(12) United States Patent
MacLachlan et al.

(10) Patent No.: US 9,006,191 B2
(45) Date of Patent: Apr. 14, 2015

(54) SILENCING OF POLO-LIKE KINASE EXPRESSION USING INTERFERING RNA

(75) Inventors: Ian MacLachlan, Mission (CA); Adam Judge, Vancouver (CA)

(73) Assignee: Protiva Biotherapeutics, Inc., Burnaby, BC (CA)

( * ) Notice: Subject to any disclaimer, the term of this patent is extended or adjusted under 35 U.S.C. 154(b) by 0 days.

(21) Appl. No.: 12/343,342

(22) Filed: Dec. 23, 2008

(65) Prior Publication Data

US 2009/0291131 A1 Nov. 26, 2009

Related U.S. Application Data

(60) Provisional application No. 61/100,653, filed on Sep. 26, 2008, provisional application No. 61/045,228, filed on Apr. 15, 2008, provisional application No. 61/017,075, filed on Dec. 27, 2007.

(51) Int. Cl.
| | |
|---|---|
| *A01N 43/04* | (2006.01) |
| *A61K 9/00* | (2006.01) |
| *A61K 9/127* | (2006.01) |
| *C12N 15/113* | (2010.01) |
| *C12N 15/88* | (2006.01) |

(52) U.S. Cl.
CPC .......... *C12N 15/1137* (2013.01); *A61K 9/0019* (2013.01); *A61K 9/127* (2013.01); *A61K 9/1271* (2013.01); *A61K 9/1272* (2013.01); *C12N 15/88* (2013.01); *C12N 2310/14* (2013.01); *C12N 2310/321* (2013.01); *C12N 2310/322* (2013.01); *C12N 2310/3231* (2013.01); *C12N 2310/3521* (2013.01); *C12N 2310/3525* (2013.01); *C12N 2310/3533* (2013.01); *C12Y 207/11021* (2013.01)

(58) Field of Classification Search
USPC ............ 435/6, 91.31, 455, 91.1, 458; 514/44; 536/23.1, 24.3, 24.5; 424/450
See application file for complete search history.

(56) References Cited

U.S. PATENT DOCUMENTS

| | | | |
|---|---|---|---|
| 5,334,761 A | 8/1994 | Gebeyehu et al. | |
| 5,578,475 A | 11/1996 | Jessee | |
| 5,627,159 A | 5/1997 | Shih et al. | |
| 5,674,908 A | 10/1997 | Haces et al. | |
| 5,736,392 A | 4/1998 | Hawley-Nelson et al. | |
| 5,877,220 A | 3/1999 | Schwartz et al. | |
| 5,958,901 A | 9/1999 | Dwyer et al. | |
| 6,020,202 A | 2/2000 | Jessee | |
| 6,020,526 A | 2/2000 | Schwartz et al. | |
| 6,034,135 A | 3/2000 | Schwartz et al. | |
| 6,051,429 A | 4/2000 | Hawley-Nelson et al. | |
| 6,075,012 A | 6/2000 | Gebeyehu et al. | |
| 6,172,049 B1 | 1/2001 | Dwyer et al. | |
| 6,251,939 B1 | 6/2001 | Schwartz et al. | |
| 6,339,173 B1 | 1/2002 | Schwartz et al. | |
| 6,376,248 B1 | 4/2002 | Hawley-Nelson et al. | |
| 6,638,529 B2 | 10/2003 | Schwartz et al. | |
| 6,671,393 B2 | 12/2003 | Hays et al. | |
| 7,166,745 B1 | 1/2007 | Chu et al. | |
| 7,479,573 B2 | 1/2009 | Chu et al. | |
| 7,507,811 B2 * | 3/2009 | Khvorova et al. | ............ 536/24.5 |
| 7,601,872 B2 | 10/2009 | Chu et al. | |
| 7,687,070 B2 | 3/2010 | Gebeyehu et al. | |
| 7,799,565 B2 | 9/2010 | MacLachlan et al. | |
| 7,807,815 B2 | 10/2010 | MacLachlan et al. | |
| 7,838,658 B2 | 11/2010 | MacLachlan et al. | |
| 7,915,450 B2 | 3/2011 | Chu et al. | |
| 8,058,068 B2 | 11/2011 | Hawley-Nelson et al. | |
| 8,158,827 B2 | 4/2012 | Chu et al. | |
| 2003/0069173 A1 | 4/2003 | Hawley-Nelson et al. | |
| 2003/0143732 A1 | 7/2003 | Fosnaugh et al. | |
| 2005/0064595 A1 | 3/2005 | MacLachlan et al. | |
| 2005/0107316 A1 | 5/2005 | Strebhardt et al. | |
| 2005/0164974 A1 * | 7/2005 | Gold et al. | ...................... 514/44 |
| 2005/0255487 A1 | 11/2005 | Khvorova et al. | |
| 2005/0260757 A1 | 11/2005 | Gebeyehu et al. | |

(Continued)

FOREIGN PATENT DOCUMENTS

| | | | |
|---|---|---|---|
| CN | 1651450 | * | 8/2005 |
| CN | 1651450 A | | 8/2005 |

(Continued)

OTHER PUBLICATIONS

Translation of CN 1651450, Ding, J., Aug. 2005.*

(Continued)

*Primary Examiner* — Jane Zara
(74) *Attorney, Agent, or Firm* — Kilpatrick Townsend & Stockton LLP

(57) ABSTRACT

The present invention provides compositions comprising interfering RNA (e.g., siRNA, aiRNA, miRNA) that target polo-like kinase 1 (PLK-1) expression and methods of using such compositions to silence PLK-1 expression. More particularly, the present invention provides unmodified and chemically modified interfering RNA molecules which silence PLK-1 expression and methods of use thereof. The present invention also provides serum-stable nucleic acid-lipid particles (e.g., SNALP) comprising an interfering RNA molecule described herein, a cationic lipid, and a non-cationic lipid, which can further comprise a conjugated lipid that inhibits aggregation of particles. The present invention further provides methods of silencing PLK-1 gene expression by administering an interfering RNA molecule described herein to a mammalian subject. The present invention additionally provides methods of identifying and/or modifying PLK-1 interfering RNA having immunostimulatory properties. Methods for sensitizing a cell such as a cancer cell to the effects of a chemotherapy drug comprising sequentially delivering PLK-1 interfering RNA followed by the chemotherapy drug are also provided.

41 Claims, 43 Drawing Sheets

(56) References Cited

U.S. PATENT DOCUMENTS

| | | |
|---|---|---|
| 2005/0282188 A1 | 12/2005 | Haeberli et al. |
| 2006/0008910 A1 | 1/2006 | MacLachlan et al. |
| 2006/0025366 A1 | 2/2006 | MacLachlan et al. |
| 2006/0134189 A1 | 6/2006 | MacLachlan et al. |
| 2006/0147514 A1 | 7/2006 | Gebeyehu et al. |
| 2006/0228406 A1 | 10/2006 | Chiou et al. |
| 2006/0240093 A1 | 10/2006 | MacLachlan et al. |
| 2007/0031844 A1 | 2/2007 | Khvorova et al. |
| 2007/0042031 A1 | 2/2007 | MacLachlan et al. |
| 2007/0054873 A1 | 3/2007 | MacLachlan et al. |
| 2007/0135370 A1 | 6/2007 | MacLachlan et al. |
| 2007/0135372 A1 | 6/2007 | MacLachlan et al. |
| 2007/0202598 A1 | 8/2007 | Chu et al. |
| 2007/0202600 A1 | 8/2007 | Chu et al. |
| 2007/0265438 A1 | 11/2007 | Khvorova et al. |
| 2008/0249046 A1 | 10/2008 | MacLachlan et al. |
| 2008/0311040 A1* | 12/2008 | Berry et al. ............... 424/9.1 |
| 2009/0143583 A1 | 6/2009 | Chu et al. |
| 2009/0149403 A1 | 6/2009 | MacLachlan et al. |
| 2009/0264511 A1* | 10/2009 | de Fougerolles et al. ... 514/44 R |
| 2009/0270481 A1 | 10/2009 | MacLachlan et al. |
| 2010/0105933 A1* | 4/2010 | Chen et al. ............... 552/544 |
| 2010/0130588 A1 | 5/2010 | Yaworski et al. |
| 2010/0159593 A1 | 6/2010 | Chu et al. |
| 2011/0076335 A1 | 3/2011 | Yaworski et al. |
| 2012/0136073 A1 | 5/2012 | Yang et al. |
| 2012/0238747 A1 | 9/2012 | Chu et al. |

FOREIGN PATENT DOCUMENTS

| | | |
|---|---|---|
| WO | WO 2004/045543 A2 | 6/2004 |
| WO | WO 2006/006948 A2 | 1/2006 |
| WO | 2006/035515 | 4/2006 |
| WO | WO 2007/051303 A1 | 5/2007 |

OTHER PUBLICATIONS

Sequence alignment data for SEQ ID No. 57.*

Cekaite et al. "Gene Expression Analysis in Blood Cells in Response to Unmodified and 2'-Modified siRNAs Reveals TLR-dependent and Independent Effects," J. Mol. Biol. 2007, vol. 365, pp. 90-108.

Judge et al. "Design of Noninflammatory Synthetic siRNA Mediating Potent Gene Silencing in Vivo," Molecular Therapy, 2006, vol. 13, No. 3, pp. 494-505.

Liu et al. "Activation of Cdc2/cyclin B and inhibition of centrosome amplification in cells depleted of Plk1 by siRNA," PNAS, 2002, vol. 99, No. 13, pp. 8672-8676.

Liu et al. "Normal Cells, but Not Cancer Cells, Survive Severe Plk1 Depletion," Molecular and Cellular Biology, 2006, vol. 26, No. 6, pp. 2093-2108.

Liu et al. "Polo-like kinase (Plk)1 depletion induces apoptosis in cancer cells," PNAS, 2003, vol. 100, No. 10, pp. 5789-5794.

Nogawa et al. "Intravesical administration of small interfering RNA targeting PLK-1 successfully prevents the growth of bladder cancer," The Journal of Clinical Investigation, 2005, vol. 115, No. 4, pp. 978-985.

Sänkuch-Schmitt et al. "Effect of RNA Silencing of Polo-Like Kinase-1 (PLK1) on Apoptosis and Spindle Formation in Human Cancer Cells," Journal of the National Cancer Institute, 2002, vol. 94, No. 24, pp. 1863-1877.

Judge, Adam et al., "Hypersensitivity and Loss of Disease Site Targeting Caused by Antibody Responses to PEGylated Liposomes," Mol Ther, Feb. 2006; 13(2):328-337.

Judge, Adam et al., "Overcoming the Innate Immune Response to Small Interfering RNA," Hum Gene Ther, Feb. 2008; 19(2):111-124.

Judge, Adam et al., "Sequence-dependent stimulation of the mammalian innate immune response by synthetic siRNA," Nature Biotechnology, 2005, vol. 23, pp. 457-462.

Robbins, Marjorie et al., "siRNA and Innate Immunity," Oligonucleotides, May 19, 2009, vol. 19, No. 2, pp. 89-101.

Ahmad, N. "Polo-like kinase (Plk) 1: a novel target for the treatment of prostate cancer," The FASEB Journal, 2004, vol. 18, No. 1, pp. 5-7.

Ahonen, L.J. et al., "Polo-like kinase 1 creates the tension-sensing 3F3/2 phosphoepitope and modulates the association of spindle-checkpoint proteins at kinetochores," Current Biology, Current Science, GB, vol. 15, No. 12, Jun. 21, 2005, pp. 1078-1089.

Zimmerman, T.S. et al, "RNA1-mediated gene silencing in non-human primates," Nature, Nature Publishing Group, London, GB, vol. 441, No. 7089, May 4, 2006, pp. 111-114.

Heyes, J. et al., "Synthesis and characterization of novel poly(ethylene glycol)-lipid conjugates suitable for use in drug delivery," Journal of Controlled Release, Elsevier, Amsterdam, NL, vol. 112, No. 2, May 15, 2006, pp. 280-290.

* cited by examiner

A

B

A

B

A

B

A

B x200 mag x400 mag x200 mag x400 mag

A

B

C

SILENCING OF POLO-LIKE KINASE EXPRESSION USING INTERFERING RNA

CROSS-REFERENCES TO RELATED APPLICATIONS

The present application claims priority to U.S. Provisional Application No. 61/017,075, filed Dec. 27, 2007, U.S. Provisional Application No. 61/045,228, filed Apr. 15, 2008, and U.S. Provisional Application No. 61/100,653, filed Sep. 26, 2008, the disclosures of which are herein incorporated by reference in their entirety for all purposes.

BACKGROUND OF THE INVENTION

Cell proliferation and programmed cell death play important roles in the growth and development of an organism. In proliferative diseases such as cancer, the processes of cell proliferation and/or programmed cell death are often perturbed. For example, a cancer cell may have unregulated cell division through either the overexpression of a positive regulator of the cell cycle or the loss of a negative regulator of the cell cycle, perhaps by mutation. Alternatively, a cancer cell may have lost the ability to undergo programmed cell death through the overexpression of a negative regulator of apoptosis. Therefore, there is a need to develop new therapeutic agents that will restore the processes of checkpoint control and programmed cell death to cancerous cells.

RNA interference (RNAi) is an evolutionarily conserved process in which recognition of double-stranded RNA (dsRNA) ultimately leads to posttranscriptional suppression of gene expression. This suppression is mediated by short dsRNA, also called small interfering RNA (siRNA), which induces specific degradation of mRNA through complementary base pairing. In several model systems, this natural response has been developed into a powerful tool for the investigation of gene function (see, e.g., Elbashir et al., *Genes Dev.*, 15:188-200 (2001); Hammond et al., *Nat. Rev. Genet.*, 2:110-119 (2001)). More recently, it was discovered that introducing synthetic 21-nucleotide dsRNA duplexes into mammalian cells could efficiently silence gene expression. Although the precise mechanism is still unclear, RNAi offers a new way to inactivate genes of interest. In particular, for the treatment of neoplastic disorders such as cancer, RNAi provides a potential new approach to modulate (e.g., reduce) the expression of certain genes, e.g., an anti-apoptotic molecule, a growth factor, a growth factor receptor, a mitotic spindle protein, a cell cycle protein, an angiogenic factor, an oncogene, an intracellular signal transducer, a molecular chaperone, and combinations thereof.

One such target is the polo-like kinase 1 (PLK-1) gene, which encodes a member of a family of serine/threonine protein kinases known as polo-like kinases (see, e.g., Nigg, *Curr. Opin. Cell. Biol.*, 10:776-783 (1998)). In eukaryotes, the regulated progression through the cell cycle is controlled by a group of genes whose expression fluctuates throughout the cycle. Cyclin-dependent kinases and their associated regulatory subunits, the cyclins, are the primary regulators of the cell cycle. These heterodimeric complexes act by phosphorylating downstream targets that, in turn, trigger signaling events that liberate nuclear proteins necessary for entry into subsequent phases of the cell cycle. Polo-like kinases such as PLK-1 contribute to the activation and inactivation of these heterodimeric complexes.

As cells progress through the cell cycle, polo-like kinases undergo fluctuations in abundance, activity, and localization to control multiple stages of the cell cycle (Hamanaka et al., *J. Biol. Chem.*, 270:21086-21091 (1995)). This family of kinases also functions in centrosome maturation (Lane et al., *J. Cell. Biol.*, 135:1701-1713 (1996)), bipolar spindle formation (Golsteyn et al., *J. Cell. Biol.*, 129:1617-1628 (1995)), DNA damage checkpoint adaptation (Arnaud et al., *Chromosoma*, 107:424-429 (1998)), and regulation of the anaphase-promoting complex (Kotani et al., *Mol. Cell*, 1:371-380 (1998)).

PLK-1 was the first member of this family of kinases to be identified as the mammalian counterpart to the *Drosophila melanogaster* gene polo, required for passage through mitosis (Golsteyn et al, *J. Cell. Sci.*, 107:1509-1517 (1994); Hamanaka et al, *Cell. Growth Differ.*, 5:249-257 (1994); Holtrich et al., *Proc. Natl. Acad. Sci. U.S.A.*, 91:1736-1740 (1994); Lake et al., *Mol. Cell. Biol.*, 13:7793-7801 (1993)). Expression of PLK-1 was shown to correlate with mitotic activity of cells (Golsteyn et al., *J. Cell. Sci.*, 107:1509-1517 (1994); Lake et al., *Mol. Cell. Biol.*, 13:7793-7801 (1993)) and to be high in tumors of several origins including lung, colon, stomach, smooth muscle, and esophagus (Holtrich et al., *Proc. Natl. Acad. Sci. U.S.A.*, 91:1736-1740 (1994)). Overexpression or constitutive expression of PLK-1 has also been shown to induce malignant transformation of mammalian cells (Mundt et al., *Biochem. Biophys. Res. Commun.*, 239:377-385 (1997); Smith et al., *Biochem. Biophys. Res. Commun.*, 234:397-405 (1997)). Microinjection of PLK-1 antisense RNA into growing mouse NIH3T3 fibroblast cells was shown to block tritiated thymidine incorporation, suggesting that PLK-1 expression is restricted to and required by proliferating cells (Hamanaka et al., *Cell. Growth Differ.*, 5:249-257 (1994)).

Further support for this conclusion is found in studies showing that elevated levels of PLK-1 expression are significant prognostic indicators of non-small cell lung cancer (Wolf et al., *Oncogene*, 14:543-549 (1997)), breast and lung cancer (Yuan et al., *Am. J. Pathol.*, 150:1165-1172 (1997)), esophageal carcinoma (Tokumitsu et al., *Int. J. Oncol.*, 15:687-692 (1999)), and squamous cell carcinomas of the head and neck (Knecht et al., *Cancer Res.*, 59:2794-2797 (1999)). The pharmacological modulation of PLK-1 activity, expression, or function may therefore be an appropriate point of therapeutic intervention in pathological conditions.

Currently, there are no known therapeutic agents which effectively inhibit the synthesis of PLK-1 and investigative strategies aimed at modulating PLK-1 function have involved the use of antibodies and antisense oligonucleotides. For example, inhibition of PLK-1 expression using antisense oligonucleotides resulted in the loss of cell viability in cultured A549 cells and anti-tumor activity in nude mice A549 xenografts (Elez et al., *Biochem. Biophys. Res. Commun.*, 209:352-356 (2000)). Similarly, U.S. Pat. No. 6,906,186 describes the inhibition of PLK-1 expression using antisense oligonucleotides in an in vitro cell culture system. However, these strategies are untested as therapeutic protocols and consequently there remains a long-felt need for agents capable of effectively inhibiting PLK-1 function in vivo.

Thus, there is a need for compositions and methods for specifically modulating PLK-1 expression. The present invention addresses these and other needs.

SUMMARY OF THE INVENTION

The present invention provides compositions comprising interfering RNA (e.g., siRNA, aiRNA, miRNA) that target polo-like kinase 1 (PLK-1) expression and methods of using such compositions to silence PLK-1 expression. More particularly, the present invention provides unmodified and chemically modified interfering RNA molecules which silence PLK-1 expression and methods of use thereof, e.g., for treating a cancer such as hepatocellular carcinoma (HCC). The present invention also provides serum-stable nucleic acid-lipid particles (e.g., SNALP) comprising an interfering RNA molecule described herein, a cationic lipid, and a non-cationic lipid, which can further comprise a conjugated lipid that inhibits aggregation of particles. The present invention further provides methods of silencing PLK-1 gene expression by administering an interfering RNA molecule described herein to a mammalian subject. The present invention additionally provides methods of identifying and/or modifying PLK-1 interfering RNA having immunostimulatory properties. Methods for sensitizing a cell such as a cancer cell to the effects of a chemotherapy drug comprising sequentially delivering PLK-1 interfering RNA followed by the chemotherapy drug are also provided.

In one aspect, the present invention provides a modified siRNA molecule comprising a double-stranded region of about 15 to about 60 nucleotides in length (e.g., about 15-60, 15-50, 15-40, 15-30, 15-25, or 19-25 nucleotides in length, or 15, 16, 17, 18, 19, 20, 21, 22, 23, 24, or 25 nucleotides in length), wherein the modified siRNA molecule is capable of silencing PLK-1 expression.

Typically, the modified siRNA molecule comprises one, two, three, four, five, six, seven, eight, nine, ten, or more modified nucleotides in the double-stranded region. In some embodiments, the modified siRNA comprises from about 1% to about 100% (e.g., about 1%, 5%, 10%, 15%, 20%, 25%, 30%, 35%, 40%, 45%, 50%, 55%, 60%, 65%, 70%, 75%, 80%, 85%, 90%, 95%, or 100%) modified nucleotides in the double-stranded region. In preferred embodiments, less than about 25% (e.g., less than about 25%, 20%, 15%, 10%, or 5%) or from about 1% to about 25% (e.g., from about 1%-25%, 5%-25%, 10%-25%, 15%-25%, 20%-25%, or 10%-20%) of the nucleotides in the double-stranded region comprise modified nucleotides.

In some embodiments, the modified siRNA comprises modified nucleotides including, but not limited to, 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In preferred embodiments, the modified siRNA comprises 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof. In certain instances, the modified siRNA does not comprise 2'OMe-cytosine nucleotides. In other embodiments, the modified siRNA comprises a hairpin loop structure.

The modified siRNA can comprise modified nucleotides in one strand (i.e., sense or antisense) or both strands of the double-stranded region of the siRNA molecule. Preferably, uridine and/or guanosine nucleotides are modified at selective positions in the double-stranded region of the siRNA duplex. With regard to uridine nucleotide modifications, at least one, two, three, four, five, six, or more of the uridine nucleotides in the sense and/or antisense strand can be a modified uridine nucleotide such as a 2'OMe-uridine nucleotide. In some embodiments, every uridine nucleotide in the sense and/or antisense strand is a 2'OMe-uridine nucleotide. With regard to guanosine nucleotide modifications, at least one, two, three, four, five, six, or more of the guanosine nucleotides in the sense and/or antisense strand can be a modified guanosine nucleotide such as a 2'OMe-guanosine nucleotide. In some embodiments, every guanosine nucleotide in the sense and/or antisense strand is a 2'OMe-guanosine nucleotide.

In some embodiments, the modified siRNA molecule is less immunostimulatory than a corresponding unmodified siRNA sequence. In certain embodiments, the modified siRNA is at least about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% less immunostimulatory than the corresponding unmodified siRNA sequence. In other embodiments, the modified siRNA is at least about 70% (e.g., 70%, 75%, 80%, 85%, 90%, 91%, 92%, 93%, 94%, 95%, 96%, 97%, 98%, 99%, or 100%) less immunostimulatory than the corresponding unmodified siRNA sequence. It will be readily apparent to those of skill in the art that the immunostimulatory properties of the modified siRNA molecule and the corresponding unmodified siRNA molecule can be determined by, for example, measuring INF-α and/or IL-6 levels about two to about twelve hours after systemic administration in a mammal or transfection of a mammalian responder cell using an appropriate lipid-based delivery system (such as the SNALP delivery system or other lipoplex systems disclosed herein).

In certain embodiments, the modified siRNA molecule has an $IC_{50}$ (i.e., half-maximal inhibitory concentration) less than or equal to ten-fold that of the corresponding unmodified siRNA (i.e., the modified siRNA has an $IC_{50}$ that is less than or equal to ten-times the $IC_{50}$ of the corresponding unmodified siRNA). In other embodiments, the modified siRNA has an $IC_{50}$ less than or equal to three-fold that of the corresponding unmodified siRNA sequence. In yet other embodiments, the modified siRNA has an $IC_{50}$ less than or equal to two-fold that of the corresponding unmodified siRNA. It will be readily apparent to those of skill in the art that a dose-response curve can be generated and the $IC_{50}$ values for the modified siRNA and the corresponding unmodified siRNA can be readily determined using methods known to those of skill in the art.

In yet another embodiments, the modified siRNA is capable of silencing at least about 5%, 10%, 15%, 20%, 25%, 30%, 35%, 40%, 45%, 50%, 55%, 60%, 65%, 70%, 75%, 80%, 85%, 90%, 95%, or 100% of the expression of the target sequence relative to the corresponding unmodified siRNA sequence.

In some embodiments, the modified siRNA does not comprise phosphate backbone modifications, e.g., in the sense and/or antisense strand of the double-stranded region. In other embodiments, the modified siRNA does not comprise 2'-deoxy nucleotides, e.g., in the sense and/or antisense strand of the double-stranded region. In certain instances, the nucleotide at the 3'-end of the double-stranded region in the sense and/or antisense strand is not a modified nucleotide. In certain other instances, the nucleotides near the 3'-end (e.g., within one, two, three, or four nucleotides of the 3'-end) of the double-stranded region in the sense and/or antisense strand are not modified nucleotides.

The modified siRNA molecules of the present invention may have 3' overhangs of one, two, three, four, or more nucleotides on one or both sides of the double-stranded region, or may lack overhangs (i.e., have blunt ends) on one or both sides of the double-stranded region. Preferably, the modified siRNA has 3' overhangs of two nucleotides on each side of the double-stranded region. In certain instances, the 3' overhang on the antisense strand has complementarity to the target sequence and the 3' overhang on the sense strand has complementarity to the complementary strand of the target sequence. Alternatively, the 3' overhangs do not have complementarity to the target sequence or the complementary strand thereof. In some embodiments, the 3' overhangs comprise one, two, three, four, or more nucleotides such as 2'-deoxy (2'H) nucleotides. In certain preferred embodiments, the 3' overhangs comprise deoxythymidine (dT) and/or uridine nucleotides. In other embodiments, one or more of the nucleotides in the 3' overhangs on one or both sides of the double-stranded region comprise modified nucleotides. Non-limiting examples of modified nucleotides are described above and include 2'OMe nucleotides, 2'-deoxy-2'F nucleotides, 2'-deoxy nucleotides, 2'-O-2-MOE nucleotides, LNA nucleotides, and mixtures thereof. In preferred embodiments, one, two, three, four, or more nucleotides in the 3' overhangs present on the sense and/or antisense strand of the siRNA comprise 2'OMe nucleotides (e.g., 2'OMe purine and/or pyrimidine nucleotides) such as, for example, 2'OMe-guanosine nucleotides, 2'OMe-uridine nucleotides, 2'OMe-adenosine nucleotides, 2'OMe-cytosine nucleotides, and mixtures thereof.

The siRNA molecules of the present invention may comprise at least one or a cocktail (e.g., at least two, three, four, five, six, seven, eight, nine, ten, or more) of modified siRNA sequences that silence PLK-1 expression. In certain instances, one or more of the modified siRNA described herein are present in a cocktail with one or more (e.g., at least two, three, four, five, six, seven, eight, nine, ten, or more) unmodified siRNA sequences that silence PLK-1 expression. In some embodiments, the modified siRNA molecule comprises a chemically modified (e.g., 2'OMe-modified) version of at least one or a cocktail of the unmodified sequences set forth in Tables 1-7. In other embodiments, the modified siRNA molecule comprises at least one or a cocktail of the modified sequences set forth in Tables 3, 6, and 10-11. Preferably, the modified siRNA molecule is selected from the group consisting of PLK1424 2/6, PLK1424 U4/GU, PLK1424 U4/G, PLK773 G/GU, PLK1425 3/5, and a mixture thereof.

In some embodiments, the corresponding unmodified siRNA sequence comprises at least one, two, three, four, five, six, seven, or more 5'-GU-3' motifs. The 5'-GU-3' motif can be in the sense strand, the antisense strand, or both strands of the unmodified siRNA sequence. The 5'-GU-3' motifs may be adjacent to each other or, alternatively, they may be separated by 1, 2, 3, 4, 5, 6, 7, 8, 9, 10, 11, 12, or more nucleotides.

In certain embodiments, the modified siRNA further comprises a carrier system, e.g., to deliver the modified siRNA into a cell of a mammal. Examples of carrier systems suitable for use in the present invention include, but are not limited to, nucleic acid-lipid particles, liposomes, micelles, virosomes, nucleic acid complexes, and mixtures thereof. In certain instances, the siRNA is complexed with a lipid such as a cationic lipid to form a lipoplex. In certain other instances, the modified siRNA is complexed with a polymer such as a cationic polymer (e.g., polyethylenimine (PEI)) to form a polyplex. The modified siRNA may also be complexed with cyclodextrin or a polymer thereof. Preferably, the modified siRNA is encapsulated in a nucleic acid-lipid particle.

The present invention also provides a pharmaceutical composition comprising a modified siRNA molecule described herein and a pharmaceutically acceptable carrier.

In another aspect, the present invention provides a nucleic acid-lipid particle that targets PLK-1 expression. The nucleic acid-lipid particle comprises a modified siRNA molecule that silences PLK-1 expression, a cationic lipid, and a non-cationic lipid. In certain instances, the nucleic acid-lipid particle further comprises a conjugated lipid that inhibits aggregation of particles. Preferably, the nucleic acid-lipid particle comprises a modified siRNA molecule that silences PLK-1 expression, a cationic lipid, a non-cationic lipid, and a conjugated lipid that inhibits aggregation of particles.

The cationic lipid may be, e.g., 1,2-dilinoleyloxy-N,N-dimethylaminopropane (DLinDMA), 1,2-dilinolenyloxy-N,N-dimethylaminopropane (DLenDMA), N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9', 1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleyoxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), or mixtures thereof. Cationic lipids such as CLinDMA, as well as additional cationic lipids, are described in U.S. Patent Publication No. 20060240554. Cationic lipids such as DLin-K-DMA, as well as additional cationic lipids, are described in U.S. Provisional Application No. 61/018, 627, filed Jan. 2, 2008, U.S. Provisional Application No. 61/049,568, filed May 1, 2008, and U.S. Provisional Application No. 61/104,219, filed Oct. 9, 2008. Cationic lipids such as DLin-K-XTC2-DMA, as well as additional cationic lipids, are described in U.S. Provisional Application No. 61/104, 212, filed Oct. 9, 2008. The cationic lipid may comprise from about 2 mol % to about 60 mol %, about 5 mol % to about 45 mol %, about 5 mol % to about 15 mol %, about 20 mol % to about 50 mol %, about 30 mol % to about 50 mol %, about 40 mol % to about 50 mol %, or about 40 mol % of the total lipid present in the particle.

The non-cationic lipid may be an anionic lipid or a neutral lipid including, but not limited to, distearoylphosphatidylcholine (DSPC), dipalmitoylphosphatidylcholine (DPPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), cholesterol, or mixtures thereof. The non-cationic lipid may comprise from about 5 mol % to about 90 mol %, about 10 mol % to about 85 mol %, about 20 mol % to about 85 mol %, about 10 mol % (e.g., phospholipid such as DSPC or DPPC only), or about 60 mol % (e.g., about 10 mol % of a phospholipid such as DSPC or DPPC and about 48 mol % cholesterol) of the total lipid present in the particle.

The conjugated lipid that inhibits aggregation of particles may be a polyethyleneglycol (PEG)-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a polyethyleneglycol-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-dilauryloxypropyl (C12), a PEG-dimyristyloxypropyl (C14), a PEG-dipalmityloxypropyl (C16), and a PEG-distearyloxypropyl (C18). Additional PEG-lipid conjugates suitable for use in the present invention include, but are not limited to, PEG-C-DOMG, described in U.S. Provisional Application No. 61/039,748, filed Mar. 26, 2008, and 1-[8'-(1,2-Dimyristoyl-3-propanoxy)-carboxamido-3',6'-dioxaoctanyl]carbamoyl-co-methyl-poly(ethylene glycol) (2KPEG-DMG), described in U.S. Pat. No. 7,404,969. In some embodiments, the conjugated lipid that inhibits aggregation of particles is a CPL that has the formula: A-W-Y, wherein A is a lipid moiety, W is a hydrophilic polymer, and Y is a polycationic moiety. W may be a polymer selected from the group consisting of polyethyleneglycol (PEG), polyamide, polylactic acid, polyglycolic acid, polylactic acid/polyglycolic acid copolymers, or combinations thereof, the polymer having a molecular weight of from about 250 to about 7000 daltons. In some embodiments, Y has at least 4 positive charges at a selected pH. In some embodiments, Y may be lysine, arginine, asparagine, glutamine, derivatives thereof, or combinations thereof. The conjugated lipid that prevents aggregation of particles may be from 0 mol % to about 20 mol %, about 0.5 mol % to about 20 mol %, about 1 mol % to about 15 mol %, about 4 mol % to about 10 mol %, or about 2 mol % of the total lipid present in the particle.

In some embodiments, the nucleic acid-lipid particle further comprises cholesterol or a derivative thereof. Examples of suitable cholesterol derivatives include, but are not limited to, cholestanol, cholestanone, cholestenone, coprostanol, cholesteryl-2'-hydroxyethyl ether, and cholesteryl-4'-hydroxybutyl ether. The cholesterol or cholesterol derivative may be from 0 mol % to about 10 mol %, about 2 mol % to about 10 mol %, about 10 mol % to about 60 mol %, about 20 mol % to about 45 mol %, about 30 mol % to about 50 mol %, or about 48 mol % of the total lipid present in the particle.

In one specific embodiment of the invention, the nucleic acid-lipid particle comprises 40 mol % DLinDMA, 10 mol % DSPC, 2 mol % PEG-cDMA, and 48 mol % cholesterol.

In other embodiments of the invention, the nucleic acid-lipid particle comprises: (a) one or more unmodified and/or modified siRNA that silence PLK-1 expression; (b) a cationic lipid comprising from about 50 mol % to about 85 mol % of the total lipid present in the particle; (c) a non-cationic lipid comprising from about 13 mol % to about 49.5 mol % of the total lipid present in the particle; and (d) a conjugated lipid that inhibits aggregation of particles comprising from about 0.5 mol % to about 2 mol % of the total lipid present in the particle. In a preferred embodiment, the siRNA is fully encapsulated within the lipid of the nucleic acid-lipid particle such that the siRNA in the nucleic acid-lipid particle is resistant in aqueous solution to degradation by a nuclease. In a preferred embodiment, the nucleic acid-lipid particle is substantially non-toxic to mammals.

In these SNALP embodiments, the nucleic acid-lipid particle may comprise one or more of the cationic lipids described above. In a preferred embodiment, the cationic lipid is DLinDMA. The cationic lipid typically comprises from about 50 mol % to about 85 mol %, about 50 mol % to about 80 mol %, about 50 mol % to about 75 mol %, about 50 mol % to about 65 mol %, or about 55 mol % to about 65 mol % of the total lipid present in the particle.

The non-cationic lipid in these SNALP embodiments may be an anionic lipid or a neutral lipid. In one embodiment, the non-cationic lipid comprises cholesterol or a derivative thereof. In this embodiment, the cholesterol or cholesterol derivative comprises from about 30 mol % to about 40 mol % of the total lipid present in the particle. In another embodiment, the non-cationic lipid comprises a phospholipid. In yet another embodiment, the non-cationic lipid comprises a mixture of a phospholipid and cholesterol or a cholesterol derivative.

Phospholipids suitable for use in these SNALP embodiments include, but are not limited to, DPPC, DSPC, DOPE, POPC, POPE, POPG, DPPE, DMPE, DSPE, monomethyl-phosphatidylethanolamine, dimethyl-phosphatidylethanolamine, DEPE, SOPE, EPC, and a mixture thereof. When the non-cationic lipid is a mixture of a phospholipid and cholesterol or a cholesterol derivative, the phospholipid comprises from about 4 mol % to about 10 mol % of the total lipid present in the particle, and the cholesterol or cholesterol derivative comprises from about 30 mol % to about 40 mol % of the total lipid present in the particle. If a cholesterol derivative is used, the cholesterol derivative includes, but is not limited to, cholestanol, cholestanone, cholestenone, coprostanol, cholesteryl-2'-hydroxyethyl ether, and cholesteryl-4'-hydroxybutyl ether. In a preferred embodiment, the phospholipid comprises DPPC.

The SNALPs of these embodiments also comprise a conjugated lipid that inhibits aggregation of the particles. Examples of suitable conjugated lipids include, but are not limited to, a PEG-lipid conjugate, a polyamide (ATTA)-lipid conjugate, a cationic-polymer-lipid conjugates (CPLs), or mixtures thereof. In one preferred embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. In a preferred embodiment, the conjugated lipid is a PEG-lipid.

Examples of suitable PEG-lipids include, but are not limited to, a PEG-DAG, a PEG-DAA, a PEG-phospholipid, a PEG-ceramide (Cer), or mixtures thereof. In a preferred embodiment, the PEG-lipid is a PEG-DAA conjugate. Examples of suitable PEG-DAA conjugates include, but are not limited to, a PEG-dilauryloxypropyl (C12), a PEG-dimyristyloxypropyl (C14), a PEG-dipalmityloxypropyl (C16), and a PEG-distearyloxypropyl (C18). In a preferred embodiment, the PEG-DAA conjugate is PEG-dimyristyloxypropyl (C14). In another preferred embodiment, the PEG-DAA conjugate is PEG-distearyloxypropyl (C18). Additional PEG-lipid conjugates include, without limitation, PEG-C-DOMG, 2KPEG-DMG, and a mixture thereof. The conjugated lipid typically comprises about 0.5 mol % to about 2 mol % of the total lipid present in the particle.

Typically, the SNALPs of these embodiments have a lipid:nucleic acid ratio of about 1 to about 100. In a preferred embodiment, these SNALPs have a lipid:nucleic acid ratio of about 5 to about 15. In another preferred embodiment, these SNALPs have a lipid:nucleic acid ratio of about 6. Typically, these SNALPs have a mean diameter of from about 50 nm to about 150 nm. In a preferred embodiment, these SNALPs have a mean diameter of from about 70 nm to about 90 nm.

In one specific embodiment of the invention, the SNALP comprises: (a) one or more unmodified and/or modified siRNA that silence PLK-1 expression; (b) a cationic lipid comprising from about 56.5 mol % to about 66.5 mol % of the total lipid present in the particle; (c) a non-cationic lipid comprising from about 31.5 mol % to about 42.5 mol % of the total lipid present in the particle; and (d) a conjugated lipid that inhibits aggregation of particles comprising from about 1 mol % to about 2 mol % of the total lipid present in the particle. This embodiment of SNALP is generally referred to herein as the "1:62" formulation. In a preferred embodiment, the cationic lipid is DLinDMA, the non-cationic lipid is cholesterol and the conjugated lipid is a PEG-DAA conjugate. Although these are preferred embodiments of the 1:62 formulation, those of skill in the art will appreciate that other cationic lipids, non-cationic lipids, including other cholesterol derivatives, and conjugated lipids can be used in the 1:62 formulation as described herein.

In another specific embodiment of the invention, the SNALP comprises: (a) one or more unmodified and/or modified siRNA that silence PLK-1 expression; (b) a cationic lipid comprising from about 52 mol % to about 62 mol % of the total lipid present in the particle; (c) a non-cationic lipid comprising from about 36 mol % to about 47 mol % of the total lipid present in the particle; and (d) a conjugated lipid that inhibits aggregation of particles comprising from about 1 mol % to about 2 mol % of the total lipid present in the particle. This embodiment of SNALP is generally referred to herein as the "1:57" formulation. In a preferred embodiment, the cationic lipid is DLinDMA, the non-cationic lipid is a mixture of a phospholipid (such as DPPC) and cholesterol, wherein the phospholipid comprises about 5 mol % to about 9 mol % of the total lipid present in the particle, and the cholesterol (or cholesterol derivative) comprises about 32 mol % to about 37 mol % of the total lipid present in the particle, and the PEG-lipid is PEG-DAA. Although these are preferred embodiments of the 1:57 formulation, those of skill in the art will appreciate that other cationic lipids, non-cationic lipids (including other phospholipids and other cholesterol derivatives) and conjugated lipids can be used in the 1:57 formulation as described herein.

In some embodiments, the nucleic acid-lipid particles comprise 1, 2, 3, 4, 5, 6, 7, 8, 9, 10, or more unmodified or modified siRNA molecules comprising or consisting of the sequences set forth in Tables 1-7 and 10-11. In other embodiments, the nucleic acid-lipid particles comprise modified siRNA molecules selected from the group consisting of PLK1424 U4/GU, PLK1424 U4/G, PLK773 G/GU, PLK1425 3/5, and mixtures thereof.

The nucleic acid-lipid particles of the invention are useful for the therapeutic delivery of siRNA molecules that silence PLK-1 expression. In one embodiment, a modified siRNA molecule described herein is formulated into nucleic acid-lipid particles, and the particles are administered to a mammal (e.g., a rodent such as a mouse or a primate such as a human, chimpanzee, or monkey) requiring such treatment. In certain instances, a therapeutically effective amount of the nucleic acid-lipid particle can be administered to the mammal, e.g., for treating a cancer such as hepatocellular carcinoma (HCC). Administration of the nucleic acid-lipid particle can be by any route known in the art, such as, e.g., oral, intranasal, intravenous, intraperitoneal, intramuscular, intra-articular, intralesional, intratracheal, subcutaneous, or intradermal.

In certain embodiments, the siRNA molecule in the nucleic acid-lipid particle is not substantially degraded after exposure of the particle to a nuclease at 37° C. for at least 20, 30, 45, or 60 minutes, or after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours.

In some embodiments, the siRNA molecule is fully encapsulated in the nucleic acid-lipid particle. In other embodiments, the siRNA molecule is complexed with the lipid portion of the particle.

The present invention further provides pharmaceutical compositions comprising the nucleic acid-lipid particles described herein and a pharmaceutically acceptable carrier.

In yet another aspect, the siRNA molecules described herein are used in methods for silencing PLK-1 expression. In particular, it is an object of the present invention to provide in vitro and in vivo methods for the treatment of a disease or disorder in a mammal by downregulating or silencing the transcription and/or translation of a PLK-1 gene. In one embodiment, the present invention provides a method for introducing an siRNA that silences expression (e.g., mRNA and/or protein levels) of a PLK-1 gene into a cell by contacting the cell with an siRNA molecule described herein. In another embodiment, the present invention provides a method for in vivo delivery of an siRNA molecule that silences expression of a PLK-1 gene by administering to a mammal an siRNA molecule described herein. Administration of the siRNA molecule can be by any route known in the art, such as, e.g., oral, intranasal, intravenous, intraperitoneal, intramuscular, intra-articular, intralesional, intratracheal, subcutaneous, or intradermal.

In these methods, the siRNA molecule that silences PLK-1 expression is typically formulated with a carrier system, and the carrier system comprising the siRNA molecule is administered to a mammal requiring such treatment. Alternatively, cells are removed from a mammal such as a human, the siRNA is delivered in vitro using a carrier system, and the cells are then administered to the mammal, such as by injection. Examples of carrier systems suitable for use in the present invention include, but are not limited to, nucleic acid-lipid particles, liposomes, micelles, virosomes, nucleic acid complexes (e.g., lipoplexes, polyplexes, etc.), and mixtures thereof. The carrier system may comprise at least one or a cocktail (e.g., at least 2, 3, 4, 5, 6, 7, 8, 9, 10, or more) of siRNA molecules that silence PLK-1 expression. In certain embodiments, the carrier system comprises at least one or a cocktail of the sequences set forth in Tables 1-7 and 10-11.

In some embodiments, the siRNA molecule that silences PLK-1 expression is in a nucleic acid-lipid particle comprising the siRNA molecule, a cationic lipid, and a non-cationic lipid. Preferably, the siRNA molecule is in a nucleic acid-lipid particle comprising the siRNA molecule, a cationic lipid, a non-cationic lipid, and a conjugated lipid that inhibits aggregation of particles. A therapeutically effective amount of the nucleic acid-lipid particle can be administered to a mammal (e.g., a rodent such as a mouse or a primate such as a human, chimpanzee, or monkey).

In some embodiments, the mammal has a cell proliferative disorder. In certain aspects of this embodiment, the mammal has a cell proliferative disorder selected from the group consisting of neoplasia (e.g., cancer), hyperplasia, restenosis, cardiac hypertrophy, immune disorders, and inflammation. Preferably, the cell proliferative disorder is a neoplastic disorder such as cancer. In some embodiments, the cancer includes, but is not limited to, hepatocellular carcinoma (HCC), papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, lung cancer, colorectal cancer, thyroid cancer, pancreatic cancer, gastric cancer, leukemia, lymphoma, Hodgkin's disease, osteosarcoma, testicular cancer, and Burkitt's disease.

In one embodiment, at least about 1%, 2%, 4%, 6%, 8%, 10%, 12%, 14%, 16%, 18%, or 20% of the total injected dose of the nucleic acid-lipid particles is present in plasma at about 1, 2, 4, 6, 8, 12, 16, 18, or 24 hours after injection. In other embodiments, more than about 20%, 30%, 40%, or as much as about 60%, 70%, or 80% of the total injected dose of the nucleic acid-lipid particles is present in plasma at about 1, 4, 6, 8, 10, 12, 20, or 24 hours after injection. In another embodiment, the effect of the siRNA molecule (e.g., downregulation of the target PLK-1 sequence) at a site proximal or distal to the site of administration is detectable at about 12, 24, 48, 72, or 96 hours, or at about 6, 8, 10, 12, 14, 16, 18, 19, 20, 22, 24, 26, or 28 days after administration of the nucleic acid-lipid particles. In a further embodiment, downregulation of expression of the target PLK-1 sequence is detectable at about 12, 24, 48, 72, or 96 hours, or at about 6, 8, 10, 12, 14, 16, 18, 19, 20, 22, 24, 26, or 28 days after administration. In some embodiments, downregulation of a PLK-1 gene is determined by detecting mRNA or protein levels in a biological sample from the mammal. In other embodiments, downregulation of expression of a PLK-1 sequence is detected by measuring cell viability or the induction of apoptosis of cells in a biological sample from the mammal.

The nucleic acid-lipid particles are suitable for use in intravenous nucleic acid delivery as they are stable in circulation, of a size required for pharmacodynamic behavior resulting in access to extravascular sites, and target cell populations. The present invention also provides pharmaceutically acceptable compositions comprising nucleic acid-lipid particles.

In a further aspect, the siRNA molecules described herein are used in methods for sensitizing a cell to the effects of a chemotherapy drug. In particular, it is an object of the present invention to provide in vitro and in vivo methods for the treatment of a cell proliferative disorder in a mammal by downregulating or silencing the transcription and/or translation of a PLK-1 gene in combination with administration of a chemotherapy drug. As described in detail herein, a mammal such as a human can be treated with a suitable dose of one or more unmodified or modified siRNA molecules (e.g., formulated in nucleic acid-lipid particles) before, during, and/or after chemotherapy drug administration. In preferred embodiments, a cell such as a cancer cell in a mammal such as a human is contacted with an siRNA that silences PLK-1 expression prior to administering the chemotherapy drug.

In an additional aspect, the present invention provides compositions comprising the asymmetrical interfering RNA (aiRNA) molecules described herein that target PLK-1 expression and methods of using such compositions to silence PLK-1 expression.

In a related aspect, the present invention provides compositions comprising the microRNA (miRNA) molecules described herein that target PLK-1 expression and methods of using such compositions to silence PLK-1 expression.

Other objects, features, and advantages of the present invention will be apparent to one of skill in the art from the following detailed description and figures.

Figure 39:
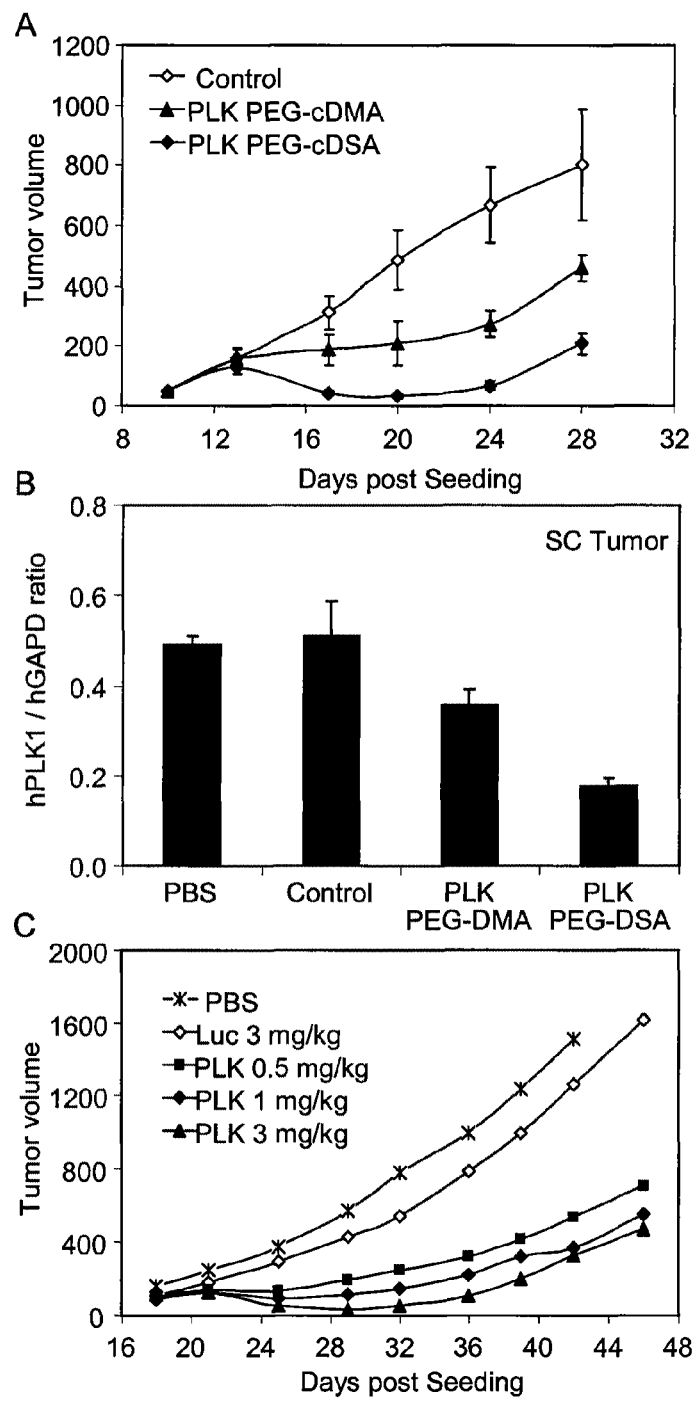

FIG. 39 illustrates data demonstrating the therapeutic activity of PLK-1 SNALP containing either C14 or C18 PEG-lipids in subcutaneous tumors. (A) Inhibition of subcutaneous tumor growth by alternate PLK1424-2/A SNALP formulations. Mice were administered PLK1424-2/A SNALP comprising either PEG-cDMA or PEG-cDSA (6×2 mg/kg intravenous) between d 10 and d 21 after Hep3B tumor seeding. Values are mean tumor volumes (mm3)+/−SD (n=5). Control=Luc-U/U siRNA SNALP (PEG-cDMA). (B) Corresponding hPLK-1:hGAPDH mRNA ratio in subcutaneous Hep3B tumors following single administration (2 mg/kg) of PLK1424-2/A or Luc-U/U siRNA; Mean+SD (n=4). (C) Dose response of PLK1424-2/A PEG-cDSA SNALP in Hep3B tumors. Mice bearing established (~100 mm$^3$) tumors were administered PLK1424-2/A PEG-cDSA SNALP (6×3, 1, or 0.5 mg/kg), Luc PEG-cDSA SNALP (6×3 mg/kg), or PBS vehicle every 2-3 days between days 18-29 after seeding. Values represent mean tumor volumes (mm$^3$) (n=5). Mean SNALP particle size and (polydispersity) were 81 (0.10), 71 (0.03), 82 (0.12), and 74 (0.05) nm for PLK1424 PEG-cDMA, PLK1424 PEG-cDSA, Luc PEG-cDMA, and Luc PEG-cDSA, respectively.

Figure 40:
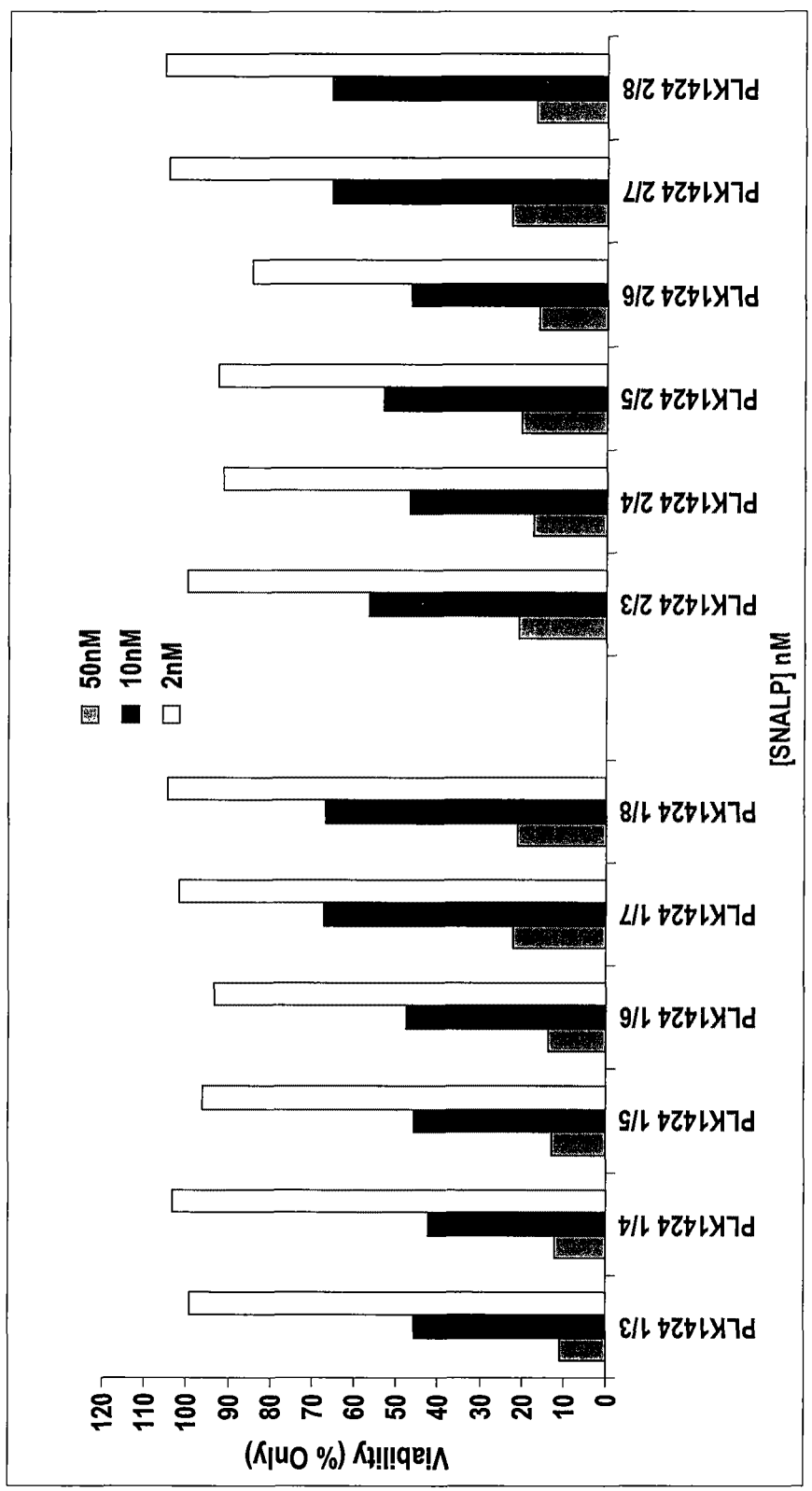

FIG. 40 illustrates data demonstrating that different chemical modification patterns in the PLK1424 siRNA sequence were well tolerated and the modified siRNA molecules retained potent activity in killing human tumor cells.

Figure 41:
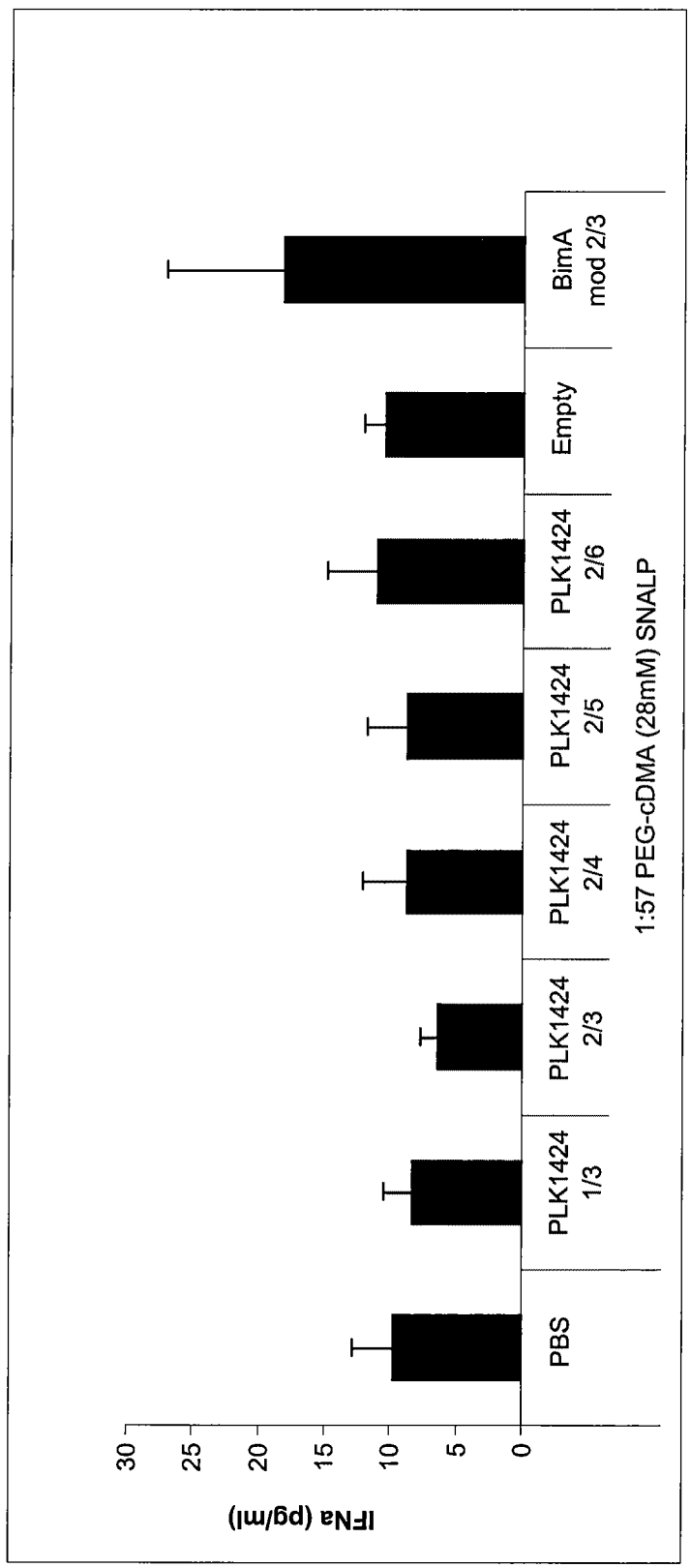

FIG. 41 illustrates data demonstrating that modified PLK1424 siRNAs did not induce an IFN-α response that was greater than the negative controls.

Figure 42:
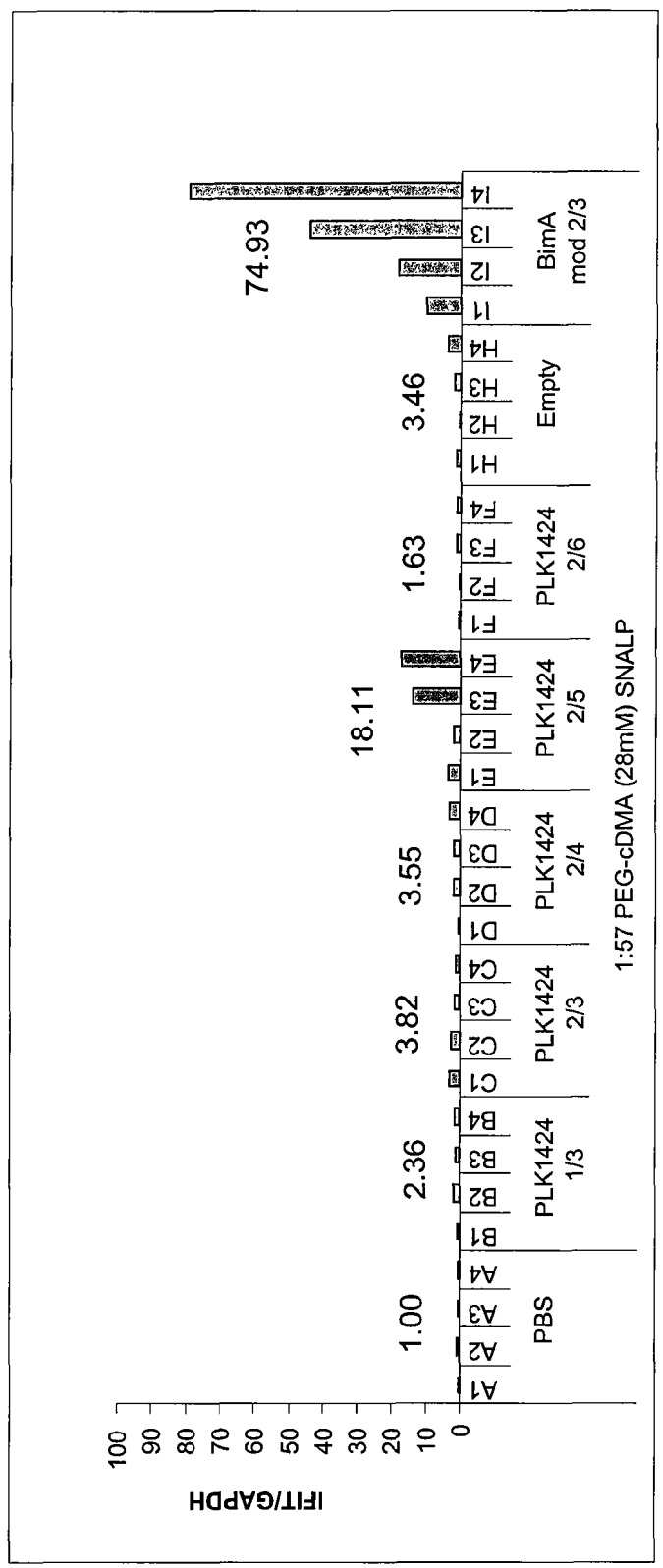

FIG. 42 illustrates data demonstrating that there was no significant IFIT1 induction above that of empty SNALP with PLK1424 1/3, PLK1424 2/3, PLK1424 2/4, and PLK1424 2/6 siRNAs.

Figure 43:
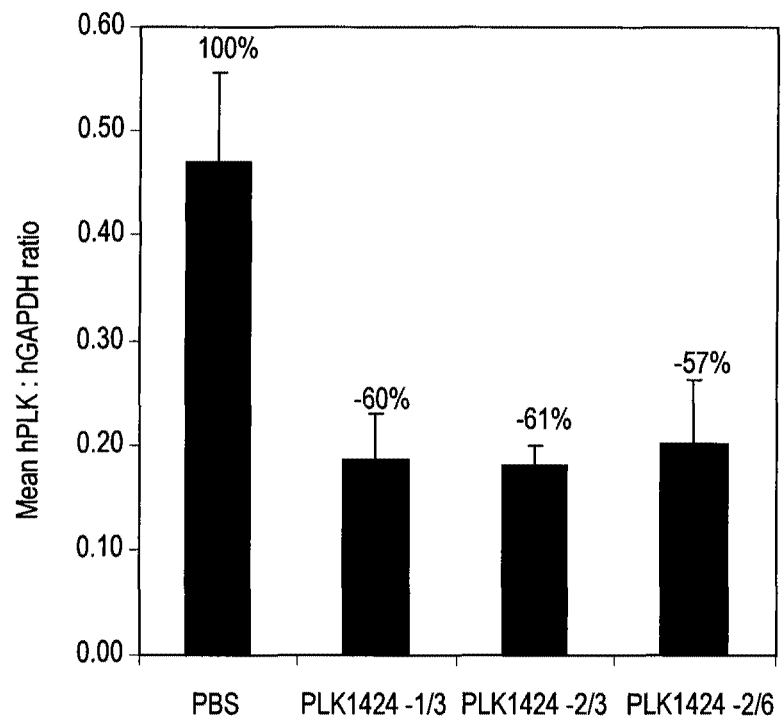

FIG. 43 illustrates data demonstrating that all PLK1424 siRNAs tested in Hep3B tumors produced an equivalent level of PLK-1 mRNA silencing in vivo.

DETAILED DESCRIPTION OF THE INVENTION

I. Introduction

Hepatocellular carcinoma (HCC) is the fifth most common solid tumor worldwide and the fourth leading cause of cancer mortality accounting for approximately 400,000 deaths annually (Thomas et al., *J. Clin. Oncol.*, 23:2892-2899 (2005)). Although several alternative treatment options exist for HCC, at present there is no effective chemotherapy regimen for HCC and the prognosis remains very poor. Surgical resection or complete liver transplantation are considered the only therapies with curative potential; however, 70-85% of HCC patients present with advanced tumors and are often compromised with underlying liver disease that contraindicates invasive surgery (Llovet et al., *J. Natl. Cancer Inst.*, 100:698-711 (2008)). Recently, the multi-kinase inhibitor Sorafenib has been approved for the treatment of unresectable HCC based on phase III data showing improvements in survival time (10.7 mo versus 7.9 mo for placebo) of patients with advanced disease (Llovet et al., *J. Hepatol.*, 48 Suppl 1:S20-37 (2008)). With no other treatment options available, it is likely that Sorafenib will become part of the standard of care for this patient population. The liver is also a common site of tumor metastatic disease; for example, approximately 50% of colorectal cancer patients develop metastases to the liver, resulting in significant increase in patient mortality (Steele et al., *Annals Surgery*, 210:127-138 (1989)). Combinatorial therapy with systemically administered conventional and targeted chemotherapeutics improves the survival times of these patients; however, the non-surgical cure for metastatic colon cancer remains elusive. It is clear that HCC and metastatic disease in the liver represent a significant unmet medical need that requires the development of novel therapeutic agents for more effective treatment options.

Short interfering RNAs are powerful, target-specific molecules designed to suppress gene expression through the endogenous cellular process of RNAi (Elbashir et al., *Nature*, 411:494-498 (2001)). Since the characterization of this fundamental gene silencing mechanism, tremendous progress has been made in developing siRNA as a potentially novel class of therapeutic agent for a broad spectrum of diseases. However, the primary barrier to realizing the potential of siRNA therapeutics is the need for drug delivery vehicles that facilitate disease site targeting and intracellular delivery of the siRNA (Zimmermann et al., *Nature*, 441:111-114 (2006); de Fougerolles et al., *Nat. Rev. Drug Discov.*, 6:443-453 (2007); Behlke, *Mol. Ther.*, 13:644-670 (2006)). While several groups have investigated the use of alternative nucleotide chemistry to improve the pharmacologic properties of siRNA (Soutschek et al., *Nature*, 432:173-178 (2004); Hall et al., *Nucleic Acids Res.*, 32:5991-6000 (2004); Morrissey et al., *Hepatology*, 41:1349-1356 (2005)), other groups have improved in vivo siRNA delivery by complexing with polycations such as polyethyleneimine (Urban-Klein et al., *Gene Ther.*, 12:461-466 (2005); Schiffelers et al., *Nucleic Acids Res.*, 32:e149 (2004)) and cyclodextrin polymers (Heidel et al., *Proc. Natl. Acad. Sci. USA*, 104:5715-5721 (2007)) or by encapsulation in lipid-based carriers (Zimmermann et al., supra; Morrissey et al., *Nat. Biotechnol.*, 23:1002-1007 (2005); Judge et al., *Mol. Ther.*, 13:494-505 (2006)). Of particular interest are those strategies that aim to take advantage of the "enhanced permeation and retention" effect (Mayer et al., *Cancer Letters*, 53:183-190 (1990); Seymour, *Crit. Rev. Ther. Drug Carrier Syst.*, 9:135-187 (1992)), also referred to as passive targeting, whereby charge neutral carriers of suitable size can pass through the fenestrated epithelium observed in sites of clinical interest such as tumors. In order to take advantage of this effect and achieve significant enrichment at the target site, carriers must be small (diameter on the order of 100 nm) and long-circulating, thereby able to bypass the microcapillary beds of the "first pass" organs, the lungs, liver and the phagocytic cells of the reticuloendothelial system. The advantage of such a system that enriches the accumulation of siRNA at the tumor target site offers the potential to develop a molecular therapeutic with additional selectivity over that of non-targeted small molecule drugs.

Many oncology targets for siRNA have been described in the literature, although direct evidence that the therapeutic effects reported in vivo are RNAi-mediated is notably lacking. Targets generally fall into three broad categories: (i) those that are involved in the cell cycle or cell division and are directly cytotoxic when down-regulated; (ii) those that support tumor cell growth, tumor progression or metastasis such as growth factors, their receptors or angiogenic factors; and (iii) those that increase tumor sensitivity to conventional therapeutic approaches such as anti-apoptotic proteins, drug resistance genes and DNA repair enzymes. The present invention is drawn to targeting the expression of an essential cell cycle protein Polo-like kinase 1 (PLK-1).

Progress through the cell cycle is controlled by kinases, such as those of the Cyclin-dependant and Polo-like kinase families. The polo-like kinases are named for Polo, a serine/ threonine kinase first identified in *Drosophila Melanogaster* and characterized by their unique phosphopeptide binding polo-box domain (Barr et al., *Nat. Rev. Mol. Cell. Biol.*, 5:429-440 (2004)). Four mammalian PLK family members, PLK-1, PLK-2 (also known as Snk), PLK-3 (also known as Prk or Fnk) and PLK-4 (also known as Sak) have been characterized and shown to have non-redundant roles in regulating the cell cycle (Barr et al., supra). All have predicted nuclear localization signals (Taniguchi et al., *J. Biol. Chem.*, 277:48884-48888 (2002)) and are thought to act in concert on nuclear substrates involved in various stages of the cell cycle. In mammalian cells, PLK-1 acts to phosphorylate Cdc25C phosphatase, cyclin B, a cohesin subunit of the mitotic spindle, subunits of the anaphase promoting complex, mammalian kinesin-like protein 1 MKLP-1 and other kinesin related proteins. This diverse array of substrates illustrates the multiple roles of PLK-1 in mitosis and cytokinesis (Barr et al., supra). Over-expression of PLK-1, observed in many human tumor types, is a negative prognosticator of patient outcome (Strebhardt et al., *Nat. Rev. Cancer*, 6:321-330 (2006)), while inhibition of PLK-1 activity rapidly induces mitotic arrest and tumor cell apoptosis (Steegmaier et al., *Curr. Biol.*, 17:316-322 (2007); Liu et al., *Proc. Natl. Acad. Sci. USA*, 100:5789-5794 (2003)). Depletion of PLK-1 also acts to sensitize cancer cells to the pro-apoptotic activity of small molecule drugs (Spankuch et al., *Oncogene*, 26:5793-5807 (2007)), likely due to its functional role in the DNA damage and spindle assembly checkpoints. These features combine to make PLK-1 an exciting target for therapeutic intervention in oncology.

As such, targeted silencing of cancer-associated genes such as PLK-1 by siRNA holds considerable promise as a novel therapeutic strategy. However, unmodified PLK-1 siRNA sequences can be immunostimulatory, e.g., stimulate potent inflammatory responses from innate immune cells, particularly when associated with delivery vehicles that facilitate intracellular uptake. This represents a significant barrier to the therapeutic development of PLK-1 siRNA molecules due to toxicity and off-target gene effects associated with the inflammatory response. The present invention overcomes these limitations by reducing or completely abrogating the immune response to PLK-1 siRNA using the selective incorporation of modified nucleotides such as 2'-O-methyl (2'OMe) uridine and/or guanosine nucleotides into either or both strands of the siRNA. In particular, the immunostimulatory properties of PLK-1 siRNA sequences and their ability to silence PLK-1 expression can be balanced or optimized by the introduction of minimal and selective 2'OMe modifications within the double-stranded region of the siRNA duplex. This can be achieved at therapeutically viable siRNA doses without cytokine induction, toxicity, and off-target effects associated with the use of unmodified siRNA.

Thus, the present invention provides chemically modified siRNA molecules which silence PLK-1 expression and methods of use thereof. The present invention also provides nucleic acid-lipid particles (e.g., SNALP) comprising a modified siRNA molecule described herein, a cationic lipid, and a non-cationic lipid, which can further comprise a conjugated lipid that inhibits aggregation of particles. The present invention further provides methods of silencing PLK-1 gene expression by administering a modified siRNA molecule described herein to a mammalian subject. In certain embodiments, the present invention provides an siRNA therapeutic targeting human PLK-1 for the treatment of liver cancers such as HCC and liver metastatic disease. The present invention additionally provides methods of identifying and/or modifying PLK-1 siRNA having immunostimulatory properties. Methods for sensitizing a cell such as a cancer cell to the effects of a chemotherapy drug comprising sequentially delivering PLK-1 siRNA followed by the chemotherapy drug are also provided.

Therefore, the present invention demonstrates that rationally designed siRNA, when delivered using a safe and effective systemic delivery vehicle, are able to affect therapeutic PLK-1 gene silencing through the confirmed mechanism of RNAi in the absence of unintended immune stimulation.

II. Definitions

As used herein, the following terms have the meanings ascribed to them unless specified otherwise.

The term "polo-like kinase 1," "PLK-1," "polo-like kinase," or "PLK" refers to a serine/threonine kinase containing two functional domains: (1) a kinase domain; and (2) a polo-box domain (see, e.g., Barr et al., *Nat. Rev. Mol. Cell. Biol.*, 5:429-440 (2004)). The activity and cellular concentration of PLK-1 are crucial for the precise regulation of cell division. PLK-1 expression and activity are low throughout the G0, G1, and S phases of the cell cycle, but begin to rise in G2 and peak during M phase. PLK-1 is essential for mitosis and cell division and contributes to the following processes: centrosome maturation and the activation of maturation-promoting factors by Cdc25C and cyclinB1 phosphorylation; bipolar spindle formation; and DNA damage checkpoint adaptation (DNA damage inhibits PLK-1 in G2 and mitosis). PLK-1 is also involved in the activation of components of the anaphase promoting complex for mitotic exit and cytokinesis. PLK-1 is overexpressed in many cancer types including hepatoma and colon cancer, and PLK-1 expression often correlates with poor patient prognosis. Overexpression of PLK-1 (wild-type or kinase inactive) results in multinucleation (genetic instability). Hyperactive PLK-1 overrides the DNA damage checkpoint. Constitutive PLK-1 expression causes transformation of NIH 3T3 cells. PLK-1 phosphorylates the p53 tumor suppressor, thereby inhibiting the pro-apoptotic effects of p53. Human PLK-1 mRNA sequences are set forth in Genbank Accession Nos. NM_005030, X73458, BC014846, BC003002, HSU01038, and L19559. A mouse PLK-1 mRNA sequence is set forth in Genbank Accession No. NM_011121. PLK-1 is also known as serine/threonine protein kinase 13 (STPK13).

The term "interfering RNA" or "RNAi" or "interfering RNA sequence" refers to single-stranded RNA (e.g., mature miRNA) or double-stranded RNA (i.e., duplex RNA such as siRNA, aiRNA, or pre-miRNA) that is capable of reducing or inhibiting expression of a target gene (i.e., by mediating the degradation or inhibiting the translation of mRNAs which are complementary to the sequence of the interfering RNA) when the interfering RNA is in the same cell as the target gene. Interfering RNA thus refers to the single-stranded RNA that is complementary to an mRNA sequence or to the double-stranded RNA formed by two complementary strands or by a single, self-complementary strand. Interfering RNA may have substantial or complete identity to the target gene or may comprise a region of mismatch (i.e., a mismatch motif). The sequence of the interfering RNA can correspond to the full length target gene, or a subsequence thereof.

Interfering RNA includes "small-interfering RNA" or "siRNA," e.g., interfering RNA of about 15-60, 15-50, or 15-40 (duplex) nucleotides in length, more typically about 15-30, 15-25, or 19-25 (duplex) nucleotides in length, and is preferably about 20-24, 21-22, or 21-23 (duplex) nucleotides in length (e.g., each complementary sequence of the double-stranded siRNA is 15-60, 15-50, 15-40, 15-30, 15-25, or 19-25 nucleotides in length, preferably about 20-24, 21-22, or 21-23 nucleotides in length, and the double-stranded siRNA is about 15-60, 15-50, 15-40, 15-30, 15-25, or 19-25 base pairs in length, preferably about 18-22, 19-20, or 19-21 base pairs in length). siRNA duplexes may comprise 3' overhangs of about 1 to about 4 nucleotides or about 2 to about 3 nucleotides and 5' phosphate termini. Examples of siRNA include, without limitation, a double-stranded polynucleotide molecule assembled from two separate stranded molecules, wherein one strand is the sense strand and the other is the complementary antisense strand; a double-stranded polynucleotide molecule assembled from a single stranded molecule, where the sense and antisense regions are linked by a nucleic acid-based or non-nucleic acid-based linker; a double-stranded polynucleotide molecule with a hairpin secondary structure having self-complementary sense and antisense regions; and a circular single-stranded polynucleotide molecule with two or more loop structures and a stem having self-complementary sense and antisense regions, where the circular polynucleotide can be processed in vivo or in vitro to generate an active double-stranded siRNA molecule.

Preferably, siRNA are chemically synthesized. siRNA can also be generated by cleavage of longer dsRNA (e.g., dsRNA greater than about 25 nucleotides in length) with the *E. coli* RNase III or Dicer. These enzymes process the dsRNA into biologically active siRNA (see, e.g., Yang et al., *Proc. Natl. Acad. Sci. USA*, 99:9942-9947 (2002); Calegari et al., *Proc. Natl. Acad. Sci. USA*, 99:14236 (2002); Byrom et al., *Ambion TechNotes*, 10(1):4-6 (2003); Kawasaki et al., *Nucleic Acids Res.*, 31:981-987 (2003); Knight et al., *Science*, 293:2269-2271 (2001); and Robertson et al., *J. Biol. Chem.*, 243:82 (1968)). Preferably, dsRNA are at least 50 nucleotides to about 100, 200, 300, 400, or 500 nucleotides in length. A dsRNA may be as long as 1000, 1500, 2000, 5000 nucleotides in length, or longer. The dsRNA can encode for an entire gene transcript or a partial gene transcript. In certain instances, siRNA may be encoded by a plasmid (e.g., transcribed as sequences that automatically fold into duplexes with hairpin loops).

As used herein, the term "mismatch motif" or "mismatch region" refers to a portion of an interfering RNA (e.g., siRNA, aiRNA, miRNA) sequence that does not have 100% complementarity to its target sequence. An interfering RNA may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

An "effective amount" or "therapeutically effective amount" of an interfering RNA is an amount sufficient to produce the desired effect, e.g., an inhibition of expression of a target sequence in comparison to the normal expression level detected in the absence of the interfering RNA. Inhibition of expression of a target gene or target sequence is achieved when the value obtained with the interfering RNA relative to the control is about 90%, 85%, 80%, 75%, 70%, 65%, 60%, 55%, 50%, 45%, 40%, 35%, 30%, 25%, 20%, 15%, 10%, 5%, or 0%. Suitable assays for measuring expression of a target gene or target sequence include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

By "decrease," "decreasing," "reduce," or "reducing" of an immune response by an interfering RNA is intended to mean a detectable decrease of an immune response to a given interfering RNA (e.g., a modified interfering RNA). The amount of decrease of an immune response by a modified interfering RNA may be determined relative to the level of an immune response in the presence of an unmodified interfering RNA. A detectable decrease can be about 5%, 10%, 15%, 20%, 25%, 30%, 35%, 40%, 45%, 50%, 55%, 60%, 65%, 70%, 75%, 80%, 85%, 90%, 95%, 100%, or more lower than the immune response detected in the presence of the unmodified interfering RNA. A decrease in the immune response to interfering RNA is typically measured by a decrease in cytokine production (e.g., IFNγ, IFNα, TNFα, IL-6, or IL-12) by a responder cell in vitro or a decrease in cytokine production in the sera of a mammalian subject after administration of the interfering RNA.

As used herein, the term "responder cell" refers to a cell, preferably a mammalian cell, that produces a detectable immune response when contacted with an immunostimulatory interfering RNA such as an unmodified siRNA. Exemplary responder cells include, e.g., dendritic cells, macrophages, peripheral blood mononuclear cells (PBMCs), splenocytes, and the like. Detectable immune responses include, e.g., production of cytokines or growth factors such as TNF-α, IFN-α, IFN-β, IFN-γ, IL-1, IL-2, IL-3, IL-4, IL-5, IL-6, IL-10, IL-12, IL-13, TGF, and combinations thereof.

"Substantial identity" refers to a sequence that hybridizes to a reference sequence under stringent conditions, or to a sequence that has a specified percent identity over a specified region of a reference sequence.

The phrase "stringent hybridization conditions" refers to conditions under which a nucleic acid will hybridize to its target sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, Ausubel et al., eds.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 55, or 60 nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of a number of contiguous positions selected from the group consisting of from about 5 to about 60, usually about 10 to about 45, more usually about 15 to about 30, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Natl. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology*, Ausubel et al., eds. (1995 supplement)).

A preferred example of algorithms that are suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids of the invention. Software for performing BLAST analyses is publicly available through the National Center for Biotechnology Information (http://www.ncbi.nlm.nih.gov/).

The BLAST algorithm also performs a statistical analysis of the similarity between two sequences (see, e.g., Karlin and Altschul, *Proc. Natl. Acad. Sci. USA*, 90:5873-5787 (1993)). One measure of similarity provided by the BLAST algorithm is the smallest sum probability (P(N)), which provides an indication of the probability by which a match between two nucleotide sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The term "nucleic acid" as used herein refers to a polymer containing at least two deoxyribonucleotides or ribonucleotides in either single- or double-stranded form and includes DNA and RNA. DNA may be in the form of, e.g., antisense molecules, plasmid DNA, pre-condensed DNA, a PCR product, vectors (P1, PAC, BAC, YAC, artificial chromosomes), expression cassettes, chimeric sequences, chromosomal DNA, or derivatives and combinations of these groups. RNA may be in the form of siRNA, asymmetrical interfering RNA (aiRNA), microRNA (miRNA), mRNA, tRNA, rRNA, tRNA, vRNA, and combinations thereof. Nucleic acids include nucleic acids containing known nucleotide analogs or modified backbone residues or linkages, which are synthetic, naturally occurring, and non-naturally occurring, and which have similar binding properties as the reference nucleic acid. Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). "Nucleotides" contain a sugar deoxyribose (DNA) or ribose (RNA), a base, and a phosphate group. Nucleotides are linked together through the phosphate groups. "Bases" include purines and pyrimidines, which further include natural compounds adenine, thymine, guanine, cytosine, uracil, inosine, and natural analogs, and synthetic derivatives of purines and pyrimidines, which include, but are not limited to, modifications which place new reactive groups such as, but not limited to, amines, alcohols, thiols, carboxylates, and alkylhalides.

The term "gene" refers to a nucleic acid (e.g., DNA or RNA) sequence that comprises partial length or entire length coding sequences necessary for the production of a polypeptide or precursor polypeptide.

"Gene product," as used herein, refers to a product of a gene such as an RNA transcript or a polypeptide.

The term "lipid" refers to a group of organic compounds that include, but are not limited to, esters of fatty acids and are characterized by being insoluble in water, but soluble in many organic solvents. They are usually divided into at least three classes: (1) "simple lipids," which include fats and oils as well as waxes; (2) "compound lipids," which include phospholipids and glycolipids; and (3) "derived lipids" such as steroids.

"Lipid vesicle" refers to any lipid composition that can be used to deliver a compound such as an interfering RNA including, but not limited to, liposomes, wherein an aqueous volume is encapsulated by an amphipathic lipid bilayer; or wherein the lipids coat an interior comprising a large molecular component, such as a plasmid comprising an interfering RNA sequence, with a reduced aqueous interior; or lipid aggregates or micelles, wherein the encapsulated component is contained within a relatively disordered lipid mixture. The term lipid vesicle encompasses any of a variety of lipid-based carrier systems including, without limitation, SPLPs, pSPLPs, SNALPs, liposomes, micelles, virosomes, lipid-nucleic acid complexes, and mixtures thereof.

As used herein, "lipid encapsulated" can refer to a lipid formulation that provides a compound, such as a nucleic acid (e.g., an interfering RNA), with full encapsulation, partial encapsulation, or both. In a preferred embodiment, the nucleic acid is fully encapsulated in the lipid formulation (e.g., to form an SPLP, pSPLP, SNALP, or other nucleic acid-lipid particle).

As used herein, the term "SNALP" refers to a stable nucleic acid-lipid particle. A SNALP represents a particle made from lipids (e.g., a cationic lipid, a non-cationic lipid and a conjugated lipid that prevents aggregation of the particle), wherein the nucleic acid (e.g., siRNA, aiRNA, miRNA, ssDNA, dsDNA, ssRNA, short hairpin RNA (shRNA), dsRNA, or a plasmid, including plasmids from which an interfering RNA is transcribed) is fully encapsulated within the lipid. As used herein, the term "SNALP" includes an SPLP, which is the term used to refer to a nucleic acid-lipid particle comprising a nucleic acid (e.g., a plasmid) encapsulated within the lipid. SNALPs and SPLPs typically contain a cationic lipid, a non-cationic lipid, and a lipid conjugate (e.g., a PEG-lipid conjugate). SNALPs and SPLPs are extremely useful for systemic applications, as they can exhibit extended circulation lifetimes following intravenous (i.v.) injection, they can accumulate at distal sites (e.g., sites physically separated from the administration site) and they can mediate expression of the transfected gene or silencing of target gene expression at these distal sites. SPLPs include "pSPLP," which comprise an encapsulated condensing agent-nucleic acid complex as set forth in PCT Publication No. WO 00/03683.

The nucleic acid-lipid particles of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids, when present in the nucleic acid-lipid particles of the present invention, are resistant in aqueous solution to degradation with a nuclease. Nucleic acid-lipid particles and their method of preparation are disclosed in, e.g., U.S. Patent Publication No. 20040142025 and U.S. Patent Publication No. 20070042031.

"Lipid formulation" or, alternatively, a "lipid-based formulation" is used herein to refer to a SNALP that can be used to deliver a nucleic acid, such as an interfering RNA, to a target site of interest. In the lipid formulation, which is typically formed from a cationic lipid, a non-cationic lipid and a lipid conjugate, the nucleic acid is encapsulated in the lipid, thereby protecting the nucleic acid from nuclease degradation.

The term "lipid conjugate" refers to a conjugated lipid that inhibits aggregation of nucleic acid-lipid particles. Such lipid conjugates include, but are not limited to, polyamide oligomers (e.g., ATTA-lipid conjugates), PEG-lipid conjugates, such as PEG coupled to dialkyloxypropyls, PEG coupled to diacylglycerols, PEG coupled to cholesterol, PEG coupled to phosphatidylethanolamines, PEG conjugated to ceramides (see, e.g., U.S. Pat. No. 5,885,613), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In preferred embodiments, non-ester containing linker moieties are used.

The term "amphipathic lipid" refers, in part, to any suitable material wherein the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine, and dilinoleoylphosphatidylcholine. Other compounds lacking in phosphorus, such as sphingolipid, glycosphingolipid families, diacylglycerols, and β-acyloxyacids, are also within the group designated as amphipathic lipids. Additionally, the amphipathic lipids described above can be mixed with other lipids including triglycerides and sterols.

The term "neutral lipid" refers to any of a number of lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" refers to any amphipathic lipid as well as any other neutral lipid or anionic lipid.

The term "anionic lipid" refers to any lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), and other anionic modifying groups joined to neutral lipids.

The term "cationic lipid" refers to any of a number of lipid species that carry a net positive charge at a selected pH, such as physiological pH (e.g., pH of about 7.0). It has been surprisingly found that cationic lipids comprising alkyl chains with multiple sites of unsaturation, e.g., at least two or three sites of unsaturation, are particularly useful for forming nucleic acid-lipid particles with increased membrane fluidity. A number of cationic lipids and related analogs, which are also useful in the present invention, have been described in U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390. Examples of cationic lipids include, but are not limited to, 1,2-dilinoleyloxy-N,N-dimethylaminopropane (DLinDMA), 1,2-dilinolenyloxy-N,N-dimethylaminopropane (DLenDMA), N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl) cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3.beta.-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and mixtures thereof. In some cases, the cationic lipids comprise a protonatable tertiary amine head group, C18 alkyl chains, ether linkages between the head group and alkyl chains, and 0 to 3 double bonds. Such lipids include, e.g., DSDMA, DLinDMA, DLenDMA, and DODMA. The cationic lipids may also comprise ether linkages and pH titratable head groups. Such lipids include, e.g., DODMA.

The term "hydrophobic lipid" refers to compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "fusogenic" refers to the ability of a liposome, a SNALP, or other drug delivery system to fuse with membranes of a cell. The membranes can be either the plasma membrane or membranes surrounding organelles, e.g., endosome, nucleus, etc.

As used herein, the term "aqueous solution" refers to a composition comprising in whole, or in part, water.

As used herein, the term "organic lipid solution" refers to a composition comprising in whole, or in part, an organic solvent having a lipid.

"Distal site," as used herein, refers to a physically separated site, which is not limited to an adjacent capillary bed, but includes sites broadly distributed throughout an organism.

"Serum-stable" in relation to nucleic acid-lipid particles means that the particle is not significantly degraded after exposure to a serum or nuclease assay that would significantly degrade free DNA or RNA. Suitable assays include, for example, a standard serum assay, a DNAse assay, or an RNAse assay.

"Systemic delivery," as used herein, refers to delivery that leads to a broad biodistribution of a compound such as an interfering RNA within an organism. Some techniques of administration can lead to the systemic delivery of certain compounds, but not others. Systemic delivery means that a useful, preferably therapeutic, amount of a compound is exposed to most parts of the body. To obtain broad biodistribution generally requires a blood lifetime such that the compound is not rapidly degraded or cleared (such as by first pass organs (liver, lung, etc.) or by rapid, nonspecific cell binding) before reaching a disease site distal to the site of administration. Systemic delivery of nucleic acid-lipid particles can be by any means known in the art including, for example, intravenous, subcutaneous, and intraperitoneal. In a preferred embodiment, systemic delivery of nucleic acid-lipid particles is by intravenous delivery.

"Local delivery," as used herein, refers to delivery of a compound such as an interfering RNA directly to a target site within an organism. For example, a compound can be locally delivered by direct injection into a disease site such as a tumor or other target site such as a site of inflammation or a target organ such as the liver, heart, pancreas, kidney, and the like.

The term "mammal" refers to any mammalian species such as a human, mouse, rat, dog, cat, hamster, guinea pig, rabbit, livestock, and the like.

The term "cancer" refers to any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, liver cancer, lung cancer, colon cancer, rectal cancer, anal cancer, bile duct cancer, small intestine cancer, stomach (gastric) cancer, esophageal cancer; gallbladder cancer, pancreatic cancer, appendix cancer, breast cancer, ovarian cancer; cervical cancer, prostate cancer, renal cancer (e.g., renal cell carcinoma), cancer of the central nervous system, glioblastoma, skin cancer, lymphomas, choriocarcinomas, head and neck cancers, osteogenic sarcomas, and blood cancers. Non-limiting examples of specific types of liver cancer include hepatocellular carcinoma, secondary liver cancer (caused by metastasis of some other non-liver cancer cell type), and hepatoblastoma. As used herein, a "tumor" comprises one or more cancerous cells.

III. Description of the Embodiments

The present invention provides compositions comprising interfering RNA (e.g., siRNA, aiRNA, miRNA, etc.) that target PLK-1 expression and methods of using such compositions to silence PLK-1 expression.

In one aspect, the present invention provides a modified siRNA molecule comprising a double-stranded region of about 15 to about 60 nucleotides in length, wherein one or more of the nucleotides in the double-stranded region comprise modified nucleotides, and wherein the modified siRNA molecule is capable of silencing PLK-1 expression.

In one embodiment, the modified siRNA molecule comprises modified nucleotides selected from the group consisting of 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In a preferred embodiment, the modified siRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

In another embodiment, the modified siRNA molecule comprises a double-stranded region of about 15 to about 30 nucleotides in length. In certain instances, the modified siRNA molecule comprises modified nucleotides in one strand of the modified siRNA molecule. In certain other instances, the modified siRNA molecule comprises modified nucleotides in both strands of the modified siRNA molecule. Typically, two, three, four, five, six, seven, or more of the nucleotides in the double-stranded region comprise modified nucleotides.

In some embodiments, less than about 25% of the nucleotides in the double-stranded region comprise modified nucleotides. In other embodiments, less than about 20% of the nucleotides in the double-stranded region comprise modified nucleotides. In yet other embodiments, less than about 15% of the nucleotides in the double-stranded region comprise modified nucleotides. In additional embodiments, from about 10% to about 20% of the nucleotides in the double-stranded region comprise modified nucleotides.

In a further embodiment, the modified siRNA molecule is less immunostimulatory than a corresponding unmodified siRNA sequence. In such embodiments, the modified siRNA molecule with reduced immunostimulatory properties advantageously retains RNAi activity against the target PLK-1 sequence. In another embodiment, the immunostimulatory properties of the modified siRNA molecules described herein and their ability to silence PLK-1 expression can be balanced or optimized by the introduction of minimal and selective 2'OMe modifications within the siRNA sequence such as, e.g., within the double-stranded region of the siRNA duplex.

In certain instances, the modified siRNA molecule is at least about 70% less immunostimulatory than the corresponding unmodified siRNA sequence. In certain other instances, the modified siRNA molecule has an $IC_{50}$ that is less than or equal to ten-fold that of the corresponding unmodified siRNA sequence.

In some instances, the modified siRNA molecule comprises 3' overhangs in one strand of the modified siRNA molecule. In other instances, the modified siRNA molecule comprises 3' overhangs in both strands of the modified siRNA molecule. In some instances, the modified siRNA molecule comprises a hairpin loop structure.

The modified siRNA molecule typically comprises a sense strand, an antisense strand, or a sense strand and an antisense strand having one or more modified nucleotides in the double-stranded region of the siRNA molecule.

In certain embodiments, the sense strand of the modified siRNA molecule comprises or consists of one of the sense strand sequences set forth in Table 1. In one preferred embodiment, the sense strand comprises or consists of the nucleic acid sequence of SEQ ID NO: 1. In another preferred embodiment, the sense strand comprises or consists of the nucleic acid sequence of SEQ ID NO:3. In certain other embodiments, the antisense strand of the modified siRNA molecule comprises or consists of one of the antisense strand sequences set forth in Table 1. In one preferred embodiment, the antisense strand comprises or consists of the nucleic acid sequence of SEQ ID NO:2. In another preferred embodiment, the antisense strand comprises or consists of the nucleic acid sequence of SEQ ID NO:4. As described herein, one or more of the nucleotides in the sense and/or antisense strand sequences set forth in Table 1 may comprise modified nucleotides, wherein the modified nucleotides are located in the double-stranded region of the siRNA molecule. In some instances, the sense and/or antisense strand contains "dTdT" or "UU" 3' overhangs. In other instances, the sense and/or antisense strand contains 3' overhangs that have complementarity to the target sequence or the complementary strand thereof. In further instances, the 3' overhang on the sense strand, antisense strand, or both strands comprises one, two, three, four, or more modified nucleotides such as those described herein (e.g., 2'OMe nucleotides).

In some embodiments, the sense strand of the modified siRNA molecule comprises or consists of one of the sense strand sequences set forth in Table 2. In other embodiments, the antisense strand of the modified siRNA molecule comprises or consists of one of the antisense strand sequences set forth in Table 2. As described herein, one or more of the nucleotides in the sense and/or antisense strand sequences set forth in Table 2 may comprise modified nucleotides, wherein the modified nucleotides are located in the double-stranded region of the siRNA molecule. In some instances, the sense and/or antisense strand contains "dTdT" or "UU" 3' overhangs. In other instances, the sense and/or antisense strand contains 3' overhangs that have complementarity to the target sequence or the complementary strand thereof. In further instances, the 3' overhang on the sense strand, antisense strand, or both strands comprises one, two, three, four, or more modified nucleotides such as those described herein (e.g., 2'OMe nucleotides).

In certain embodiments, the sense strand of the modified siRNA molecule comprises or consists of one of the unmodified sense strand sequences set forth in Table 3. In one preferred embodiment, the sense strand comprises or consists of the nucleic acid sequence of SEQ ID NO:51. In another preferred embodiment, the sense strand comprises or consists of the nucleic acid sequence of SEQ ID NO:58. In yet another preferred embodiment, the sense strand comprises or consists of the nucleic acid sequence of SEQ ID NO:65. In certain other embodiments, the antisense strand of the modified siRNA molecule comprises or consists of one of the unmodified antisense strand sequences set forth in Table 3. In one preferred embodiment, the antisense strand comprises or consists of the nucleic acid sequence of SEQ ID NO:52. In another preferred embodiment, the antisense strand comprises or consists of the nucleic acid sequence of SEQ ID NO:59. In yet another preferred embodiment, the antisense strand comprises or consists of the nucleic acid sequence of SEQ ID NO:66. As described herein, one or more of the nucleotides in the unmodified sense and/or antisense strand sequences set forth in Table 3 may comprise modified nucleotides, wherein the modified nucleotides are located in the double-stranded region of the siRNA molecule. In some instances, the sense and/or antisense strand contains "dTdT" or "UU" 3' overhangs. In other instances, the sense and/or antisense strand contains 3' overhangs that have complementarity to the target sequence or the complementary strand thereof. In further instances, the 3' overhang on the sense strand, antisense strand, or both strands comprises one, two, three, four, or more modified nucleotides such as those described herein (e.g., 2'OMe nucleotides).

In some embodiments, the sense strand of the modified siRNA molecule comprises or consists of one of the modified sense strand sequences set forth in Table 3. In one preferred embodiment, the sense strand comprises or consists of the nucleic acid sequence of SEQ ID NO:57. In another preferred embodiment, the sense strand comprises or consists of the nucleic acid sequence of SEQ ID NO:64. In yet another preferred embodiment, the sense strand comprises or consists of the nucleic acid sequence of SEQ ID NO:67. In some instances, the sense strand contains "dTdT" or "UU" 3' overhangs. In other instances, the sense strand contains 3' overhangs that have complementarity to the complementary strand of the target sequence. In further instances, the 3' overhang on the sense strand comprises one, two, three, four, or more modified nucleotides such as those described herein (e.g., 2'OMe nucleotides).

In other embodiments, the antisense strand of the modified siRNA molecule comprises or consists of one of the modified antisense strand sequences set forth in Table 3. In one preferred embodiment, the antisense strand comprises or consists of the nucleic acid sequence of SEQ ID NO:54. In another preferred embodiment, the antisense strand comprises or consists of the nucleic acid sequence of SEQ ID NO:56. In yet another preferred embodiment, the antisense strand comprises or consists of the nucleic acid sequence of SEQ ID NO:63. In an additional preferred embodiment, the antisense strand comprises or consists of the nucleic acid sequence of SEQ ID NO:68. In some instances, the antisense strand contains "dTdT" or "UU" 3' overhangs. In other instances, the antisense strand contains 3' overhangs that have complementarity to the target sequence. In further instances, the 3' overhang on the antisense strand comprises one, two, three, four, or more modified nucleotides such as those described herein (e.g., 2'OMe nucleotides).

In some embodiments, the sense strand of the modified siRNA molecule comprises or consists of one of the sense strand sequences set forth in Tables 4-5. In certain other embodiments, the antisense strand of the modified siRNA molecule comprises or consists of one of the antisense strand sequences set forth in Tables 4-5. As described herein, one or more of the nucleotides in the sense and/or antisense strand sequences set forth in Tables 4-5 may comprise modified nucleotides, wherein the modified nucleotides are located in the double-stranded region of the siRNA molecule. In some instances, the sense and/or antisense strand contains "dTdT" or "UU" 3' overhangs. In other instances, the sense and/or antisense strand contains 3' overhangs that have complementarity to the target sequence or the complementary strand thereof. In further instances, the 3' overhang on the sense strand, antisense strand, or both strands comprises one, two, three, four, or more modified nucleotides such as those described herein (e.g., 2'OMe nucleotides).

In certain embodiments, the sense strand of the modified siRNA molecule comprises or consists of one of the unmodified sense strand sequences set forth in Table 6. In one preferred embodiment, the sense strand comprises or consists of the nucleic acid sequence of SEQ ID NO:211. In another preferred embodiment, the sense strand comprises or consists of the nucleic acid sequence of SEQ ID NO:218. In certain other embodiments, the antisense strand of the modified siRNA molecule comprises or consists of one of the unmodified antisense strand sequences set forth in Table 6. In one preferred embodiment, the antisense strand comprises or consists of the nucleic acid sequence of SEQ ID NO:212. In another preferred embodiment, the antisense strand comprises or consists of the nucleic acid sequence of SEQ ID NO:219. As described herein, one or more of the nucleotides in the unmodified sense and/or antisense strand sequences set forth in Table 6 may comprise modified nucleotides, wherein the modified nucleotides are located in the double-stranded region of the siRNA molecule. In some instances, one or both of the uridine nucleotides in the "UU" 3' overhang on the sense and/or antisense strand comprises modified nucleotides such as those described herein (e.g., 2'OMe-uridine nucleotides).

In some embodiments, the sense strand of the modified siRNA molecule comprises or consists of one of the modified sense strand sequences set forth in Table 6. In one preferred embodiment, the sense strand comprises or consists of the nucleic acid sequence of SEQ ID NO:214. In another preferred embodiment, the sense strand comprises or consists of the nucleic acid sequence of SEQ ID NO:220. In some instances, one or both of the uridine nucleotides in the "UU" 3' overhang on the sense strand comprises modified nucleotides such as those described herein (e.g., 2'OMe-uridine nucleotides).

In other embodiments, the antisense strand of the modified siRNA molecule comprises or consists of one of the modified antisense strand sequences set forth in Table 6. In one preferred embodiment, the antisense strand comprises or consists of the nucleic acid sequence of SEQ ID NO:215. In another preferred embodiment, the antisense strand comprises or consists of the nucleic acid sequence of SEQ ID NO:216. In yet another preferred embodiment, the antisense strand comprises or consists of the nucleic acid sequence of SEQ ID NO:223. In some instances, one or both of the uridine nucleotides in the "UU" 3' overhang on the antisense strand comprises modified nucleotides such as those described herein (e.g., 2'OMe-uridine nucleotides).

In some embodiments, the sense strand of the modified siRNA molecule comprises or consists of one of the sense strand sequences set forth in Table 7. In other embodiments, the antisense strand of the modified siRNA molecule comprises or consists of a sequence that is complementary to one of the sense strand sequences set forth in Table 7 (except for the "UU" 3' overhang). As described herein, one or more of the nucleotides in the sense sequences set forth in Table 7 and/or the complementary antisense strand sequences may comprise modified nucleotides, wherein the modified nucleotides are located in the double-stranded region of the siRNA molecule. In some instances, one or both of the uridine nucleotides in the "UU" 3' overhang on the sense and/or antisense strand comprises modified nucleotides such as those described herein (e.g., 2'OMe-uridine nucleotides).

In some embodiments, the sense strand of the modified siRNA molecule comprises or consists of one of the modified sense strand sequences set forth in Table 10. In one preferred embodiment, the sense strand comprises or consists of the nucleic acid sequence of SEQ ID NO:400. In other embodiments, the antisense strand of the modified siRNA molecule comprises or consists of one of the modified antisense strand sequences set forth in Table 10. In one preferred embodiment, the antisense strand comprises or consists of the nucleic acid sequence of SEQ ID NO:403. In some instances, one or both of the nucleotides in the 3' overhang on the sense and/or antisense strand comprises modified nucleotides such as those described herein (e.g., 2'OMe-uridine nucleotides).

In certain embodiments, the modified siRNA molecule is selected from the group consisting of any one or more of the siRNA molecules set forth in Table 11. In preferred embodiments, the modified siRNA molecule is PLK1424 2/6.

In certain other embodiments, the modified siRNA molecule is selected from the group consisting of PLK1424 2/6, PLK1424 U4/GU, PLK1424 U4/G, PLK773 G/GU, PLK1425 3/5, and a mixture thereof.

In another embodiment, the modified siRNA molecule further comprises a carrier system. In certain instances, the carrier system is selected from the group consisting of a nucleic acid-lipid particle, a liposome, a micelle, a virosome, a nucleic acid complex, and mixtures thereof. Generally, the nucleic acid complex may comprise the modified siRNA complexed with a cationic lipid, a cationic polymer, a cyclodextrin, or mixtures thereof. As a non-limiting example, the modified siRNA molecule may be complexed with a cationic polymer, wherein the cationic polymer is polyethylenimine (PEI). In preferred embodiments, the carrier system is a nucleic acid-lipid particle.

In other embodiments, the present invention provides a pharmaceutical composition comprising a modified siRNA molecule described herein and a pharmaceutically acceptable carrier.

In another aspect, the present invention provides a nucleic acid-lipid particle comprising:
a modified siRNA molecule described herein;
a cationic lipid; and
a non-cationic lipid.

In some embodiments, the cationic lipid is a member selected from the group consisting of 1,2-Dilinoleyloxy-N,N-dimethylaminopropane (DLinDMA), 1,2-Dilinolenyloxy-N,N-dimethylaminopropane (DLenDMA), N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), distearyldimethylammonium (DSDMA), N-(1-(2,3-dioleyloxy)propyl)-N,N,N-trimethylammonium chloride (DOTMA), N,N-dimethyl-2,3-dioleyloxypropylamine (DODMA), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and a mixture thereof. In a preferred embodiment, the cationic lipid is DLinDMA.

In certain embodiments, the non-cationic lipid is an anionic lipid. In certain other embodiments, the non-cationic lipid is a neutral lipid.

In some embodiments, the non-cationic lipid is a member selected from the group consisting of distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylcholine (DPPC), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), cholesterol, and a mixture thereof. In a preferred embodiment, the non-cationic lipid is DSPC, DPPC, or DSPE.

In another embodiment, the nucleic acid-lipid particle further comprises a conjugated lipid that inhibits aggregation of particles. In certain instances, the conjugated lipid that inhibits aggregation of particles is a member selected from the group consisting of a polyethyleneglycol (PEG)-lipid conjugate, a polyamide (ATTA)-lipid conjugate, and a mixture thereof. In some embodiments, the PEG-lipid conjugate is a member selected from the group consisting of a PEG-diacylglycerol, a PEG dialkyloxypropyl, a PEG-phospholipid, a PEG-ceramide, and a mixture thereof. In a preferred embodiment, the conjugated lipid that inhibits aggregation of particles comprises a PEG-dialkyloxypropyl (PEG-DAA) conjugate. In certain instances, the PEG-DAA conjugate is a member selected from the group consisting of a PEG-dilauryloxypropyl ($C_{12}$) conjugate, a PEG-dimyristyloxypropyl ($C_{14}$) conjugate, a PEG-dipalmityloxypropyl ($C_{16}$) conjugate, and a PEG-distearyloxypropyl ($C_{18}$) conjugate. In a preferred embodiment, the PEG-DAA conjugate is a PEG-dimyristyloxypropyl ($C_{14}$) conjugate. Additional PEG-lipid conjugates include, e.g., PEG-C-DOMG, 2KPEG-DMG, or mixtures thereof.

In some embodiments, the cationic lipid comprises from about 20 mol % to about 50 mol % of the total lipid present in the particle. In a preferred embodiment, the cationic lipid comprises about 40 mol % of the total lipid present in the particle.

In other embodiments, the non-cationic lipid comprises from about 5 mol % to about 90 mol % of the total lipid present in the particle. In certain instances, the non-cationic lipid comprises about 10 mol % of the total lipid present in the particle. In certain other instances, the non-cationic lipid comprises about 60 mol % of the total lipid present in the particle.

In further embodiments, the PEG-DAA conjugate comprises from 0 mol % to about 20 mol % of the total lipid present in the particle. In a preferred embodiment, the PEG-DAA conjugate comprises about 2 mol % of the total lipid present in the particle.

In additional embodiments, the nucleic acid-lipid particle further comprises cholesterol. In certain instances, the cholesterol comprises from about 10 mol % to about 60 mol % of the total lipid present in the particle. In a preferred embodiment, the cholesterol comprises about 48 mol % of the total lipid present in the particle.

In another embodiment, the modified siRNA in the nucleic acid-lipid particle is not substantially degraded after exposure of the particle to a nuclease at 37° C. for 20 minutes. In a related embodiment, the modified siRNA in the nucleic acid-lipid particle is not substantially degraded after incubation of the particle in serum at 37° C. for 30 minutes. In a preferred embodiment, the modified siRNA is fully encapsulated in the nucleic acid-lipid particle.

In certain instances, the particle has an siRNA:lipid mass ratio of from about 0.01 to about 0.2. In certain other instances, the particle has an siRNA:lipid mass ratio of from about 0.02 to about 0.1. In yet other instances, the particle has an siRNA:lipid mass ratio of about 0.08.

In some instances, the particle has a median diameter of from about 50 nm to about 150 nm. In other instances, the particle has a median diameter of from about 70 nm to about 90 nm.

In yet another aspect, the present invention provides a nucleic acid-lipid particle comprising:
(a) an siRNA molecule that silences PLK-1 expression;
(b) a cationic lipid comprising from about 50 mol % to about 85 mol % of the total lipid present in the particle;
(c) a non-cationic lipid comprising from about 13 mol % to about 49.5 mol % of the total lipid present in the particle; and
(d) a conjugated lipid that inhibits aggregation of particles comprising from about 0.5 mol % to about 2 mol % of the total lipid present in the particle.

In one embodiment, the siRNA molecule comprises a double-stranded region of about 15 to about 60 nucleotides in length. In another embodiment, the siRNA molecule comprises at least one of the sequences set forth in Tables 1-7 and 10-11.

In certain embodiments, the cationic lipid is a member selected from the group consisting of DLinDMA, DLenDMA, DODAC, DDAB, DOTAP, DSDMA, DOTMA, DODMA, DC-Chol, DMRIE, DOSPA, DOGS, CLinDMA, CpLinDMA, DMOBA, DOcarbDAP, DLinDAP, DLincarb-DAP, DLinCDAP, DLin-K-DMA, DLin-K-XTC2-DMA, and a mixture thereof. In a preferred embodiment, the cationic lipid comprises DLinDMA.

In another embodiment, the non-cationic lipid comprises cholesterol or a derivative thereof. In certain instances, the cholesterol or derivative thereof comprises from about 30 mol % to about 45 mol % of the total lipid present in the particle. Generally, the cholesterol derivative is a member selected from the group consisting of cholestanol, cholestanone, cholestenone, coprostanol, cholesteryl-2'-hydroxyethyl ether, and cholesteryl-4'-hydroxybutyl ether.

In one alternative embodiment, the non-cationic lipid comprises a phospholipid. In another alternative embodiment, the non-cationic lipid comprises a mixture of a phospholipid and cholesterol or a derivative thereof. In such embodiments, the phospholipid may be a member selected from the group consisting of DPPC, DSPC, DOPE, POPC, POPE, POPG, DPPE, DMPE, DSPE, DEPE, SOPE, EPC, monomethyl-phosphatidylethanolamine, dimethyl-phosphatidylethanolamine, and a mixture thereof. In certain instances, the phospholipid comprises from about 4 mol % to about 10 mol % of the total lipid present in the particle and the cholesterol comprises from about 30 mol % to about 40 mol % of the total lipid present in the particle. In a preferred embodiment, the phospholipid comprises DPPC.

In yet another embodiment, the conjugated lipid that inhibits aggregation of particles is a member selected from the group consisting of a polyethyleneglycol (PEG)-lipid conjugate, a polyamide (ATTA)-lipid conjugate, and a mixture thereof. In some embodiments, the PEG-lipid conjugate is a member selected from the group consisting of a PEG-diacylglycerol, a PEG dialkyloxypropyl, a PEG-phospholipid, a PEG-ceramide, and a mixture thereof. In a preferred embodiment, the conjugated lipid that inhibits aggregation of particles comprises a PEG-dialkyloxypropyl (PEG-DAA) conjugate. In certain instances, the PEG-DAA conjugate is a member selected from the group consisting of a PEG-dilauryloxypropyl ($C_{12}$) conjugate, a PEG-dimyristyloxypropyl ($C_{14}$) conjugate, a PEG-dipalmityloxypropyl ($C_{16}$) conjugate, and a PEG-distearyloxypropyl ($C_{18}$) conjugate. In one preferred embodiment, the PEG-DAA conjugate is a PEG-dimyristyloxypropyl ($C_{14}$) conjugate. In another preferred embodiment, the PEG-DAA conjugate comprises a PEG-distearyloxypropyl ($C_{18}$) conjugate. Additional PEG-lipid conjugates include, e.g., PEG-C-DOMG, 2KPEG-DMG, or mixtures thereof.

In a further embodiment, the nucleic acid in the nucleic acid-lipid particle is not substantially degraded after exposure of the particle to a nuclease at 37° C. for 20 minutes. In a related embodiment, the nucleic acid in the nucleic acid-lipid particle is not substantially degraded after incubation of the particle in serum at 37° C. for 30 minutes. In a preferred embodiment, the nucleic acid is fully encapsulated in the nucleic acid-lipid particle.

In certain embodiments, the particle has a lipid:siRNA mass ratio of from about 1 to about 100. In certain other embodiments, the particle has a lipid:siRNA mass ratio of from about 5 to about 15. Preferably, the particle has a lipid:siRNA mass ratio of about 6. In some instances, the particle has a median diameter of from about 50 nm to about 150 nm. In other instances, the particle has a median diameter of from about 70 nm to about 90 nm.

In one preferred embodiment, the present invention provides a nucleic acid-lipid particle comprising:
(a) an siRNA molecule that silences PLK-1 expression;
(b) a cationic lipid comprising from about 56.5 mol % to about 66.5 mol % of the total lipid present in the particle;
(c) a non-cationic lipid comprising from about 31.5 mol % to about 42.5 mol % of the total lipid present in the particle; and
(d) a conjugated lipid that inhibits aggregation of particles comprising from about 1 mol % to about 2 mol % of the total lipid present in the particle.

In one embodiment, the siRNA molecule comprises a double-stranded region of about 15 to about 60 nucleotides in length. In another embodiment, the siRNA molecule comprises at least one of the sequences set forth in Tables 1-7 and 10-11.

In certain embodiments, the cationic lipid is a member selected from the group consisting of DLinDMA, DLenDMA, DODAC, DDAB, DOTAP, DSDMA, DOTMA, DODMA, DC-Chol, DMRIE, DOSPA, DOGS, CLinDMA, CpLinDMA, DMOBA, DOcarbDAP, DLinDAP, DLincarb-DAP, DLinCDAP, DLin-K-DMA, DLin-K-XTC2-DMA, and a mixture thereof. Preferably, the cationic lipid comprises DLinDMA.

In other embodiments, the non-cationic lipid comprises cholesterol a derivative thereof. Preferably, the non-cationic lipid comprises cholesterol.

In further embodiments, the conjugated lipid that inhibits aggregation of particles is a PEG-lipid conjugate selected from the group consisting of a PEG-diacylglycerol, a PEG dialkyloxypropyl, a PEG-phospholipid, a PEG-ceramide, and a mixture thereof. Preferably, the conjugated lipid that inhibits aggregation of particles comprises a PEG-DAA conjugate. Additional PEG-lipid conjugates include, e.g., PEG-C-DOMG, 2KPEG-DMG, or mixtures thereof.

In another preferred embodiment, the present invention provides a nucleic acid-lipid particle, comprising:
(a) an siRNA molecule that silences PLK-1 expression;
(b) a cationic lipid comprising from about 52 mol % to about 62 mol % of the total lipid present in the particle;
(c) a non-cationic lipid comprising from about 36 mol % to about 47 mol % of the total lipid present in the particle; and
(d) a conjugated lipid that inhibits aggregation of particles comprising from about 1 mol % to about 2 mol % of the total lipid present in the particle.

In one embodiment, the siRNA molecule comprises a double-stranded region of about 15 to about 60 nucleotides in length. In another embodiment, the siRNA molecule comprises at least one of the sequences set forth in Tables 1-7 and 10-11.

In certain embodiments, the cationic lipid is a member selected from the group consisting of DLinDMA, DLenDMA, DODAC, DDAB, DOTAP, DSDMA, DOTMA, DODMA, DC-Chol, DMRIE, DOSPA, DOGS, CLinDMA, CpLinDMA, DMOBA, DOcarbDAP, DLinDAP, DLincarb-DAP, DLinCDAP, DLin-K-DMA, DLin-K-XTC2-DMA, and a mixture thereof. Preferably, the cationic lipid comprises DLinDMA.

In certain other embodiments, the non-cationic lipid comprises a phospholipid. In alternative embodiments, the non-cationic lipid comprises a mixture of a phospholipid and cholesterol or a derivative thereof. The phospholipid may be, for example, DPPC, DSPC, DOPE, POPC, POPE, POPG, DPPE, DMPE, DSPE, DEPE, SOPE, EPC, monomethyl-phosphatidylethanolamine, dimethyl-phosphatidylethanolamine, or a mixture thereof. Preferably, the non-cationic lipid comprises a mixture of DPPC and cholesterol. In such instances, the DPPC typically comprises from about 5 mol % to about 9 mol % of the total lipid present in the particle and the cholesterol typically comprises from about 32 mol % to about 37 mol % of the total lipid present in the particle.

In further embodiments, the conjugated lipid that inhibits aggregation of particles is a PEG-lipid conjugate selected from the group consisting of a PEG-diacylglycerol, a PEG dialkyloxypropyl, a PEG-phospholipid, a PEG-ceramide, and a mixture thereof. Preferably, the conjugated lipid that inhibits aggregation of particles comprises a PEG-DAA conjugate. Additional PEG-lipid conjugates include, e.g., PEG-C-DOMG, 2KPEG-DMG, or mixtures thereof.

In a further aspect, the present invention provides a pharmaceutical composition comprising a nucleic acid-lipid particle described herein and a pharmaceutically acceptable carrier.

In another aspect, the present invention provides a method for introducing an siRNA that silences PLK-1 expression into a cell, comprising contacting the cell with a nucleic acid-lipid particle described herein.

In one embodiment, the cell is in a mammal. Preferably, the mammal is a human.

In yet another aspect, the present invention provides a method for the in vivo delivery of a nucleic acid, comprising administering to a mammalian subject a nucleic acid-lipid particle described herein.

In some embodiments, the administration is selected from the group consisting of oral, intranasal, intravenous, intraperitoneal, intramuscular, intra-articular, intralesional, intratracheal, subcutaneous, and intradermal. In a preferred embodiment, the mammalian subject is a human.

In a further aspect, the present invention provides a method for treating cancer in a mammalian subject in need thereof, comprising administering to the mammalian subject a therapeutically effective amount of a nucleic acid-lipid particle described herein.

In certain embodiments, the cancer is liver cancer (e.g., hepatocellular carcinoma). In a preferred embodiment, the mammalian subject is a human.

In another aspect, the present invention provides a method for introducing an siRNA that silences PLK-1 expression into a cell, the method comprising contacting the cell with a modified siRNA molecule described herein.

In one embodiment, the modified siRNA molecule is in a carrier system. The carrier system may be, for example, a nucleic acid-lipid particle, a liposome, a micelle, a virosome, a nucleic acid complex, or a mixture thereof. Typically, the nucleic acid complex comprises the modified siRNA molecule complexed with a cationic lipid, a cationic polymer, a cyclodextrin, or a mixture thereof. In certain instances, the modified siRNA molecule is complexed with a cationic polymer, wherein the cationic polymer is polyethylenimine (PEI). In a preferred embodiment, the carrier system is a nucleic acid-lipid particle comprising: the modified siRNA molecule; a cationic lipid; and a non-cationic lipid.

In certain embodiments, the nucleic acid-lipid particle further comprises a conjugated lipid that prevents aggregation of particles. In other embodiments, the presence of the nucleic acid-lipid particle is detectable at least 1 hour after administration of the particle. In yet other embodiments, more than 10% of a plurality of the particles are present in the plasma of a mammal about 1 hour after administration. In further embodiments, the cell is in a mammal. Preferably, the mammal is a human.

In yet another aspect, the present invention provides a method for in vivo delivery of an siRNA that silences PLK-1 expression, the method comprising administering to a mammalian subject a modified siRNA molecule described herein.

In one embodiment, the modified siRNA molecule is in a carrier system. The carrier system may be, for example, a nucleic acid-lipid particle, a liposome, a micelle, a virosome, a nucleic acid complex, or a mixture thereof. Typically, the nucleic acid complex comprises the modified siRNA molecule complexed with a cationic lipid, a cationic polymer, a cyclodextrin, or a mixture thereof. In certain instances, the modified siRNA molecule is complexed with a cationic polymer, wherein the cationic polymer is polyethylenimine (PEI). In a preferred embodiment, the carrier system is a nucleic acid-lipid particle comprising: the modified siRNA molecule; a cationic lipid; and a non-cationic lipid.

In certain embodiments, the nucleic acid-lipid particle further comprises a conjugated lipid that prevents aggregation of particles. In other embodiments, the administration is selected from the group consisting of oral, intranasal, intravenous, intraperitoneal, intramuscular, intra-articular, intralesional, intratracheal, subcutaneous, and intradermal. In a preferred embodiment, the mammalian subject is a human.

In still yet another aspect, the present invention provides a method for treating cancer in a mammalian subject in need thereof, comprising administering to the mammalian subject a therapeutically effective amount of a modified siRNA molecule described herein.

In certain embodiments, the cancer is liver cancer (e.g., hepatocellular carcinoma). In a preferred embodiment, the mammalian subject is a human.

In a further aspect, the present invention provides a method for modifying an immunostimulatory siRNA that silences PLK-1 expression, the method comprising:
(a) providing an unmodified siRNA sequence capable of silencing PLK-1 expression, wherein the unmodified siRNA sequence has immunostimulatory properties and comprises a double-stranded sequence of about 15 to about 60 nucleotides in length; and
(b) modifying the unmodified siRNA sequence by substituting one or more nucleotides with modified nucleotides,
thereby generating a modified siRNA molecule that is less immunostimulatory than the unmodified siRNA sequence and is capable of silencing PLK-1 expression.

In one embodiment, the modified siRNA molecule comprises modified nucleotides selected from the group consisting of 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In a preferred embodiment, the modified siRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

Typically, two, three, four, five, six, seven, or more of the nucleotides in the unmodified siRNA sequence are substituted with modified nucleotides. In some embodiments, less than about 25% of the nucleotides in the double-stranded region of the unmodified siRNA sequence are substituted with modified nucleotides. In other embodiments, less than about 20% of the nucleotides in the double-stranded region of the unmodified siRNA sequence are substituted with modified nucleotides. In yet other embodiments, less than about 15% of the nucleotides in the double-stranded region of the unmodified siRNA sequence are substituted with modified nucleotides. In additional embodiments, from about 10% to about 20% of the nucleotides in the double-stranded region of the unmodified siRNA sequence are substituted with modified nucleotides.

In certain instances, the modified siRNA molecule is at least about 70% less immunostimulatory than the unmodified siRNA sequence. In certain other instances, the modified siRNA molecule has an $IC_{50}$ that is less than or equal to ten-fold that of the unmodified siRNA sequence.

In some embodiments, the method further comprises: (c) confirming that the modified siRNA molecule is less immunostimulatory by contacting the modified siRNA molecule with a mammalian responder cell under conditions suitable for the responder cell to produce a detectable immune response.

In a related aspect, the present invention provides a method for identifying and modifying an immunostimulatory siRNA that silences PLK-1 expression, the method comprising:
(a) contacting an unmodified siRNA sequence capable of silencing PLK-1 expression with a mammalian responder cell under conditions suitable for the responder cell to produce a detectable immune response;
(b) identifying the unmodified siRNA sequence as an immunostimulatory siRNA by the presence of a detectable immune response in the responder cell; and
(c) modifying the unmodified siRNA sequence by substituting one or more nucleotides with modified nucleotides, thereby generating a modified siRNA molecule that is less immunostimulatory than the unmodified siRNA sequence.

In one embodiment, the modified siRNA molecule comprises modified nucleotides selected from the group consisting of 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In a preferred embodiment, the modified siRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

Typically, two, three, four, five, six, seven, or more of the nucleotides in the unmodified siRNA sequence are substituted with modified nucleotides. In some embodiments, less than about 25% of the nucleotides in the double-stranded region of the unmodified siRNA sequence are substituted with modified nucleotides. In other embodiments, less than about 20% of the nucleotides in the double-stranded region of the unmodified siRNA sequence are substituted with modified nucleotides. In yet other embodiments, less than about 15% of the nucleotides in the double-stranded region of the unmodified siRNA sequence are substituted with modified nucleotides. In additional embodiments, from about 10% to about 20% of the nucleotides in the double-stranded region of the unmodified siRNA sequence are substituted with modified nucleotides.

In certain instances, the modified siRNA molecule is at least about 70% less immunostimulatory than the unmodified siRNA sequence. In certain other instances, the modified siRNA molecule has an $IC_{50}$ that is less than or equal to ten-fold that of the unmodified siRNA sequence.

In some embodiments, the mammalian responder cell is a peripheral blood mononuclear cell or dendritic cell. In other embodiments, the detectable immune response comprises production of a cytokine or growth factor selected from the group consisting of TNF-α, IFN-α, IFN-β, IFN-γ, IL-6, IL-12, and combinations thereof. In further embodiments, the detectable immune response comprises induction of interferon-induced protein with tetratricopeptide repeats 1 (IFIT1) mRNA.

In another aspect, the present invention provides a method for sensitizing a cell to the effects of a chemotherapy drug, the method comprising contacting the cell with an siRNA molecule that silences PLK-1 expression prior to administering the chemotherapy drug.

In one embodiment, the siRNA molecule comprises a double-stranded region of about 15 to about 60 nucleotides in length. In another embodiment, the cell is contacted with a modified siRNA molecule that silences PLK-1 expression. In certain instances, one or more of the nucleotides in the double-stranded region comprise modified nucleotides. Preferably, the modified nucleotides are selected from the group consisting of 2'OMe-guanosine nucleotides, 2'OMe-uridine nucleotides, and mixtures thereof. In certain other instances, the modified siRNA molecule is less immunostimulatory than a corresponding unmodified siRNA sequence.

In some embodiments, the siRNA molecule is in a carrier system. Non-limiting examples of carrier systems include a nucleic acid-lipid particle, a liposome, a micelle, a virosome, a nucleic acid complex, and a mixture thereof. In a preferred embodiment, the carrier system is a nucleic acid-lipid particle comprising: the siRNA molecule; a cationic lipid; and a non-cationic lipid.

In other embodiments, the nucleic acid-lipid particle further comprises a conjugated lipid that prevents aggregation of particles. In certain instances, the cell is a cancer cell. In a further embodiment, the cancer cell is in a mammal. Preferably, the mammal is a human.

In certain embodiments, the chemotherapy drug is selected from the group consisting of paclitaxel, fluorouracil (5-FU), irinotecan, sorafenib, and mixtures thereof.

In further aspects, the present invention provides compositions comprising the asymmetrical interfering RNA (aiRNA) molecules described herein that target PLK-1 expression and methods of using such compositions to silence PLK-1 expression.

In one embodiment, the aiRNA molecule comprises a double-stranded (duplex) region of about 10 to about 25 (base paired) nucleotides in length,
wherein the aiRNA molecule comprises an antisense strand comprising 5' and 3' overhangs, and
wherein the aiRNA molecule is capable of silencing PLK-1 expression.

In certain instances, the aiRNA molecule comprises a double-stranded (duplex) region of about 12-20, 12-19, 12-18, 13-17, or 14-17 (base paired) nucleotides in length, more typically 12, 13, 14, 15, 16, 17, 18, 19, or 20 (base paired) nucleotides in length. In certain other instances, the 5' and 3' overhangs on the antisense strand comprise sequences that are complementary to the target PLK-1 mRNA, and may optionally further comprise nontargeting sequences. In some embodiments, each of the 5' and 3' overhangs on the antisense strand comprises or consists of one, two, three, four, five, six, seven, or more nucleotides. Exemplary aiRNA molecules targeting PLK-1 mRNA are provided in Table 8.

In other embodiments, the aiRNA molecule comprises modified nucleotides selected from the group consisting of 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In a preferred embodiment, the aiRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

In related aspects, the present invention provides compositions comprising the microRNA (miRNA) molecules described herein that target PLK-1 expression and methods of using such compositions to silence PLK-1 expression.

In one embodiment, the miRNA molecule comprises about 15 to about 60 nucleotides in length, wherein the miRNA molecule is capable of silencing PLK-1 expression.

In certain instances, the miRNA molecule comprises about 15-50, 15-40, or 15-30 nucleotides in length, more typically about 15-25 or 19-25 nucleotides in length, and are preferably about 20-24, 21-22, or 21-23 nucleotides in length. In a preferred embodiment, the miRNA molecule is a mature miRNA molecule targeting PLK-1 mRNA. Exemplary miRNA molecules targeting PLK-1 mRNA are provided in Table 9.

In some embodiments, the miRNA molecule comprises modified nucleotides selected from the group consisting of 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, locked nucleic acid (LNA) nucleotides, and mixtures thereof. In a preferred embodiment, the miRNA molecule comprises 2'OMe nucleotides. As a non-limiting example, the 2'OMe nucleotides may be selected from the group consisting of 2'OMe-guanosine nucleotides, 2'OMe-uridine nucleotides, and mixtures thereof.

IV. Interfering RNA

A. siRNAs

The unmodified and modified siRNA molecules of the present invention are capable of silencing PLK-1 expression and are typically about 15 to 60 nucleotides in length. The modified siRNA molecules are generally less immunostimulatory than a corresponding unmodified siRNA sequence and retain RNAi activity against the target PLK-1 sequence. In some embodiments, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide. In preferred embodiments, one or more of the uridine and/or guanosine nucleotides are modified. The modified nucleotides can be present in one strand (i.e., sense or antisense) or both strands of the siRNA. The siRNA sequences may have overhangs (e.g., 3' or 5' overhangs as described in Elbashir et al., Genes Dev., 15:188 (2001) or Nykanen et al., Cell, 107:309 (2001)), or may lack overhangs (i.e., have blunt ends).

The modified siRNA generally comprises from about 1% to about 100% (e.g., about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 65%, 70%, 75%, 80%, 85%, 90%, 95%, or 100%) modified nucleotides in the double-stranded region of the siRNA duplex. In certain embodiments, one, two, three, four, five, six, seven, eight, nine, ten, or more of the nucleotides in the double-stranded region of the siRNA comprise modified nucleotides.

In some embodiments, less than about 25% (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%) of the nucleotides in the double-stranded region of the siRNA comprise modified nucleotides.

In other embodiments, from about 1% to about 25% (e.g., from about 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15%-25%, 16%-25%, 17%-25%, 18%-25%, 19%-25%, 20%-25%, 21%-25%, 22%-25%, 23%-25%, or 24%-25%) or from about 1% to about 20% (e.g., from about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15%-20%, 16%-20%, 17%-20%, 18%-20%, or 19%-20%) of the nucleotides in the double-stranded region of the siRNA comprise modified nucleotides.

In further embodiments, e.g., when one or both strands of the siRNA are selectively modified at uridine and/or guanosine nucleotides, the resulting modified siRNA can comprise less than about 30% modified nucleotides (e.g., less than about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or from about 1% to about 30% modified nucleotides (e.g., from about 1%-30%, 2%-30%, 3%-30%, 4%-30%, 5%-30%, 6%-30%, 7%-30%, 8%-30%, 9%-30%, 10%-30%, 11%-30%, 12%-30%, 13%-30%, 14%-30%, 15%-30%, 16%-30%, 17%-30%, 18%-30%, 19%-30%, 20%-30%, 21%-30%, 22%-30%, 23%-30%, 24%-30%, 25%-30%, 26%-30%, 27%-30%, 28%-30%, or 29%-30% modified nucleotides).

1. Selection of siRNA Sequences

Suitable siRNA sequences can be identified using any means known in the art. Typically, the methods described in Elbashir et al., Nature, 411:494-498 (2001) and Elbashir et al., EMBO J., 20:6877-6888 (2001) are combined with rational design rules set forth in Reynolds et al., Nature Biotech., 22(3):326-330 (2004). Generally, the nucleotide sequence 3' of the AUG start codon of a transcript from the target gene of interest is scanned for dinucleotide sequences (e.g., AA, NA, CC, GG, or UU, wherein N=C, G, or U) (see, e.g., Elbashir et al., EMBO J., 20:6877-6888 (2001)). The nucleotides immediately 3' to the dinucleotide sequences are identified as potential siRNA sequences (i.e., a target sequence or a sense strand sequence). Typically, the 19, 21, 23, 25, 27, 29, 31, 33, 35, or more nucleotides immediately 3' to the dinucleotide sequences are identified as potential siRNA sequences. In some embodiments, the dinucleotide sequence is an AA or NA sequence and the 19 nucleotides immediately 3' to the AA or NA dinucleotide are identified as a potential siRNA sequences. siRNA sequences are usually spaced at different positions along the length of the target gene. To further enhance silencing efficiency of the siRNA sequences, potential siRNA sequences may be analyzed to identify sites that do not contain regions of homology to other coding sequences, e.g., in the target cell or organism. For example, a suitable siRNA sequence of about 21 base pairs typically will not have more than 16-17 contiguous base pairs of homology to coding sequences in the target cell or organism. If the siRNA sequences are to be expressed from an RNA Pol III promoter, siRNA sequences lacking more than 4 contiguous A's or T's are selected.

Once a potential siRNA sequence has been identified, a complementary sequence (i.e., an antisense strand sequence) can be designed. A potential siRNA sequence can also be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found at, e.g., http://boz094.ust.hk/RNAi/siRNA. One of skill in the art will appreciate that sequences with one or more of the foregoing characteristics may be selected for further analysis and testing as potential siRNA sequences.

Additionally, potential siRNA sequences with one or more of the following criteria can often be eliminated as siRNA: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA sequences may be further analyzed based on siRNA duplex asymmetry as described in, e.g., Khvorova et al., Cell, 115:209-216 (2003); and Schwarz et al., Cell, 115:199-208 (2003). In other embodiments, potential siRNA sequences may be further analyzed based on secondary structure at the mRNA target site as described in, e.g., Luo et al., Biophys. Res. Commun., 318:303-310 (2004). For example, mRNA secondary structure can be modeled using the Mfold algorithm (available at http://www.bioinfo.rpi.edu/applications/mfold/rna/form1.cgi) to select siRNA sequences which favor accessibility at the mRNA target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs (e.g., 5'-GU-3',5'-UGU-3',5'-GUGU-3',5'-UGUGU-3', etc.) can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naïve mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, IFN-α, IFN-β, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 30% (e.g., less than about 30%, 25%, 20%, 15%, 10%, or 5%) of the nucleotides in the double-stranded region of the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "Western blot" method of Gordon et al. (U.S. Pat. No. 4,452,901); immunoprecipitation of labeled ligand (Brown et al., J. Biol. Chem., 255:4980-4983 (1980)); enzyme-linked immunosorbent assays (ELISA) as described, for example, by Raines et al., J. Biol. Chem., 257:5154-5160 (1982); immunocytochemical techniques, including the use of fluorochromes (Brooks et al., Clin. Exp. Immunol, 39:477 (1980)); and neutralization of activity (Bowen-Pope et al., Proc. Natl. Acad. Sci. USA, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

A non-limiting example of an in vivo model for detecting an immune response includes an in vivo mouse cytokine induction assay as described in, e.g., Judge et al., Mol. Ther., 13:494-505 (2006). In certain embodiments, the assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturer's instructions (e.g., mouse and human IFN-α (PBL Biomedical; Piscataway, N.J.); human IL-6 and TNF-α (eBioscience; San Diego, Calif.); and mouse IL-6, TNF-α, and IFN-γ (BD Biosciences; San Diego, Calif.)).

Monoclonal antibodies that specifically bind cytokines and growth factors are commercially available from multiple sources and can be generated using methods known in the art (see, e.g., Kohler et al., Nature, 256: 495-497 (1975) and Harlow and Lane, ANTIBODIES, A LABORATORY MANUAL, Cold Spring Harbor Publication, New York (1999)). Generation of monoclonal antibodies has been previously described and can be accomplished by any means known in the art (Buhring et al., in Hybridoma, Vol. 10, No. 1, pp. 77-78 (1991)). In some methods, the monoclonal antibody is labeled (e.g., with any composition detectable by spectroscopic, photochemical, biochemical, electrical, optical, or chemical means) to facilitate detection.

2. Generating siRNA Molecules siRNA can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al., Genes Dev., 15:188 (2001) or Nykanen et al., Cell, 107:309 (2001), or may lack overhangs (i.e., to have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Methods for isolating RNA, synthesizing RNA, hybridizing nucleic acids, making and screening cDNA libraries, and performing PCR are well known in the art (see, e.g., Gubler and Hoffman, *Gene,* 25:263-269 (1983); Sambrook et al., supra; Ausubel et al., supra), as are PCR methods (see, U.S. Pat. Nos. 4,683,195 and 4,683,202; *PCR Protocols: A Guide to Methods and Applications* (Innis et al., eds, 1990)). Expression libraries are also well known to those of skill in the art. Additional basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994).

Preferably, siRNA are chemically synthesized. The oligonucleotides that comprise the siRNA molecules of the present invention can be synthesized using any of a variety of techniques known in the art, such as those described in Usman et al., *J. Am. Chem. Soc.,* 109:7845 (1987); Scaringe et al., *Nucl. Acids Res.,* 18:5433 (1990); Wincott et al., *Nucl. Acids Res.,* 23:2677-2684 (1995); and Wincott et al., *Methods Mol. Bio.,* 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 μmol scale protocol. Alternatively, syntheses at the 0.2 μmol scale can be performed on a 96-well plate synthesizer from Protogene (Palo Alto, Calif.). However, a larger or smaller scale of synthesis is also within the scope of the present invention. Suitable reagents for oligonucleotide synthesis, methods for RNA deprotection, and methods for RNA purification are known to those of skill in the art.

The siRNA molecules of the present invention can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, siRNA molecules can be synthesized as a single continuous oligonucleotide fragment, where the self-complementary sense and antisense regions hybridize to form an siRNA duplex having hairpin secondary structure.

3. Modifying siRNA Sequences

In certain aspects, the siRNA molecules of the present invention comprise a duplex having two strands and at least one modified nucleotide in the double-stranded region, wherein each strand is about 15 to about 60 nucleotides in length. Advantageously, the modified siRNA is less immunostimulatory than a corresponding unmodified siRNA sequence, but retains the capability of silencing the expression of a target sequence. In preferred embodiments, the degree of chemical modifications introduced into the siRNA molecule strikes a balance between reduction or abrogation of the immunostimulatory properties of the siRNA and retention of RNAi activity. As a non-limiting example, an siRNA molecule that targets PLK-1 can be minimally modified (e.g., less than about 30%, 25%, 20%, 15%, 10%, or 5% modified) at selective uridine and/or guanosine nucleotides within the siRNA duplex to eliminate the immune response generated by the siRNA while retaining its capability to silence PLK-1 expression.

Examples of modified nucleotides suitable for use in the present invention include, but are not limited to, ribonucleotides having a 2'-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a Northern conformation such as those described in, e.g., Saenger, *Principles of Nucleic Acid Structure*, Springer-Verlag Ed. (1984), are also suitable for use in the siRNA molecules of the present invention. Such modified nucleotides include, without limitation, locked nucleic acid (LNA) nucleotides (e.g., 2'-O, 4'-C-methylene-(D-ribofuranosyl) nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2'Cl) nucleotides, and 2'-azido nucleotides. In certain instances, the siRNA molecules of the present invention include one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., *J. Am. Chem. Soc.,* 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, *Nucl. Acids Res.,* 29:2437-2447 (2001)) can be incorporated into the siRNA molecules of the present invention.

In certain embodiments, the siRNA molecules of the present invention further comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-amino-alkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., *Tetrahedron* 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., *Nucleic Acid Analogues: Synthesis and Properties*, in *Modern Synthetic Methods*, VCH, 331-417 (1995); Mesmaeker et al., *Novel Backbone Replacements for Oligonucleotides*, in *Carbohydrate Modifications in Antisense Research*, ACS, 24-39 (1994)). Such chemical modifications can occur at the 5'-end and/or 3'-end of the sense strand, antisense strand, or both strands of the siRNA.

In some embodiments, the sense and/or antisense strand of the siRNA molecule can further comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into the modified siRNA molecules of the present invention are described, e.g., in UK Patent No. GB 2,397,818 B and U.S. Patent Publication Nos. 20040192626, 20050282188, and 20070135372.

The modified siRNA molecules of the present invention can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the chemically-modified siRNA molecule. The conjugate can be attached at the 5' and/or 3'-end of the sense and/or antisense strand of the chemically-modified siRNA via a covalent attachment such as, e.g., a biodegradable linker. The conjugate can also be attached to the chemically-modified siRNA, e.g., through a carbamate group or other linking group (see, e.g., U.S. Patent Publication Nos. 20050074771, 20050043219, and 20050158727). In certain instances, the conjugate is a molecule that facilitates the delivery of the chemically-modified siRNA into a cell. Examples of conjugate molecules suitable for attachment to the chemically-modified siRNA of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the chemically-modified siRNA molecule can be evaluated for improved pharmacokinetic profiles, bioavailability, and/or stability of the siRNA while retaining RNAi activity. As such, one skilled in the art can screen chemically-modified siRNA molecules having various conjugates attached thereto to identify ones having improved properties and full RNAi activity using any of a variety of well-known in vitro cell culture or in vivo animal models.

B. aiRNAs

Like siRNA, asymmetrical interfering RNA (aiRNA) can recruit the RNA-induced silencing complex (RISC) and lead to effective silencing of a variety of genes in mammalian cells by mediating sequence-specific cleavage of the target mRNA between nucleotide 10 and 11 relative to the 5' end of the antisense strand (Sun et al., *Nat. Biotech.*, 26:1379-1382 (2008)). Typically, an aiRNA molecule comprises a short RNA duplex having a sense strand and an antisense strand, wherein the duplex contains overhangs at the 3' and 5' ends of the antisense strand. The aiRNA is generally asymmetric because the sense strand is shorter on both ends when compared to the complementary antisense strand. In some aspects, the aiRNA molecules of the present invention may be designed, synthesized, and annealed under conditions similar to those used for siRNA molecules. As a non-limiting example, aiRNA sequences may be selected and generated using the methods described above for selecting siRNA sequences.

In another embodiment, aiRNA duplexes of various lengths (e.g., about 10-25, 12-20, 12-19, 12-18, 13-17, or 14-17 base pairs, more typically 12, 13, 14, 15, 16, 17, 18, 19, or base pairs) may be designed with overhangs at the 3' and 5' ends of the antisense strand to target an mRNA of interest. In certain instances, the sense strand of the aiRNA molecule is about 10-25, 12-20, 12-19, 12-18, 13-17, or 14-17 nucleotides in length, more typically 12, 13, 14, 15, 16, 17, 18, 19, or 20 nucleotides in length. In certain other instances, the antisense strand of the aiRNA molecule is about 15-60, 15-50, or 15-40 nucleotides in length, more typically about 15-30, 15-25, or 19-25 nucleotides in length, and is preferably about 20-24, 21-22, or 21-23 nucleotides in length.

In some embodiments, the 5' antisense overhang contains one, two, three, four, or more nontargeting nucleotides (e.g., "AA", "UU", "dTdT", etc.). In other embodiments, the 3' antisense overhang contains one, two, three, four, or more nontargeting nucleotides (e.g., "AA", "UU", "dTdT", etc.). In certain aspects, the aiRNA molecules described herein may comprise one or more modified nucleotides, e.g., in the double-stranded (duplex) region and/or in the antisense overhangs. As a non-limiting example, aiRNA sequences may comprise one or more of the modified nucleotides described above for siRNA sequences. In a preferred embodiment, the aiRNA molecule comprises 2'OMe nucleotides such as, for example, 2'OMe-guanosine nucleotides, 2'OMe-uridine nucleotides, or mixtures thereof.

In certain embodiments, the aiRNA molecule of the present invention comprises an antisense strand which corresponds to the antisense strand of an siRNA molecule, e.g., one of the siRNA molecules described herein which displays PLK-1 silencing activity. In some instances, aiRNAs targeting PLK-1 mRNA are administered using a carrier system described herein such as a nucleic acid-lipid particle. In a preferred embodiment, the nucleic acid-lipid particle comprises: (a) one or more aiRNA molecules targeting PLK-1 mRNA; (b) a cationic lipid (e.g., DLinDMA); and (c) a non-cationic lipid (e.g., DSPC, DPPC, DSPE, and/or cholesterol). In certain instances, the nucleic acid-lipid particle may further comprise a conjugated lipid that prevents aggregation of particles (e.g., PEG-DAA). Non-limiting examples of aiRNA molecules suitable for modulating (e.g., silencing) PLK-1 expression are provided in Table 8 of Example 17.

C. miRNAs

Generally, microRNAs (miRNA) are single-stranded RNA molecules of about 21-23 nucleotides in length which regulate gene expression. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules, and their main function is to downregulate gene expression. The identification of miRNAs is described, e.g., in Lagos-Quintana et al., *Science,* 294:853-858; Lau et al., *Science,* 294:858-862; and Lee et al., *Science,* 294:862-864.

The genes encoding miRNAs are much longer than the processed mature miRNA molecule. miRNAs are first transcribed as primary transcripts or pri-miRNA with a cap and poly-A tail and processed to short, ~70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha (Denli et al., *Nature,* 432:231-235 (2004)). These pre-miRNAs are then processed to mature miRNAs in the cytoplasm by interaction with the endonuclease Dicer, which also initiates the formation of the RNA-induced silencing complex (RISC) (Bernstein et al., *Nature,* 409:363-366 (2001). Either the sense strand or antisense strand of DNA can function as templates to give rise to miRNA.

When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end (Preall et al., *Curr. Biol.,* 16:530-535 (2006)). The remaining strand, known as the anti-guide or passenger strand, is degraded as a RISC complex substrate (Gregory et al., *Cell,* 123:631-640 (2005)). After integration into the active RISC complex, miRNAs base pair with their complementary mRNA molecules and induce target mRNA degradation and/or translational silencing.

Mammalian miRNAs are usually complementary to a site in the 3' UTR of the target mRNA sequence. In certain instances, the annealing of the miRNA to the target mRNA inhibits protein translation by blocking the protein translation machinery. In certain other instances, the annealing of the miRNA to the target mRNA facilitates the cleavage and degradation of the target mRNA through a process similar to RNA interference (RNAi). miRNAs may also target methylation of genomic sites which correspond to targeted mRNAs. Generally, miRNAs function in association with a complement of proteins collectively termed the miRNP.

In certain aspects, the miRNA molecules described herein are about 15-100, 15-90, 15-80, 15-75, 15-70, 15-60, 15-50, or 15-40 nucleotides in length, more typically about 15-30, 15-25, or 19-25 nucleotides in length, and are preferably about 20-24, 21-22, or 21-23 nucleotides in length. In certain other aspects, the miRNA molecules described herein may comprise one or more modified nucleotides. As a non-limiting example, miRNA sequences may comprise one or more of the modified nucleotides described above for siRNA sequences. In a preferred embodiment, the miRNA molecule comprises 2'OMe nucleotides such as, for example, 2'OMe-guanosine nucleotides, 2'OMe-uridine nucleotides, or mixtures thereof.

In some embodiments, miRNAs targeting PLK-1 mRNA are administered using a carrier system described herein such as a nucleic acid-lipid particle. In a preferred embodiment, the nucleic acid-lipid particle comprises: (a) one or more miRNA molecules targeting PLK-1 mRNA; (b) a cationic lipid (e.g., DLinDMA); and (c) a non-cationic lipid (e.g., DSPC, DPPC, DSPE, and/or cholesterol). In certain instances, the nucleic acid-lipid particle may further comprise a conjugated lipid that prevents aggregation of particles (e.g., PEG-DAA). Non-limiting examples of miRNA molecules suitable for modulating (e.g., silencing) PLK-1 expression are provided in Table 9 of Example 18.

In other embodiments, one or more agents that block the activity of a miRNA targeting PLK-1 mRNA are administered using a carrier system described herein (e.g., a nucleic acid-lipid particle). Examples of blocking agents include, but are not limited to, steric blocking oligonucleotides, locked nucleic acid oligonucleotides, and Morpholino oligonucleotides. Such blocking agents may bind directly to the miRNA or to the miRNA binding site on the target mRNA.

V. Carrier Systems Containing Interfering RNA

In one aspect, the present invention provides carrier systems containing one or more interfering RNA described herein, e.g., unmodified or modified siRNA, aiRNA, or miRNA. In some embodiments, the carrier system is a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a stabilized nucleic acid-lipid particle such as a SNALP or SPLP. One skilled in the art will appreciate that the interfering RNA of the present invention can also be delivered as a naked molecule.

A. Stabilized Nucleic Acid-Lipid Particles

The stabilized nucleic acid-lipid particles (SNALP) of the present invention typically comprise an interfering RNA molecule as described herein, a cationic lipid (e.g., a cationic lipid of Formula I or II), and a non-cationic lipid. The SNALP can further comprise a lipid conjugate (i.e., a conjugated lipid that inhibits aggregation of the particles). In some embodiments, the SNALP may comprise at least 1, 2, 3, 4, 5, 6, 7, 8, 9, 10, or more of the modified interfering RNA molecules described herein, alone or in combination with at least 1, 2, 3, 4, 5, 6, 7, 8, 9, 10, or more unmodified interfering RNA molecules.

The SNALP of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids are resistant in aqueous solution to degradation with a nuclease when present in the nucleic acid-lipid particles. Nucleic acid-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Publication No. WO 96/40964.

1. Cationic Lipids

Any of a variety of cationic lipids may be used in the stabilized nucleic acid-lipid particles of the present invention, either alone or in combination with one or more other cationic lipid species or non-cationic lipid species.

Cationic lipids which are useful in the present invention can be any of a number of lipid species which carry a net positive charge at physiological pH. Such lipids include, but are not limited to, N,N-dioleyl-N,N-dimethylammonium chloride (DODAC), dioctadecyldimethylammonium (DODMA), distearyldimethylammonium (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3.beta.-oxy)-3'-oxapentoxy)-3-dimethyl-1-(cis,cis-9',1-2'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), and mixtures thereof. A number of these lipids and related analogs have been described in U.S. Patent Publication Nos. 20060083780 and 20060240554; U.S. Pat. Nos. 5,208,036; 5,264,618; 5,279,833; 5,283,185; 5,753,613; and 5,785,992; and PCT Publication No. WO 96/10390. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

Furthermore, cationic lipids of Formula I having the following structures are useful in the present invention.

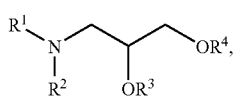

(I)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradecatrienyl ($C_{14}$) and $R^4$ is linoleyl ($C_{18}$). In a preferred embodiment, the cationic lipid of Formula I is symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienoyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradecatrienyl, hexadecatrienyl, linolenyl, and icosatrienyl. In particularly preferred embodiments, the cationic lipid of Formula I is 1,2-dilinoleyloxy-N,N-dimethylaminopropane (DLinDMA) or 1,2-dilinolenyloxy-N,N-dimethylaminopropane (DLenDMA).

Moreover, cationic lipids of Formula II having the following structures are useful in the present invention.

(II)

wherein $R^1$ and $R^2$ are independently selected and are H or $C_1$-$C_3$ alkyls, $R^3$ and $R^4$ are independently selected and are alkyl groups having from about 10 to about 20 carbon atoms, and at least one of $R^3$ and $R^4$ comprises at least two sites of unsaturation. In certain instances, $R^3$ and $R^4$ are both the same, i.e., $R^3$ and $R^4$ are both linoleyl ($C_{18}$), etc. In certain other instances, $R^3$ and $R^4$ are different, i.e., $R^3$ is tetradecatrienyl ($C_{14}$) and $R^4$ is linoleyl ($C_{18}$). In a preferred embodiment, the cationic lipids of the present invention are symmetrical, i.e., $R^3$ and $R^4$ are both the same. In another preferred embodiment, both $R^3$ and $R^4$ comprise at least two sites of unsaturation. In some embodiments, $R^3$ and $R^4$ are independently selected from the group consisting of dodecadienyl, tetradecadienoyl, hexadecadienyl, linoleyl, and icosadienyl. In a preferred embodiment, $R^3$ and $R^4$ are both linoleyl. In some embodiments, $R^3$ and $R^4$ comprise at least three sites of unsaturation and are independently selected from, e.g., dodecatrienyl, tetradecatrienyl, hexadecatrienyl, linolenyl, and icosatrienyl.

In some embodiments, the cationic lipid comprises from about 2 mol % to about 60 mol %, from about 5 mol % to about 50 mol %, from about 10 mol % to about 50 mol %, from about 20 mol % to about 50 mol %, from about 20 mol % to about 40 mol %, from about 30 mol % to about 40 mol %, or about 40 mol % of the total lipid present in the particle.

In other embodiments, the cationic lipid comprises from about 50 mol % to about 85 mol %, about 50 mol % to about 80 mol %, about 50 mol % to about 75 mol %, about 50 mol % to about 65 mol %, or about 55 mol % to about 65 mol % of the total lipid present in the particle.

It will be readily apparent to one of skill in the art that depending on the intended use of the particles, the proportions of the components can be varied and the delivery efficiency of a particular formulation can be measured using, e.g., an endosomal release parameter (ERP) assay.

2. Non-Cationic Lipids

The non-cationic lipids used in the stabilized nucleic acid-lipid particles of the present invention can be any of a variety of neutral uncharged, zwitterionic, or anionic lipids capable of producing a stable complex.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lyso-phosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof such as cholestanol, cholestanone, cholestenone, and coprostanol.

In some embodiments, the non-cationic lipid present in the SNALP comprises or consists of cholesterol, e.g., a phospholipid-free SNALP. In other embodiments, the non-cationic lipid present in the SNALP comprises or consists of one or more phospholipids, e.g., a cholesterol-free SNALP. In further embodiments, the non-cationic lipid present in the SNALP comprises or consists of a mixture of one or more phospholipids and cholesterol.

Other examples of non-cationic lipids suitable for use in the present invention include nonphosphorous containing lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyoxylated fatty acid amides, dioctadecyldimethyl ammonium bromide, ceramide, sphingomyelin, and the like.

In some embodiments, the non-cationic lipid comprises from about 5 mol % to about 90 mol %, from about 10 mol % to about 85 mol %, from about 20 mol % to about 80 mol %, about 10 mol % (e.g., phospholipid only), or about 60 mol % (e.g., phospholipid and cholesterol) of the total lipid present in the particle. If present, the cholesterol or cholesterol derivative typically comprises from about 0 mol % to about 10 mol %, from about 2 mol % to about 10 mol %, from about 10 mol % to about 60 mol %, from about 12 mol % to about 58 mol %, from about 20 mol % to about 55 mol %, from about 30 mol % to about 50 mol %, or about 48 mol % of the total lipid present in the particle.

In other embodiments, the non-cationic lipid comprises from about 13 mol % to about 49.5 mol %, about 20 mol % to about 45 mol %, about 25 mol % to about 45 mol %, about 30 mol % to about 45 mol %, about 35 mol % to about 45 mol %, about 20 mol % to about 40 mol %, about 25 mol % to about 40 mol %, or about 30 mol % to about 40 mol % of the total lipid present in the particle.

In certain embodiments, the cholesterol present in phospholipid-free nucleic acid-lipid particles comprises from about 30 mol % to about 45 mol %, about 30 mol % to about 40 mol %, about 35 mol % to about 45 mol %, or about 35 mol % to about 40 mol % of the total lipid present in the particle. As a non-limiting example, a phospholipid-free nucleic acid-lipid particle may comprise cholesterol at about 37 mol % of the total lipid present in the particle.

In certain other embodiments, the cholesterol present in nucleic acid-lipid particles containing a mixture of phospholipid and cholesterol comprises from about 30 mol % to about 40 mol %, about 30 mol % to about 35 mol %, or about 35 mol % to about 40 mol % of the total lipid present in the particle. As a non-limiting example, a nucleic acid-lipid particle comprising a mixture of phospholipid and cholesterol may comprise cholesterol at about 34 mol % of the total lipid present in the particle.

In embodiments where the nucleic acid-lipid particles contain a mixture of phospholipid and cholesterol, the phospholipid may comprise from about 2 mol % to about 12 mol %, about 4 mol % to about 10 mol %, about 5 mol % to about 10 mol %, about 5 mol % to about 9 mol %, or about 6 mol % to about 8 mol % of the total lipid present in the particle. As a non-limiting example, a nucleic acid-lipid particle comprising a mixture of phospholipid and cholesterol may comprise a phospholipid such as DPPC at about 7 mol % of the total lipid present in the particle.

3. Lipid Conjugate

In addition to cationic and non-cationic lipids, the stabilized nucleic acid-lipid particles of the present invention may comprise a lipid conjugate. The conjugated lipid is useful in that it prevents the aggregation of particles. Suitable conjugated lipids include, but are not limited to, PEG-lipid conjugates, ATTA-lipid conjugates, cationic-polymer-lipid conjugates (CPLs), and mixtures thereof. In certain embodiments, the particles comprise either a PEG-lipid conjugate or an ATTA-lipid conjugate together with a CPL.

In a preferred embodiment, the lipid conjugate is a PEG-lipid. Examples of PEG-lipids include, but are not limited to, PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides as described in, e.g., U.S. Pat. No. 5,885,613, PEG conjugated to cholesterol or a derivative thereof, and mixtures thereof. Additional PEG-lipids include, without limitation, PEG-C-DOMG, 2KPEG-DMG, and a mixture thereof.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). Other PEGs such as those described in U.S. Pat. Nos. 6,774,180 and 7,053,150 (e.g., mPEG (20 KDa) amine) are also useful for preparing the PEG-lipid conjugates of the present invention. In addition, monomethoxypolyethyleneglycol-acetic acid (MePEG-CH$_2$COOH) is particularly useful for preparing PEG-lipid conjugates including, e.g., PEG-DAA conjugates.

In a preferred embodiment, the PEG has an average molecular weight of from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons. The PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinimidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available, or can be isolated or synthesized using conventional techniques known to those of skill in the art. Phosphatidyl-ethanolamines containing saturated or unsaturated fatty acids with carbon chain lengths in the range of C$_{10}$ to C$_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

The term "ATTA" or "polyamide" refers to, without limitation, compounds disclosed in U.S. Pat. Nos. 6,320,017 and 6,586,559. These compounds include a compound having the formula:

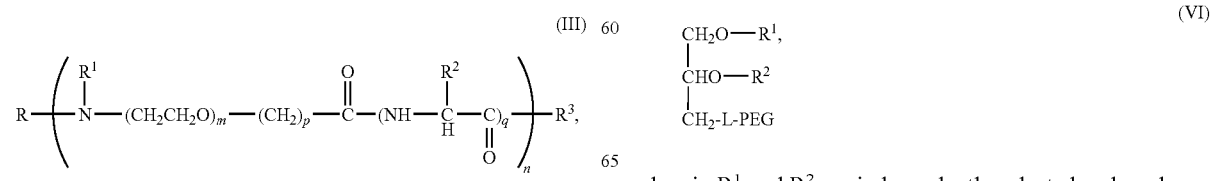

wherein R is a member selected from the group consisting of hydrogen, alkyl and acyl; R$^1$ is a member selected from the group consisting of hydrogen and alkyl; or optionally, R and R$^1$ and the nitrogen to which they are bound form an azido moiety; R$^2$ is a member of the group selected from hydrogen, optionally substituted alkyl, optionally substituted aryl and a side chain of an amino acid; R$^3$ is a member selected from the group consisting of hydrogen, halogen, hydroxy, alkoxy, mercapto, hydrazino, amino and NR$^4$R$^5$, wherein R$^4$ and R$^5$ are independently hydrogen or alkyl; n is 4 to 80; m is 2 to 6; p is 1 to 4; and q is 0 or 1. It will be apparent to those of skill in the art that other polyamides can be used in the compounds of the present invention.

The term "diacylglycerol" refers to a compound having 2 fatty acyl chains, R$^1$ and R$^2$, both of which have independently between 2 and 30 carbons bonded to the 1- and 2-position of glycerol by ester linkages. The acyl groups can be saturated or have varying degrees of unsaturation. Suitable acyl groups include, but are not limited to, lauroyl (C$_{12}$), myristoyl (C$_{14}$), palmitoyl (C$_{16}$), stearoyl (C$_{18}$), and icosoyl (C$_{20}$). In preferred embodiments, R$^1$ and R$^2$ are the same, i.e., R$^1$ and R$^2$ are both myristoyl (i.e., dimyristoyl), R$^1$ and R$^2$ are both stearoyl (i.e., distearoyl), etc. Diacylglycerols have the following general formula:

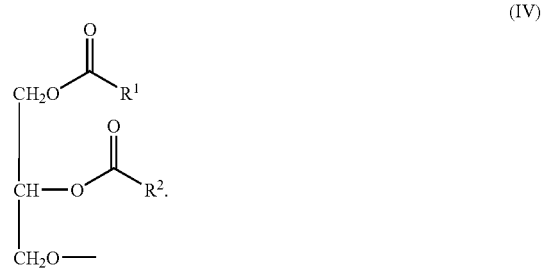

The term "dialkyloxypropyl" refers to a compound having 2 alkyl chains, R$^1$ and R$^2$, both of which have independently between 2 and 30 carbons. The alkyl groups can be saturated or have varying degrees of unsaturation. Dialkyloxypropyls have the following general formula:

wherein R$^1$ and R$^2$ are independently selected and are long-chain alkyl groups having from about 10 to about 22 carbon atoms.

In a preferred embodiment, the PEG-lipid is a PEG-DAA conjugate having the following formula:

$$\begin{array}{l} CH_2O-R^1, \\ CHO-R^2 \\ CH_2\text{-L-PEG} \end{array} \quad (VI)$$

wherein R$^1$ and R$^2$ are independently selected and are long-chain alkyl groups having from about 10 to about 22 carbon atoms; PEG is a polyethyleneglycol; and L is a non-ester containing linker moiety or an ester containing linker moiety as described above. The long-chain alkyl groups can be saturated or unsaturated. Suitable alkyl groups include, but are not limited to, lauryl ($C_{12}$), myristyl ($C_{14}$), palmityl ($C_{16}$), stearyl ($C_{18}$), and icosyl ($C_{20}$). In preferred embodiments, $R^1$ and $R^2$ are the same, i.e., $R^1$ and $R^2$ are both myristyl (i.e., dimyristoyl), $R^1$ and $R^2$ are both stearyl (i.e., distearyl), etc.

In Formula VI above, the PEG has an average molecular weight ranging from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons. The PEG can be optionally substituted with alkyl, alkoxy, acyl, or aryl. In a preferred embodiment, the terminal hydroxyl group is substituted with a methoxy or methyl group.

In a preferred embodiment, "L" is a non-ester containing linker moiety. Suitable non-ester containing linkers include, but are not limited to, an amido linker moiety, an amino linker moiety, a carbonyl linker moiety, a carbamate linker moiety, a urea linker moiety, an ether linker moiety, a disulphide linker moiety, a succinimidyl linker moiety, and combinations thereof. In a preferred embodiment, the non-ester containing linker moiety is a carbamate linker moiety (i.e., a PEG-C-DAA conjugate). In another preferred embodiment, the non-ester containing linker moiety is an amido linker moiety (i.e., a PEG-A-DAA conjugate). In yet another preferred embodiment, the non-ester containing linker moiety is a succinimidyl linker moiety (i.e., a PEG-S-DAA conjugate).

The PEG-DAA conjugates are synthesized using standard techniques and reagents known to those of skill in the art. It will be recognized that the PEG-DAA conjugates will contain various amide, amine, ether, thio, carbamate, and urea linkages. Those of skill in the art will recognize that methods and reagents for forming these bonds are well known and readily available. See, e.g., March, ADVANCED ORGANIC CHEMISTRY (Wiley 1992); Larock, COMPREHENSIVE ORGANIC TRANSFORMATIONS (VCH 1989); and Furniss, VOGEL'S TEXTBOOK OF PRACTICAL ORGANIC CHEMISTRY, 5th ed. (Longman 1989). It will also be appreciated that any functional groups present may require protection and deprotection at different points in the synthesis of the PEG-DAA conjugates. Those of skill in the art will recognize that such techniques are well known. See, e.g., Green and Wuts, PROTECTIVE GROUPS IN ORGANIC SYNTHESIS (Wiley 1991).

Preferably, the PEG-DAA conjugate is a dilauryloxypropyl ($C_{12}$)-PEG conjugate, dimyristyloxypropyl ($C_{14}$)-PEG conjugate, a dipalmityloxypropyl ($C_{16}$)-PEG conjugate, or a distearyloxypropyl ($C_{18}$)-PEG conjugate. Those of skill in the art will readily appreciate that other dialkyloxypropyls can be used in the PEG-DAA conjugates of the present invention.

In addition to the foregoing, it will be readily apparent to those of skill in the art that other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl methacrylamide, polymethacrylamide and polydimethylacrylamide, polylactic acid, polyglycolic acid, and derivatized celluloses such as hydroxymethylcellulose or hydroxyethylcellulose.

In addition to the foregoing components, the particles (e.g., SNALPs or SPLPs) of the present invention can further comprise cationic poly(ethylene glycol) (PEG) lipids or CPLs (see, e.g., Chen et al., *Bioconj. Chem.*, 11:433-437 (2000)). Suitable SPLPs and SPLP-CPLs for use in the present invention, and methods of making and using SPLPs and SPLP-CPLs, are disclosed, e.g., in U.S. Pat. No. 6,852,334 and PCT Publication No. WO 00/62813.

Suitable CPLs include compounds of Formula VII:

$$A\text{-}W\text{-}Y \qquad\qquad\qquad (VII),$$

wherein A, W, and Y are as described below.

With reference to Formula VII, "A" is a lipid moiety such as an amphipathic lipid, a neutral lipid, or a hydrophobic lipid that acts as a lipid anchor. Suitable lipid examples include, but are not limited to, diacylglycerolyls, dialkylglycerolyls, N—N-dialkylaminos, 1,2-diacryloxy-3-aminopropanes, and 1,2-dialkyl-3-aminopropanes.

"W" is a polymer or an oligomer such as a hydrophilic polymer or oligomer. Preferably, the hydrophilic polymer is a biocompatible polymer that is nonimmunogenic or possesses low inherent immunogenicity. Alternatively, the hydrophilic polymer can be weakly antigenic if used with appropriate adjuvants. Suitable nonimmunogenic polymers include, but are not limited to, PEG, polyamides, polylactic acid, polyglycolic acid, polylactic acid/polyglycolic acid copolymers, and combinations thereof. In a preferred embodiment, the polymer has a molecular weight of from about 250 to about 7,000 daltons.

"Y" is a polycationic moiety. The term polycationic moiety refers to a compound, derivative, or functional group having a positive charge, preferably at least 2 positive charges at a selected pH, preferably physiological pH. Suitable polycationic moieties include basic amino acids and their derivatives such as arginine, asparagine, glutamine, lysine, and histidine; spermine; spermidine; cationic dendrimers; polyamines; polyamine sugars; and amino polysaccharides. The polycationic moieties can be linear, such as linear tetralysine, branched or dendrimeric in structure. Polycationic moieties have between about 2 to about 15 positive charges, preferably between about 2 to about 12 positive charges, and more preferably between about 2 to about 8 positive charges at selected pH values. The selection of which polycationic moiety to employ may be determined by the type of particle application which is desired.

The charges on the polycationic moieties can be either distributed around the entire particle moiety, or alternatively, they can be a discrete concentration of charge density in one particular area of the particle moiety e.g., a charge spike. If the charge density is distributed on the particle, the charge density can be equally distributed or unequally distributed. All variations of charge distribution of the polycationic moiety are encompassed by the present invention.

The lipid "A" and the nonimmunogenic polymer "W" can be attached by various methods and preferably by covalent attachment. Methods known to those of skill in the art can be used for the covalent attachment of "A" and "W." Suitable linkages include, but are not limited to, amide, amine, carboxyl, carbonate, carbamate, ester, and hydrazone linkages. It will be apparent to those skilled in the art that "A" and "W" must have complementary functional groups to effectuate the linkage. The reaction of these two groups, one on the lipid and the other on the polymer, will provide the desired linkage. For example, when the lipid is a diacylglycerol and the terminal hydroxyl is activated, for instance with NHS and DCC, to form an active ester, and is then reacted with a polymer which contains an amino group, such as with a polyamide (see, e.g., U.S. Pat. Nos. 6,320,017 and 6,586,559), an amide bond will form between the two groups.

In certain instances, the polycationic moiety can have a ligand attached, such as a targeting ligand or a chelating moiety for complexing calcium. Preferably, after the ligand is attached, the cationic moiety maintains a positive charge. In certain instances, the ligand that is attached has a positive charge. Suitable ligands include, but are not limited to, a compound or device with a reactive functional group and include lipids, amphipathic lipids, carrier compounds, bioaffinity compounds, biomaterials, biopolymers, biomedical devices, analytically detectable compounds, therapeutically active compounds, enzymes, peptides, proteins, antibodies, immune stimulators, radiolabels, fluorogens, biotin, drugs, haptens, DNA, RNA, polysaccharides, liposomes, virosomes, micelles, immunoglobulins, functional groups, other targeting moieties, or toxins.

In some embodiments, the lipid conjugate (e.g., PEG-lipid) comprises from about 0 mol % to about 20 mol %, from about 0.5 mol % to about 20 mol %, from about 1.5 mol % to about 18 mol %, from about 4 mol % to about 15 mol %, from about 5 mol % to about 12 mol %, or about 2 mol % of the total lipid present in the particle.

In other embodiments, the lipid conjugate (e.g., PEG-lipid) comprises from about 0.1 mol % to about 10 mol %, about 0.1 mol % to about 5 mol %, about 0.2 mol % to about 5 mol %, about 0.3 mol % to about 5 mol %, about 0.4 mol % to about 5 mol %, about 0.5 mol % to about 5 mol %, about 0.5 mol % to about 2 mol %, about 0.5 mol % to about 1.5 mol %, about 0.5 mol % to about 1 mol %, about 1 mol % to about 2 mol %, or about 1.5 mol % of the total lipid present in the particle.

One of ordinary skill in the art will appreciate that the concentration of the lipid conjugate can be varied depending on the lipid conjugate employed and the rate at which the nucleic acid-lipid particle is to become fusogenic.

By controlling the composition and concentration of the lipid conjugate, one can control the rate at which the lipid conjugate exchanges out of the nucleic acid-lipid particle and, in turn, the rate at which the nucleic acid-lipid particle becomes fusogenic. For instance, when a PEG-phosphatidylethanolamine conjugate or a PEG-ceramide conjugate is used as the lipid conjugate, the rate at which the nucleic acid-lipid particle becomes fusogenic can be varied, for example, by varying the concentration of the lipid conjugate, by varying the molecular weight of the PEG, or by varying the chain length and degree of saturation of the acyl chain groups on the phosphatidylethanolamine or the ceramide. In addition, other variables including, for example, pH, temperature, ionic strength, etc. can be used to vary and/or control the rate at which the nucleic acid-lipid particle becomes fusogenic. Other methods which can be used to control the rate at which the nucleic acid-lipid particle becomes fusogenic will become apparent to those of skill in the art upon reading this disclosure.

B. Additional Carrier Systems

Non-limiting examples of additional lipid-based carrier systems suitable for use in the present invention include lipoplexes (see, e.g., U.S. Patent Publication No. 20030203865; and Zhang et al., J. Control Release, 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., interfering RNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., interfering RNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropyleneimine (PPI), polyvinylpyrrolidone (PVP), poly-L-lysine (PLL), diethylaminoethyl (DEAE)-dextran, poly(β-amino ester) (PAE) polymers (see, e.g., Lynn et al., J. Am. Chem. Soc., 123:8155-8156 (2001)), chitosan, polyamidoamine (PAMAM) dendrimers (see, e.g., Kukowska-Latallo et al., Proc. Natl. Acad. Sci. USA, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., J. Control Release, 100:165-180 (2004); and Tiera et al., Curr. Gene Ther., 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the interfering RNA may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091, 192; and the cyclodextrin polymer-complexing agent-nucleic acid complexes described in U.S. Pat. No. 7,018,609. In certain other instances, the interfering RNA may be complexed with a peptide or polypeptide. An example of a protein-based carrier system includes, but is not limited to, the cationic oligopeptide-nucleic acid complex described in PCT Publication No. WO95/21931.

VI. Preparation of Nucleic Acid-Lipid Particles

The serum-stable nucleic acid-lipid particles of the present invention, in which the interfering RNA described herein is encapsulated in a lipid bilayer and is protected from degradation, can be formed by any method known in the art including, but not limited to, a continuous mixing method, a direct dilution process, a detergent dialysis method, or a modification of a reverse-phase method which utilizes organic solvents to provide a single phase during mixing of the components.

In preferred embodiments, the cationic lipids are lipids of Formula I and II or combinations thereof. In other preferred embodiments, the non-cationic lipids are egg sphingomyelin (ESM), distearoylphosphatidylcholine (DSPC), dioleoylphosphatidylcholine (DOPC), 1-palmitoyl-2-oleoyl-phosphatidylcholine (POPC), dipalmitoyl-phosphatidylcholine (DPPC), monomethyl-phosphatidylethanolamine, dimethyl-phosphatidylethanolamine, 14:0 PE (1,2-dimyristoyl-phosphatidylethanolamine (DMPE)), 16:0 PE (1,2-dipalmitoyl-phosphatidylethanolamine (DPPE)), 18:0 PE (1,2-distearoyl-phosphatidylethanolamine (DSPE)), 18:1 PE (1,2-dioleoyl-phosphatidylethanolamine (DOPE)), 18:1 trans PE (1,2-dielaidoyl-phosphatidylethanolamine (DEPE)), 18:0-18:1 PE (1-stearoyl-2-oleoyl-phosphatidylethanolamine (SOPE)), 16:0-18:1 PE (1-palmitoyl-2-oleoyl-phosphatidylethanolamine (POPE)), polyethylene glycol-based polymers (e.g., PEG 2000, PEG 5000, PEG-modified diacylglycerols, or PEG-modified dialkyloxypropyls), cholesterol, or combinations thereof. In still other preferred embodiments, the organic solvents are methanol, chloroform, methylene chloride, ethanol, diethyl ether, or combinations thereof.

In a preferred embodiment, the present invention provides for nucleic acid-lipid particles produced via a continuous mixing method, e.g., process that includes providing an aqueous solution comprising a nucleic acid such as an interfering RNA in a first reservoir, providing an organic lipid solution in a second reservoir, and mixing the aqueous solution with the organic lipid solution such that the organic lipid solution mixes with the aqueous solution so as to substantially instantaneously produce a liposome encapsulating the nucleic acid (e.g., interfering RNA). This process and the apparatus for carrying this process are described in detail in U.S. Patent Publication No. 20040142025.

The action of continuously introducing lipid and buffer solutions into a mixing environment, such as in a mixing chamber, causes a continuous dilution of the lipid solution with the buffer solution, thereby producing a liposome substantially instantaneously upon mixing. As used herein, the phrase "continuously diluting a lipid solution with a buffer solution" (and variations) generally means that the lipid solution is diluted sufficiently rapidly in a hydration process with sufficient force to effectuate vesicle generation. By mixing the aqueous solution comprising a nucleic acid with the organic lipid solution, the organic lipid solution undergoes a continuous stepwise dilution in the presence of the buffer solution (i.e., aqueous solution) to produce a nucleic acid-lipid particle.

The serum-stable nucleic acid-lipid particles formed using the continuous mixing method typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In another embodiment, the present invention provides for nucleic acid-lipid particles produced via a direct dilution process that includes forming a liposome solution and immediately and directly introducing the liposome solution into a collection vessel containing a controlled amount of dilution buffer. In preferred aspects, the collection vessel includes one or more elements configured to stir the contents of the collection vessel to facilitate dilution. In one aspect, the amount of dilution buffer present in the collection vessel is substantially equal to the volume of liposome solution introduced thereto. As a non-limiting example, a liposome solution in 45% ethanol when introduced into the collection vessel containing an equal volume of dilution buffer will advantageously yield smaller particles.

In yet another embodiment, the present invention provides for nucleic acid-lipid particles produced via a direct dilution process in which a third reservoir containing dilution buffer is fluidly coupled to a second mixing region. In this embodiment, the liposome solution formed in a first mixing region is immediately and directly mixed with dilution buffer in the second mixing region. In preferred aspects, the second mixing region includes a T-connector arranged so that the liposome solution and the dilution buffer flows meet as opposing 180° flows; however, connectors providing shallower angles can be used, e.g., from about 27° to about 180°. A pump mechanism delivers a controllable flow of buffer to the second mixing region. In one aspect, the flow rate of dilution buffer provided to the second mixing region is controlled to be substantially equal to the flow rate of liposome solution introduced thereto from the first mixing region. This embodiment advantageously allows for more control of the flow of dilution buffer mixing with the liposome solution in the second mixing region, and therefore also the concentration of liposome solution in buffer throughout the second mixing process. Such control of the dilution buffer flow rate advantageously allows for small particle size formation at reduced concentrations.

These processes and the apparatuses for carrying out these direct dilution processes are described in detail in U.S. Patent Publication No. 20070042031.

The serum-stable nucleic acid-lipid particles formed using the direct dilution process typically have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

In some embodiments, the particles are formed using detergent dialysis. Without intending to be bound by any particular mechanism of formation, a nucleic acid such as an interfering RNA is contacted with a detergent solution of cationic lipids to form a coated nucleic acid complex. These coated nucleic acids can aggregate and precipitate. However, the presence of a detergent reduces this aggregation and allows the coated nucleic acids to react with excess lipids (typically, non-cationic lipids) to form particles in which the nucleic acid is encapsulated in a lipid bilayer. Thus, the serum-stable nucleic acid-lipid particles can be prepared as follows:

(a) combining a nucleic acid with cationic lipids in a detergent solution to form a coated nucleic acid-lipid complex;

(b) contacting non-cationic lipids with the coated nucleic acid-lipid complex to form a detergent solution comprising a nucleic acid-lipid complex and non-cationic lipids; and (c) dialyzing the detergent solution of step (b) to provide a solution of serum-stable nucleic acid-lipid particles, wherein the nucleic acid is encapsulated in a lipid bilayer and the particles are serum-stable and have a size of from about 50 nm to about 150 nm.

An initial solution of coated nucleic acid-lipid complexes is formed by combining the nucleic acid with the cationic lipids in a detergent solution. In these embodiments, the detergent solution is preferably an aqueous solution of a neutral detergent having a critical micelle concentration of 15-300 mM, more preferably 20-50 mM. Examples of suitable detergents include, for example, N,N'-((octanoylimino)-bis-(trimethylene))-bis-(D-gluconamide) (BIGCHAP); BRIJ 35; Deoxy-BIGCHAP; dodecylpoly(ethylene glycol) ether; Tween 20; Tween 40; Tween 60; Tween 80; Tween 85; Mega 8; Mega 9; Zwittergent® 3-08; Zwittergent® 3-10; Triton X-405; hexyl-, heptyl-, octyl- and nonyl-β-D-glucopyranoside; and heptylthioglucopyranoside; with octyl β-D-glucopyranoside and Tween-20 being the most preferred. The concentration of detergent in the detergent solution is typically about 100 mM to about 2 M, preferably from about 200 mM to about 1.5 M.

The cationic lipids and nucleic acids will typically be combined to produce a charge ratio (+/−) of about 1:1 to about 20:1, in a ratio of about 1:1 to about 12:1, or in a ratio of about 2:1 to about 6:1. Additionally, the overall concentration of nucleic acid in solution will typically be from about 25 µg/ml to about 1 mg/ml, from about 25 µg/ml to about 200 µg/ml, or from about 50 µg/ml to about 100 µg/ml. The combination of nucleic acids and cationic lipids in detergent solution is kept, typically at room temperature, for a period of time which is sufficient for the coated complexes to form. Alternatively, the nucleic acids and cationic lipids can be combined in the detergent solution and warmed to temperatures of up to about 37° C., about 50° C., about 60° C., or about 70° C. For nucleic acids which are particularly sensitive to temperature, the coated complexes can be formed at lower temperatures, typically down to about 4° C.

The detergent solution of the coated nucleic acid-lipid complexes is then contacted with non-cationic lipids to provide a detergent solution of nucleic acid-lipid complexes and non-cationic lipids. The non-cationic lipids which are useful in this step include, diacylphosphatidylcholine, diacylphosphatidylethanolamine, ceramide, sphingomyelin, cephalin, cardiolipin, and cerebrosides. In preferred embodiments, the non-cationic lipids are diacylphosphatidylcholine, diacylphosphatidylethanolamine, ceramide, or sphingomyelin. The acyl groups in these lipids are preferably acyl groups derived from fatty acids having $C_{10}$-$C_{24}$ carbon chains. More preferably, the acyl groups are lauroyl, myristoyl, palmitoyl, stearoyl, or oleoyl. In particularly preferred embodiments, the non-cationic lipids are DSPC, DOPE, POPC, egg phosphatidylcholine (EPC), cholesterol, or a mixture thereof. In the most preferred embodiments, the nucleic acid-lipid particles are fusogenic particles with enhanced properties in vivo and the non-cationic lipid is DSPC or DOPE. In addition, the nucleic acid-lipid particles of the present invention may further comprise cholesterol. In other preferred embodiments, the non-cationic lipids can further comprise polyethylene glycol-based polymers such as PEG 2,000, PEG 5,000, and PEG conjugated to a diacylglycerol, a ceramide, or a phospholipid, as described in, e.g., U.S. Pat. No. 5,820,873 and U.S. Patent Publication No. 20030077829. In further preferred embodiments, the non-cationic lipids can further comprise polyethylene glycol-based polymers such as PEG 2,000, PEG 5,000, and PEG conjugated to a dialkyloxypropyl.

The amount of non-cationic lipid which is used in the present methods is typically from about 2 to about 20 mg of total lipids to 50 µg of nucleic acid. Preferably, the amount of total lipid is from about 5 to about 10 mg per 50 µg of nucleic acid.

Following formation of the detergent solution of nucleic acid-lipid complexes and non-cationic lipids, the detergent is removed, preferably by dialysis. The removal of the detergent results in the formation of a lipid-bilayer which surrounds the nucleic acid providing serum-stable nucleic acid-lipid particles which have a size of from about 50 nm to about 150 nm, from about 60 nm to about 130 nm, from about 70 nm to about 110 nm, or from about 70 nm to about 90 nm. The particles thus formed do not aggregate and are optionally sized to achieve a uniform particle size.

The serum-stable nucleic acid-lipid particles can be sized by any of the methods available for sizing liposomes. The sizing may be conducted in order to achieve a desired size range and relatively narrow distribution of particle sizes.

Several techniques are available for sizing the particles to a desired size. One sizing method, used for liposomes and equally applicable to the present particles, is described in U.S. Pat. No. 4,737,323. Sonicating a particle suspension either by bath or probe sonication produces a progressive size reduction down to particles of less than about 50 nm in size. Homogenization is another method which relies on shearing energy to fragment larger particles into smaller ones. In a typical homogenization procedure, particles are recirculated through a standard emulsion homogenizer until selected particle sizes, typically between about 60 and about 80 nm, are observed. In both methods, the particle size distribution can be monitored by conventional laser-beam particle size discrimination, or QELS.

Extrusion of the particles through a small-pore polycarbonate membrane or an asymmetric ceramic membrane is also an effective method for reducing particle sizes to a relatively well-defined size distribution. Typically, the suspension is cycled through the membrane one or more times until the desired particle size distribution is achieved. The particles may be extruded through successively smaller-pore membranes, to achieve a gradual reduction in size.

In another group of embodiments, the serum-stable nucleic acid-lipid particles can be prepared as follows:

(a) preparing a mixture comprising cationic lipids and non-cationic lipids in an organic solvent;

(b) contacting an aqueous solution of nucleic acid with the mixture in step (a) to provide a clear single phase; and (c) removing the organic solvent to provide a suspension of nucleic acid-lipid particles, wherein the nucleic acid is encapsulated in a lipid bilayer and the particles are stable in serum and have a size of from about 50 nm to about 150 nm.

The nucleic acids (e.g., interfering RNA), cationic lipids, and non-cationic lipids which are useful in this group of embodiments are as described for the detergent dialysis methods above.

The selection of an organic solvent will typically involve consideration of solvent polarity and the ease with which the solvent can be removed at the later stages of particle formation. The organic solvent, which is also used as a solubilizing agent, is in an amount sufficient to provide a clear single phase mixture of nucleic acid and lipids. Suitable solvents include, but are not limited to, chloroform, dichloromethane, diethylether, cyclohexane, cyclopentane, benzene, toluene, methanol, or other aliphatic alcohols such as propanol, isopropanol, butanol, tert-butanol, iso-butanol, pentanol and hexanol. Combinations of two or more solvents may also be used in the present invention.

Contacting the nucleic acid with the organic solution of cationic and non-cationic lipids is accomplished by mixing together a first solution of nucleic acid, which is typically an aqueous solution, and a second organic solution of the lipids. One of skill in the art will understand that this mixing can take place by any number of methods, for example, by mechanical means such as by using vortex mixers.

After the nucleic acid has been contacted with the organic solution of lipids, the organic solvent is removed, thus forming an aqueous suspension of serum-stable nucleic acid-lipid particles. The methods used to remove the organic solvent will typically involve evaporation at reduced pressures or blowing a stream of inert gas (e.g., nitrogen or argon) across the mixture.

The serum-stable nucleic acid-lipid particles thus formed will typically be sized from about 50 nm to about 150 nm, from about 60 nm to about 130 nm, from about 70 nm to about 110 nm, or from about 70 nm to about 90 nm. To achieve further size reduction or homogeneity of size in the particles, sizing can be conducted as described above.

In other embodiments, the methods will further comprise adding non-lipid polycations which are useful to effect the delivery to cells using the present compositions. Examples of suitable non-lipid polycations include, but are limited to, hexadimethrine bromide (sold under the brand name POLYBRENE®, from Aldrich Chemical Co., Milwaukee, Wis., USA) or other salts of heaxadimethrine. Other suitable polycations include, for example, salts of poly-L-ornithine, poly-L-arginine, poly-L-lysine, poly-D-lysine, polyallylamine, and polyethyleneimine.

In certain embodiments, the formation of the nucleic acid-lipid particles can be carried out either in a mono-phase system (e.g., a Bligh and Dyer monophase or similar mixture of aqueous and organic solvents) or in a two-phase system with suitable mixing.

When formation of the complexes is carried out in a mono-phase system, the cationic lipids and nucleic acids are each dissolved in a volume of the mono-phase mixture. Combination of the two solutions provides a single mixture in which the complexes form. Alternatively, the complexes can form in two-phase mixtures in which the cationic lipids bind to the nucleic acid (which is present in the aqueous phase), and "pull" it into the organic phase.

In another embodiment, the serum-stable nucleic acid-lipid particles can be prepared as follows:

(a) contacting nucleic acids with a solution comprising non-cationic lipids and a detergent to form a nucleic acid-lipid mixture;

(b) contacting cationic lipids with the nucleic acid-lipid mixture to neutralize a portion of the negative charge of the nucleic acids and form a charge-neutralized mixture of nucleic acids and lipids; and (c) removing the detergent from the charge-neutralized mixture to provide the nucleic acid-lipid particles in which the nucleic acids are protected from degradation.

In one group of embodiments, the solution of non-cationic lipids and detergent is an aqueous solution. Contacting the nucleic acids with the solution of non-cationic lipids and detergent is typically accomplished by mixing together a first solution of nucleic acids and a second solution of the lipids and detergent. One of skill in the art will understand that this mixing can take place by any number of methods, for example, by mechanical means such as by using vortex mixers. Preferably, the nucleic acid solution is also a detergent solution. The amount of non-cationic lipid which is used in the present method is typically determined based on the amount of cationic lipid used, and is typically of from about 0.2 to about 5 times the amount of cationic lipid, preferably from about 0.5 to about 2 times the amount of cationic lipid used.

In some embodiments, the nucleic acids are precondensed as described in, e.g., U.S. patent application Ser. No. 09/744,103.

The nucleic acid-lipid mixture thus formed is contacted with cationic lipids to neutralize a portion of the negative charge which is associated with the nucleic acids (or other polyanionic materials) present. The amount of cationic lipids used will typically be sufficient to neutralize at least 50% of the negative charge of the nucleic acid. Preferably, the negative charge will be at least 70% neutralized, more preferably at least 90% neutralized. Cationic lipids which are useful in the present invention, include, for example, DLinDMA and DLenDMA. These lipids and related analogs are described in U.S. Patent Publication No. 20060083780.

Contacting the cationic lipids with the nucleic acid-lipid mixture can be accomplished by any of a number of techniques, preferably by mixing together a solution of the cationic lipid and a solution containing the nucleic acid-lipid mixture. Upon mixing the two solutions (or contacting in any other manner), a portion of the negative charge associated with the nucleic acid is neutralized. Nevertheless, the nucleic acid remains in an uncondensed state and acquires hydrophilic characteristics.

After the cationic lipids have been contacted with the nucleic acid-lipid mixture, the detergent (or combination of detergent and organic solvent) is removed, thus forming the nucleic acid-lipid particles. The methods used to remove the detergent will typically involve dialysis. When organic solvents are present, removal is typically accomplished by evaporation at reduced pressures or by blowing a stream of inert gas (e.g., nitrogen or argon) across the mixture.

The particles thus formed will typically be sized from about 50 nm to several microns, about 50 nm to about 150 nm, from about 60 nm to about 130 nm, from about 70 nm to about 110 nm, or from about 70 nm to about 90 nm. To achieve further size reduction or homogeneity of size in the particles, the nucleic acid-lipid particles can be sonicated, filtered, or subjected to other sizing techniques which are used in liposomal formulations and are known to those of skill in the art.

In other embodiments, the methods will further comprise adding non-lipid polycations which are useful to effect the lipofection of cells using the present compositions. Examples of suitable non-lipid polycations include, hexadimethrine bromide (sold under the brand name POLYBRENE®, from Aldrich Chemical Co., Milwaukee, Wis., USA) or other salts of hexadimethrine. Other suitable polycations include, for example, salts of poly-L-ornithine, poly-L-arginine, poly-L-lysine, poly-D-lysine, polyallylamine, and polyethyleneimine. Addition of these salts is preferably after the particles have been formed.

In another aspect, the serum-stable nucleic acid-lipid particles can be prepared as follows:

(a) contacting an amount of cationic lipids with nucleic acids in a solution; the solution comprising from about 15%-35% water and about 65%-85% organic solvent and the amount of cationic lipids being sufficient to produce a +/−charge ratio of from about 0.85 to about 2.0, to provide a hydrophobic nucleic acid-lipid complex;

(b) contacting the hydrophobic, nucleic acid-lipid complex in solution with non-cationic lipids, to provide a nucleic acid-lipid mixture; and (c) removing the organic solvents from the nucleic acid-lipid mixture to provide nucleic acid-lipid particles in which the nucleic acids are protected from degradation.

The nucleic acids (e.g., interfering RNA), non-cationic lipids, cationic lipids, and organic solvents which are useful in this aspect of the invention are the same as those described for the methods above which used detergents. In one group of embodiments, the solution of step (a) is a mono-phase. In another group of embodiments, the solution of step (a) is two-phase.

In preferred embodiments, the non-cationic lipids are ESM, DSPC, DOPC, POPC, DPPC, monomethyl-phosphatidylethanolamine, dimethyl-phosphatidylethanolamine, DMPE, DPPE, DSPE, DOPE, DEPE, SOPE, POPE, PEG-based polymers (e.g., PEG 2000, PEG 5000, PEG-modified diacylglycerols, or PEG-modified dialkyloxypropyls), cholesterol, or combinations thereof. In still other preferred embodiments, the organic solvents are methanol, chloroform, methylene chloride, ethanol, diethyl ether or combinations thereof.

In one embodiment, the nucleic acid is an interfering RNA as described herein; the cationic lipid is DLindMA, DLenDMA, DODAC, DDAB, DOTMA, DOSPA, DMRIE, DOGS, or combinations thereof; the non-cationic lipid is ESM, DOPE, PEG-DAG, DSPC, DPPC, DPPE, DMPE, monomethyl-phosphatidylethanolamine, dimethyl-phosphatidylethanolamine, DSPE, DEPE, SOPE, POPE, cholesterol, or combinations thereof (e.g., DSPC and PEG-DAA); and the organic solvent is methanol, chloroform, methylene chloride, ethanol, diethyl ether or combinations thereof.

As above, contacting the nucleic acids with the cationic lipids is typically accomplished by mixing together a first solution of nucleic acids and a second solution of the lipids, preferably by mechanical means such as by using vortex mixers. The resulting mixture contains complexes as described above. These complexes are then converted to particles by the addition of non-cationic lipids and the removal of the organic solvent. The addition of the non-cationic lipids is typically accomplished by simply adding a solution of the non-cationic lipids to the mixture containing the complexes. A reverse addition can also be used. Subsequent removal of organic solvents can be accomplished by methods known to those of skill in the art and also described above.

The amount of non-cationic lipids which is used in this aspect of the invention is typically an amount of from about 0.2 to about 15 times the amount (on a mole basis) of cationic lipids which was used to provide the charge-neutralized nucleic acid-lipid complex. Preferably, the amount is from about 0.5 to about 9 times the amount of cationic lipids used.

In one embodiment, the nucleic acid-lipid particles prepared according to the above-described methods are either net charge neutral or carry an overall charge which provides the particles with greater gene lipofection activity. Preferably, the nucleic acid component of the particles is a nucleic acid which interferes with the production of an undesired protein. In other preferred embodiments, the non-cationic lipid may further comprise cholesterol.

In some embodiments, the nucleic acid to lipid ratios (mass/mass ratios) in a formed nucleic acid-lipid particle will range from about 0.01 to about 0.2, from about 0.02 to about 0.1, from about 0.03 to about 0.1, or from about 0.01 to about 0.08. The ratio of the starting materials also falls within this range. In other embodiments, the nucleic acid-lipid particle preparation uses about 400 µg nucleic acid per 10 mg total lipid or a nucleic acid to lipid mass ratio of about 0.01 to about 0.08 and, more preferably, about 0.04, which corresponds to 1.25 mg of total lipid per 50 µg of nucleic acid. In other preferred embodiments, the particle has a nucleic acid:lipid mass ratio of about 0.08.

In other embodiments, the lipid to nucleic acid ratios (mass/mass ratios) in a formed nucleic acid-lipid particle will range from about 1 (1:1) to about 100 (100:1), from about 5 (5:1) to about 100 (100:1), from about 1 (1:1) to about 50 (50:1), from about 2 (2:1) to about 50 (50:1), from about 3 (3:1) to about 50 (50:1), from about 4 (4:1) to about 50 (50:1), from about 5 (5:1) to about 50 (50:1), from about 1 (1:1) to about 25 (25:1), from about 2 (2:1) to about 25 (25:1), from about 3 (3:1) to about 25 (25:1), from about 4 (4:1) to about 25 (25:1), from about 5 (5:1) to about 25 (25:1), from about 5 (5:1) to about 20 (20:1), from about 5 (5:1) to about 15 (15:1), from about 5 (5:1) to about 10 (10:1), about 5 (5:1), 6 (6:1), 7 (7:1), 8 (8:1), 9 (9:1), 10 (10:1), 11 (11:1), 12 (12:1), 13 (13:1), 14 (14:1), or 15 (15:1). The ratio of the starting materials also falls within this range.

As previously discussed, the conjugated lipid may further include a CPL. A variety of general methods for making SNALP-CPLs (CPL-containing SNALPs) are discussed herein. Two general techniques include "post-insertion" technique, that is, insertion of a CPL into for example, a preformed SNALP, and the "standard" technique, wherein the CPL is included in the lipid mixture during for example, the SNALP formation steps. The post-insertion technique results in SNALPs having CPLs mainly in the external face of the SNALP bilayer membrane, whereas standard techniques provide SNALPs having CPLs on both internal and external faces. The method is especially useful for vesicles made from phospholipids (which can contain cholesterol) and also for vesicles containing PEG-lipids (such as PEG-DAAs and PEG-DAGs). Methods of making SNALP-CPL, are taught, for example, in U.S. Pat. Nos. 5,705,385; 6,586,410; 5,981, 501; 6,534,484; and 6,852,334; U.S. Patent Publication No. 20020072121; and PCT Publication No. WO 00/62813.

VII. Kits

The present invention also provides nucleic acid-lipid particles in kit form. The kit may comprise a container which is compartmentalized for holding the various elements of the nucleic acid-lipid particles (e.g., the nucleic acids and the individual lipid components of the particles). In some embodiments, the kit may further comprise an endosomal membrane destabilizer (e.g., calcium ions). The kit typically contains the nucleic acid-lipid particle compositions of the present invention, preferably in dehydrated form, with instructions for their rehydration and administration.

As explained herein, the SNALPs of the present invention can be tailored to preferentially target particular tissues or organs of interest. Preferential targeting of SNALPs is carried out by controlling the composition of the SNALP itself. For instance, as set forth in Examples 14 and 15, it has been found that the 1:57 PEG-cDSA SNALP formulation can be used to preferentially target tumors outside of the liver, whereas the 1:57 PEG-cDMA SNALP formulation can be used to preferentially target the liver. In certain instances, however, it may be desirable to have a targeting moiety attached to the surface of the particle to further enhance the targeting of the SNALP. Methods of attaching targeting moieties (e.g., antibodies, proteins) to lipids (such as those used in the present particles) are known to those of skill in the art.

VIII. Administration of Nucleic Acid-Lipid Particles

Once formed, the serum-stable nucleic acid-lipid particles (SNALP) of the present invention are useful for the introduction of nucleic acids (e.g., interfering RNA) into cells. Accordingly, the present invention also provides methods for introducing a nucleic acid (e.g., interfering RNA) into a cell. The methods are carried out in vitro or in vivo by first forming the particles as described above and then contacting the particles with the cells for a period of time sufficient for delivery of the nucleic acid to the cells to occur.

The nucleic acid-lipid particles of the present invention can be adsorbed to almost any cell type with which they are mixed or contacted. Once adsorbed, the particles can either be endocytosed by a portion of the cells, exchange lipids with cell membranes, or fuse with the cells. Transfer or incorporation of the nucleic acid portion of the particle can take place via any one of these pathways. In particular, when fusion takes place, the particle membrane is integrated into the cell membrane and the contents of the particle combine with the intracellular fluid.

The nucleic acid-lipid particles of the present invention can be administered either alone or in a mixture with a pharmaceutically-acceptable carrier (e.g., physiological saline or phosphate buffer) selected in accordance with the route of administration and standard pharmaceutical practice. Generally, normal buffered saline (e.g., 135-150 mM NaCl) will be employed as the pharmaceutically-acceptable carrier. Other suitable carriers include, e.g., water, buffered water, 0.4% saline, 0.3% glycine, and the like, including glycoproteins for enhanced stability, such as albumin, lipoprotein, globulin, etc. Additional suitable carriers are described in, e.g., REMINGTON'S PHARMACEUTICAL SCIENCES, Mack Publishing Company, Philadelphia, Pa., 17th ed. (1985). As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The phrase "pharmaceutically-acceptable" refers to molecular entities and compositions that do not produce an allergic or similar untoward reaction when administered to a human.

The pharmaceutically-acceptable carrier is generally added following particle formation. Thus, after the particle is formed, the particle can be diluted into pharmaceutically-acceptable carriers such as normal buffered saline.

The concentration of particles in the pharmaceutical formulations can vary widely, i.e., from less than about 0.05%, usually at or at least about 2 to 5%, to as much as about 10 to 90% by weight, and will be selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, particles composed of irritating lipids may be diluted to low concentrations to lessen inflammation at the site of administration.

The pharmaceutical compositions of the present invention may be sterilized by conventional, well-known sterilization techniques. Aqueous solutions can be packaged for use or filtered under aseptic conditions and lyophilized, the lyophilized preparation being combined with a sterile aqueous solution prior to administration. The compositions can contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, and calcium chloride. Additionally, the particle suspension may include lipid-protective agents which protect lipids against free-radical and lipid-peroxidative damages on storage. Lipophilic free-radical quenchers, such as alphatocopherol and water-soluble iron-specific chelators, such as ferrioxamine, are suitable.

A. In Vivo Administration

Systemic delivery for in vivo therapy, i.e., delivery of a therapeutic nucleic acid to a distal target cell via body systems such as the circulation, has been achieved using nucleic acid-lipid particles such as those disclosed in PCT Publication Nos. WO 05/007196, WO 05/121348, WO 05/120152, and WO 04/002453. The present invention also provides fully encapsulated nucleic acid-lipid particles that protect the nucleic acid from nuclease degradation in serum, are nonimmunogenic, are small in size, and are suitable for repeat dosing.

For in vivo administration, administration can be in any manner known in the art, e.g., by injection, oral administration, inhalation (e.g., intransal or intratracheal), transdermal application, or rectal administration. Administration can be accomplished via single or divided doses. The pharmaceutical compositions can be administered parenterally, i.e., intraarticularly, intravenously, intraperitoneally, subcutaneously, or intramuscularly. In some embodiments, the pharmaceutical compositions are administered intravenously or intraperitoneally by a bolus injection (see, e.g., U.S. Pat. No. 5,286,634). Intracellular nucleic acid delivery has also been discussed in Straubringer et al., *Methods Enzymol.,* 101:512 (1983); Mannino et al., *Biotechniques,* 6:682 (1988); Nicolau et al., *Crit. Rev. Ther. Drug Carrier Syst.,* 6:239 (1989); and Behr, *Acc. Chem. Res.,* 26:274 (1993). Still other methods of administering lipid-based therapeutics are described in, for example, U.S. Pat. Nos. 3,993,754; 4,145,410; 4,235,871; 4,224,179; 4,522,803; and 4,588,578. The lipid-nucleic acid particles can be administered by direct injection at the site of disease or by injection at a site distal from the site of disease (see, e.g., Culver, HUMAN GENE THERAPY, MaryAnn Liebert, Inc., Publishers, New York. pp. 70-71 (1994)).

The compositions of the present invention, either alone or in combination with other suitable components, can be made into aerosol formulations (i.e., they can be "nebulized") to be administered via inhalation (e.g., intranasally or intratracheally) (see, Brigham et al, *Am. J. Sci.,* 298:278 (1989)). Aerosol formulations can be placed into pressurized acceptable propellants, such as dichlorodifluoromethane, propane, nitrogen, and the like.

In certain embodiments, the pharmaceutical compositions may be delivered by intranasal sprays, inhalation, and/or other aerosol delivery vehicles. Methods for delivering nucleic acid compositions directly to the lungs via nasal aerosol sprays have been described, e.g., in U.S. Pat. Nos. 5,756,353 and 5,804,212. Likewise, the delivery of drugs using intranasal microparticle resins and lysophosphatidyl-glycerol compounds (U.S. Pat. No. 5,725,871) are also well-known in the pharmaceutical arts. Similarly, transmucosal drug delivery in the form of a polytetrafluoroethylene support matrix is described in U.S. Pat. No. 5,780,045.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions are preferably administered, for example, by intravenous infusion, orally, topically, intraperitoneally, intravesically, or intrathecally.

Generally, when administered intravenously, the nucleic acid-lipid formulations are formulated with a suitable pharmaceutical carrier. Many pharmaceutically acceptable carriers may be employed in the compositions and methods of the present invention. Suitable formulations for use in the present invention are found, for example, in REMINGTON'S PHARMACEUTICAL SCIENCES, Mack Publishing Company, Philadelphia, Pa., 17th ed. (1985). A variety of aqueous carriers may be used, for example, water, buffered water, 0.4% saline, 0.3% glycine, and the like, and may include glycoproteins for enhanced stability, such as albumin, lipoprotein, globulin, etc. Generally, normal buffered saline (135-150 mM NaCl) will be employed as the pharmaceutically acceptable carrier, but other suitable carriers will suffice. These compositions can be sterilized by conventional liposomal sterilization techniques, such as filtration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc. These compositions can be sterilized using the techniques referred to above or, alternatively, they can be produced under sterile conditions. The resulting aqueous solutions may be packaged for use or filtered under aseptic conditions and lyophilized, the lyophilized preparation being combined with a sterile aqueous solution prior to administration.

In certain applications, the nucleic acid-lipid particles disclosed herein may be delivered via oral administration to the individual. The particles may be incorporated with excipients and used in the form of ingestible tablets, buccal tablets, troches, capsules, pills, lozenges, elixirs, mouthwash, suspensions, oral sprays, syrups, wafers, and the like (see, e.g., U.S. Pat. Nos. 5,641,515, 5,580,579, and 5,792,451). These oral dosage forms may also contain the following: binders, gelatin; excipients, lubricants, and/or flavoring agents. When the unit dosage form is a capsule, it may contain, in addition to the materials described above, a liquid carrier. Various other materials may be present as coatings or to otherwise modify the physical form of the dosage unit. Of course, any material used in preparing any unit dosage form should be pharmaceutically pure and substantially non-toxic in the amounts employed.

Typically, these oral formulations may contain at least about 0.1% of the nucleic acid-lipid particles or more, although the percentage of the particles may, of course, be varied and may conveniently be between about 1% or 2% and about 60% or 70% or more of the weight or volume of the total formulation. Naturally, the amount of particles in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Formulations suitable for oral administration can consist of: (a) liquid solutions, such as an effective amount of the packaged nucleic acid (e.g., interfering RNA) suspended in diluents such as water, saline, or PEG 400; (b) capsules, sachets, or tablets, each containing a predetermined amount of the nucleic acid (e.g., interfering RNA), as liquids, solids, granules, or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the nucleic acid (e.g., interfering RNA) in a flavor, e.g., sucrose, as well as pastilles comprising the nucleic acid (e.g., interfering RNA) in an inert base, such as gelatin and glycerin or sucrose and acacia emulsions, gels, and the like containing, in addition to the nucleic acid (e.g., interfering RNA), carriers known in the art.

In another example of their use, nucleic acid-lipid particles can be incorporated into a broad range of topical dosage forms. For instance, the suspension containing the nucleic acid-lipid particles can be formulated and administered as gels, oils, emulsions, topical creams, pastes, ointments, lotions, foams, mousses, and the like.

When preparing pharmaceutical preparations of the nucleic acid-lipid particles of the invention, it is preferable to use quantities of the particles which have been purified to reduce or eliminate empty particles or particles with nucleic acid associated with the external surface.

The methods of the present invention may be practiced in a variety of hosts. Preferred hosts include mammalian species, such as primates (e.g., humans and chimpanzees as well as other nonhuman primates), canines, felines, equines, bovines, ovines, caprines, rodents (e.g., rats and mice), lagomorphs, and swine.

The amount of particles administered will depend upon the ratio of nucleic acid to lipid, the particular nucleic acid used, the disease state being diagnosed, the age, weight, and condition of the patient, and the judgment of the clinician, but will generally be between about 0.01 and about 50 mg per kilogram of body weight, preferably between about 0.1 and about 5 mg/kg of body weight, or about $10^8$-$10^{10}$ particles per administration (e.g., injection).

B. In Vitro Administration

For in vitro applications, the delivery of nucleic acids (e.g., interfering RNA) can be to any cell grown in culture, whether of plant or animal origin, vertebrate or invertebrate, and of any tissue or type. In preferred embodiments, the cells are animal cells, more preferably mammalian cells, and most preferably human cells.

Contact between the cells and the nucleic acid-lipid particles, when carried out in vitro, takes place in a biologically compatible medium. The concentration of particles varies widely depending on the particular application, but is generally between about 1 μmol and about 10 mmol. Treatment of the cells with the nucleic acid-lipid particles is generally carried out at physiological temperatures (about 37° C.) for periods of time of from about 1 to 48 hours, preferably of from about 2 to 4 hours.

In one group of preferred embodiments, a nucleic acid-lipid particle suspension is added to 60-80% confluent plated cells having a cell density of from about $10^3$ to about $10^5$ cells/ml, more preferably about $2\times10^4$ cells/ml. The concentration of the suspension added to the cells is preferably of from about 0.01 to 0.2 μg/ml, more preferably about 0.1 μg/ml.

Using an Endosomal Release Parameter (ERP) assay, the delivery efficiency of the SNALP or other lipid-based carrier system can be optimized. An ERP assay is described in detail in U.S. Patent Publication No. 20030077829. More particularly, the purpose of an ERP assay is to distinguish the effect of various cationic lipids and helper lipid components of SNALPs based on their relative effect on binding/uptake or fusion with/destabilization of the endosomal membrane. This assay allows one to determine quantitatively how each component of the SNALP or other lipid-based carrier system affects delivery efficiency, thereby optimizing the SNALPs or other lipid-based carrier systems. Usually, an ERP assay measures expression of a reporter protein (e.g., luciferase, β-galactosidase, green fluorescent protein (GFP), etc.), and in some instances, a SNALP formulation optimized for an expression plasmid will also be appropriate for encapsulating an interfering RNA. In other instances, an ERP assay can be adapted to measure downregulation of transcription or translation of a target sequence in the presence or absence of an interfering RNA (e.g., siRNA). By comparing the ERPs for each of the various SNALPs or other lipid-based formulations, one can readily determine the optimized system, e.g., the SNALP or other lipid-based formulation that has the greatest uptake in the cell.

C. Cells for Delivery of Interfering RNA

The compositions and methods of the present invention are used to treat a wide variety of cell types, in vivo and in vitro. Suitable cells include, e.g., hematopoietic precursor (stem) cells, fibroblasts, keratinocytes, hepatocytes, endothelial cells, skeletal and smooth muscle cells, osteoblasts, neurons, quiescent lymphocytes, terminally differentiated cells, slow or noncycling primary cells, parenchymal cells, lymphoid cells, epithelial cells, bone cells, and the like. In preferred embodiments, an interfering RNA (e.g., siRNA) is delivered to cancer cells such as, e.g., lung cancer cells, colon cancer cells, rectal cancer cells, anal cancer cells, bile duct cancer cells, small intestine cancer cells, stomach (gastric) cancer cells, esophageal cancer cells, gallbladder cancer cells, liver cancer cells, pancreatic cancer cells, appendix cancer cells, breast cancer cells, ovarian cancer cells, cervical cancer cells, prostate cancer cells, renal cancer cells, cancer cells of the central nervous system, glioblastoma tumor cells, skin cancer cells, lymphoma cells, choriocarcinoma tumor cells, head and neck cancer cells, osteogenic sarcoma tumor cells, and blood cancer cells.

In vivo delivery of nucleic acid-lipid particles encapsulating an interfering RNA (e.g., siRNA) is suited for targeting cells of any cell type. The methods and compositions can be employed with cells of a wide variety of vertebrates, including mammals, such as, e.g, canines, felines, equines, bovines, ovines, caprines, rodents (e.g., mice, rats, and guinea pigs), lagomorphs, swine, and primates (e.g. monkeys, chimpanzees, and humans).

To the extent that tissue culture of cells may be required, it is well-known in the art. For example, Freshney, Culture of Animal Cells, a Manual of Basic Technique, 3rd Ed., Wiley-Liss, New York (1994), Kuchler et al., Biochemical Methods in Cell Culture and Virology, Dowden, Hutchinson and Ross, Inc. (1977), and the references cited therein provide a general guide to the culture of cells. Cultured cell systems often will be in the form of monolayers of cells, although cell suspensions are also used.

D. Detection of SNALP

In some embodiments, the nucleic acid-lipid particles are detectable in the subject at about 8, 12, 24, 48, 60, 72, or 96 hours, or 6, 8, 10, 12, 14, 16, 18, 19, 22, 24, 25, or 28 days after administration of the particles. The presence of the particles can be detected in the cells, tissues, or other biological samples from the subject. The particles may be detected, e.g., by direct detection of the particles, detection of the interfering RNA (e.g., siRNA) sequence, detection of the target sequence of interest (i.e., by detecting expression or reduced expression of the sequence of interest), or a combination thereof.

1. Detection of Particles

Nucleic acid-lipid particles can be detected using any methods known in the art. For example, a label can be coupled directly or indirectly to a component of the SNALP or other carrier system using methods well-known in the art. A wide variety of labels can be used, with the choice of label depending on sensitivity required, ease of conjugation with the SNALP component, stability requirements, and available instrumentation and disposal provisions. Suitable labels include, but are not limited to, spectral labels such as fluorescent dyes (e.g., fluorescein and derivatives, such as fluorescein isothiocyanate (FITC) and Oregon Green™; rhodamine and derivatives such Texas red, tetrarhodimine isothiocynate (TRITC), etc., digoxigenin, biotin, phycoerythrin, AMCA, CyDyes™, and the like; radiolabels such as $^3$H, $^{125}$I, $^{35}$S, $^{14}$C, $^{32}$P, $^{33}$P, etc.; enzymes such as horse radish peroxidase, alkaline phosphatase, etc.; spectral calorimetric labels such as colloidal gold or colored glass or plastic beads such as polystyrene, polypropylene, latex, etc. The label can be detected using any means known in the art.

2. Detection of Nucleic Acids

Nucleic acids (e.g., interfering RNA) are detected and quantified herein by any of a number of means well-known to those of skill in the art. The detection of nucleic acids proceeds by well-known methods such as Southern analysis, Northern analysis, gel electrophoresis, PCR, radiolabeling, scintillation counting, and affinity chromatography. Additional analytic biochemical methods such as spectrophotometry, radiography, electrophoresis, capillary electrophoresis, high performance liquid chromatography (HPLC), thin layer chromatography (TLC), and hyperdiffusion chromatography may also be employed.

The selection of a nucleic acid hybridization format is not critical. A variety of nucleic acid hybridization formats are known to those skilled in the art. For example, common formats include sandwich assays and competition or displacement assays. Hybridization techniques are generally described in, e.g., "Nucleic Acid Hybridization, A Practical Approach," Eds. Hames and Higgins, IRL Press (1985).

The sensitivity of the hybridization assays may be enhanced through use of a nucleic acid amplification system which multiplies the target nucleic acid being detected. In vitro amplification techniques suitable for amplifying sequences for use as molecular probes or for generating nucleic acid fragments for subsequent subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA™) are found in Sambrook et al., In *Molecular Cloning: A Laboratory Manual*, Cold Spring Harbor Laboratory Press (2000); and Ausubel et al., SHORT PROTOCOLS IN MOLECULAR BIOLOGY, eds., Current Protocols, Greene Publishing Associates, Inc. and John Wiley & Sons, Inc. (2002); as well as U.S. Pat. No. 4,683,202; PCR Protocols, A Guide to Methods and Applications (Innis et al. eds.) Academic Press Inc. San Diego, Calif. (1990); Arnheim & Levinson (Oct. 1, 1990), *C&EN* 36; *The Journal Of NIH Research*, 3:81 (1991); Kwoh et al., *Proc. Natl. Acad. Sci. USA*, 86:1173 (1989); Guatelli et al., *Proc. Natl. Acad. Sci. USA*, 87:1874 (1990); Lomell et al., *J. Clin. Chem.*, 35:1826 (1989); Landegren et al, *Science*, 241:1077 (1988); Van Brunt, *Biotechnology*, 8:291 (1990); Wu and Wallace, *Gene*, 4:560 (1989); Barringer et al., *Gene*, 89:117 (1990); and Sooknanan and Malek, *Biotechnology*, 13:563 (1995). Improved methods of cloning in vitro amplified nucleic acids are described in U.S. Pat. No. 5,426,039. Other methods described in the art are the nucleic acid sequence based amplification (NASBA™, Cangene, Mississauga, Ontario) and Qβ-replicase systems. These systems can be used to directly identify mutants where the PCR or LCR primers are designed to be extended or ligated only when a select sequence is present. Alternatively, the select sequences can be generally amplified using, for example, nonspecific PCR primers and the amplified target region later probed for a specific sequence indicative of a mutation.

Nucleic acids for use as probes, e.g., in in vitro amplification methods, for use as gene probes, or as inhibitor components are typically synthesized chemically according to the solid phase phosphoramidite triester method described by Beaucage et al., *Tetrahedron Letts.*, 22:1859 1862 (1981), e.g., using an automated synthesizer, as described in Needham VanDevanter et al., *Nucleic Acids Res.*, 12:6159 (1984). Purification of polynucleotides, where necessary, is typically performed by either native acrylamide gel electrophoresis or by anion exchange HPLC as described in Pearson et al., *J. Chrom.*, 255:137 149 (1983). The sequence of the synthetic poluyucleotides can be verified using the chemical degradation method of Maxam and Gilbert (1980) in Grossman and Moldave (eds.) Academic Press, New York, *Methods in Enzymology*, 65:499.

An alternative means for determining the level of transcription is in situ hybridization. In situ hybridization assays are well-known and are generally described in Angerer et al., *Methods Enzymol.*, 152:649 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

IX. Administration of Chemotherapeutic Agents

In some embodiments, the present invention provides methods for sensitizing a cell to the effects of a chemotherapy drug by administering a PLK-1 interfering RNA (e.g., using a suitable carrier system) in combination with the chemotherapy drug. The methods can be carried out in vitro using standard tissue culture techniques or in vivo by administering the interfering RNA and chemotherapy drug as described herein or using any means known in the art. In preferred embodiments, this combination of therapeutic agents is delivered to a cancer cell in a mammal such as a human.

In certain aspects, a patient about to begin chemotherapy is first pretreated with a suitable dose of one or more nucleic acid-lipid particles (e.g., SNALP) containing PLK-1 interfering RNA (e.g., siRNA). The patient can be pretreated with a suitable dose of one or more nucleic acid-lipid particles at any reasonable time prior to chemotherapy drug administration. As non-limiting examples, the dose of one or more nucleic acid-lipid particles can be administered about 96, 84, 72, 60, 48, 36, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 hours, or any interval thereof, before chemotherapy drug administration.

Additionally, a patient about to begin chemotherapy can be pretreated with more than one dose of nucleic acid-lipid particles (e.g., SNALP) containing PLK-1 interfering RNA (e.g., siRNA) at different times before chemotherapy drug administration. As such, the methods of the present invention can further comprise administering a second dose of nucleic acid-lipid particles prior to chemotherapy drug administration. In certain instances, the nucleic acid-lipid particles of the first dose are the same as the nucleic acid-lipid particles of the second dose. In certain other instances, the nucleic acid-lipid particles of the first dose are different from the nucleic acid-lipid particles of the second dose. Preferably, the two pretreatment doses use the same nucleic acid-lipid particles, e.g., SNALP containing the same PLK-1 interfering RNA sequence. One skilled in the art will appreciate that the second dose of nucleic acid-lipid particles can occur at any reasonable time following the first dose. As a non-limiting example, if the first dose was administered about 12 hours before chemotherapy drug administration, the second dose can be administered about 11, 10, 9, 8, 7, 6, 5, 4, 3, 2, 1, 0.9, 0.8, 0.7, 0.6, 0.5, 0.4, 0.3, 0.2, or 0.1 hours, or any interval thereof, before chemotherapy drug administration. One skilled in the art will also appreciate that the second dose of nucleic acid-lipid particles can be the same or a different dose. In additional embodiments of the present invention, the patient can be pretreated with a third, fourth, fifth, sixth, seventh, eighth, ninth, tenth, or more dose of the same or different nucleic acid-lipid particles prior to chemotherapy drug administration.

A patient can also be treated with a suitable dose of one or more nucleic acid-lipid particles (e.g., SNALP) containing PLK-1 interfering RNA (e.g., siRNA) at any reasonable time during chemotherapy drug administration. As such, the methods of the present invention can further comprise administering a dose of nucleic acid-lipid particles during chemotherapy drug administration. One skilled in the art will appreciate that more than one dose of nucleic acid-lipid particles can be administered at different times during chemotherapy drug administration. As a non-limiting example, a SNALP containing an unmodified and/or modified PLK-1 siRNA sequence can be administered at the beginning of chemotherapy drug administration, while chemotherapy drug administration is in progress, and/or at the end of chemotherapy drug administration. One skilled in the art will also appreciate that the pretreatment and intra-treatment (i.e., during chemotherapy drug administration) doses of nucleic acid-lipid particles can be the same or a different dose.

In addition, a patient can be treated with a suitable dose of one or more nucleic acid-lipid particles (e.g., SNALP) containing PLK-1 interfering RNA (e.g., siRNA) at any reasonable time following chemotherapy drug administration. As such, the methods of the present invention can further comprise administering a dose of nucleic acid-lipid particles after chemotherapy drug administration. As non-limiting examples, the dose of one or more nucleic acid-lipid particles can be administered about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 36, 48, 60, 72, 84, 96, 108, or more hours, or any interval thereof, after chemotherapy drug administration. In certain instances, the same nucleic acid-lipid particle is used before and after chemotherapy drug administration. In certain other instances, a different nucleic acid-lipid particle is used following chemotherapy drug administration. One skilled in the art will appreciate that more than one dose of nucleic acid-lipid particles can be administered at different times following chemotherapy drug administration. One skilled in the art will also appreciate that the pretreatment and posttreatment (i.e., following chemotherapy drug administration) doses of nucleic acid-lipid particles can be the same or a different dose.

Chemotherapy drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that a chemotherapy drug is administered at the same time, just prior to, or just after the administration of a second drug or therapeutic agent (e.g., a nucleic acid-lipid particle, another chemotherapy drug, a drug useful for reducing the side-effects associated with chemotherapy, a radiotherapeutic agent, a hormonal therapeutic agent, an immunotherapeutic agent, etc.).

Non-limiting examples of chemotherapy drugs suitable for use in the present invention include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil (5-FU), azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel (taxol), docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), tyrosine kinase inhibitors (e.g., gefitinib (Iressa®), sunitinib (Sutent®; SU11248), erlotinib (Tarceva®; OSI-1774), lapatinib (GW572016; GW2016), canertinib (CI 1033), semaxinib (SU5416), vatalanib (PTK787/ZK222584), sorafenib (BAY 43-9006), imatinib (Gleevec®; STI571), dasatinib (BMS-354825), leflunomide (SU101), vandetanib (Zactima™; ZD6474), etc.), pharmaceutically acceptable salts thereof, stereoisomers thereof, derivatives thereof, analogs thereof, and combinations thereof.

The nucleic acid-lipid particles and/or chemotherapy drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the nucleic acid-lipid particles and/or chemotherapy drugs described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the nucleic acid-lipid particles and/or chemotherapy drugs described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

A therapeutically effective amount of a chemotherapy drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages. One skilled in the art will appreciate that administered dosages of chemotherapy drugs will vary depending on a number of factors, including, but not limited to, the particular chemotherapy drug or set of chemotherapy drugs to be administered, the mode of administration, the type of application, the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage.

As used herein, the term "unit dosage form" refers to physically discrete units suitable as unitary dosages for human subjects and other mammals, each unit containing a predetermined quantity of a chemotherapy drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the chemotherapy drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a chemotherapy drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. A chemotherapy drug can also be formulated into a suppository disposed, for example, in a polyethylene glycol (PEG) carrier.

Liquid dosage forms can be prepared by dissolving or dispersing a chemotherapy drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. A chemotherapy drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, a chemotherapy drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

X. Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLE 1

Materials and Methods siRNA: All siRNA molecules used in these studies were chemically synthesized by the University of Calgary (Calgary, AB), Dharmacon Inc. (Lafayette, Colo.), or Integrated DNA Technologies (Coralville, Iowa). The siRNAs were desalted and annealed using standard procedures.

Lipid Encapsulation of siRNA: Unless otherwise indicated, siRNA molecules were encapsulated into nucleic acid-lipid particles composed of the following lipids: synthetic cholesterol (Sigma-Aldrich Corp.; St. Louis, Mo.); the phospholipid DSPC (1,2-distearoyl-sn-glycero-3-phosphocholine; Avanti Polar Lipids; Alabaster, Ala.); the PEG-lipid PEG-cDMA (3-N-[(-Methoxy poly(ethylene glycol)2000) carbamoyl]-1,2-dimyrestyloxy-propylamine); and the cationic lipid DLinDMA (1,2-Dilinoleyloxy-3-(N,N-dimethyl) aminopropane) in the molar ratio 48:10:2:40, respectively. In other words, unless otherwise indicated, siRNAs were encapsulated into liposomes of the following "2:40" SNALP formulation: 2% PEG-cDMA; 40% DLinDMA; 10% DSPC; and 48% cholesterol. In some embodiments, siRNA molecules were encapsulated into nucleic acid-lipid particles composed of the following lipids: the lipid conjugate PEG-cDMA; the cationic lipid DLinDMA; the phospholipid DPPC (1,2-dipalmitoyl-sn-glycero-3-phosphocholine; Avanti Polar Lipids; Alabaster, Ala.); and synthetic cholesterol in the molar ratio 1.4:57.1:7.1:34.3, respectively. In other words, siRNAs were encapsulated into SNALPs of the following "1:57" formulation: 1.4% PEG-cDMA; 57.1% DLinDMA; 7.1% DPPC; and 34.3% cholesterol. In other embodiments, siRNA molecules were encapsulated into phospholipid-free SNALPs composed of the following lipids: the lipid conjugate PEG-cDMA; the cationic lipid DLinDMA; and synthetic cholesterol in the molar ratio 1.5:61.5:36.9, respectively. In other words, siRNAs were encapsulated into phospholipid-free SNALPs of the following "1:62" formulation: 1.5% PEG-cDMA; 61.5% DLinDMA; and 36.9% cholesterol. For vehicle controls, empty particles with identical lipid composition were formed in the absence of siRNA. It should be understood that the 1:57 formulation and 1:62 formulation are target formulations, and that the amount of lipid (both cationic and non-cationic) present and the amount of lipid conjugate present in the formulation may vary. Typically, in the 1:57 formulation, the amount of cationic lipid will be 57 mol %±5 mol %, and the amount of lipid conjugate will be 1.5 mol %±0.5 mol %, with the balance of the 1:57 formulation being made up of non-cationic lipid (e.g., phospholipid, cholesterol, or a mixture of the two). Similarly, in the 1:62 formulation, the amount of cationic lipid will be 62 mol %±5 mol %, and the amount of lipid conjugate will be 1.5 mol %±0.5 mol %, with the balance of the 1:62 formulation being made up of the non-cationic lipid (e.g., cholesterol).

Cell Viability Assay: Cell viability of in vitro cell cultures was assessed using the commercial reagent CellTiter-Blue® (Promega Corp.; Madison, Wis.), a resazurin dye that is reduced by metabolically active cells to the fluorogenic product resorufin. Various cancer cell lines were cultured in vitro using standard tissue culture techniques. 48-72 hours after treatment with siRNA formulations and/or chemotherapy drugs, the CellTiter-Blue® reagent was added to the culture to quantify the metabolic activity of the cells, which is a measure of cell viability.

Target mRNA Quantitation: The QuantiGene® branched DNA assay (Panomics, Inc.; Fremont, Calif.) was used to quantify the reduction of target mRNA in cell cultures treated with SNALP. Cell lysates were prepared according to the manufacturer's instructions and used directly for PLK1 mRNA quantification. Relative PLK-1 mRNA levels are expressed relative to the vehicle (PBS) treated control cells. Specific probe sets used for detection of mRNA were designed to target human PLK-1 mRNA (Genbank Accession No. NM_005030). These probe sets are cross reactive with mouse PLK-1.

Apoptosis/Caspase 3/7 Assay: The level of Caspase 3 and 7 enzyme activity in siRNA treated cells was assessed using the commercial reagent Apo-ONE® (Promega Corp., Madison, Wis.). This assay is based on the specific enzymatic cleavage of the Caspase 3/7 substrate (Z-DEVD)-2-Rhodamine 110 to a fluorogenic product and is used to quantify the level of apoptosis in cultured cells. The relative level of Caspase 3/7 activity was assessed in a number of cancer cell lines at 24-48 hours after treatment with siRNA formulations and/or chemotherapy drugs.

Cytokine Induction Assays: Flt3-ligand derived murine dendritic cells (Flt3L DC) were generated as described by Gilliet et al. (J. Exp. Med., 195:953-958) using 100 ng/ml murine Flt3-ligand (PeproTech Inc.; Rocky Hill, N.J.) supplemented media. Femurs and tibiae of female Balb/C mice were isolated and rinsed in sterile PBS. The ends of bones were cut and marrow harvested in complete media (RPMI 1640, 10% heat inactivated FBS, 1% penicillin/streptomycin, 2 mM L-glutamine, 1 mM sodium pyruvate, 25 mM HEPES, 50 µM 2-mercaptoethanol). Bone marrow cells were passed through a 70 µm strainer, centrifuged at 1000 rpm for 7 minutes, and resuspended in complete media supplemented with 100 ng/ml murine Flt3L to 2×10⁶ cells/ml. 2 mls of cells were seeded in 6-well plates and 1 ml fresh complete media added every two or three days. On day 9 of culture, non-adherent cells were washed in complete media and plated into 96-well plates at concentrations ranging from 0.5 to 2.5×10⁵ cells/well. 2'OMe-modified and unmodified (0/0) PLK-1 SNALP were diluted in PBS and added to Flt3L DC cultures at 5 µg/ml siRNA. Cells were incubated for 24 hours at 37° C. before supernatants were assayed for cytokines by ELISA.

Cytokine ELISA: Interferon-α and IL-6 in culture supernatants were quantified using sandwich ELISA kits according to manufacturer's instructions. These were mouse IFN-α (PBL Biomedical; Piscataway, N.J.) and mouse IL-6 (eBioscience; San Diego, Calif.).

EXAMPLE 2

Selection of Candidate PLK-1 siRNA Molecules

Candidate PLK-1 siRNA sequences were identified by imputing the human PLK-1 mRNA sequence (Genbank Accession No. NM_005030) or the mouse PLK-1 mRNA sequence (Genbank Accession No. NM_011121) into the Whitehead Institute for Biomedical Research siRNA design algorithm (see, e.g., Elbashir et al., *Genes Dev.*, 15:188-200 (2001); Schwarz et al., *Cell*, 115:199-208 (2003); and Khvorova et al *Cell,* 115: 209-216 (2003); available at http://jura.wi.mit.edu/bioc/siRNAext/home.php). siRNA fulfilling the following criteria were selected: (1) NN(N19)NN target sequences; (2) thermodynamically less stable 5' antisense end (Difference <−2.0); (3) G/C content between 30-70%; and (4) no four nucleotide stretches of the same base. Selected sequences were verified and the positions within both human and mouse target sequences were identified.

BLASTn searches against the human and mouse sequence databases were then performed on all selected sequences. Sequences were eliminated that cross-hybridized with >15 of its internal nucleotides.

The candidate sequences are shown in Tables 1-2.

TABLE 1 siRNA sequences that target human PLK-1 expression.

| siRNA | Sense Strand (5'→3') | SEQ ID NO: | Antisense Strand (5'→3') | SEQ ID NO: |
|---|---|---|---|---|
| PLK1424 | AGAUCACCCUCCUUAAAUA | 1 | UAUUUAAGGAGGGUGAUCU | 2 |
| PLK773 | AGACCUACCUCCGGAUCAA | 3 | UUGAUCCGGAGGUAGGUCU | 4 |
| PLK126 | GGUCCUAGUGGACCCACGC | 5 | GCGUGGGUCCACUAGGACC | 6 |
| PLK412 | CUCCUGGAGCUGCACAAGA | 7 | UCUUGUGCAGCUCCAGGAG | 8 |
| PLK694 | GUGGAUGUGUGGUCCAUUG | 9 | CAAUGGACCACACAUCCAC | 10 |
| PLK772 | GAGACCUACCUCCGGAUCA | 11 | UGAUCCGGAGGUAGGUCUC | 12 |
| PLK832 | GCCGCCUCCCUCAUCCAGA | 13 | UCUGGAUGAGGGAGGCGGC | 14 |
| PLK837 | CUCCCUCAUCCAGAAGAUG | 15 | CAUCUUCUGGAUGAGGGAG | 16 |
| PLK1081 | CCAGUGGUUCGAGAGACAG | 17 | CUGUCUCUCGAACCACUGG | 18 |
| PLK1195 | GAGGCUGAGGAUCCUGCCU | 19 | AGGCAGGAUCCUCAGCCUC | 20 |
| PLK1229 | GGGUCAGCAAGUGGGUGGA | 21 | UCCACCCACUUGCUGACCC | 22 |
| PLK1232 | UCAGCAAGUGGGUGGACUA | 23 | UAGUCCACCCACUUGCUGA | 24 |
| PLK1233 | CAGCAAGUGGGUGGACUAU | 25 | AUAGUCCACCCACUUGCUG | 26 |
| PLK1242 | GGUGGACUAUUCGGACAAG | 27 | CUUGUCCGAAUAGUCCACC | 28 |
| PLK1345 | GACAGCCUGCAGUACAUAG | 29 | CUAUGUACUGCAGGCUGUC | 30 |
| PLK1556 | GCGCCAUCAUCCUGCACCU | 31 | AGGUGCAGGAUGAUGGCGC | 32 |

The number after "PLK" in Table 1 refers to the nucleotide position of the 5' base of the sense strand relative to the start codon (ATG) of the human PLK-1 mRNA sequence NM_005030. In certain embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In some instances, the sense and/or antisense strand contains "dTdT" or "UU" 3' overhangs. In other instances, the sense and/or antisense strand contains 3' overhangs that have complementarity to the target sequence or the complementary strand thereof. As a non-limiting example, the PLK1424 sense strand (SEQ ID NO:1) may contain a "UU" 3' overhang and the PLK1424 antisense strand (SEQ ID NO:2) may contain a "UC" 3' overhang. As another non-limiting example, the PLK773 sense strand (SEQ ID NO:3) may contain a "GA" 3' overhang and the PLK773 antisense strand (SEQ ID NO:4) may contain a "CU" 3' overhang. In further embodiments, the 3' overhang on the sense strand, antisense strand, or both strands may comprise one, two, three, four, or more modified nucleotides such as those described above.

TABLE 2 siRNA sequences that target mouse PLK-1 expression.

| siRNA | Sense Strand (5'→3') | SEQ ID NO: | Antisense Strand (5'→3') | SEQ ID NO: |
|---|---|---|---|---|
| mPLK1399 | CCCAUCCCAAUUCCUUGAU | 33 | AUCAAGGAAUUGGGAUGGG | 34 |
| mPLK1424 | AGAUCACUCUCCUCAACUA | 35 | UAGUUGAGGAGAGUGAUCU | 36 |
| mPLK1425 | GAUCACUCUCCUCAACUAU | 37 | AUAGUUGAGGAGAGUGAUC | 38 |
| mPLK1428 | CACUCUCCUCAACUAUUUC | 39 | GAAAUAGUUGAGGAGAGUG | 40 |
| mPLK1434 | CCUCAACUAUUUCCGCAAU | 41 | AUUGCGGAAAUAGUUGAGG | 42 |
| mPLK1607 | AGGACCACACCAAACUUAU | 43 | AUAAGUUUGGUGUGGUCCU | 44 |
| mPLK1608 | GGACCACACCAAACUUAUC | 45 | GAUAAGUUUGGUGUGGUCC | 46 |
| mPLK1650 | GACCUACAUCAACGAGAAG | 47 | CUUCUCGUUGAUGUAGGUC | 48 |
| mPLK1668 | GAGGGACUUCCAAACGUAC | 49 | GUACGUUUGGAAGUCCCUC | 50 |

The number after "mPLK" in Table 2 refers to the nucleotide position of the 5' base of the sense strand relative to the start codon (ATG) of the mouse PLK-1 mRNA sequence NM_011121. In certain embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In some instances, the sense and/or antisense strand contains "dTdT" or "UU" 3' overhangs. In other instances, the sense and/or antisense strand contains 3' overhangs that have complementarity to the target sequence or the complementary strand thereof. In further embodiments, the 3' overhangs may comprise modified nucleotides such as those described above.

EXAMPLE 3 siRNAs Targeting PLK-1 Inhibit the Growth of Cancer Cells

Figure 1:
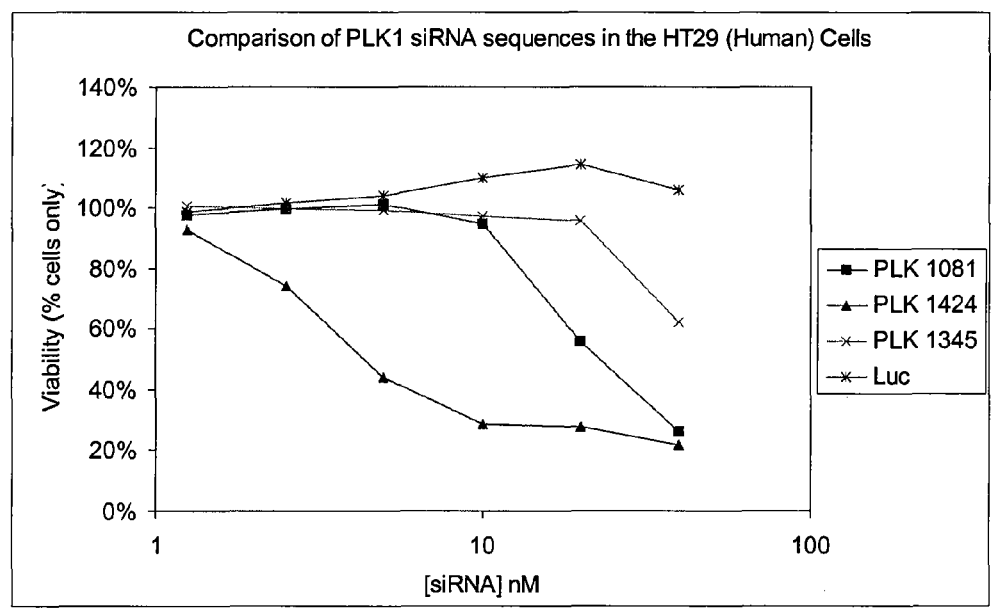
FIG. 1 illustrates data demonstrating the RNAi activity of selected SNALP-formulated PLK-1 siRNA sequences in HT29 and Neuro2A cells.
Figure 1:
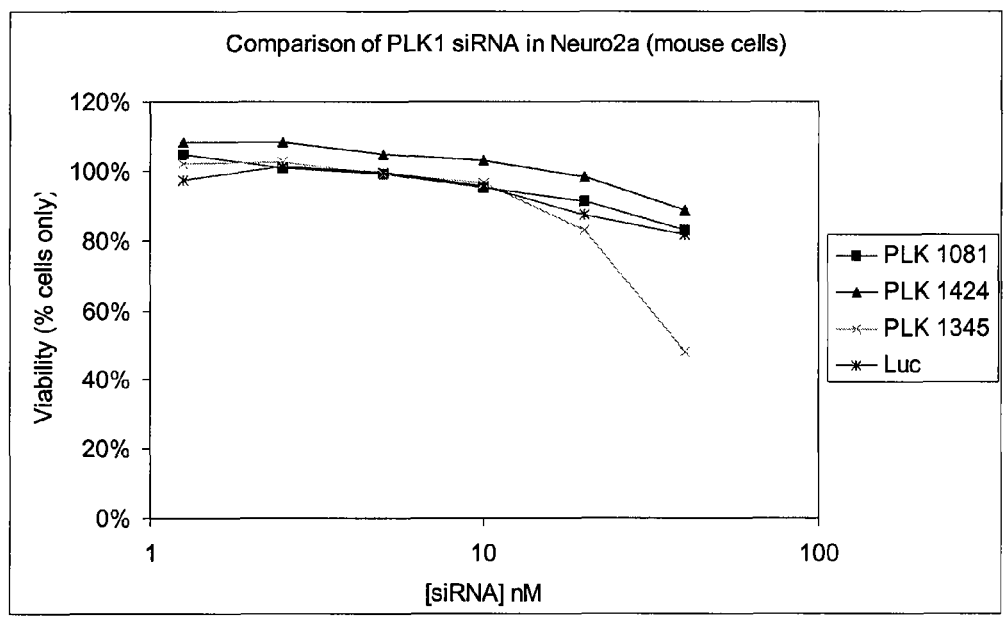

Various PLK-1 siRNAs were formulated as SNALP ("2:40" SNALP formulation: 2% PEG-cDMA; 40% DLinDMA; 10% DSPC; and 48% cholesterol) and evaluated for their inhibitory effects on cell growth in vitro. HT29 (human colon adenocarcinoma) or Neuro2A (mouse neuroblastoma) cells were treated with various PLK-1 SNALP at a range of siRNA concentrations and their effect on cell viability was evaluated. Viability of cell cultures is expressed as % viability relative to PBS treated controls. FIG. 1A shows that SNALP containing PLK1424 were highly potent at killing human tumor cells. This siRNA sequence is specific to human PLK-1, as shown by its inactivity in the mouse cell line (FIG. 1B). SNALP containing either PLK1081 or PLK1345 also inhibited the growth of human tumor cells, but at higher siRNA concentrations (FIG. 1A). PLK1345, which was designed to be conserved between murine and human PLK-1, was effective at inhibiting the growth of mouse Neuro2A cells at higher siRNA concentrations (FIG. 1B). siRNA targeting Luciferase (Luc) was used as a control SNALP.

EXAMPLE 4

Dose-Dependent Silencing of PLK-1 mRNA in Cancer Cells by siRNAs Targeting PLK-1

Figure 2:
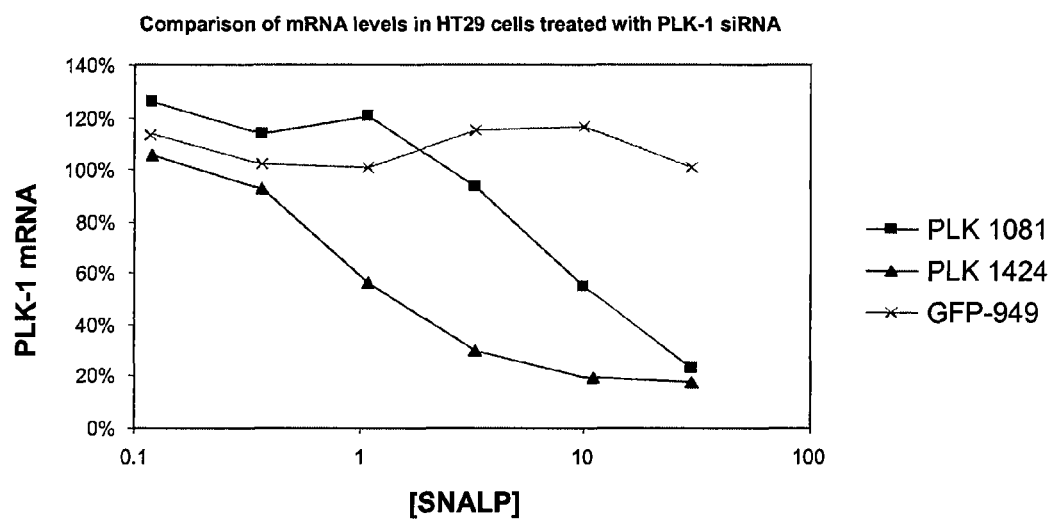
FIG. 2 illustrates data demonstrating that the potent effects of PLK-1 SNALP on cell viability is due to the silencing of PLK-1 mRNA.
Figure 2:
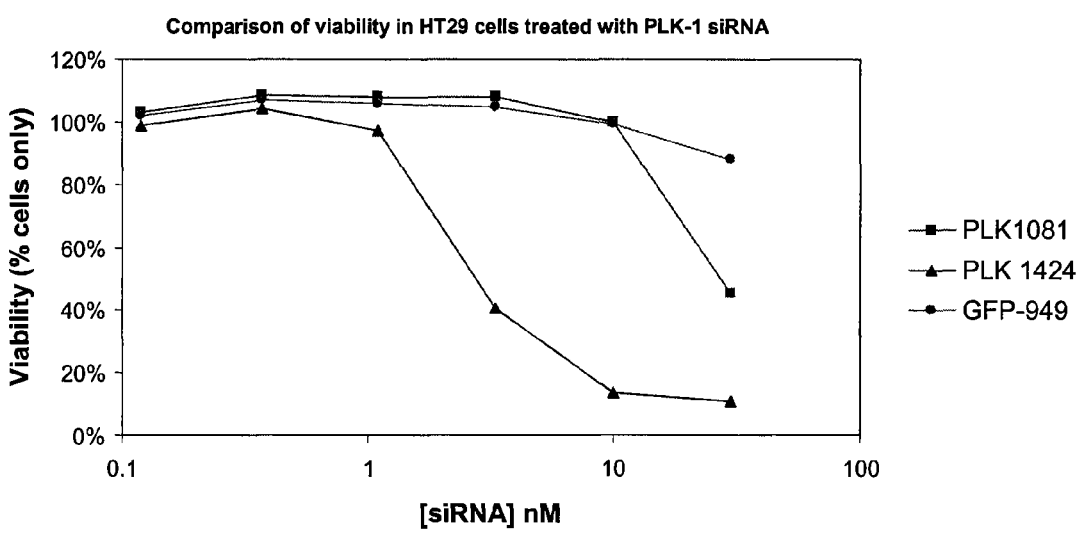

PLK-1 SNALP ("2:40" SNALP formulation: 2% PEG-cDMA; 40% DLinDMA; 10% DSPC; and 48% cholesterol) were tested for their ability to silence PLK-1 mRNA in HT29 cells. Cells were plated in duplicates at relatively high concentrations (~10,000 cells/well). QuantiGene® analysis was performed at 24 hours following transfection to detect the level of mRNA down-regulation. A visual score of the transfected cells was obtained at 48 hours following transfection. Cell viability analysis was performed at 72 hours following transfection. FIG. 2A shows the relative silencing of PLK-1 mRNA by PLK1424 and PLK1081 at 24 hours versus a non-targeting (GFP) siRNA control. FIG. 2B shows the subsequent effects of these siRNA on cell viability at 72 hours. The results confirm that the potent effects of PLK-1 SNALP on cell viability is due to the silencing of PLK-1 mRNA.

EXAMPLE 5

Additional siRNAs Targeting PLK-1 Inhibit the Growth of Cancer Cells

Figure 3:
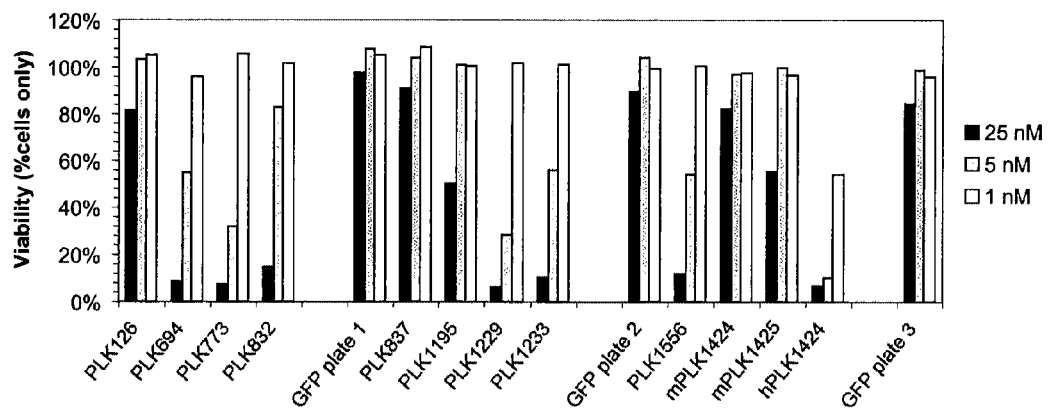
FIG. 3 illustrates data demonstrating the RNAi activity of additional SNALP-formulated PLK-1 siRNA sequences in HT29 and Neuro2A cells.
Figure 3:
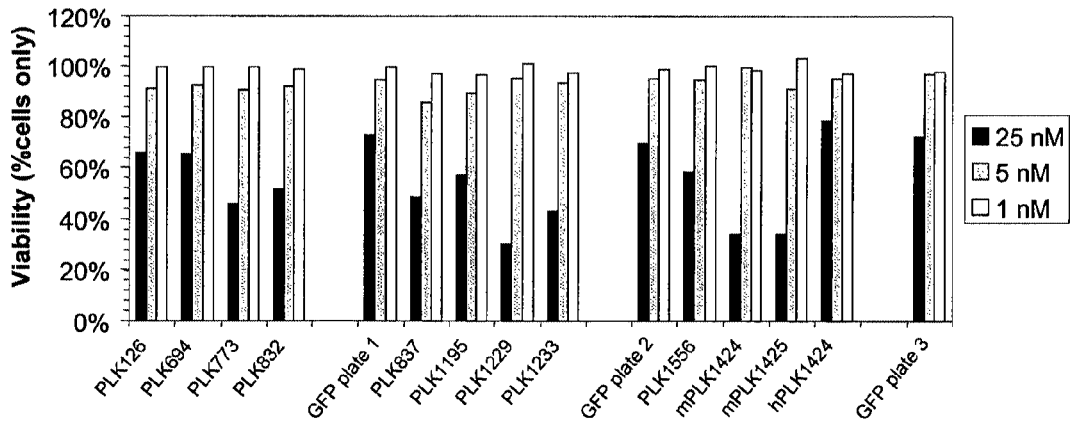

Additional PLK-1 siRNA molecules were formulated as SNALP ("2:40" SNALP formulation: 2% PEG-cDMA; 40% DLinDMA; 10% DSPC; and 48% cholesterol) and evaluated for their inhibitory effects on cell growth in vitro. HT29 or Neuro2A cells were plated in triplicate at 5000 cells/well and 2500 cells/well, respectively. PLK-1 SNALP dosages were as follows: 25 nM; 5 nM; and 1 nM. Cell viability analysis was performed at 72 hours following transfection. SNALP containing a non-targeting (GFP) siRNA were used as a negative control. FIG. 3A shows that PLK694, PLK773, PLK832, PLK1195, PLK1229, PLK1233, PLK1424, and PLK1556 were effective at killing human tumor cells, with PLK1424 demonstrating the most potent effects. FIG. 3B shows that mPLK1424 and mPLK1425 were the most active mouse-specific siRNA sequences. PLK773 and PLK1229 were the most potent human/mouse cross-reactive siRNA molecules.

EXAMPLE 6 siRNAs Targeting PLK-1 Are Active in Different Colon Cancer Cell Lines

Figure 4:
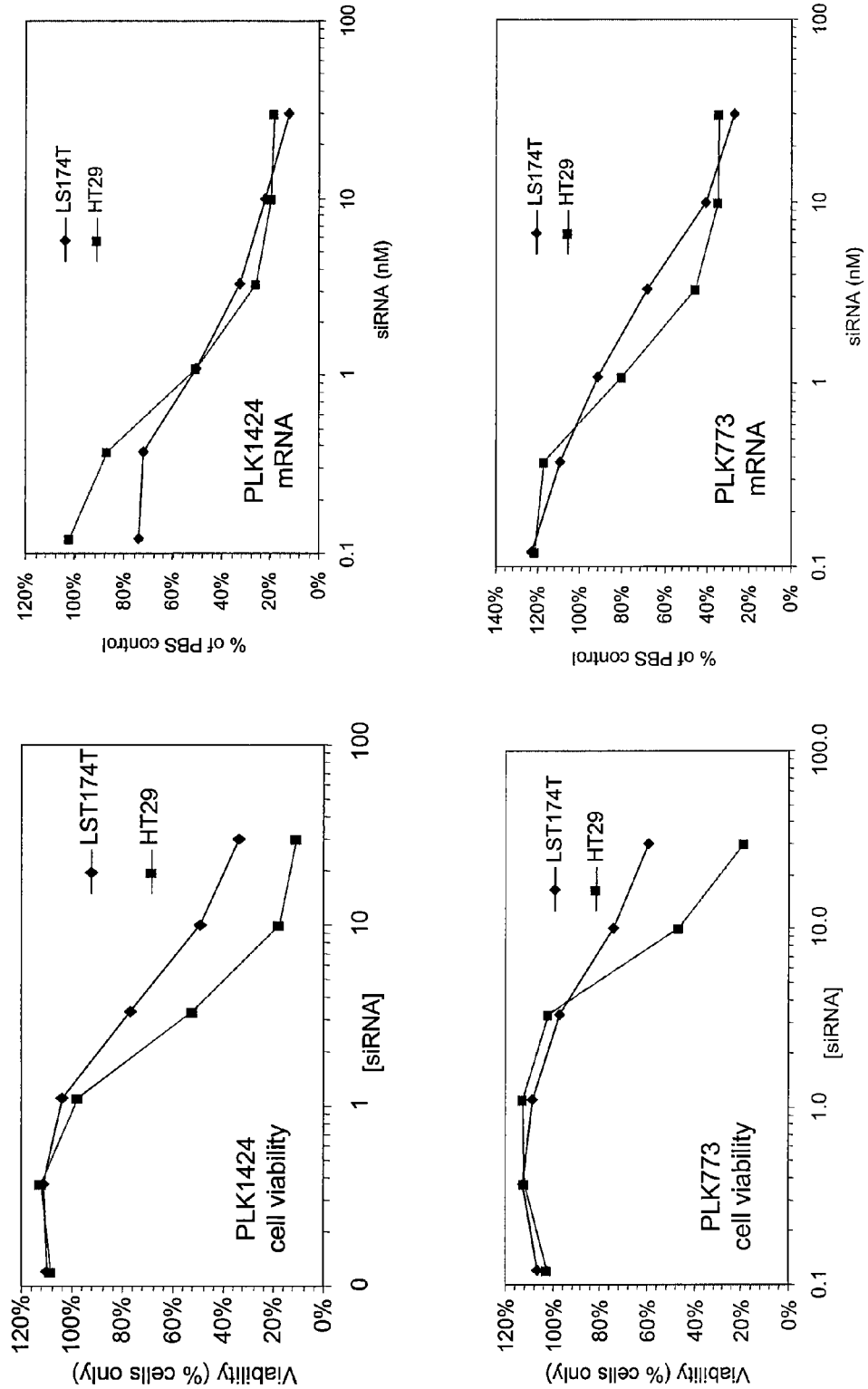
FIG. 4 illustrates data demonstrating the activity of SNALP-formulated PLK1424 and PLK773 in HT29 and LS174T cells.

SNALP containing PLK1424 or PLK773 siRNA ("2:40" SNALP formulation: 2% PEG-cDMA; 40% DLinDMA; 10% DSPC; and 48% cholesterol) were tested for their effects on cell viability and silencing of PLK-1 mRNA in HT29 and LS174T human colon cancer cells. Cells were plated in triplicate at ~10,000 cells/well. SNALP dosages were as follows: 30 nM; 10 nM; 3.3 nM; 1.1 nM; 0.37 nM; and 0.12 nM. Branched DNA mRNA assays were performed 24 hours following transfection. Cell viability assays were performed at 72 hours following transfection. SNALP containing a non-targeting (GFP) siRNA were used as a negative control. FIG. 4 shows that PLK1424 and PLK773 SNALP were effective at reducing PLK-1 mRNA levels and inhibiting cell growth in both HT29 and LS174T cells. The effects on cell viability correlated with silencing of the target PLK-1 mRNA.

EXAMPLE 7 siRNAs Targeting PLK-1 Induce Apoptosis in Colon Cancer Cells

Figure 5:
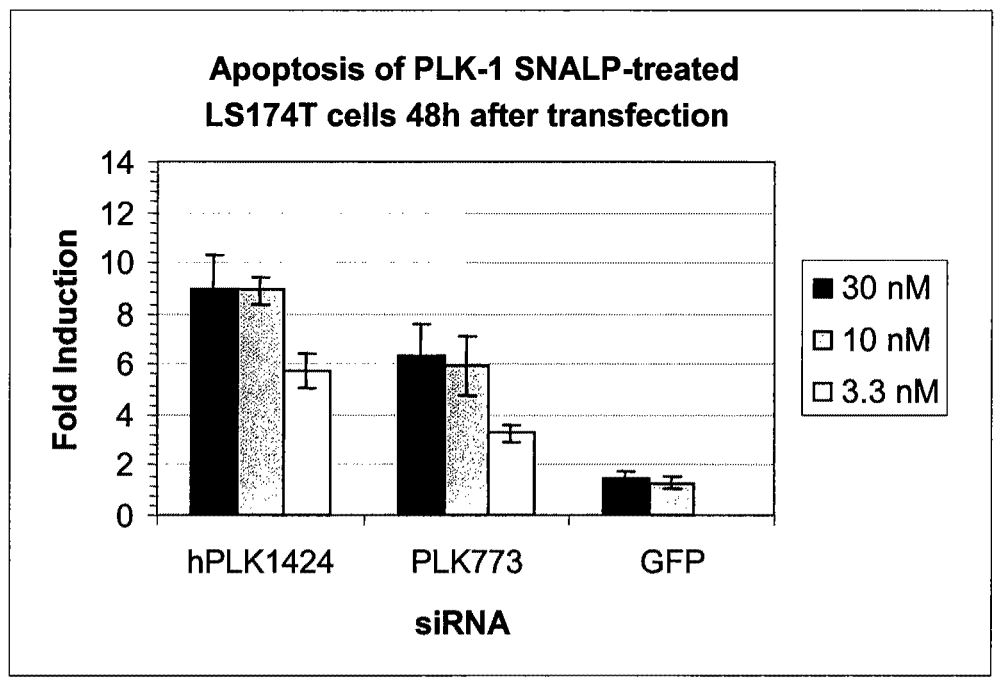
FIG. 5 illustrates data demonstrating that SNALP-formulated PLK1424 and PLK773 induce apoptosis in LS174T cells.

SNALP containing PLK1424 or PLK773 siRNA ("2:40" SNALP formulation: 2% PEG-cDMA; 40% DLinDMA; 10% DSPC; and 48% cholesterol) were further tested for their effects on inducing the apoptosis of LS174T cells. Cells were plated in triplicate at ~10,000 cells/well. SNALP dosages were as follows: 30 nM; 10 nM; and 3.3 nM. Caspase 3/7 assays were performed at 24, 48, and 72 hours following transfection. SNALP containing a non-targeting (GFP) siRNA were used as a negative control. FIG. 5 shows that PLK1424 and PLK773 SNALP induced a significant amount of apoptosis in LS174T cells at all SNALP doses tested.

EXAMPLE 8

Additional siRNAs Targeting PLK-1 Inhibit the Growth of Cancer Cells

Figure 6:
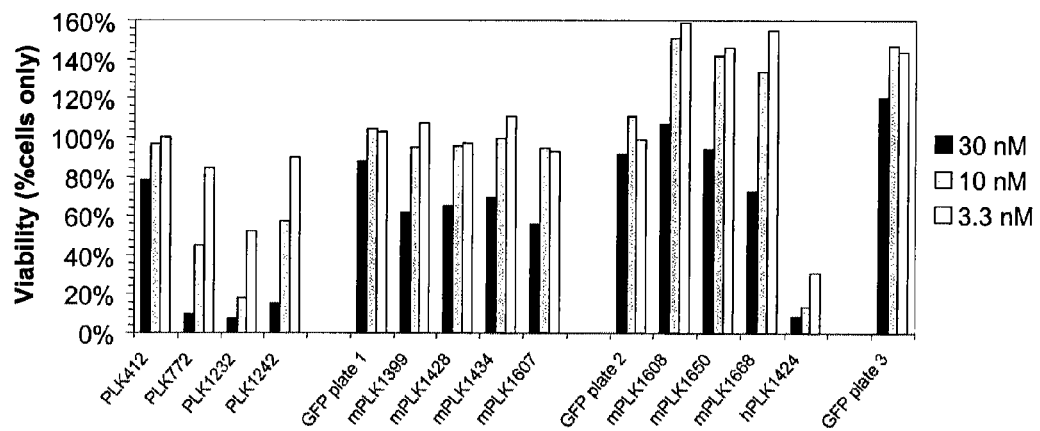
FIG. 6 illustrates data demonstrating the RNAi activity of additional SNALP-formulated PLK-1 siRNA sequences in HT29 and Neuro2A cells.
Figure 6:
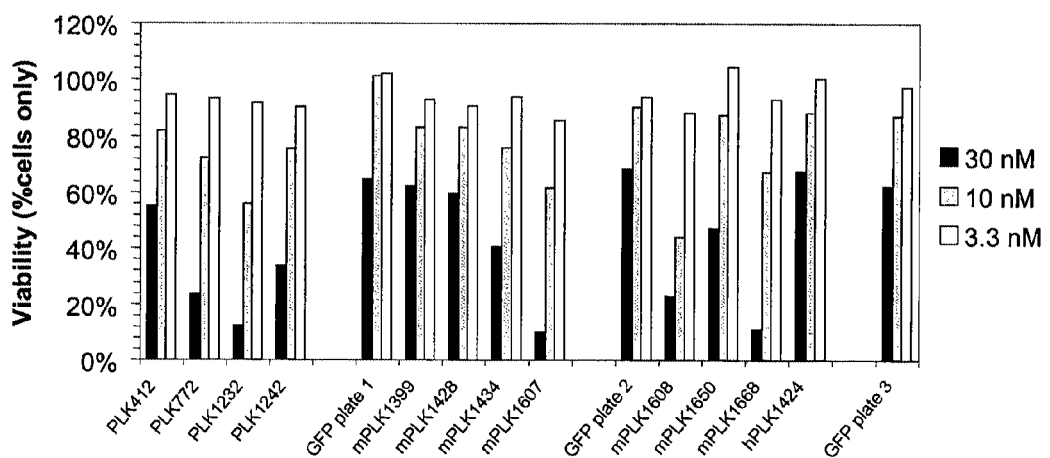

Additional PLK-1 siRNA molecules were formulated as SNALP ("2:40" SNALP formulation: 2% PEG-cDMA; 40% DLinDMA; 10% DSPC; and 48% cholesterol) and evaluated for their inhibitory effects on cell growth in vitro. HT29 or Neuro2A cells were plated in triplicate at 5000 cells/well and 2500 cells/well, respectively. PLK-1 SNALP dosages were as follows: 30 nM; 10 nM; and 3.3 nM. Cell viability analysis was performed at 72 hours following transfection. SNALP containing a non-targeting (GFP) siRNA were used as a negative control. FIG. 6A shows that PLK772, PLK1232, PLK1242, and PLK1424 were effective at killing human tumor cells, with PLK1424 demonstrating the most potent effects. FIG. 6B shows that mPLK1607, mPLK1608, and mPLK1668 were the most active mouse-specific PLK-1 siRNA sequences. PLK1232 was the most potent human/mouse cross-reactive siRNA molecule.

EXAMPLE 9

Modified PLK-1 siRNAs Are Non-Immunostimulatory and Inhibit the Growth of Cancer Cells PLK-1 siRNA molecules containing 2'-O-methyl (2'OMe) nucleotides at selective positions within the double-stranded region of the siRNA duplex were formulated as SNALP ("2:40" SNALP formulation: 2% PEG-cDMA; 40% DLinDMA; 10% DSPC; and 48% cholesterol) and evaluated for their inhibitory effects on cell growth in vitro. The modified PLK-1 siRNA sequences are shown in Table 3. HT29 cells were plated in triplicate at 5000 cells/well. Cell viability analysis was performed at 72 hours following transfection with a range of PLK-1 SNALP dosages. SNALP containing a non-targeting (GFP) siRNA were used as a negative control.

TABLE 3 siRNA duplexes comprising sense and antisense PLK-1 RNA polynucleotides.

| siRNA | PLK-1 siRNA Sequence | | % Modified in DS Region |
|---|---|---|---|
| PLK1424 | 5'-AGAUCACCCUCCUUAAAUANN-3'<br>3'-NNUCUAGUGGGAGGAAUUUAU-5' | (SEQ ID NO: 51)<br>(SEQ ID NO: 52) | 0/38 = 0% |
| PLK1424 U3/GU | 5'-AGA<u>U</u>CACCC<u>U</u>CCU<u>U</u>AAAUANN-3'<br>3'-NNUC<u>U</u>AGUGGGAG<u>G</u>AAUUUAU-5' | (SEQ ID NO: 53)<br>(SEQ ID NO: 54) | 5/38 = 13.2% |
| PLK1424 U3/UG | 5'-AGA<u>U</u>CACCC<u>U</u>CCU<u>U</u>AAAUANN-3'<br>3'-NNUC<u>U</u>AG<u>U</u>G<u>GG</u>AGGAA<u>U</u>UUAU-5' | (SEQ ID NO: 53)<br>(SEQ ID NO: 55) | 7/38 = 18.4% |
| PLK1424 U3/G | 5'-AGA<u>U</u>CACCC<u>U</u>CCU<u>U</u>AAAUANN-3'<br>3'-NNUCUA<u>G</u>U<u>GG</u>GA<u>G</u>GAAUUUAU-5' | (SEQ ID NO: 53)<br>(SEQ ID NO: 56) | 6/38 = 15.8% |
| PLK1424 U4/GU | 5'-AGA<u>U</u>CACCC<u>U</u>CCU<u>U</u>AAA<u>U</u>ANN-3'<br>3'-NNUC<u>U</u>AGUGGGAG<u>G</u>AAUUUAU-5' | (SEQ ID NO: 57)<br>(SEQ ID NO: 54) | 6/38 = 15.8% |
| PLK1424 U4/UG | 5'-AGA<u>U</u>CACCC<u>U</u>CCU<u>U</u>AAA<u>U</u>ANN-3'<br>3'-NNUC<u>U</u>AG<u>U</u>G<u>GG</u>AGGAA<u>U</u>UUAU-5' | (SEQ ID NO: 57)<br>(SEQ ID NO: 55) | 8/38 = 21% |
| PLK1424 U4/G | 5'-AGA<u>U</u>CACCC<u>U</u>CCU<u>U</u>AAA<u>U</u>ANN-3'<br>3'-NNUCUA<u>G</u>U<u>GG</u>GA<u>G</u>GAAUUUAU-5' | (SEQ ID NO: 57)<br>(SEQ ID NO: 56) | 7/38 = 18.4% |
| PLK773 | 5'-AGACCUACCUCCGGAUCANN-3'<br>3'-NNUCUGGAUGGAGGCCUAGUU-5' | (SEQ ID NO: 58)<br>(SEQ ID NO: 59) | 0/38 = 0% |
| PLK773 U/U | 5'-AGACC<u>U</u>ACC<u>U</u>CCGGA<u>U</u>CANN-3'<br>3'-NNUC<u>U</u>GGA<u>U</u>GGAGGCC<u>U</u>AGUU-5' | (SEQ ID NO: 60)<br>(SEQ ID NO: 61) | 6/38 = 15.8% |

TABLE 3-continued siRNA duplexes comprising sense and antisense PLK-1 RNA polynucleotides.

| siRNA | PLK-1 siRNA Sequence | | % Modified in DS Region |
|---|---|---|---|
| PLK773 U/G | 5'-AGACCUACCUCCGGAUCAANN-3'<br>3'-NNUCUGGAUGGAGGCCUAGUU-5' | (SEQ ID NO: 60)<br>(SEQ ID NO: 62) | 7/38 = 18.4% |
| PLK773 U/GU | 5'-AGACCUACCUCCGGAUCAANN-3'<br>3'-NNUCUGGAUGGAGGCCUAGUU-5' | (SEQ ID NO: 60)<br>(SEQ ID NO: 63) | 6/38 = 15.8% |
| PLK773 G/U | 5'-AGACCUACCUCCGGAUCAANN-3'<br>3'-NNUCUGGAUGGAGGCCUAGUU-5' | (SEQ ID NO: 64)<br>(SEQ ID NO: 61) | 5/38 = 13.2% |
| PLK773 G/G | 5'-AGACCUACCUCCGGAUCAANN-3'<br>3'-NNUCUGGAUGGAGGCCUAGUU-5' | (SEQ ID NO: 64)<br>(SEQ ID NO: 62) | 6/38 = 15.8% |
| PLK773 G/GU | 5'-AGACCUACCUCCGGAUCAANN-3'<br>3'-NNUCUGGAUGGAGGCCUAGUU-5' | (SEQ ID NO: 64)<br>(SEQ ID NO: 63) | 5/38 = 13.2% |
| PLK1425 | 5'-GAUCACCCUCCUUAAAUAUNN-3'<br>3'-NNCUAGUGGGAGGAAUUUAUA-5' | (SEQ ID NO: 65)<br>(SEQ ID NO: 66) | 0/38 = 0% |
| PLK1425 3/2 | 5'-GAUCACCCUCCUUAAAUAUNN-3'<br>3'-NNCUAGUGGGAGGAAUUUAUA-5' | (SEQ ID NO: 67)<br>(SEQ ID NO: 66) | 3/38 = 7.9% |
| PLK1425 3/5 | 5'-GAUCACCCUCCUUAAAUAUNN-3'<br>3'-NNCUAGUGGGAGGAAUUUAUA-5' | (SEQ ID NO: 67)<br>(SEQ ID NO: 68) | 5/38 = 13/2% |
| PLK1425 3/6 | 5'-GAUCACCCUCCUUAAAUAUNN-3'<br>3'-NNCUAGUGGGAGGAAUUUAUA-5' | (SEQ ID NO: 67)<br>(SEQ ID NO: 69) | 6/38 = 15.8% |
| PLK1425 3/7 | 5'-GAUCACCCUCCUUAAAUAUNN-3'<br>3'-NNCUAGUGGGAGGAAUUUUAUA-5' | (SEQ ID NO: 67)<br>(SEQ ID NO: 70) | 7/38 = 18.4% |
| PLK1425 3/8 | 5'-GAUCACCCUCCUUAAAUAUNN-3'<br>3'-NNCUAGUGGGAGGAAUUUAUA-5' | (SEQ ID NO: 67)<br>(SEQ ID NO: 71) | 7/38 = 18.4% |
| PLK1425 4/2 | 5'-GAUCACCCUCCUUAAAUAUNN-3'<br>3'-NNCUAGUGGGAGGAAUUUAUA-5' | (SEQ ID NO: 72)<br>(SEQ ID NO: 66) | 4/38 = 10.5% |
| PLK1425 4/5 | 5'-GAUCACCCUCCUUAAAUAUNN-3'<br>3'-NNCUAGUGGGAGGAAUUUAUA-5' | (SEQ ID NO: 72)<br>(SEQ ID NO: 68) | 6/38 = 15.8% |
| PLK1425 4/6 | 5'-GAUCACCCUCCUUAAAUAUNN-3'<br>3'-NNCUAGUGGGAGGAAUUUAUA-5' | (SEQ ID NO: 72)<br>(SEQ ID NO: 69) | 7/38 = 18.4% |
| PLK1425 4/7 | 5'-GAUCACCCUCCUUAAAUAUNN-3'<br>3'-NNCUAGUGGGAGGAAUUUUAUA-5' | (SEQ ID NO: 72)<br>(SEQ ID NO: 70) | 8/38 = 21% |
| PLK1425 4/8 | 5'-GAUCACCCUCCUUAAAUAUNN-3'<br>3'-NNCUAGUGGGAGGAAUUUAUA-5' | (SEQ ID NO: 72)<br>(SEQ ID NO: 71) | 8/38 = 21% |

Column 1: The number after "PLK" refers to the nucleotide position of the 5' base of the sense strand relative to the start codon (ATG) of the human PLK-1 mRNA sequence NM_005030.
Column 2: 2'-O-methyl (2'OMe) nucleotides are indicated in bold and underlined. The siRNA can alternatively or additionally comprise 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. N = deoxythymidine (dT) nucleotide, modified or unmodified uridine (U) ribonucleotide, or modified or unmodified ribonucleotide having complementarity to the target sequence or the complementary strand thereof.
Column 3: The number and percentage of modified nucleotides in the double-stranded (DS) region of the siRNA duplex are provided.

Figure 7:
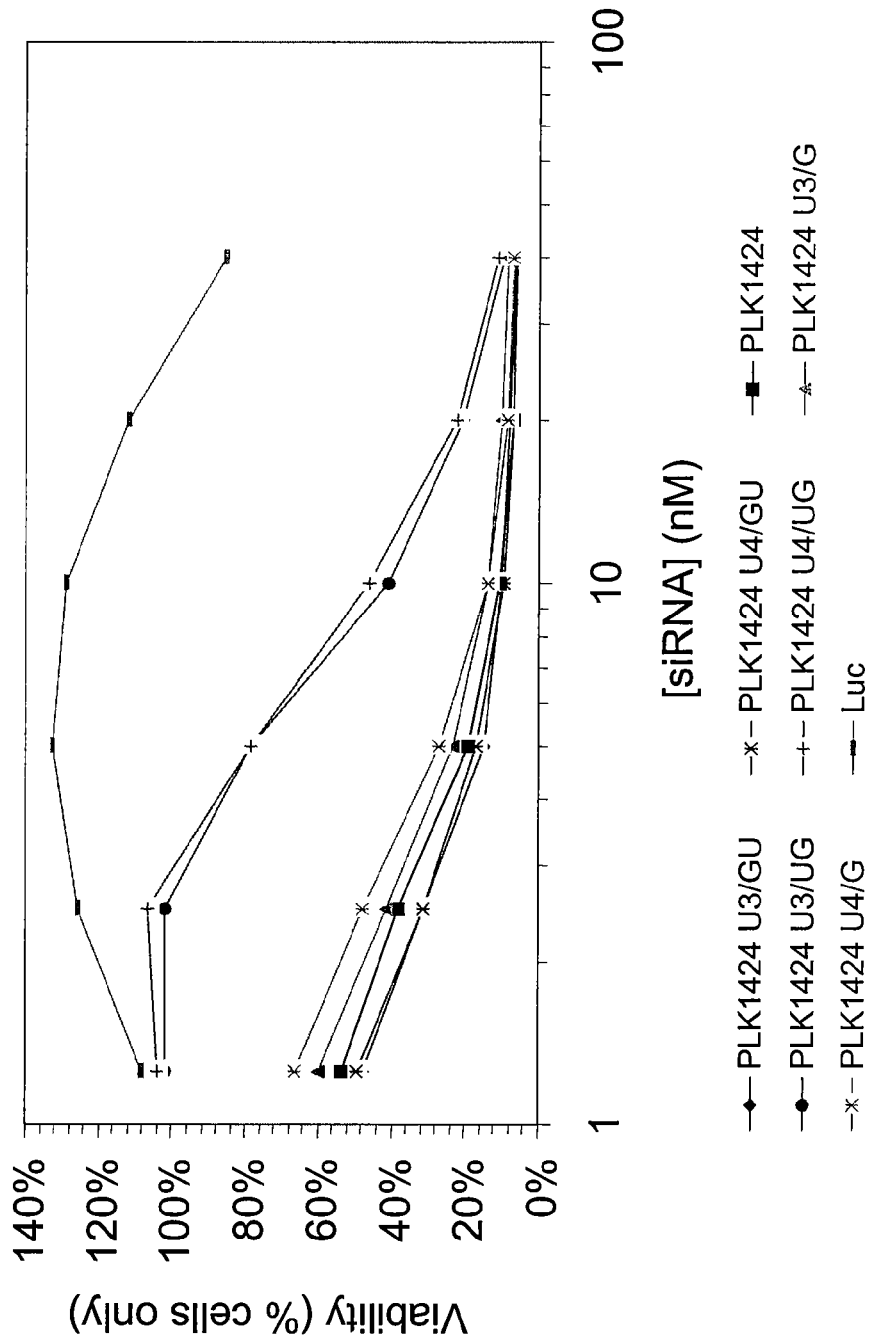
FIG. 7 illustrates data demonstrating that different 2'OMe modification patterns in the PLK1424 siRNA sequence were well tolerated and the modified siRNA molecules retained potent activity.
Figure 8:
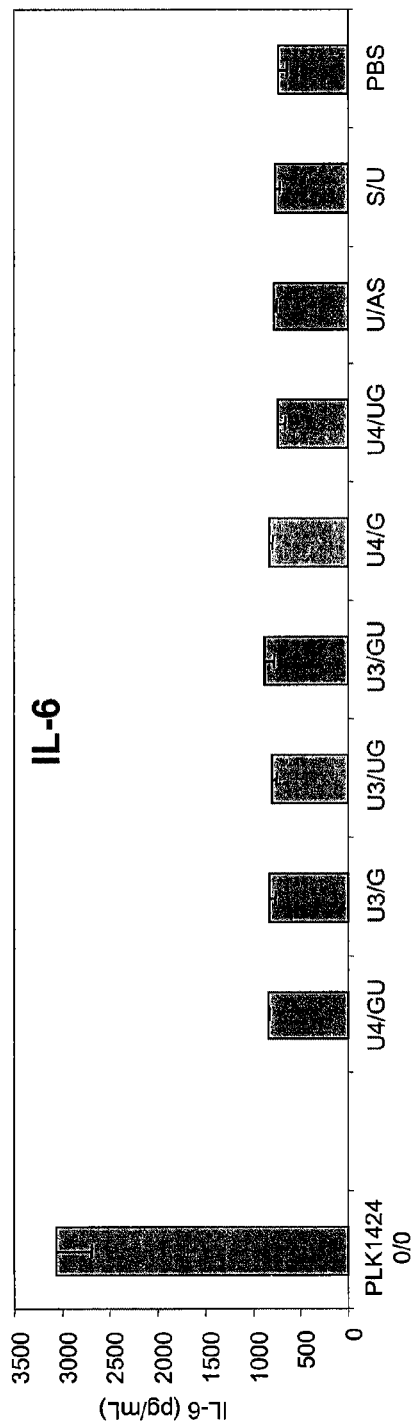
FIG. 8 illustrates data demonstrating that 2'OMe-modified PLK1424 siRNAs induced no detectable IL-6 or IFN-α response in murine FLT3L DC cultures.
Figure 8:
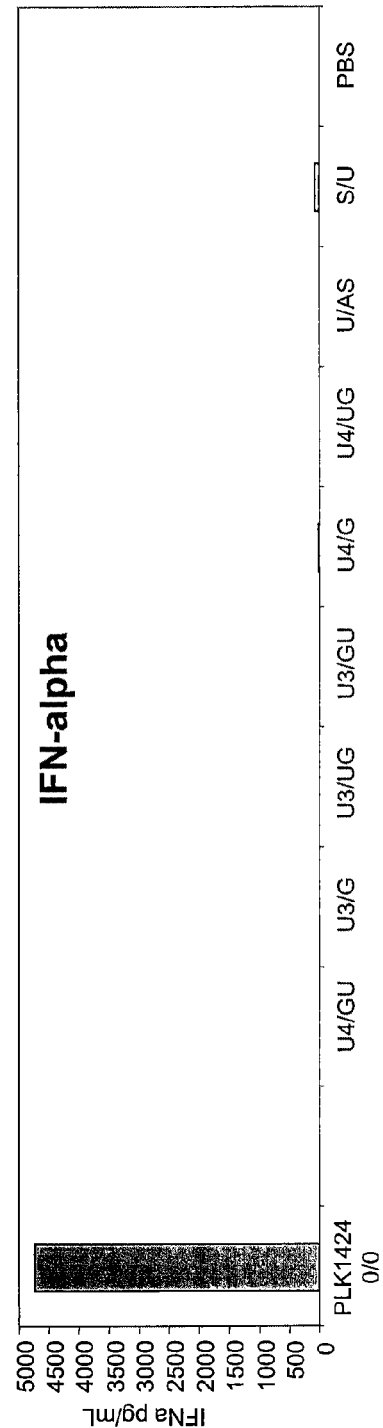

FIG. 7 shows that different chemical modification patterns in the PLK1424 siRNA sequence were well tolerated and the modified siRNA molecules retained potent activity. The most active modified siRNA molecules, PLK1424 U4/GU and PLK1424 U3/GU, were as potent as the unmodified PLK1424 sequence in killing human tumor cells. PLK1424 U4/G and PLK1424 U3/G showed similar activity to that of the unmodified PLK1424 sequence. SNALP containing 2'OMe-modified PLK1424 siRNAs were also tested for immunostimulatory activity in murine FLT3L DC cultures. FIG. 8 shows that modified PLK1424 siRNAs induced no detectable cytokine (i.e., IL-6 or IFN-α) response in this cell culture system.

Figure 9:
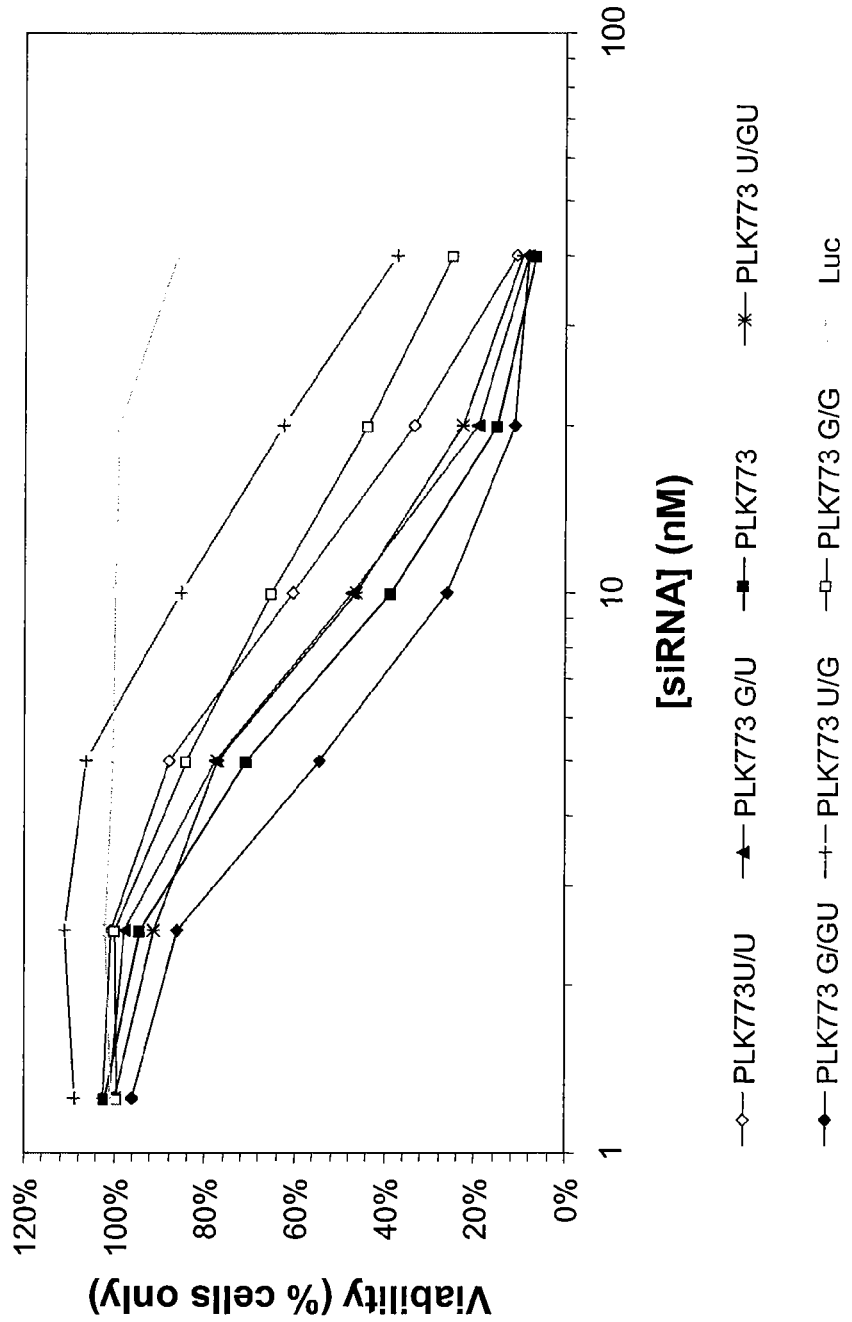
FIG. 9 illustrates data demonstrating that different 2'OMe modification patterns in the PLK773 siRNA sequence were well tolerated and the modified siRNA molecules retained potent activity.

FIG. 9 shows that different chemical modification patterns in the PLK773 siRNA sequence were well tolerated and the modified siRNA molecules retained potent activity. The most active modified siRNA molecule, PLK773 G/GU, was more potent than the unmodified PLK1424 sequence in killing human tumor cells. PLK773 G/U and PLK773 U/GU showed similar activity to that of the unmodified PLK773 sequence.

Figure 10:
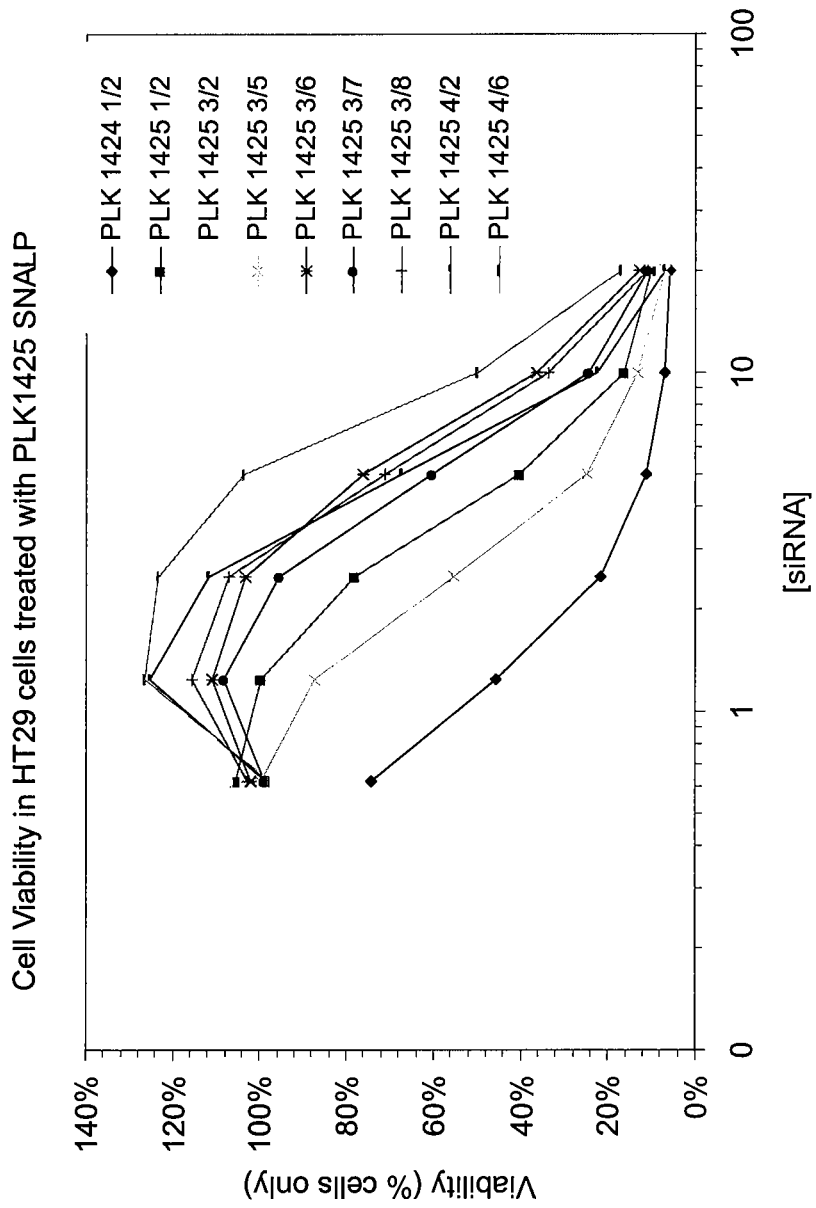
FIG. 10 illustrates data demonstrating that different 2'OMe modification patterns in the PLK1425 siRNA sequence were well tolerated and the modified siRNA molecules retained potent activity.

FIG. 10 shows that different chemical modification patterns in the PLK1425 siRNA sequence were well tolerated and the modified siRNA molecules retained potent activity. The most active modified siRNA molecule, PLK1425 3/5, was more potent than the unmodified PLK1425 sequence in killing human tumor cells. PLK1425 siRNAs containing modified antisense strand 5, 7, or 8 retained RNAi activity.

This example illustrates that minimal 2'OMe modifications at selective positions in the PLK-1 siRNA duplex are sufficient to decrease the immunostimulatory properties of PLK-1 siRNAs while retaining RNAi activity. In particular, selective 2'OMe-uridine and/or 2'OMe-guanosine modifications at less than about 25% of the nucleotide positions in the double-stranded region provide PLK-1 siRNAs with a desirable combination of silencing and non-immunostimulatory properties.

EXAMPLE 10

PLK-1 SNALP Pretreatment Sensitizes Cancer Cells to the Effects of Chemotherapy Drugs SNALP containing PLK1424 U4/GU or PLK773 G/GU siRNA ("2:40" SNALP formulation: 2% PEG-cDMA; 40% DLinDMA; 10% DSPC; and 48% cholesterol) were evaluated to determine whether sequential dosing of the SNALP before chemotherapy drug treatment produces synergistic effects in vitro in human and mouse cell lines. HepG2 (human hepatocellular liver carcinoma) and Neuro2A cells were plated in triplicate at 10,000 cells/well and 5000 cells/well, respectively. SNALP containing the modified PLK-1 siRNA molecules were added to the cells 24 hours after plating at a range of dosages. Media was changed and chemotherapy drugs were added to the cells 24 hours after SNALP treatment at a range of dosages. For example, paclitaxel (taxol) doses ranged from between 0.31 nM-10 nM for human cells and 6.25 nM-200 nM for mouse cells. Cell viability analysis or an apoptosis assay was performed at 48 or 24 hours following chemotherapy drug treatment, respectively. SNALP containing a non-targeting (Luc) siRNA were used as a negative control.

Figure 11:
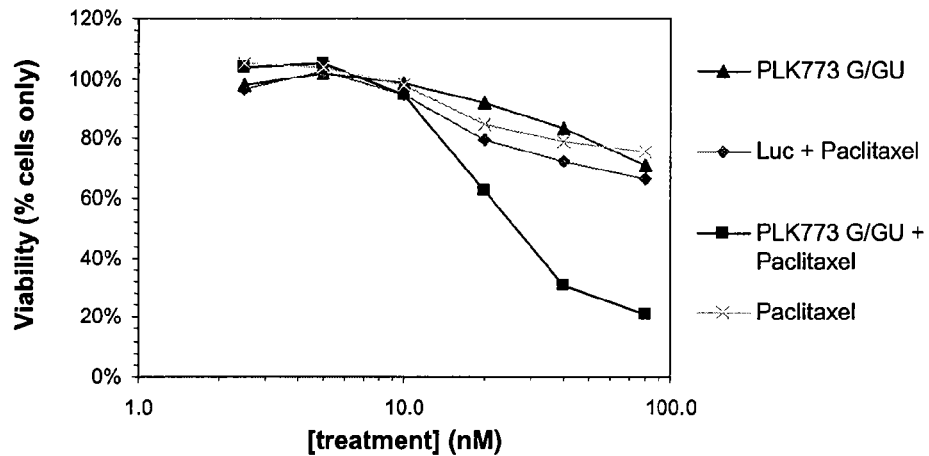
FIG. 11 illustrates data demonstrating that sequential combination treatment with PLK-1 SNALP and paclitaxel (taxol) significantly enhanced the inhibition of Neuro2A and HepG2 cell growth.
Figure 11:
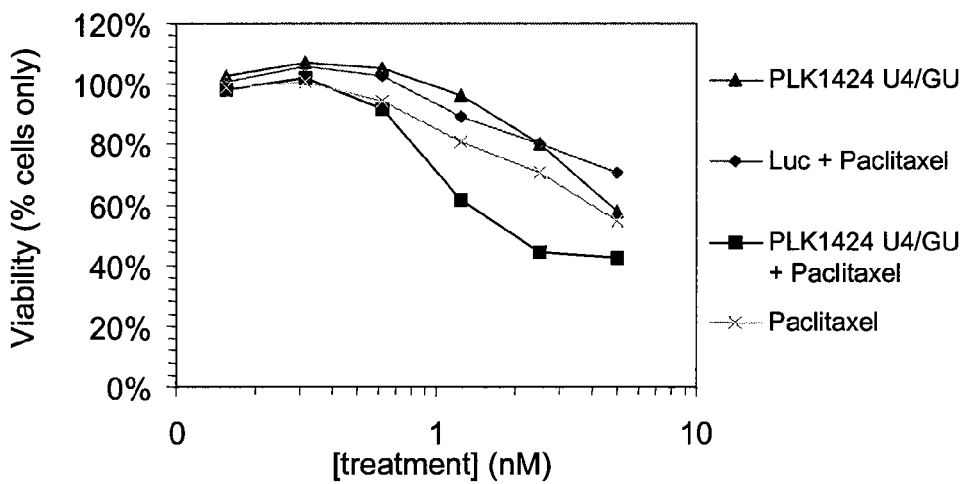
Figure 12:
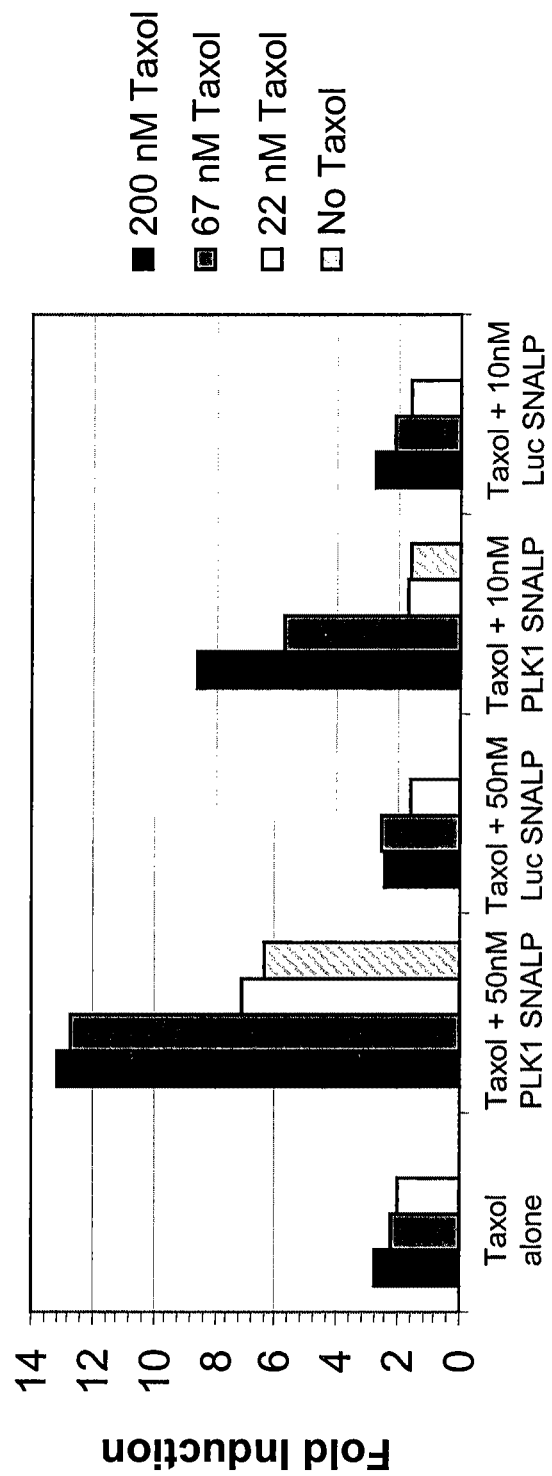
FIG. 12 illustrates data demonstrating that sequential combination treatment with PLK-1 SNALP and paclitaxel (taxol) significantly enhanced the level of apoptosis induced in Neuro2A cells.

FIG. 11 shows that the sequential administration of PLK-1 SNALP followed by paclitaxel significantly enhanced the killing of both Neuro2A and HepG2 cells. In particular, suboptimal doses of PLK-1 SNALP and paclitaxel were more effective than either agent alone. Similar synergistic effects were observed for sequential combination therapy with PLK-1 SNALP followed by fluorouracil (5-FU) or irinotecan at higher SNALP doses. FIG. 12 shows that the sequential combination dosing of PLK-1 SNALP followed by paclitaxel significantly enhanced the level of apoptosis induction at both SNALP concentrations. The increased apoptosis correlated with the enhanced effects of this drug combination on cell viability.

This example illustrates that pretreatment with SNALP containing PLK-1 siRNA sensitizes cancer cells to the toxic effects of chemotherapy drugs such as paclitaxel, 5-FU, and irinotecan. This example further illustrates that the sequential administration of PLK-1 SNALP followed by chemotherapy drugs induces significant levels of apoptosis in cancer cells, correlating with the decreases in cell viability observed with this combination of dosing.

EXAMPLE 11

Selection of Additional Candidate Human PLK-1 siRNA Molecules

Additional human PLK-1 siRNA sequences were designed. Candidate PLK-1 siRNA sequences were identified by imputing the human PLK-1 mRNA sequence (Genbank Accession No. NM_005030) into the Whitehead Institute for Biomedical Research siRNA design algorithm (see, e.g., Elbashir et al., *Genes Dev.*, 15:188-200 (2001); Schwarz et al., *Cell*, 115:199-208 (2003); and Khvorova et al *Cell*, 115: 209-216 (2003); available at http://jura.wi.mit.edu/bioc/siR-NAext/home.php). siRNA fulfilling the following criteria were selected (Table 4): (1) NA(N19)NN target sequences; (2) thermodynamically less stable 5' antisense end (Difference <-2.0); (3) G/C content between 30-70%; and (4) no four nucleotide stretches of the same base. A second set of siRNA (Table 5) were selected on the following criteria: (1) NN(N19)NN target sequences; (2) thermodynamically less stable 5' antisense end (Difference <-2.0); (3) Thermodynamics of 5' antisense end >-6 (-6 to 0); (4) G/C content between 30-70%; and (5) no four nucleotide stretches of the same base. Selected sequences were verified and the positions within the human PLK-1 target sequence were identified.

BLASTn searches against the human and mouse sequence databases were then performed on all selected sequences. Sequences were eliminated that cross-hybridized with >17 of its internal nucleotides.

The candidate sequences are shown in Tables 4-5.

TABLE 4

Additional siRNA sequences that target human PLK-1 expression.

| siRNA | Sense Strand (5'→3') | SEQ ID NO: | Antisense Strand (5'→3') | SEQ ID NO: |
|---|---|---|---|---|
| PLK (-23) | GGUCUGCAGCGCAGCUUCG | 73 | CGAAGCUGCGCUGCAGACC | 74 |
| PLK (-15) | GCGCAGCUUCGGGAGCAUG | 75 | CAUGCUCCCGAAGCUGCGC | 76 |
| PLK272 | AGCCGCACCAGAGGGAGAA | 77 | UUCUCCCUCUGGUGCGGCU | 78 |
| PLK273 | GCCGCACCAGAGGGAGAAG | 79 | CUUCUCCCUCUGGUGCGGC | 80 |
| PLK288 | GAAGAUGUCCAUGGAAAUA | 81 | UAUUUCCAUGGACAUCUUC | 82 |
| PLK363 | GGACAACGACUUCGUGUUC | 83 | GAACACGAAGUCGUUGUCC | 84 |
| PLK420 | GCUGCACAAGAGGAGGAAA | 85 | UUUCCUCCUCUUGUGCAGC | 86 |
| PLK429 | GAGGAGGAAAGCCCUGACU | 87 | AGUCAGGGCUUUCCUCCUC | 88 |
| PLK431 | GGAGGAAAGCCCUGACUGA | 89 | UCAGUCAGGGCUUUCCUCC | 90 |
| PLK438 | AGCCCUGACUGAGCCUGAG | 91 | CUCAGGCUCAGUCAGGGCU | 92 |

TABLE 4-continued

Additional siRNA sequences that target human PLK-1 expression.

| siRNA | Sense Strand (5'→3') | SEQ ID NO: | Antisense Strand (5'→3') | SEQ ID NO: |
|---|---|---|---|---|
| PLK439 | GCCCUGACUGAGCCUGAGG | 93 | CCUCAGGCUCAGUCAGGGC | 94 |
| PLK450 | GCCUGAGGCCCGAUACUAC | 95 | GUAGUAUCGGGCCUCAGGC | 96 |
| PLK456 | GGCCCGAUACUACCUACGG | 97 | CCGUAGGUAGUAUCGGGCC | 98 |
| PLK498 | CCUGCACCGAAACCGAGUU | 99 | AACUCGGUUUCGGUGCAGG | 100 |
| PLK504 | CCGAAACCGAGUUAUUCAU | 101 | AUGAAUAACUCGGUUUCGG | 102 |
| PLK589 | CUGGCAACCAAAGUCGAAU | 103 | AUUCGACUUUGGUUGCCAG | 104 |
| PLK618 | GAGGAAGAAGACCCUGUGU | 105 | ACACAGGGUCUUCUUCCUC | 106 |
| PLK627 | GACCCUGUGUGGGACUCCU | 107 | AGGAGUCCCACACAGGGUC | 108 |
| PLK629 | CCCUGUGUGGGACUCCUAA | 109 | UUAGGAGUCCCACACAGGG | 110 |
| PLK663 | GGUGCUGAGCAAGAAAGGG | 111 | CCCUUUCUUGCUCAGCACC | 112 |
| PLK693 | GGUGGAUGUGUGGUCCAUU | 113 | AAUGGACCACACAUCCACC | 114 |
| PLK710 | UUGGGUGUAUCAUGUAUAC | 115 | GUAUACAUGAUACACCCAA | 116 |
| PLK736 | GUGGGCAAACCACCUUUUG | 117 | CAAAAGGUGGUUUGCCCAC | 118 |
| PLK744 | ACCACCUUUUGAGACUUCU | 119 | AGAAGUCUCAAAAGGUGGU | 120 |
| PLK745 | CCACCUUUUGAGACUUCUU | 121 | AAGAAGUCUCAAAAGGUGG | 122 |
| PLK774 | GACCUACCUCCGGAUCAAG | 123 | CUUGAUCCGGAGGUAGGUC | 124 |
| PLK776 | CCUACCUCCGGAUCAAGAA | 125 | UUCUUGAUCCGGAGGUAGG | 126 |
| PLK780 | CCUCCGGAUCAAGAAGAAU | 127 | AUUCUUCUUGAUCCGGAGG | 128 |
| PLK884 | CCAUUAACGAGCUGCUUAA | 129 | UUAAGCAGCUCGUUAAUGG | 130 |
| PLK894 | GCUGCUUAAUGACGAGUUC | 131 | GAACUCGUCAUUAAGCAGC | 132 |
| PLK903 | UGACGAGUUCUUUACUUCU | 133 | AGAAGUAAAGAACUCGUCA | 134 |
| PLK1024 | GUCCUCAAUAAAGGCUUGG | 135 | CCAAGCCUUUAUUGAGGAC | 136 |
| PLK1137 | GCAGCUGCACAGUGUCAAU | 137 | AUUGACACUGUGCAGCUGC | 138 |
| PLK1235 | GCAAGUGGGUGGACUAUUC | 139 | GAAUAGUCCACCCACUUGC | 140 |
| PLK1319 | CACGCCUCAUCCUCUACAA | 141 | UUGUAGAGGAUGAGGCGUG | 142 |
| PLK1321 | CGCCUCAUCCUCUACAAUG | 143 | CAUUGUAGAGGAUGAGGCG | 144 |
| PLK1347 | CAGCCUGCAGUACAUAGAG | 145 | CUCUAUGUACUGCAGGCUG | 146 |
| PLK1363 | GAGCGUGACGGCACUGAGU | 147 | ACUCAGUGCCGUCACGCUC | 148 |
| PLK1404 | UCCCAACUCCUUGAUGAAG | 149 | CUUCAUCAAGGAGUUGGGA | 150 |
| PLK1409 | ACUCCUUGAUGAAGAAGAU | 151 | AUCUUCUUCAUCAAGGAGU | 152 |
| PLK1422 | GAAGAUCACCCUCCUUAAA | 153 | UUUAAGGAGGGUGAUCUUC | 154 |
| PLK1430 | CCCUCCUUAAAUAUUUCCG | 155 | CGGAAAUAUUUAAGGAGGG | 156 |
| PLK1457 | UGAGCGAGCACUUGCUGAA | 157 | UUCAGCAAGUGCUCGCUCA | 158 |
| PLK1550 | CCCGCAGCGCCAUCAUCCU | 159 | AGGAUGAUGGCGCUGCGGG | 160 |
| PLK1577 | GCAACGGCAGCGUGCAGAU | 161 | AUCUGCACGCUGCCGUUGC | 162 |
| PLK1580 | ACGGCAGCGUGCAGAUCAA | 163 | UUGAUCUGCACGCUGCCGU | 164 |

TABLE 4-continued

Additional siRNA sequences that target human PLK-1 expression.

| siRNA | Sense Strand (5'→3') | SEQ ID NO: | Antisense Strand (5'→3') | SEQ ID NO: |
|---|---|---|---|---|
| PLK1581 | CGGCAGCGUGCAGAUCAAC | 165 | GUUGAUCUGCACGCUGCCG | 166 |
| PLK1586 | GCGUGCAGAUCAACUUCUU | 167 | AAGAAGUUGAUCUGCACGC | 168 |
| PLK1620 | GCUCAUCUUGUGCCCACUG | 169 | CAGUGGGCACAAGAUGAGC | 170 |
| PLK1640 | UGGCAGCCGUGACCUACAU | 171 | AUGUAGGUCACGGCUGCCA | 172 |
| PLK1645 | GCCGUGACCUACAUCGACG | 173 | CGUCGAUGUAGGUCACGGC | 174 |
| PLK1658 | UCGACGAGAAGCGGGACUU | 175 | AAGUCCCGCUUCUCGUCGA | 176 |
| PLK1667 | AGCGGGACUUCCGCACAUA | 177 | UAUGUGCGGAAGUCCCGCU | 178 |
| PLK1668 | GCGGGACUUCCGCACAUAC | 179 | GUAUGUGCGGAAGUCCCGC | 180 |
| PLK1704 | GGAGUACGGCUGCUGCAAG | 181 | CUUGCAGCAGCCGUACUCC | 182 |
| PLK1775 | GCUCACGCUCGGCCAGCAA | 183 | UUGCUGGCCGAGCGUGAGC | 184 |
| PLK1794 | CCGUCUCAAGGCCUCCUAA | 185 | UUAGGAGGCCUUGAGACGG | 186 |

The number after "PLK" in Table 4 refers to the nucleotide position of the 5' base of the sense strand relative to the start codon (ATG) of the human PLK-1 mRNA sequence NM_005030. In certain embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides. In some instances, the sense and/or antisense strand contains "dTdT" or "UU" 3' overhangs. In other instances, the sense and/or antisense strand contains 3' overhangs that have complementarity to the target sequence or the complementary strand thereof. In further embodiments, the 3' overhangs may comprise modified nucleotides such as those described above.

TABLE 5

Additional siRNA sequences that target human PLK-1 expression.

| siRNA | Sense Strand (5'→3') | SEQ ID NO: | Antisense Strand (5'→3') | SEQ ID NO: |
|---|---|---|---|---|
| PLK287 | AGAAGAUGUCCAUGGAAAU | 187 | AUUUCCAUGGACAUCUUCU | 188 |
| PLK461 | GAUACUACCUACGGCAAAU | 189 | AUUUGCCGUAGGUAGUAUC | 190 |
| PLK500 | UGCACCGAAACCGAGUUAU | 191 | AUAACUCGGUUUCGGUGCA | 192 |
| PLK591 | GGCAACCAAAGUCGAAUAU | 193 | AUAUUCGACUUUGGUUGCC | 194 |
| PLK630 | CCUGUGUGGGACUCCUAAU | 195 | AUUAGGAGUCCCACACAGG | 196 |
| PLK632 | UGUGUGGGACUCCUAAUUA | 197 | UAAUUAGGAGUCCCACACA | 198 |
| PLK1016 | CCCUCACAGUCCUCAAUAA | 199 | UUAUUGAGGACUGUGAGGG | 200 |
| PLK1017 | CCUCACAGUCCUCAAUAAA | 201 | UUUAUUGAGGACUGUGAGG | 202 |
| PLK1018 | CUCACAGUCCUCAAUAAAG | 203 | CUUUAUUGAGGACUGUGAG | 204 |
| PLK1795 | CGUCUCAAGGCCUCCUAAU | 205 | AUUAGGAGGCCUUGAGACG | 206 |
| PLK1796 | GUCUCAAGGCCUCCUAAUA | 207 | UAUUAGGAGGCCUUGAGAC | 208 |
| PLK1797 | UCUCAAGGCCUCCUAAUAG | 209 | CUAUUAGGAGGCCUUGAGA | 210 |

The number after "PLK" in Table 5 refers to the nucleotide position of the 5' base of the sense strand relative to the start codon (ATG) of the human PLK-1 mRNA sequence NM_005030. In certain embodiments, the sense and/or antisense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE)

nucleotides, and/or locked nucleic acid (LNA) nucleotides. In some instances, the sense and/or antisense strand contains "dTdT" or "UU" 3' overhangs. In other instances, the sense and/or antisense strand contains 3' overhangs that have complementarity to the target sequence or the complementary strand thereof. In further embodiments, the 3' overhangs may comprise modified nucleotides such as those described above.

EXAMPLE 12 siRNAs Targeting PLK-1 Increase Survival of Hep3B Tumor-Bearing Mice

SNALP containing PLK-1 siRNA ("1:57" SNALP formulation: 1.4% PEG-cDMA; 57.1% DLinDMA; 7.1% DPPC; and 34.3% cholesterol) were tested for their effects on the survival of CD1 nu/nu mice bearing Hep3B liver tumors.

Experimental Groups

20 CD1 nu/nu mice were seeded as follows:

| Group | # Mice | Tumor seeding | SNALP | # Mice | SNALP dosing IV | SNALP dose | Sacrifice | Assay |
|---|---|---|---|---|---|---|---|---|
| A | 20 to seed | I.H. 1.5 × 10⁶ Hep3B | Luc 1:57 PLK 1424 1:57 | 9 9 | Days 11, 14, 17, 21, 25, 28, 32, 35, 39, 42 | 10 × 2 mg/kg | When moribund | Survival Body Weights |
| B | | | | | | | | |

Test Articles

All samples were filter-sterilized prior to dilution to working concentration. All tubes were labeled with the formulation date, lipid composition, and nucleic acid concentration. SNALP samples were provided at 0.2 mg/ml nucleic acid. A minimum of 20 ml of each SNALP was required to perform the study. Formulations for this study contained:

| Group | Test Article Description |
|---|---|
| A | Luc U/U SNALP 1:57 (28 mM lipid) |
| B | PLK1424 U4/GU SNALP 1:57 (28 mM lipid) |
| | PLK1424 U4/G SNALP 1:57 (28 mM lipid) |

Procedures

| | |
|---|---|
| Day 0 | Mice will receive Anafen by SC injection (100 μg in 20 μl saline) immediately prior to surgery. Individual mice are anesthetized by isoflourane gas inhalation and eye lube applied to prevent excessive eye drying. While maintained under gas anesthesia from a nose cone, a single 1.5 cm incision across the midline will be made below the sternum. The left lateral hepatic lobe is then exteriorized using an autoclaved cotton wool bud. 25 μl of tumor cells suspended in PBS is injected into the lobe at a shallow angle using a leur tip Hamilton syringe (50 μl) and 30 G (³⁄₈") needle. Cells will be injected slowly (~30 s) and a swab applied to the puncture wound immediately after needle withdrawal. After any bleeding has stopped (~1 min), the incision is closed with 5-6 sutures in the muscle wall and 3-4 skin clips. Cell suspensions will be thoroughly mixed immediately prior to each injection. Mice will recover from anesthesia in a clean cage lined with paper towel and monitored closely for 2-4 hours. Animals are then returned to normal housing. |
| Day 1 | All mice will be lightly anesthetized by isoflourane gas and the sutures examined. Animals will then receive Anafen by SC injection (100 μg in 20 μl saline). |
| Day 10 | Mice will be randomized into the appropriate treatment groups. |
| Day 11 | Groups A, B - Day 11: All Animals will be administered SNALP at 2 mg/kg by IV injection via the lateral tail vein. Mice will be dosed according to body weight (10 ml/kg). Dosing will be repeated for 5 consecutive days based on initial weight. |
| Day 14-35 | Groups A, B - Days 14, 17, 21, 25, 28, 32, 35: All Animals will be re-administered SNALP at 2 mg/kg by IV injection via the lateral tail vein. Mice will be dosed according to body weight (10 ml/kg). Body weights Groups: Mice will be weighed on the day of dosing for 5 weeks, then twice weekly until close of the study. Endpoint: Tumor burden and formulations are expected to be well tolerated. Mice that exhibit signs of distress associated with the treatment or tumor burden are terminated at the discretion of the vivarium staff. |
| Termination: | Mice are anesthetized with a lethal dose of ketamine/xylazine followed by cervical dislocation. |
| Data Analysis: | Survival and body weights are assayed. |

Results

Figure 13:
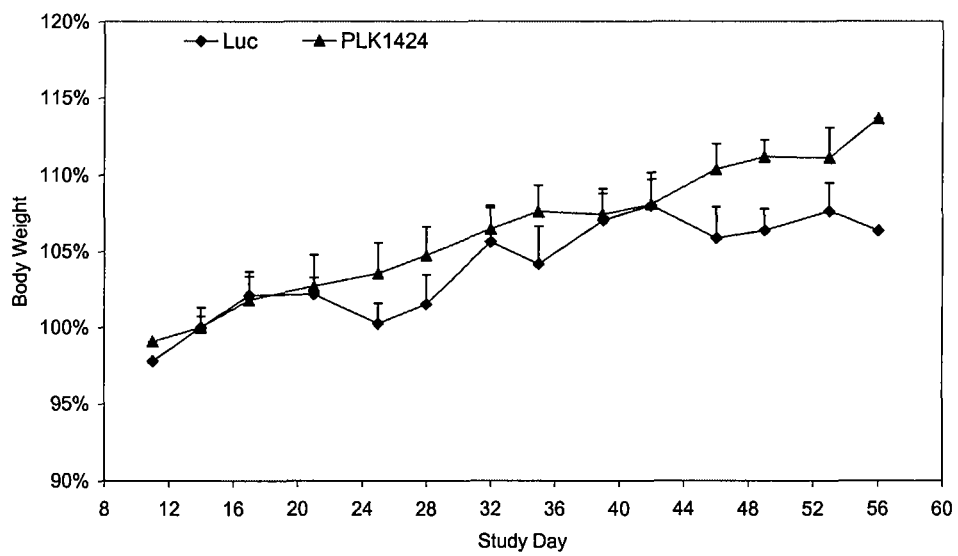
FIG. 13 illustrates data demonstrating that a treatment regimen of SNALP-formulated PLK1424 is well tolerated with no apparent signs of treatment related toxicity in mice bearing Hep3B liver tumors.

FIG. 13 shows the mean body weights of mice during therapeutic dosing of PLK1424 SNALP in the Hep3B intrahepatic (I.H.) tumor model. The treatment regimen was well tolerated with no apparent signs of treatment-related toxicity.

Figure 14:
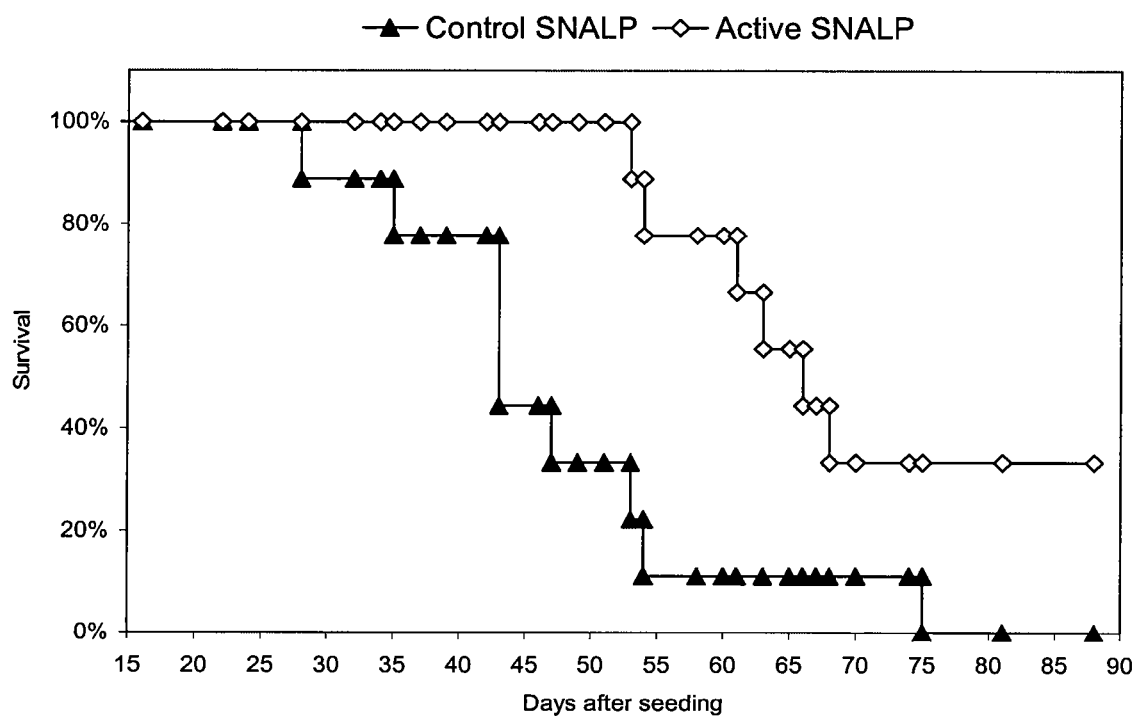
FIG. 14 illustrates data demonstrating that treatment with SNALP-formulated PLK1424 caused a significant increase in the survival of Hep3B tumor-bearing mice.

FIG. 14 shows that treatment with SNALP-formulated PLK1424 caused a significant increase in the survival of Hep3B tumor-bearing mice. This in vivo anti-tumor effect was observed in the absence of any apparent toxicity or immune stimulation.

EXAMPLE 13 siRNAs Targeting PLK-1 Increase Survival of Hep3B Tumor-Bearing Mice

The objectives of this study were as follows:
1. To determine the level of mRNA silencing in established Hep3B liver tumors following a single IV administration of PLK1424 SNALP.
2. To confirm the mechanism of mRNA silencing by detecting specific RNA cleavage products using RACE-PCR.
3. To confirm induction of tumor cell apoptosis by histopathology.

The "1:57" SNALP formulation (1.4% PEG-cDMA; 57.1% DLinDMA; 7.1% DPPC; and 34.3% cholesterol) was used for this study.

Experimental Groups

20 SCID/beige mice were seeded as follows:

| Group | # Mice | Tumor seeding | SNALP | # Mice | SNALP dosing IV | Sacrifice | Assay |
|---|---|---|---|---|---|---|---|
| A | 20 to seed | I.H. 1 × 10⁶ Hep3B | PBS Luc 1:57 PLK 1424 1:57 | 6 7 7 | 1 × 2 mg/kg Day 20 | 24 h after treatment | Tumor QG Tumor RACE-PCR Histopathology |
| B | | | | | | | |
| C | | | | | | | |

Test Articles

All samples were filter-sterilized prior to dilution to working concentration. All tubes were labeled with the formulation date, lipid composition, and nucleic acid concentration. SNALP samples were provided at 0.2 mg/ml nucleic acid. A minimum of 2 ml of SNALP was required to perform the study. Formulations for this study contained:

| Group | Test Article Description |
|---|---|
| A | PBS |
| B | Luc U/U 1:57 SNALP |
| C | PLK1424 U4/GU 1:57 SNALP |

Procedures

| | |
|---|---|
| Day 0 | Mice will receive Anafen by SC injection (100 µg in 20 µl saline) immediately prior to surgery. Individual mice are anesthetized by isoflourane gas inhalation and eye lube applied to prevent excessive eye drying. While maintained under gas anesthesia from a nose cone, a single 1.5 cm incision across the midline will be made below the sternum. The left lateral hepatic lobe is then exteriorized using an autoclaved cotton wool bud. 25 µl of tumor cells suspended in PBS is injected into the lobe at a shallow angle using a leur tip Hamilton syringe (50 µl) and 30 G (⅜") needle. Cells will be injected slowly (~30 s) and a swab applied to the puncture wound immediately after needle withdrawal. After any bleeding has stopped (~1 min), the muscle wall incision is closed with 5-6 sutures. The skin incision is then closed with 3-4 metal skin clips. Cell suspensions will be thoroughly mixed immediately prior to each injection. Mice will recover from anesthesia in a clean cage lined with paper towel and monitored closely for 2-4 hours. Animals are then returned to normal housing. |
| Day 1 | All mice will be lightly anesthetized by isoflourane gas and the sutures examined. Animals will then receive Anafen by SC injection (100 µg in 20 µl saline). |
| Day 7 | Mice will be randomized into the appropriate treatment groups. |
| Day 20 | Groups A-C: Mice will be weighed and then administered either PBS, Luc, or PLK1424 SNALP by IV injection via the lateral tail vein. SNALP will be dosed at 2 mg/kg or equivalent volume (10 ml/kg) according to body weight. |
| Day 21 | Groups A-C: All mice will be weighed and then euthanized by lethal anesthesia.<br>Tumor bearing liver lobes from all mice in each group will be weighed and collected into RNALater for RNA analysis.<br>Endpoint: Tumor burden and formulations are expected to be well |

| | |
|---|---|
| | tolerated. Mice that exhibit signs of distress associated with the treatment or tumor burden are terminated at the discretion of the vivarium staff. |
| Termination: | Mice are anaesthetized with a lethal dose of ketamine/xylazine followed by cervical dislocation. |
| Data Analysis: | mRNA analysis of liver tumors by bDNA (QG) assay and RACE-PCR. Tumor cell apoptosis by histopathology. |

Results

Body weights were monitored from day 14 onwards to assess tumor progression. On Day 20, 6 mice showing greatest weight loss were randomized into each of the 3 groups and treated. All six mice had substantial-large I.H. tumors at sacrifice (Day 21). Treatment of the remaining 14 mice was therefore initiated on the Day 21 (sacrifice Day 22). 10/14 mice had substantial tumors; 2/14 mice had small/probable tumors; and 2/14 mice had no visible tumor burden.

Figure 15:
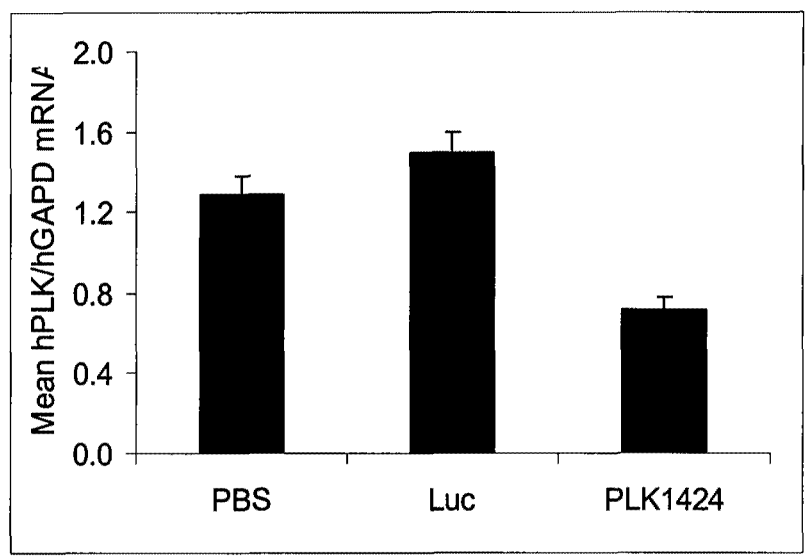
FIG. 15 illustrates data demonstrating that treatment with SNALP-formulated PLK1424 reduced PLK-1 mRNA levels by 50% in intrahepatic Hep3B tumors growing in mice 24 hours after SNALP administration.

FIG. 15 shows data from Quantigene assays used to measure human (tumor)-specific PLK-1 mRNA levels. A single 2 mg/kg dose of PLK1424 U4/GU SNALP reduced PLK-1 mRNA levels by about 50% in intrahepatic Hep3B tumors growing in mice.

Figure 16:
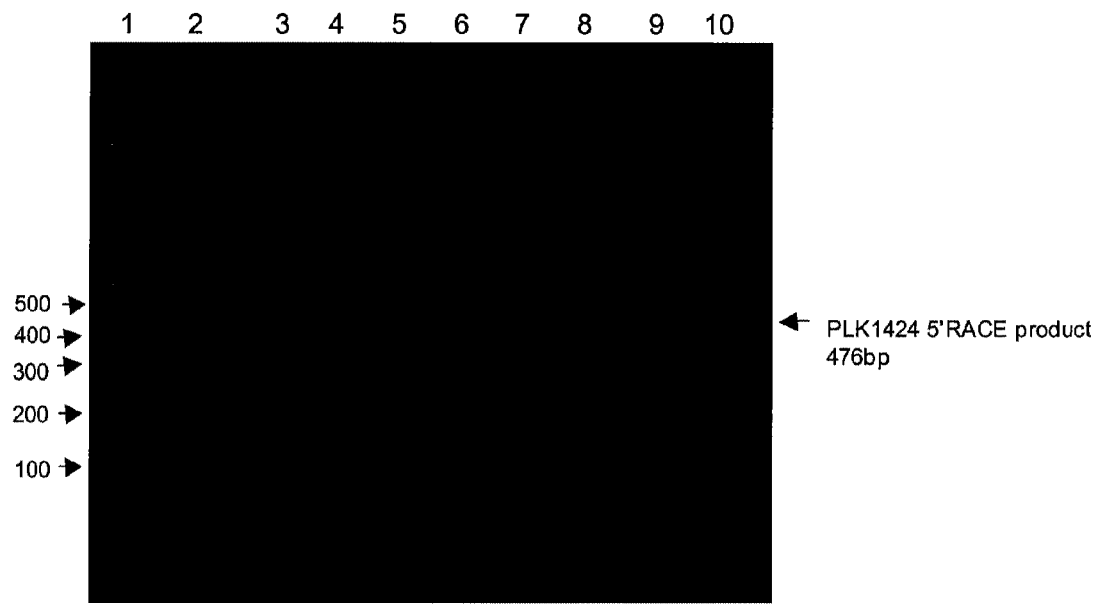
FIG. 16 illustrates data demonstrating that a specific cleavage product of PLK-1 mRNA was detectable in mice treated with PLK1424 SNALP by 5' RACE-PCR. 10 μl PCR product/well were loaded onto a 1.5% agarose gel. Lane Nos.: (1) molecular weight (MW) marker; (2) PBS mouse 1; (3) PBS mouse 2; (4) PBS mouse 3; (5) Luc SNALP mouse 1; (6) Luc SNALP mouse 2; (7) PLK SNALP mouse 1; (8) PLK SNALP mouse 2; (9) PLK SNALP mouse 3; and (10) no template control.

FIG. 16 shows that a specific cleavage product of PLK-1 mRNA was detectable in mice treated with PLK1424 SNALP by 5' RACE-PCR. No specific PCR product was detectable in mice treated with either PBS or control (Luc) SNALP. Nucleotide sequencing of the PCR product confirmed the predicted cleavage site by PLK1424 siRNA-mediated RNA interference in the PLK-1 mRNA.

Figure 17:
FIG. 17 illustrates data demonstrating that control (Luc) SNALP-treated mice displayed normal mitoses in Hep3B tumors (top panels), whereas PLK1424 SNALP-treated mice exhibited numerous aberrant mitoses and tumor cell apoptosis in Hep3B tumors (bottom panels).
Figure 17:
Figure 17:
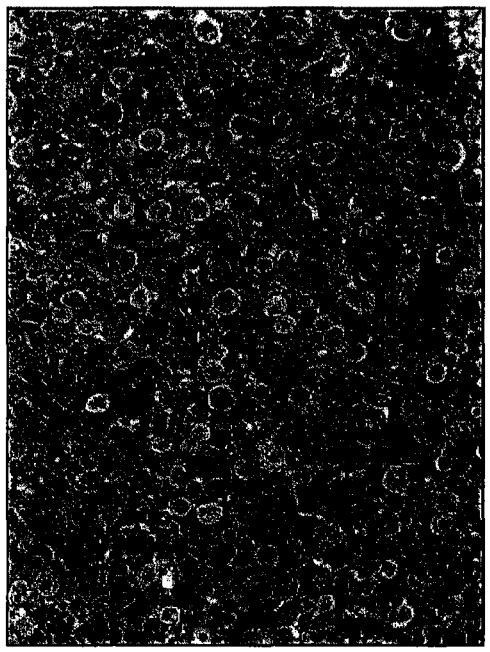
Figure 17:
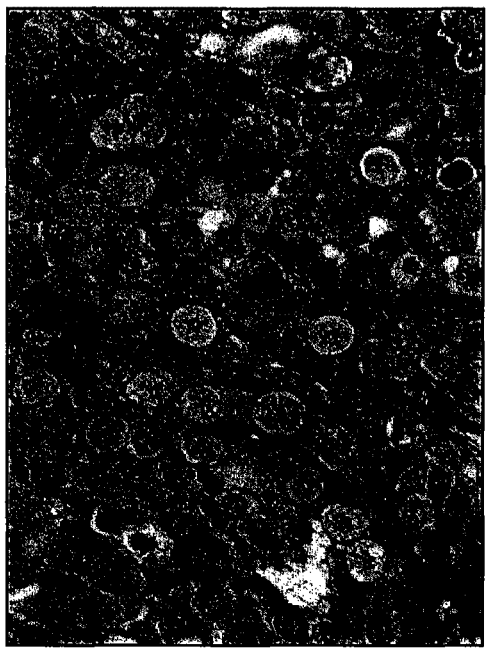

FIG. 17 shows Hep3B tumor histology in mice treated with either Luc SNALP (top) or PLK1424 SNALP (bottom). Luc SNALP-treated mice displayed normal mitoses in Hep3B tumors, whereas PLK1424 SNALP-treated mice exhibited numerous aberrant mitoses and tumor cell apoptosis in Hep3B tumors.

Conclusion

This example illustrates that a single administration of PLK1424 SNALP to Hep3B tumor-bearing mice induced significant in vivo silencing of PLK-1 mRNA. This reduction in PLK-1 mRNA was confirmed to be mediated by RNA interference using 5' RACE-PCR analysis. Importantly, PLK-1 mRNA silencing by SNALP-formulated PLK1424 profoundly disrupted tumor cell proliferation (mitosis), causing subsequent apoptosis of tumor cells. As demonstrated in the previous example, this anti-tumor effect translated into extended survival times in the tumor-bearing mice.

EXAMPLE 14

Comparison of PLK-1 SNALP Containing Either Peg-cDMA or PEG-cDSA in a Subcutaneous Hep3B Tumor Model This example demonstrates the utility of the PEG-lipid PEG-cDSA (3-N-[(-Methoxypoly(ethylene glycol)2000)carbamoyl]-1,2-distearyloxypropylamine) in the 1:57 formulation for systemically targeting distal (e.g., subcutaneous) tumors. In particular, this example compares the tumor targeting ability of PLK-1 SNALPs containing either PEG-cDMA ($C_{14}$) or PEG-cDSA ($C_{18}$). Readouts are tumor growth inhibition and PLK1 mRNA silencing. The PLK-1 siRNA used was PLK1424 U4/GU, the sequence of which is provided in Table 3.

Subcutaneous (S.C.) Hep3B tumors were established in scid/beige mice. Multi-dose anti-tumor efficacy of PLK-1 SNALP was evaluated for the following groups (n=5 for each group): (1) "Luc-cDMA"-PEG-cDMA Luc SNALP; (2) "PLK-cDMA"-PEG-cDMA PLK-1 SNALP; and (3) "PLK-cDSA"-PEG-cDSA PLK-1 SNALP. Administration of 6×2 mg/kg siRNA was initiated once tumors reached about 5 mm in diameter (Day 10). Dosing was performed on Days 10, 12, 14, 17, 19, and 21. Tumors were measured by caliper twice weekly.

Figure 18:
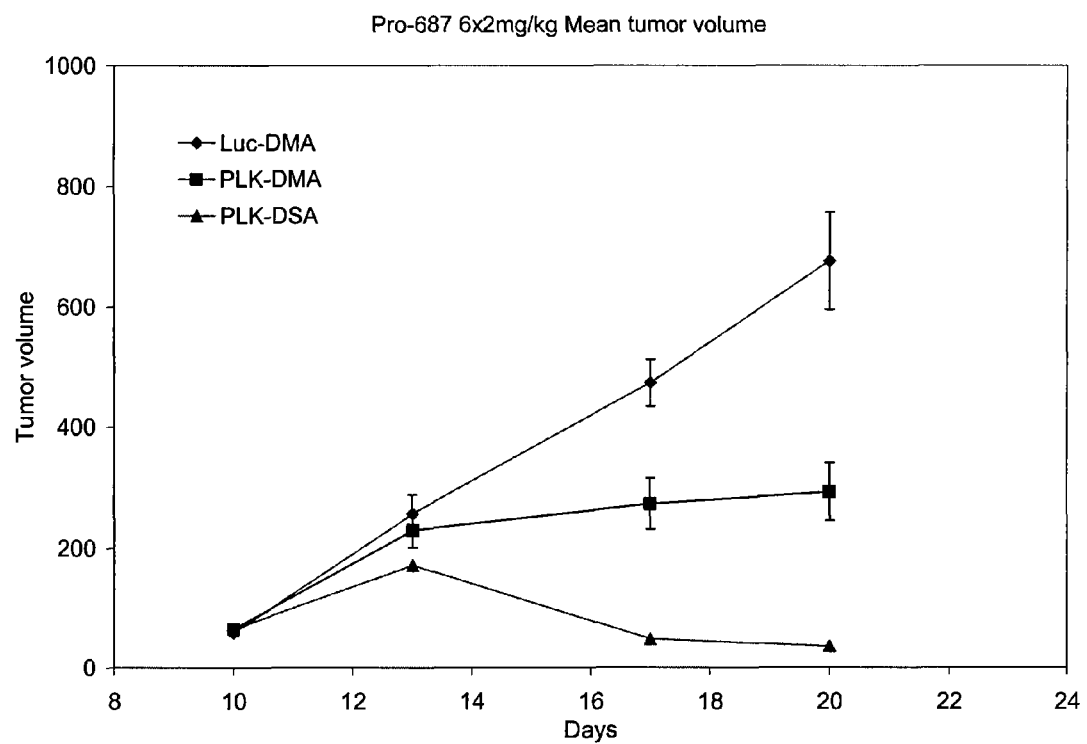
FIG. 18 illustrates data demonstrating that multiple doses of 1:57 PLK-1 SNALP containing PEG-cDSA induced the regression of established Hep3B subcutaneous (S.C.) tumors.

FIG. 18 shows that multiple doses of PLK-1 SNALP containing PEG-cDSA induced the regression of established Hep3B S.C. tumors. In particular, 5/5 tumors in the PLK1-cDSA treated mice appeared flat, measurable only by discoloration at the tumor site.

Figure 19:
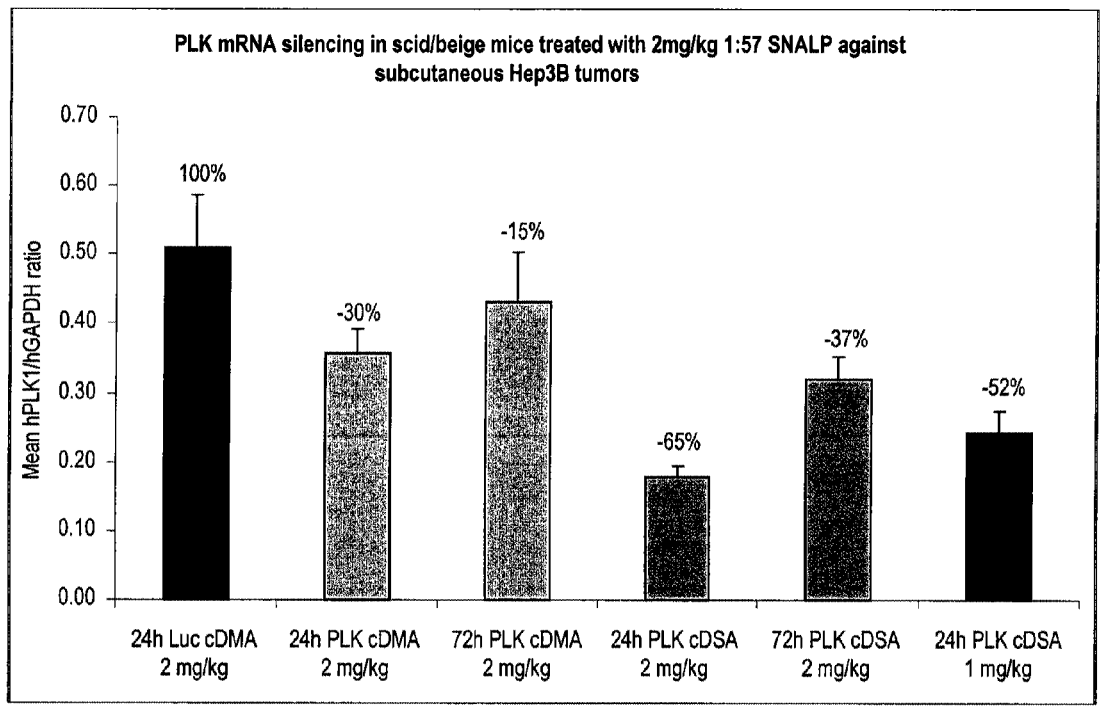
FIG. 19 illustrates data demonstrating mRNA silencing of 1:57 PLK SNALP in S.C. Hep3B tumors following a single intravenous SNALP administration.

FIG. 19 shows the mRNA silencing of PLK SNALP in S.C. Hep3B tumors following a single intravenous SNALP administration. The extent of silencing observed with the PLK1-cDSA SNALP correlated with the anti-tumor activity in the multi-dose study shown in FIG. 18.

Figure 20:
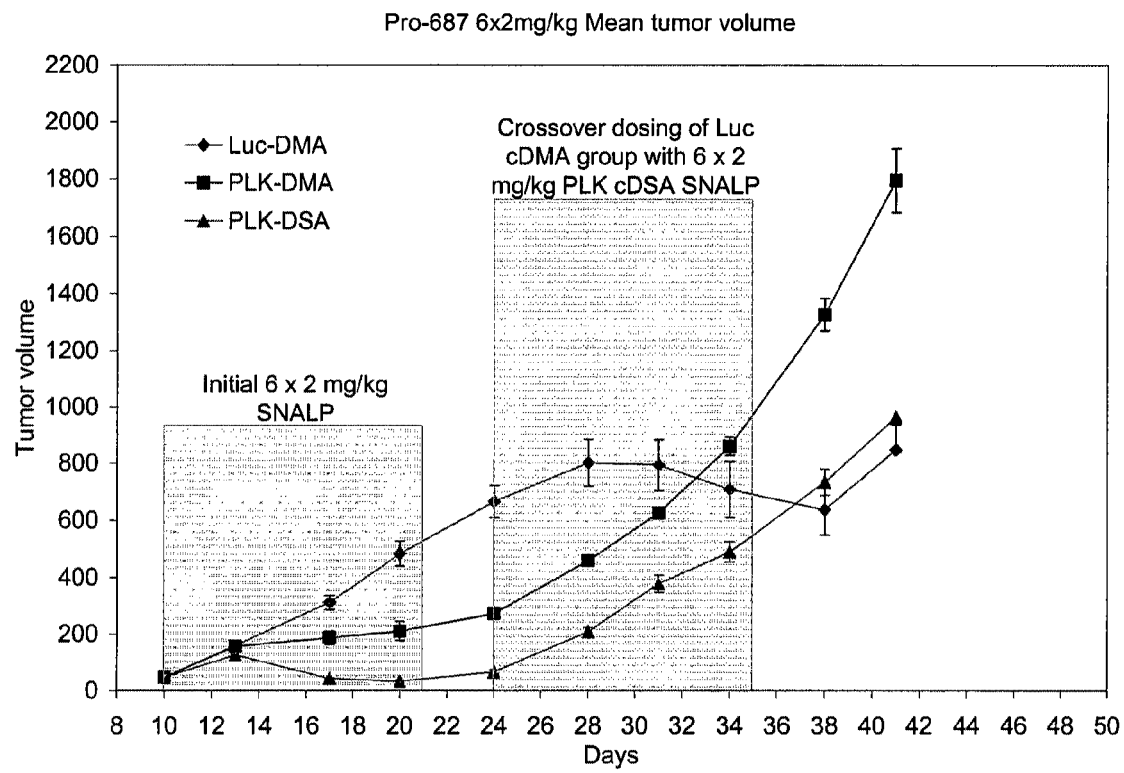
FIG. 20 illustrates data demonstrating that PLK1-cDSA SNALP inhibited the growth of large S.C. Hep3B tumors.

The Luc-cDMA SNALP-treated group, which had developed large S.C. tumors at Day 24, were then administered PLK-cDSA SNALP on Days 24, 26, 28, 31, 33, and 35. There was no additional dosing of the original PLK-1 SNALP-treated groups. The results from this crossover doing study with large established tumors is provided in FIG. 20, which shows that PLK1-cDSA SNALP inhibited the growth of large S.C. Hep3B tumors.

A comparison of the effect of PEG-cDMA and PEG-cDSA 1:57 SNALPs on PLK-1 mRNA silencing was performed using established intrahepatic Hep3B tumors in scid/beige mice. A single 2 mg/kg dose of PLK-1 SNALP containing either PEG-cDMA or PEG-cDSA was administered intravenously. Liver/tumor samples were collected at 24 and 96 hours after SNALP treatment. Control=2 mg/kg Luc-cDMA SNALP at 24 hours.

Figure 21:
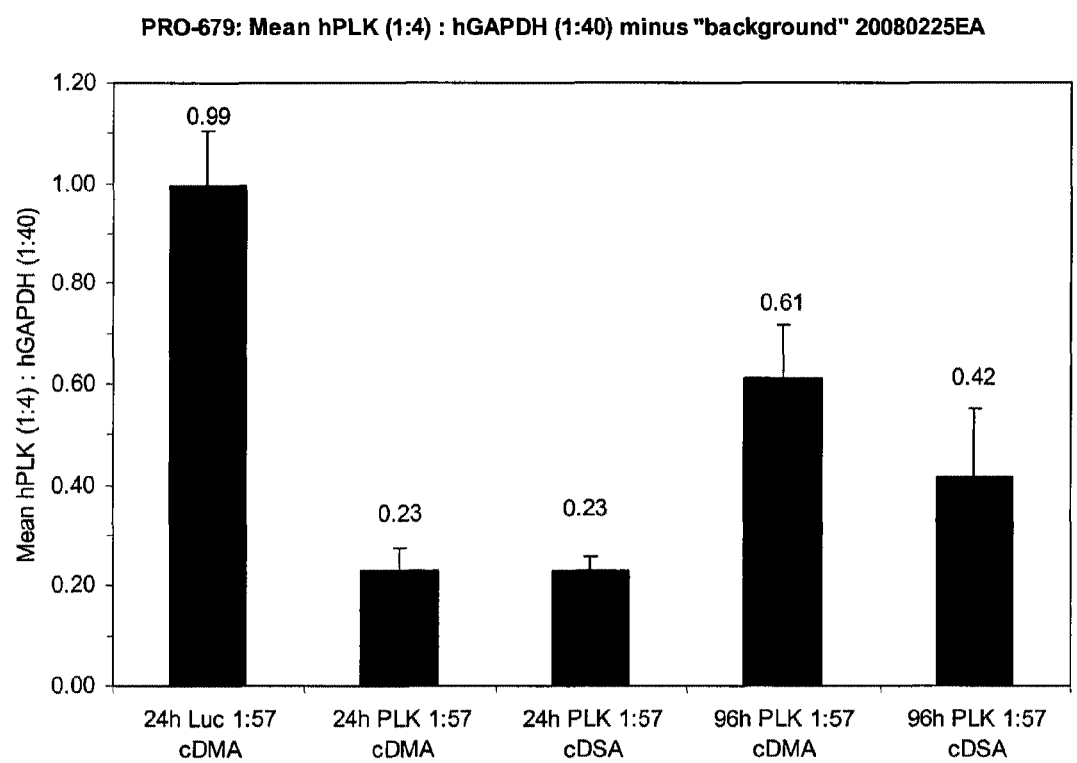
FIG. 21 illustrates data demonstrating tumor-derived PLK-1 mRNA silencing in Hep3B intrahepatic tumors.

FIG. 21 shows that PLK-cDMA SNALP and PLK-cDSA SNALP had similar silencing activities after 24 hours, but that the PLK-cDSA SNALP may increase the duration of mRNA silencing in intrahepatic tumors.

Figure 22:
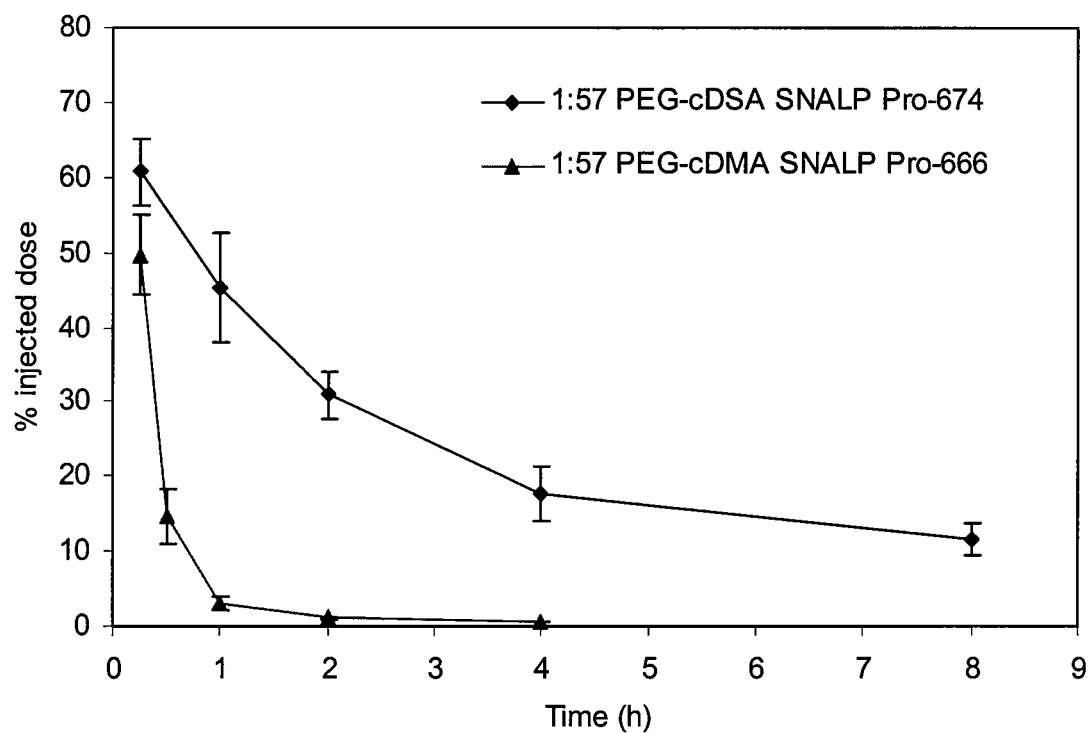
FIG. 22 illustrates data demonstrating the blood clearance profile of 1:57 PLK-1 SNALP containing either PEG-cDMA or PEG-cDSA.

FIG. 22 shows the blood clearance profile of PLK-1 SNALP containing either PEG-cDMA or PEG-cDSA. The extended blood circulation times observed for the PLK-cDSA SNALP may enable the increased accumulation and activity at distal (e.g., subcutaneous) tumor sites.

Thus, this study shows that the PEG-cDSA SNALP formulation can be used to preferentially target tumors outside of the liver, whereas the PEG-cDMA SNALP can be used to preferentially target the liver.

EXAMPLE 15

Confirming the RNAi-Mediated Mechanism of Action of siRNA-Based Cancer Therapeutics Short interfering RNAs (siRNA) that specifically silence the expression of cancer-related genes offer a novel therapeutic approach in oncology. However, it remains critical to delineate the true mechanism underlying their therapeutic activity. This example describes the development of chemically-modified siRNA targeting the essential cell cycle proteins Polo-like kinase1 (PLK-1) and kinesin spindle protein (KSP; also known as Eg5). siRNA formulated in lipid nanoparticles (SNALP) displayed potent anti-tumor efficacy in both hepatic and subcutaneous tumor models, exhibiting a degree of target gene silencing following a single intravenous administration that was sufficient to cause extensive mitotic disruption and tumor cell apoptosis. Specificity and siRNA mechanism of action was confirmed by: (1) the use of appropriately designed siRNA formulations that induced no measurable immune response, therefore excluding the potential for non-specific efficacy; (2) induction of RNAi-specific mRNA cleavage products in tumor cells; (3) correlation of this active RNAi signature with the duration of target mRNA silencing; and (4) confirmation of functional target inhibition by histologic biomarkers. This example provides results which represent a significant advance in the development of siRNA-based cancer therapeutics, and serves to highlight the technical requirements needed to support a conclusion that RNAi is the primary mechanism of siRNA-mediated therapeutic effects.

Introduction

Short interfering RNA (siRNA) are target-specific double-stranded RNA molecules designed to suppress gene expression through the endogenous cellular process of RNA interference (RNAi) (1). Since the characterization of this fundamental gene silencing mechanism, tremendous progress has been made in developing siRNA as a potentially novel class of therapeutic agent for a broad spectrum of diseases including cancer, viral infection, and metabolic disorders.

Many siRNA targets in oncology have been described in the literature, although direct evidence that their therapeutic effects in tumor models are mediated by RNAi is notably lacking. The interpretation of anti-tumor activity attributable to siRNA is problematic due to the potential for off-target effects of the nucleic acids, including their propensity to activate immune responses through TLR-dependent (2-4) and independent mechanisms (5, 6). These types of response are known to elicit anti-tumor effects, primarily through the actions of interferons and inflammatory cytokines that exert anti-angiogenic, pro-apoptotic, and adjuvant effects that enhance cellular immunity (7, 8). Many of these mechanisms remain active in the immunodeficient mouse strains typically used as hosts for human tumor xenografts, including SCID/beige mice that lack functional lymphocyte and NK cell populations (9, 10). Induction of the innate immune response by nucleic acids can also have significant toxicologic consequences (11). Clinical experience with certain recombinant cytokines and TLR agonists (12, 13) including liposomal plasmid DNA has shown that human subjects can be exquisitely sensitive to the toxic effects of these agents when compared to preclinical models. Therefore, additional caution is required if considering an immune stimulatory siRNA for clinical development (14, 15).

The incorporation of modified nucleotide chemistries into siRNA has been widely utilized to improve their pharmacologic and nuclease resistant properties (16). We first reported that extensive chemical modification to siRNA molecules could provide the additional benefit of preventing their recognition by the mammalian immune system (17). This has led to the rational design of 2'-O-methyl (2'OMe) modified siRNA constructs that have inherently low immunostimulatory potential in vivo (18).

To establish proof that systemically administered siRNA can elicit RNAi-mediated anti-cancer efficacy in the absence of measurable immune activation, we have selected the essential cell cycle proteins kinesin spindle protein (KSP, Eg5) (19) and Polo-like kinase 1 (PLK-1) (20) as validated cancer targets with well characterized mechanisms of direct tumor cell killing. KSP is a mitotic spindle motor protein that drives chromosome segregation during mitosis. Inhibition of KSP blocks the formation of bipolar mitotic spindles, causing cell cycle arrest, activation of the mitotic checkpoint and induction of apoptosis (21). In mammalian cells, PLK-1 acts to phosphorylate a number of cell cycle proteins, including Cdc25C, cyclin B, cohesin subunit SCC-1, subunits of the anaphase promoting complex, mammalian kinesin-like protein 1, and other kinesin-related proteins. This diverse array of substrates reflects the multiple roles of PLK-1 in mitosis and cytokinesis (22). Over-expression of PLK-1, observed in many human tumor types, is a negative prognosticator of patient outcome (20), while inhibition of PLK-1 activity rapidly induces mitotic arrest and tumor cell apoptosis (23, 24). Depletion of PLK-1 may also sensitize cancer cells to the pro-apoptotic activity of small molecule drugs (25), likely due to the role of PLK-1 in the DNA damage and spindle assembly checkpoints.

One of the primary barriers to realizing the potential of siRNA therapeutics is the requirement for drug delivery vehicles to facilitate disease site targeting, cellular uptake, and cytoplasmic delivery of the siRNA (26-28). Common approaches to delivery include complexing the siRNA with polycations such as polyethyleneimine (29, 30) and cyclodextrin polymers (31) or incorporation into cationic lipid-based carriers (17, 18, 26, 32). We have previously described the development of stable nucleic acid-lipid particles (SNALP) as an effective systemic delivery vehicle for targeting siRNA to the murine and non-human primate liver and have demonstrated therapeutic effects in silencing endogenous hepatocyte (18, 26) and viral gene transcripts (17). The accumulation of SNALP within tissues of clinical interest takes advantage of passive disease site targeting (33, 34), whereby charge neutral carriers of suitable size (around 100 nm diameter or smaller) can pass through the fenestrated epithelium of tumors, sites of inflammation, and the healthy liver. This avoids the requirement for active targeting moieties such as peptides, antibodies, and receptor ligands that may otherwise be candidates for incorporation into siRNA delivery vehicles to enhance target cell selectivity (31, 35, 36).

This example describes the development of SNALP formulated siRNA as novel cancer therapeutics. Results demonstrate that rationally designed siRNA targeting PLK-1 or KSP, when delivered with an effective systemic delivery vehicle, are able to affect therapeutic gene silencing in solid tumors. The specificity and mechanism of action is confirmed using a combination of methodologies that demonstrate RNAi-mediated silencing of target mRNA causing mitotic disruption in tumor cells typical of target inhibition. This can be achieved in the complete absence of immune stimulation through the use of appropriately designed, chemically modified siRNA.

Results

In Vitro Characterization of PLK-1 siRNA Activity

Figure 23:
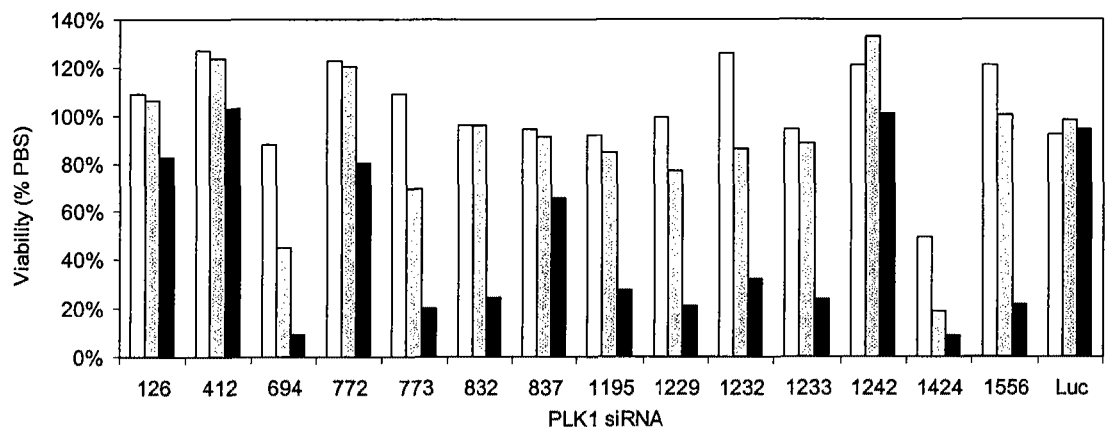
FIG. 23 illustrates data demonstrating an in vitro activity screen of PLK-1 siRNA sequences. Activity of native PLK-1 siRNA sequences targeting human PLK-1 mRNA were assessed in the HT29 cell viability assay. Cells were treated with SNALP formulated PLK-1 or Luc siRNA at 1 nM (white bar), 5 nM (grey bar), and 25 nM (black bar). Cell viability was assessed at 72 h using CellTiter Blue resazurin dye. Two rounds of siRNA design (A & B, C) were conducted. Sequence numbers represent the siRNA target site in the hPLK-1 mRNA open reading frame (Genbank Accession No. NM_005030).
Figure 23:
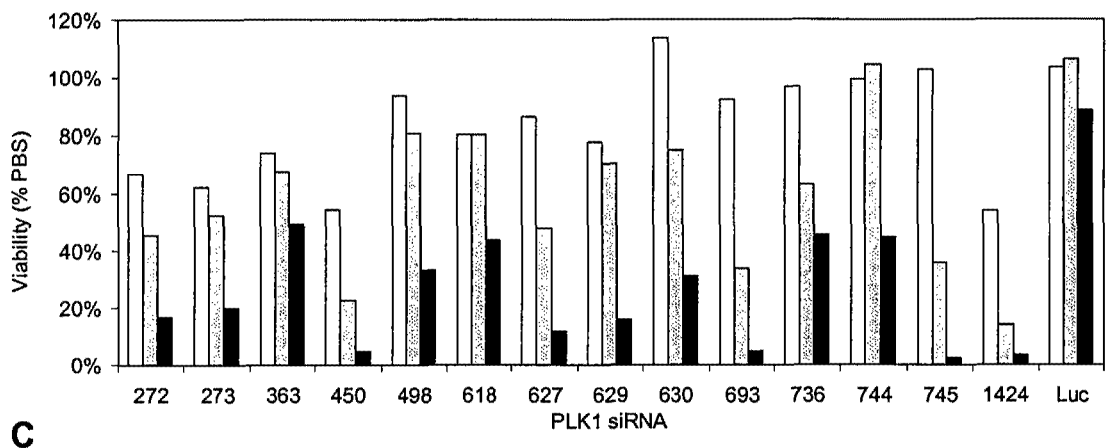
Figure 23:
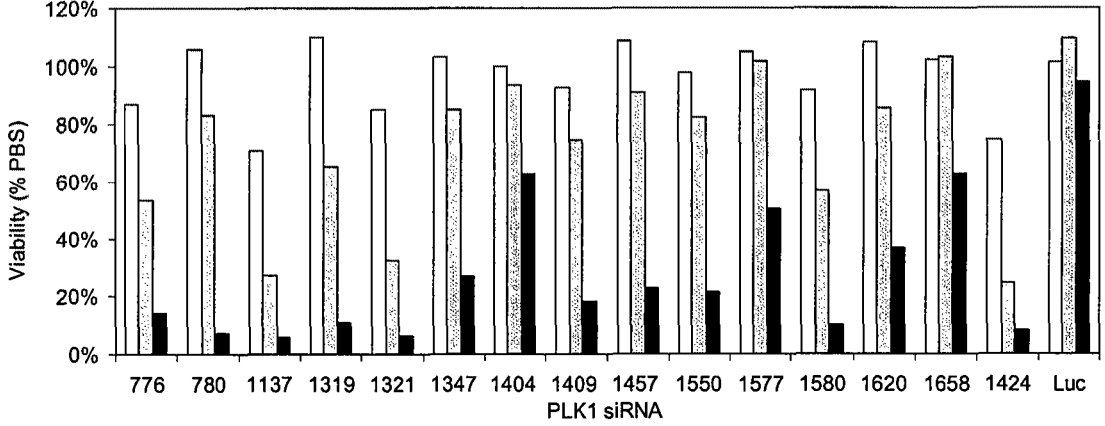
Figure 24:
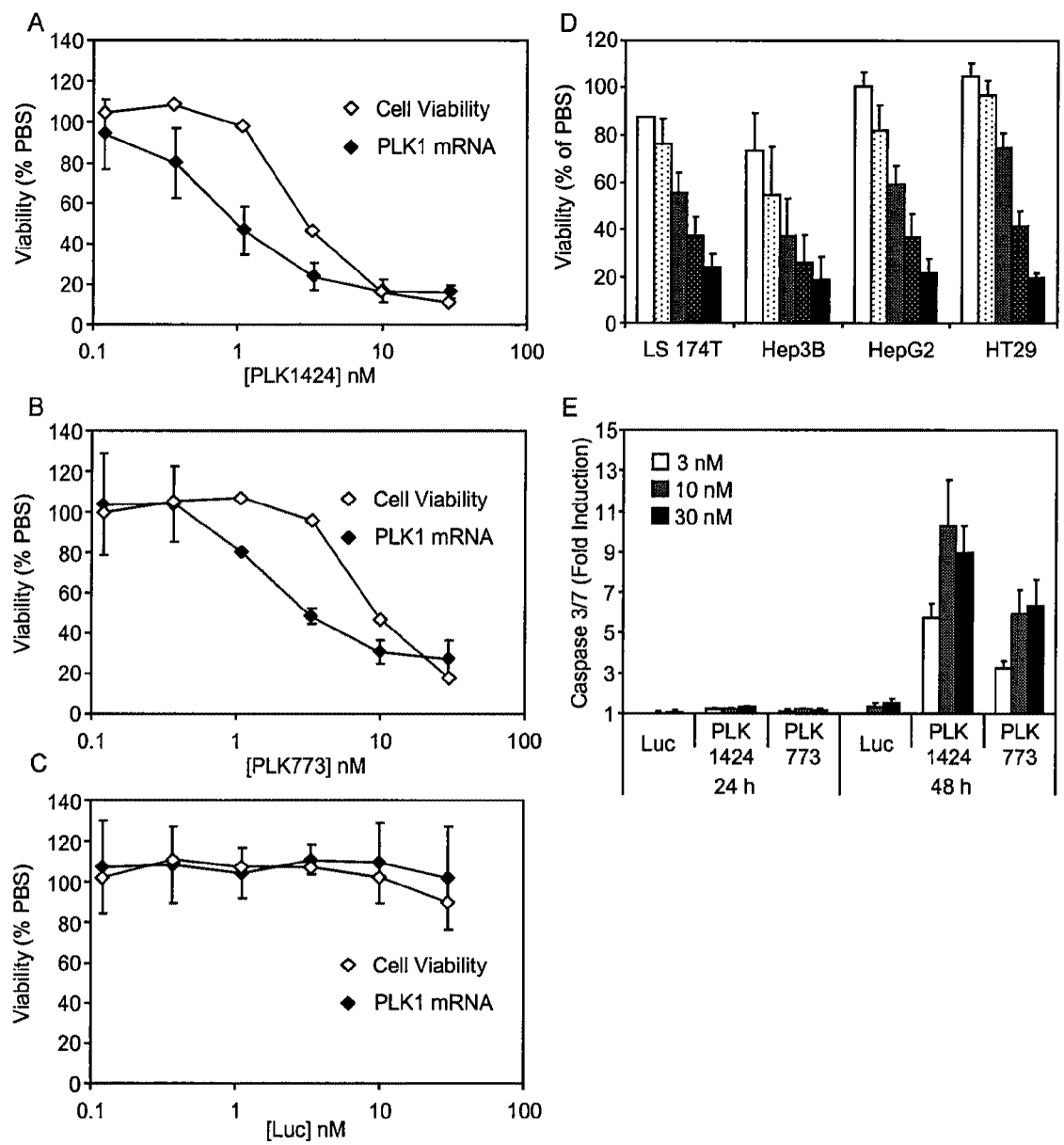
FIG. 24 illustrates data demonstrating the activity of PLK-1 siRNAs in vitro. Correlation between mRNA silencing and HT29 cell viability for (A) PLK1424, (B) PLK773, or (C) Luc siRNA treatments. PLK-1 mRNA was determined by bDNA analysis at 24 h. Duplicate plates were assessed for cell viability at 72 h. (D) PLK1424 siRNA causes dose dependent reductions in viability of LS174T, HT29, Hep3B, and HepG2 cell cultures. Cells were treated for 72 h with PLK1424 SNALP at 5 (black bar), 2.5, 1.25, 0.63, and 0.31 (white bar) nM siRNA. Values in (A)-(D) are expressed as % viability or PLK-1 mRNA relative to PBS control and reflect mean of 3 separate experiments (+/−SD) conducted in triplicate cultures. (E) Decreased cell viability is associated with the induction of apoptosis. Caspase 3/7 activity in LS174T cells was assessed 24 h and 48 h after treatment with SNALP encapsulated PLK773, PLK1424, or Luc control siRNA. Data represents fold induction over PBS in triplicate cultures (mean+/−SD triplicate cultures).

PLK-1 represents a validated gene target in oncology whose inhibition is known to cause mitotic arrest and apoptosis in proliferating tumor cell cultures (20). We designed and screened a panel of novel PLK-1 siRNA for anti-proliferative activity in the human HT29 colon cancer cell line (FIG. 23). This screen identified PLK1424 as the most potent human siRNA and PLK773 as the most potent mouse, rat, and human cross-reactive siRNA based on PLK-1 sequence homology. These lead siRNA were formulated into a SNALP composition that has been shown to effectively target siRNA to the liver of rodents and non-human primates (26). Treatment of HT29 cells with formulated PLK1424 and PLK773 siRNA caused a dose-dependent decrease in cell viability that correlated with the degree of PLK-1 mRNA silencing (FIG. 24A-C). PLK1424 siRNA displayed potent activity in a range of human cancer cell lines, including LS174T colon carcinoma and HepG2 and He3B hepatocellular carcinoma (HCC) cell lines (FIG. 24D), that was associated with the dose-dependent induction of apoptosis 48 h after siRNA transfection (FIG. 24E).

Design of PLK-1 and KSP siRNA for In Vivo Applications

Figure 25:
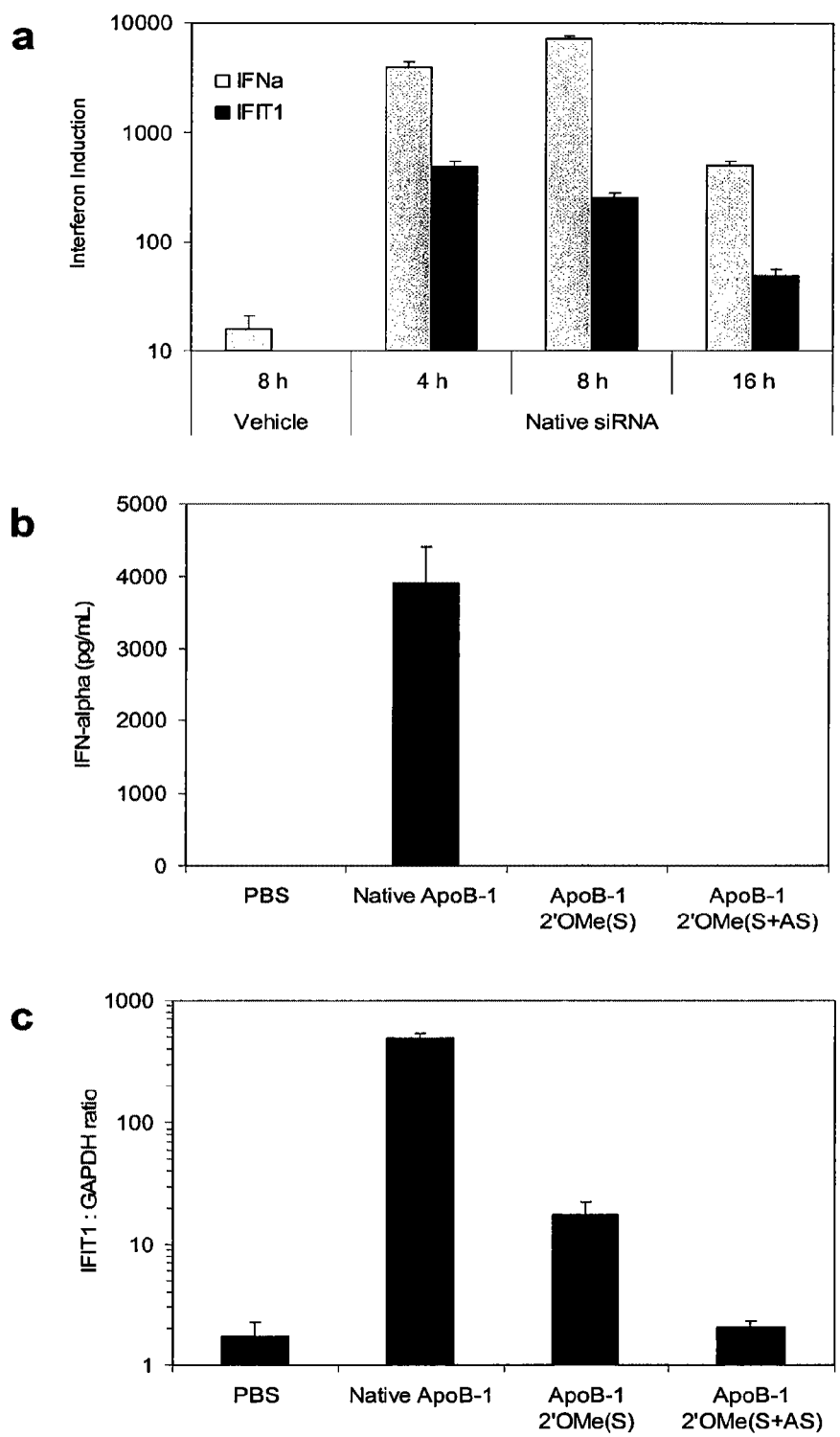
FIG. 25 illustrates data demonstrating the in vivo characterization of the interferon response induced by SNALP-formulated siRNA. (a) Time course for the induction of serum IFNα and liver IFIT1 mRNA after i.v. administration of SNALP formulated native (unmodified) ApoB1 siRNA. Balb/c mice (n=4 per group) were administered 2.5 mg/kg siRNA or lipid vehicle; serum IFNα (pg/mL) and IFIT1 mRNA (relative to GAPDH) from whole liver lysates were assessed after 4, 8, and 16 h by ELISA and bDNA assay, respectively. (b,c) Measurement of IFIT1 mRNA induction in target tissues can resolve residual immunostimulatory activity within siRNAs. Mice were treated with the native ApoB-1 siRNA or ApoB-1 siRNAs containing selective 2′OMe nucleotides in either the sense (S) strand or both strands (S+AS). (b) Serum IFNα and (c) liver IFIT1 mRNA were assessed 4 h after administration (mean+SD, n=4). Residual immunostimulatory activity in the absence of systemic cytokine induction was evident by IFIT1 mRNA induction in ApoB-1 2′OMe(S) treated mice. This response was fully abrogated by the incorporation of additional 2′OMe nucleotides into the AS strand of the siRNA duplex. All siRNAs retained full RNAi activity.

Prior to the in vivo assessment of synthetic siRNA, it is essential to anticipate the potential effects of immune stimulation on the biological system under consideration and take steps to mitigate this risk (11). We have previously reported that the selective introduction of 2'OMe-guanosine or 2'OMe-uridine residues into siRNA abrogates its capacity to activate an immune response (18, 37). This original strategy proposed restricting 2'OMe modifications to the siRNA sense strand in order to minimize the potential of negatively impacting RNAi activity (18). While this approach remains broadly applicable for synthetic siRNA (37), we have found through extensions to our original studies that certain siRNA sequences incorporating a 2'OMe-modified sense strand, for example the U(S)-ApoB1 duplex (18), may retain low-grade immunostimulatory activity. This was only evidenced by the induction of IFN-inducible p56 IFIT1 mRNA in the liver and spleen following intravenous administration of SNALP-formulated U(S)-ApoB1 siRNA in mice, despite there being no measurable serum cytokine response (FIG. 25). This residual IFIT1 induction, however, could be fully abrogated by the selective introduction of 2'OMe nucleotides to the antisense (AS) strand of the duplex (FIG. 25). These findings provided the rationale for our design and testing of 2'OMe siRNA against oncology targets.

Figure 26:
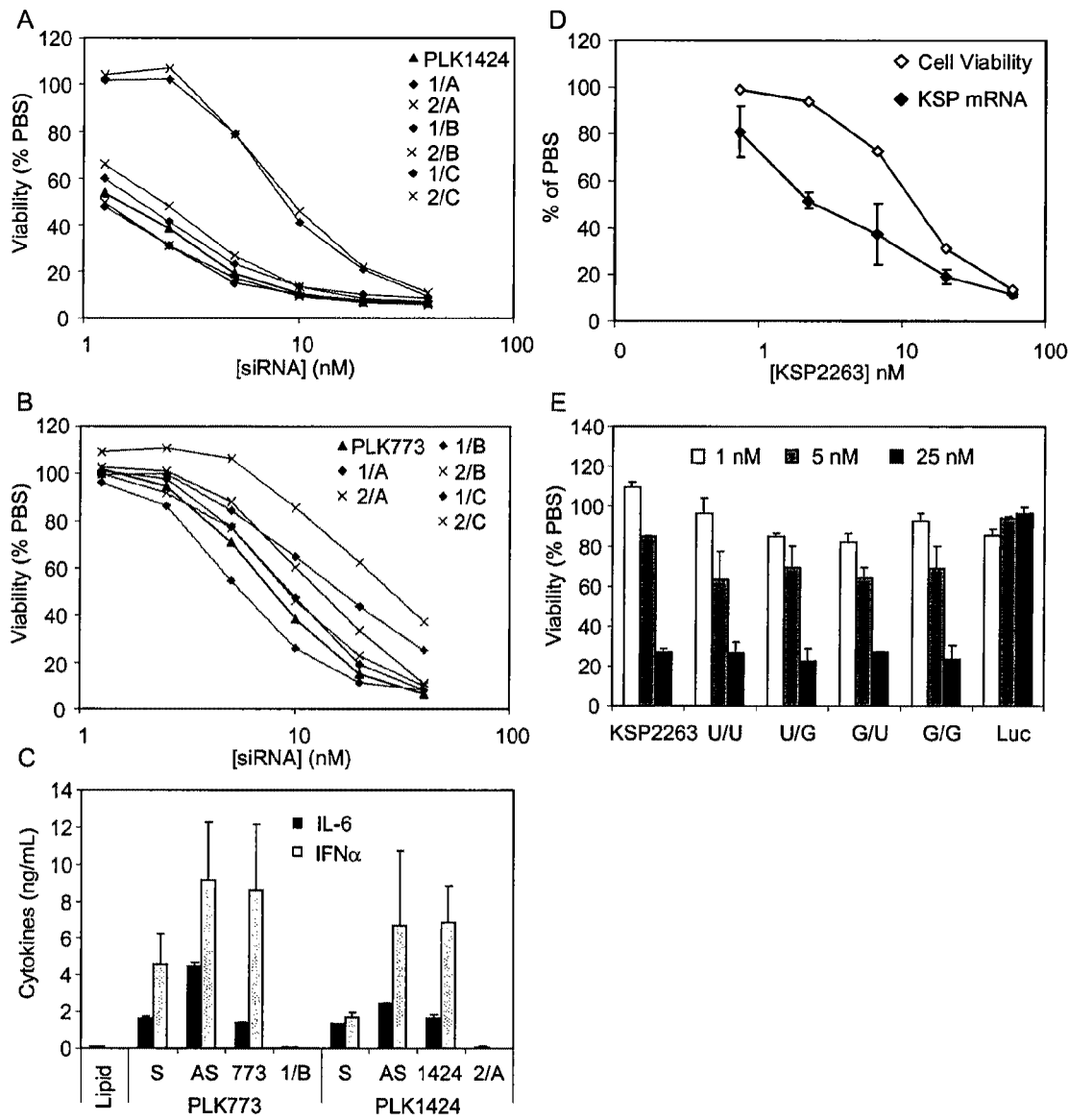
FIG. 26 illustrates data demonstrating the in vitro activity of unmodified versus 2′OMe-modified PLK-1 and KSP siRNA. Activity of the 2′OMe-modified panels of (A) PLK1424 and (B) PLK773 siRNA. Unmodified PLK1424 or PLK773 siRNA (black) were compared in the Hep3B cell viability assay to the 2′OMe modified duplexes 1/A, 2/A, 1/B, 2/B, 1/C, or 2/C that comprise the respective 2′OMe sense/antisense oligonucleotides (see, Table 6). Data are mean viability of triplicate cultures relative to PBS treated cells and representative of 2 independent experiments using SNALP-formulated siRNA. (C) Cytokine induction by unmodified and 2′OMe PLK-1 siRNA in vitro. Murine Flt3L DC were treated with 5 µg/mL unmodified PLK773 or PLK1424 siRNA duplexes (773, 1424) and their constituent sense (S) or antisense (AS) oligonucleotides or the 2′OMe siRNA duplexes PLK773-1/B and PLK1424-2/A formulated in SNALP. IFNα and IL-6 were assayed in culture supernates at 24 h. Values are mean+SD of 3 separate experiments conducted in triplicate cultures. (D,E) Activity of SNALP-formulated KSP2263 siRNA in murine Neuro2a cells. (D) Correlation between KSP mRNA silencing and cell viability relative to PBS control. KSP mRNA was determined by bDNA analysis at 24 h. Duplicate plates were assessed for cell viability at 72 h. (E) Activity screen comparing the unmodified KSP2263 siRNA to the panel of 2′OMe-modified duplexes (see, Table 6) in the Neuro2a cell viability assay. Data represents mean+/−SD triplicate cultures, relative to PBS treatment.

A similar approach to siRNA design was applied to PLK1424 and PLK773 to generate duplexes that possessed no measurable immune stimulatory effects yet retaining full RNAi activity. This step was regarded as a pre-requisite to conducting in vivo studies in order to conclude the specificity of anti-tumor effects that may be observed. 2'OMe-U or 2'OMe-G nucleotides were substituted into the native sense and AS oligonucleotides to form a panel of modified PLK1424 and PLK773 duplexes (Table 6) that were then screened for the preservation of RNAi activity. 2'OMe-PLK1424 duplexes containing the modified AS strands A or B showed similar anti-proliferative activity to the native PLK1424 sequence when paired with either of the modified sense strands 1 or 2. 2'OMe-PLK1424 containing AS strand C displayed anti-proliferative activity at higher concentrations (FIG. 26A). The panel of 2'OMe-PLK773 duplexes displayed modest differences in activity compared to the native PLK773 sequence (FIG. 26B). We selected PLK1424-2/A and PLK773-1/B siRNA duplexes (comprising the designated 2'OMe-modified sense/AS strands) for evaluation in an in vitro immune stimulation model. As expected, native PLK1424 and PLK773 siRNA and their constituent single stranded RNA (ssRNA) stimulated murine Flt3-ligand derived dendritic cells to produce high levels of both IFNα and IL-6 (FIG. 26C), whereas this immune reactivity was completely abrogated in the PLK1424-2/A and PLK773-1/B duplexes.

TABLE 6

PLK-1, KSP, and Luc siRNA sequences with 2'OMe modification patterns.

| Name | Strand | Sequence (5'-3' 21 mer) | SEQ ID NO: |
|---|---|---|---|
| PLK1424 | S | AGAUCACCCUCCUUAAAUAUU | 211 |
| PLK1424 | AS | UAUUUAAGGAGGGUGAUCUUU | 212 |
| PLK1424-1 | S | AGAUCACCCUCCUUAAAUAUU | 213 |
| PLK1424-2 | S | AGAUCACCCUCCUUAAAUAUU | 214 |
| PLK1424-A | AS | UAUUUAAGGAGGGUGAUCUUU | 215 |
| PLK1424-B | AS | UAUUUAAGGAGGGUGAUCUUU | 216 |
| PLK1424-C | AS | UAUUUAAGGAGGGUGAUCUUU | 217 |
| PLK773 | S | AGACCUACCUCCGGAUCAAUU | 218 |
| PLK773 | AS | UUGAUCCGGAGGUAGGUCUUU | 219 |
| PLK773-1 | S | AGACCUACCUCCGGAUCAAUU | 220 |
| PLK773-2 | S | AGACCUACCUCCGGAUCAAUU | 221 |
| PLK773-A | AS | UUGAUCCGGAGGUAGGUCUUU | 222 |
| PLK773-B | AS | UUGAUCCGGAGGUAGGUCUUU | 223 |
| PLK773-C | AS | UUGAUCCGGAGGUAGGUCUUU | 224 |
| KSP2263 | S | CUGAAGACCUGAAGACAAUdTdT | 225 |
| KSP2263 | AS | AUUGUCUUCAGGUCUUCAGdTdT | 226 |
| KSP2263-U | S | CUGAAGACCUGAAGACAAUdTdT | 227 |
| KSP2263-G | S | CUGAAGACCUGAAGACAAUdTdT | 228 |
| KSP2263-U | AS | AUUGUCUUCAGGUCUUCAGdTdT | 229 |
| KSP2263-G | AS | AUUGUCUUCAGGUCUUCAGdTdT | 230 |
| Luc | S | GAUUAUGUCCGGUUAUGUAUU | 231 |
| Luc | AS | UACAUAACCGGACAUAAUCUU | 232 |
| Luc-U | S | GAUUAUGUCCGGUUAUGUAUU | 233 |
| Luc-U | AS | UACAUAACCGGACAUAAUCUU | 234 |

2'-O-methyl (2'OMe) nucleotides are indicated in bold and underlined. The sense (S) or antisense (AS) strand can alternatively or additionally comprise 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides.

To demonstrate the utility of this approach to siRNA design, the same methodology was applied to a published siRNA targeting KSP (38). The selected KSP siRNA (termed KSP2263 from its original description) has full sequence homology to mouse and human KSP mRNA and showed potent anti-proliferative effects in both human and mouse cancer cell lines. As an example, treatment of mouse Neuro2a cells with SNALP-formulated KSP2263 induced dose-dependent reductions in KSP mRNA 24 h after transfection, correlating with a subsequent loss of cell viability at 72 h (FIG. 26D). A panel of modified KSP2263 duplexes containing 2'OMe-U or 2'OMe-G nucleotides (Table 6) was then screened in this assay. In this case, each combination of the two modified sense and AS strands generated a duplex with equivalent potency to the native KSP2263 sequence, confirming preservation of RNAi activity (FIG. 26E). We selected the 2'OMe-modified variant KSP2263-U/U for further characterization.

Confirmation of the RNAi Mechanism by 5'RACE-PCR

Figure 27:
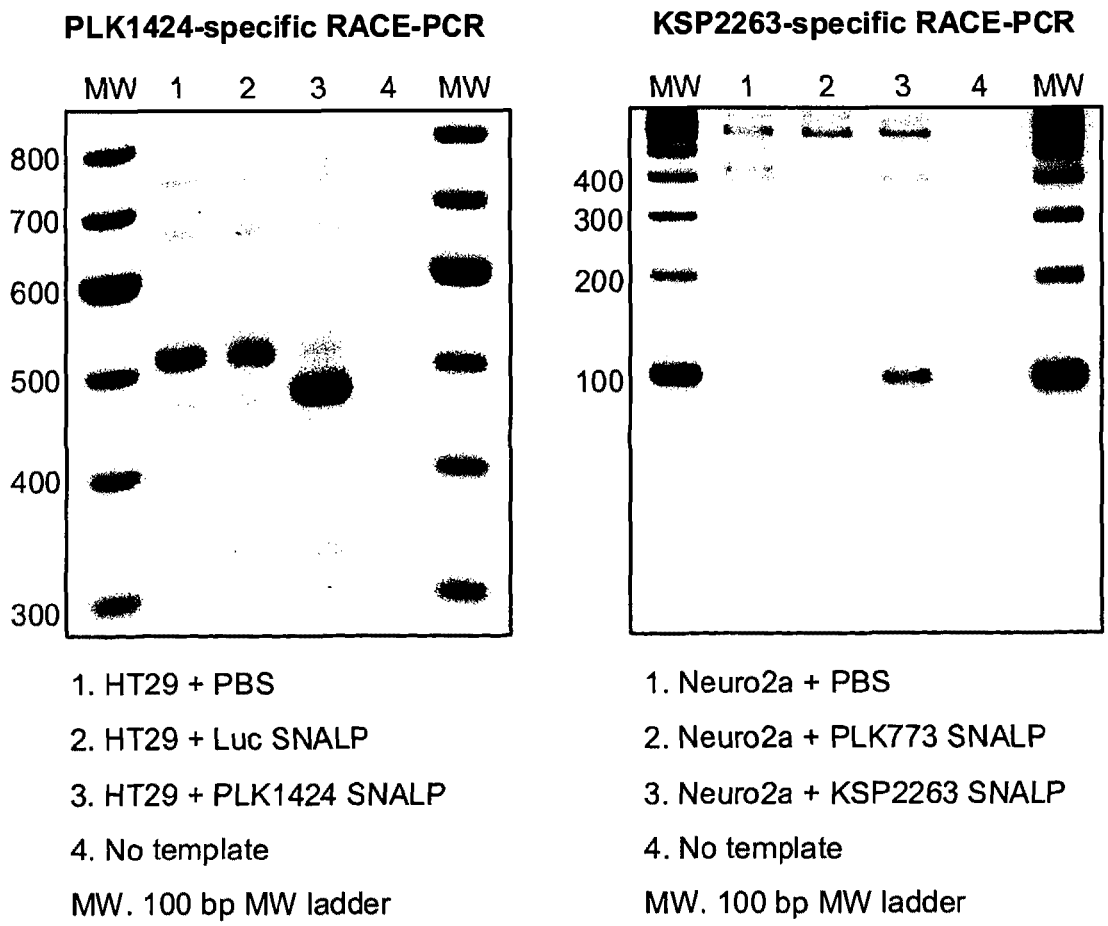
FIG. 27 illustrates data demonstrating the detection of the PLK1424-specific and KSP2263-specific mRNA cleavage products and by 5′RACE-PCR in vitro. (A) HT29 cells were treated with 10 nM SNALP-formulated PLK1424, Luc siRNA or PBS. RNA was isolated 24 hours after transfection and assayed for the specific PLK-1 mRNA cleavage product by 5′-RACE-PCR. (B) Neuro2a cells were treated with SNALP-formulated KSP2263, PLK773 siRNA or PBS. RNA was isolated 24 hours after transfection and assayed for the specific mouse KSP mRNA cleavage product by 5′-RACE-PCR. The identity of the RNAi-specific 476 bp PLK-1 mRNA and 102 bp KSP mRNA cleavage products were confirmed by direct oligonucleotide sequencing.

The detection of specific RNA cleavage products generated by RISC-mediated hydrolysis of target mRNA is the definitive marker confirming RNAi as the mechanism of gene silencing (39, 40). Activated RISC cleaves target mRNA precisely between the nucleotides complementary to positions 10 and 11 of the siRNA AS strand generating an mRNA cleavage product that is unique to the siRNA sequence. This can be detected in cells using an appropriately designed 5'-rapid amplification of cDNA ends-PCR method (RACE-PCR). We developed RACE-PCR assays to detect the PLK1424-specific cleavage product of human PLK-1 mRNA and the KSP2263-specific cleavage product of mouse KSP mRNA. Treatment of HT29 cells with PLK1424-2/A generated the predicted 476 bp 5' RACE-PCR product and oligonucleotide sequencing across the 5' ligation site confirmed its identity as the human PLK-1 mRNA product cleaved at the 5' position 1433 (relative to ATG start site) (FIG. 27). Similarly, a predicted 102 bp RACE-PCR product was amplified from Neuro2a cells treated with KSP2263-U/U siRNA that corresponded to mouse KSP mRNA cleaved at position 2129 (FIG. 27).

Characterization of the Immune Response to 2'OMe PLK-1 and KSP siRNA In Vivo

Figure 28:
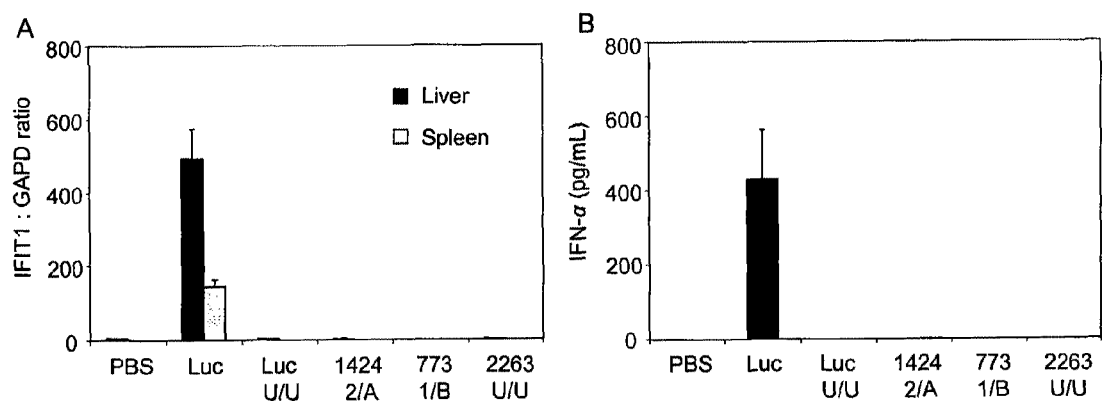
FIG. 28 illustrates data demonstrating that 2′OMe-modified PLK-1, KSP, or Luc siRNA induce no measurable IFN response in mice. SNALP-formulated Luc (unmodified) and the 2′OMe-modified Luc-U/U, PLK1424-2/A, PLK773-1/B, or KSP2263-U/U siRNA were administered at 2 mg/kg i.v. to Balb/C mice. (A) IFIT1 relative to GAPDH mRNA in liver and spleen was assessed at 4 h by bDNA analysis. (B). Serum IFNα was assessed at 6 h by ELISA. SNALP-formulated 2′OMe siRNAs induced no detectable increase in either IFNα protein or IFIT1 mRNA relative to PBS vehicle. Values represent mean+SD (n=4).

To confirm the abrogation of immune stimulation by the 2'OMe siRNA in vivo, Balb/c mice were treated intravenously with SNALP-formulated PLK1424-2/A, PLK773-1/B, KSP2263-U/U, or a control 2'OMe siRNA targeting luciferase (Luc-U/U). IFIT1 mRNA and serum cytokines were assessed 4-6 h after SNALP administration based on the approximate time of peak response for these markers. In these studies, SNALP-formulated native Luc siRNA (Table 6) was used as a positive control for immune stimulation. Intravenous administration of this unmodified siRNA induced 83-fold and 247-fold increases in IFIT1 mRNA in the liver and spleen, respectively, compared to PBS treated controls (FIG. 28A). This was consistent with the detection of systemic IFNα in these animals (FIG. 28B). In contrast, the PLK1424-2/A, PLK773-1/B, KSP2263-U/U, or Luc-U/U siRNAs induced no measurable IFNα or increase in IFIT1 mRNA in the liver or spleen relative to PBS treated animals, confirming that these SNALP-formulated siRNA caused no discernable IFN signaling in either the liver as primary target organ for this formulation or in secondary lymphoid tissues (FIG. 28). As previously reported (18), the administration of SNALP-formulated 2'OMe siRNA induced no increase in other serum cytokines including IL-6, IL-10, IL-12, TNF, or IFNγ and displayed a similar lack of immune reactivity in primary human immune cell cultures.

This siRNA design and screening approach can be applied to any given sequence to rapidly identify siRNA in which the chemical modifications are well tolerated with respect to RNAi activity and predicted to fully abrogate immune stimulation. Unlike other chemical modification strategies for siRNA, enhancing nuclease resistance was not a primary design consideration since SNALP, the intended delivery vehicle for in vivo studies, is known to protect unmodified siRNA from nuclease degradation for greater than 24 h in serum (18). However, the 2'OMe modification pattern can take into account the avoidance of: (1) position 9 in the sense strand based on the observation that efficient activation of RISC involves initial cleavage of the siRNA sense strand between positions 9-10 and this can be inhibited by the introduction of nuclease resistant chemistries at this linkage (41, 42); and (2) the 5' antisense terminus where modified chemistries may interfere with effective RNA loading into RISC (43, 44).

Therapeutic Inhibition of Tumor Growth by Systemic siRNA Administration

Orthotopic liver tumor models were established to examine the pharmacodynamics and therapeutic efficacy of SNALP-formulated PLK1424-2/A and KSP2263-U/U siRNA. These were a Hep3B xenograft in scid/beige mice as a representative model of human HCC and a syngeneic Neuro2a tumor model in immune competent A/J mice. Tumor cells were injected directly into the left lateral liver lobe to establish primary intrahepatic tumors (45). This procedure resulted in histologically distinct, localized tumor nodules in greater than 90% of mice in both models.

Figure 29:
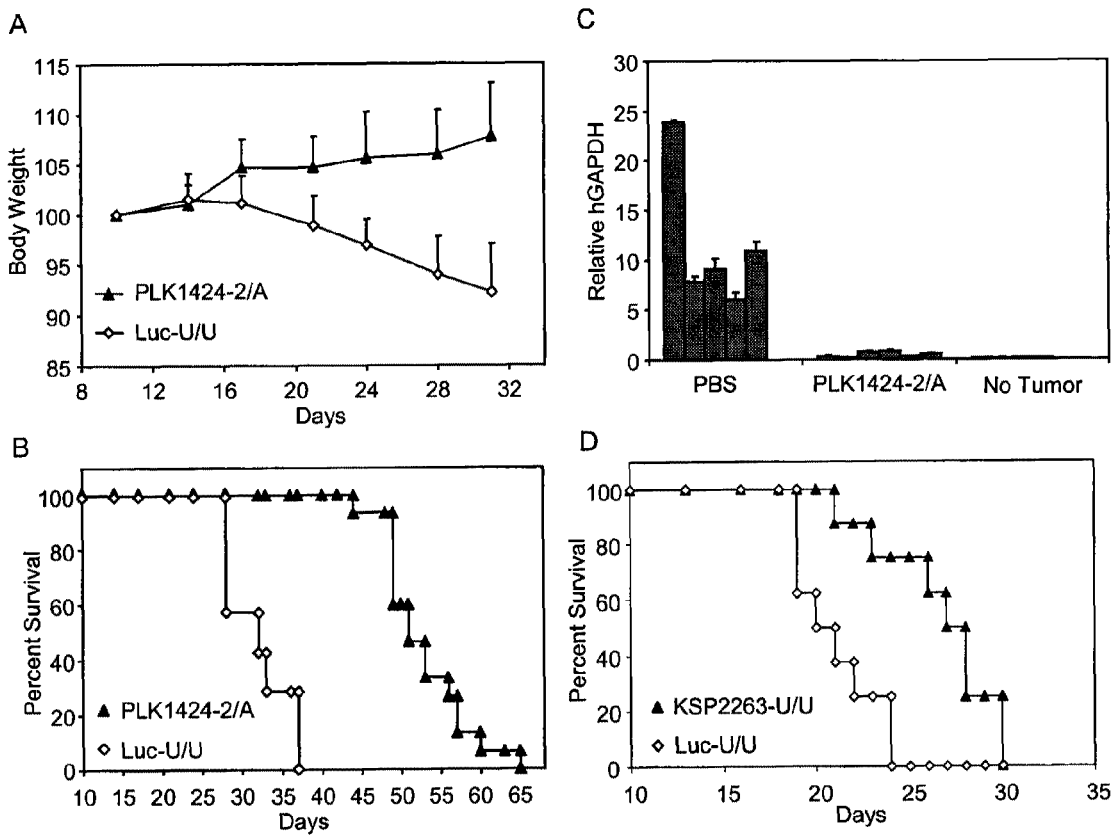
FIG. 29 illustrates data demonstrating the therapeutic activity of PLK-1 and KSP siRNA in hepatic tumors. PLK1424-2/A treatment confers significant survival advantages in scid/beige mice bearing hepatic Hep3B tumors. Mice were administered SNALP-formulated PLK1424-2/A (n=15) or Luc-U/U (n=8) at 6×2 mg/kg, intravenous twice weekly (d 10 to d 28). (A) Body weights (mean+SD) over the dosing period expressed as % of initial weight on d 10. (B) Kaplan-Meier plot of days to euthanization due to tumor burden. PLK1424-2/A treatment provided significant survival advantage over control treatment. (p=0.03, Log-rank Mantel Cox test). (C) Residual hepatic Hep3B tumor burden in mice 24 h after final administration of PLK1424-2/A siRNA (5×2 mg/kg siRNA on d 8, 11, 14, 18 & 21). Bars represent hGAPDH mRNA/mg liver of individual mice (mean+/−SD of triplicate analyses) determined by human-specific bDNA assay (No tumor=livers from non-tumor seeded mice). See FIG. 32 for additional data. (D) KSP2263-U/U treatment confers survival advantages in A/J mice bearing hepatic Neuro2a tumors. Mice were administered SNALP-formulated KSP2263-U/U or Luc-U/U (n=8) at 5×4 mg/kg, intravenous (q3d×5 from d 8 to d 21 after tumor seeding). A Kaplan-Meier plot of days to euthanization due to tumor burden and endpoints are based on clinical scores as a humane surrogate for survival. Mean SNALP particle size and (polydispersity) were 83 (0.09), and 90 (0.12) nm for PLK1424 and Luc formulations, respectively.
Figure 30:
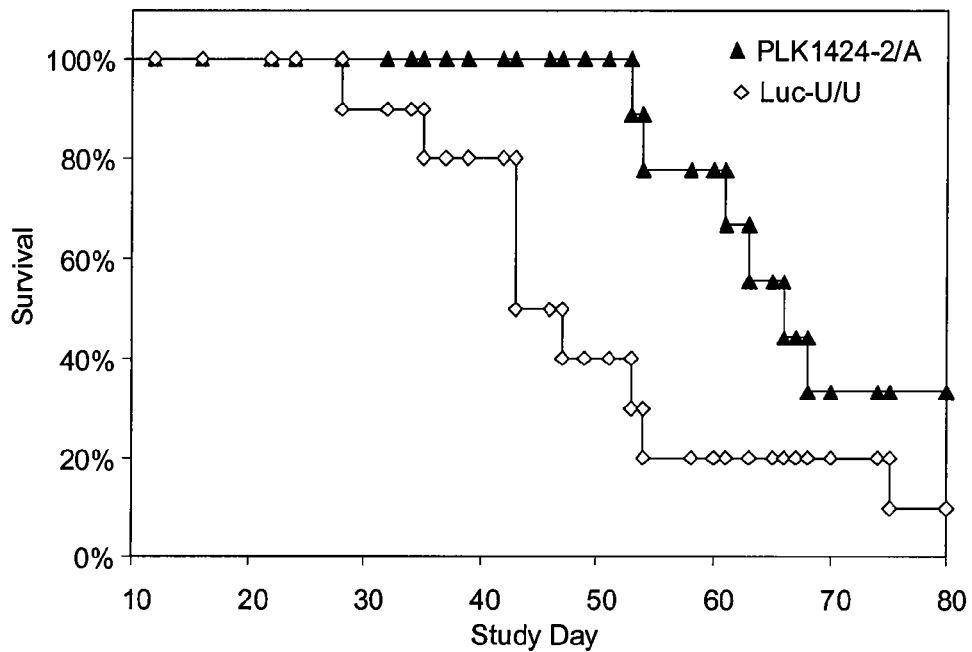
FIG. 30 illustrates data demonstrating that PLK1424 SNALP confers significant survival advantages in the hepatic Hep3B-nu/nu mouse model. Mice bearing established hepatic tumors were treated with PLK1424-2/A or Luc-U/U SNALP (2 mg/kg twice weekly between d11 and d28 after tumor seeding) and monitored for tumor burden until euthanasia defined by humane endpoints. Data represent 2 independent studies. Median survival of PLK1424 vs Luc in Study (A)=d 45 and d 67, respectively; p=0.02. and study (B)=d 42 and undefined, respectively, p=0.008, Log-rank Mantel Cox test. All animals surviving beyond day 80 were found to be tumor free at termination of the study on day 100.
Figure 30:
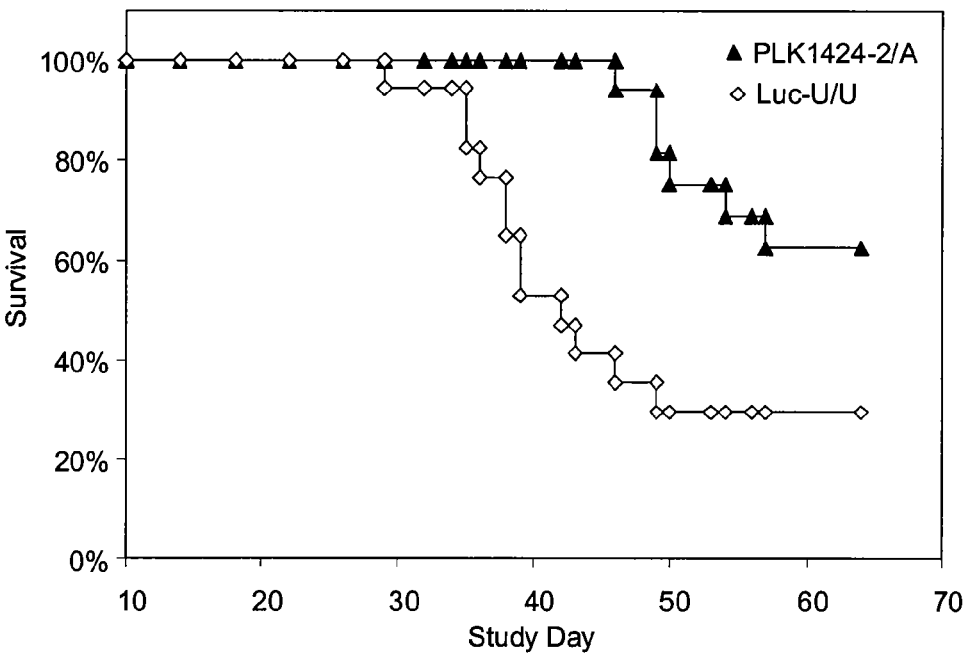

To evaluate the therapeutic efficacy of SNALP formulated PLK1 siRNA, mice bearing established Hep3B liver tumors were treated with 2 mg/kg PLK1424-2/A or Luc-U/U siRNA by intravenous administration twice weekly for 3 weeks, until control groups displayed symptoms of extensive tumor burden. We have found progressive body weight loss to be a good indicator of hepatic tumor burden in the Hep3B-scid/beige mouse model. Weight loss in Luc-U/U treated mice was evident 12-16 days after tumor implantation and proceeded throughout the remainder of the study (FIG. 29A). In contrast, PLK1424-2/A SNALP treated mice typically maintained body weight over the duration of treatment, indicating that the siRNA formulation was well tolerated and suggesting therapeutic benefit. Death is not an acceptable endpoint in animal studies; therefore, a humane endpoint was defined according to daily clinical scores which were an aggregate of weight loss, body condition, and abdominal distension. In this aggressive orthotopic model, the time until first euthanization in the Luc-U/U group was 28 d after tumor seeding with a median survival time of 32 d. By comparison, the times to first euthanization and median survival in the PLK1424-2/A SNALP treated mice were significantly extended to 44 d and 51 d, respectively ($p<0.05$; FIG. 29B). Similar extensions to survival times were observed in repeat studies utilizing athymic nu/nu mice as hosts (FIG. 30).

Figure 31:
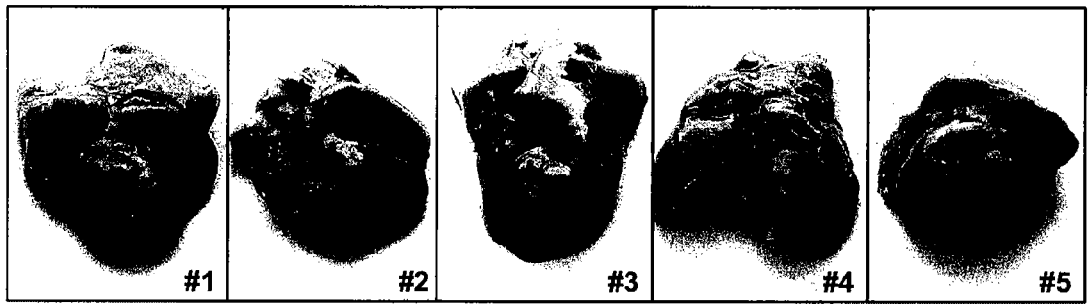
FIG. 31 illustrates data demonstrating that PLK1424-2/A SNALP significantly reduces macroscopic tumor burden after completion of dosing. Results are from individual mice described in FIG. 37C. Livers from (A) PBS control and (B) PLK1424-2/A SNALP treated mice showing macroscopic tumor burden in the left lateral hepatic lobe. (C) Body weights of individual mice shown in (A) and (B) over the duration of the study from day 8-day 21 after tumor seeding. Loss of body weight directly correlated with tumor burden in individual mice.
Figure 31:
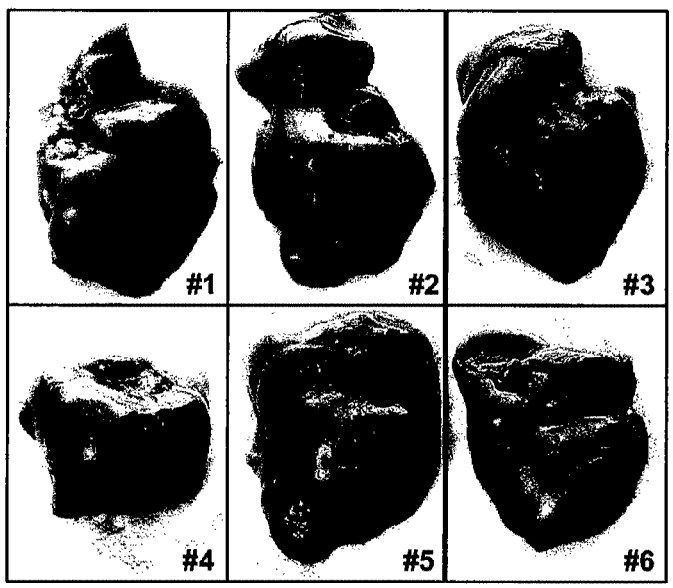
Figure 31:
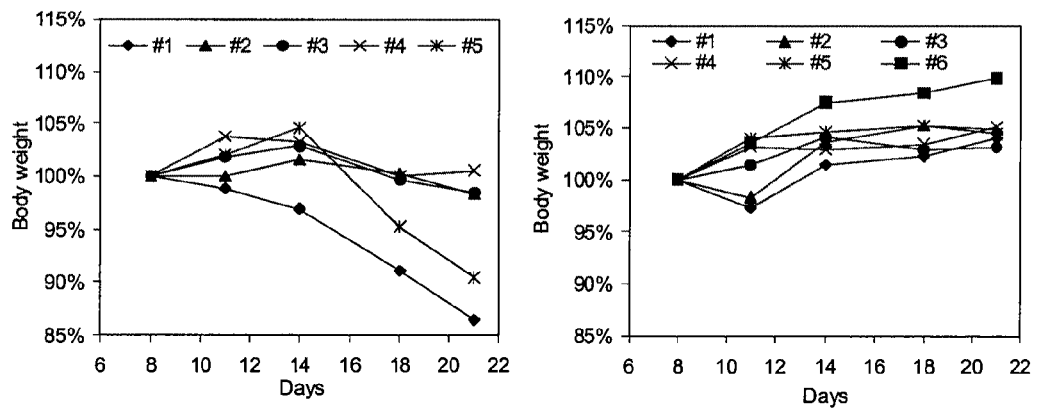

The extent of Hep3B liver tumor burden was then assessed at the completion of dosing with PLK1424-2/A on day 22 after tumor implantation (1 day after the fifth siRNA dose). At autopsy, only 2 of 6 PLK1424-2/A treated mice had visible tumors localized around the site of cell implantation into the liver lobe, compared to extensive macroscopic tumor burden in corresponding control animals (FIG. 31). Species-specific probe sets to human GAPDH (hGAPDH) mRNA detected low levels of this tumor-derived signal in 5 of 6 PLK1424-2/A treated mice, ranging from 2 to 6-fold above the background signal from normal mouse liver (FIG. 29C), indicating that tumor growth was significantly suppressed but not completely eradicated by this treatment regime.

Figure 32:
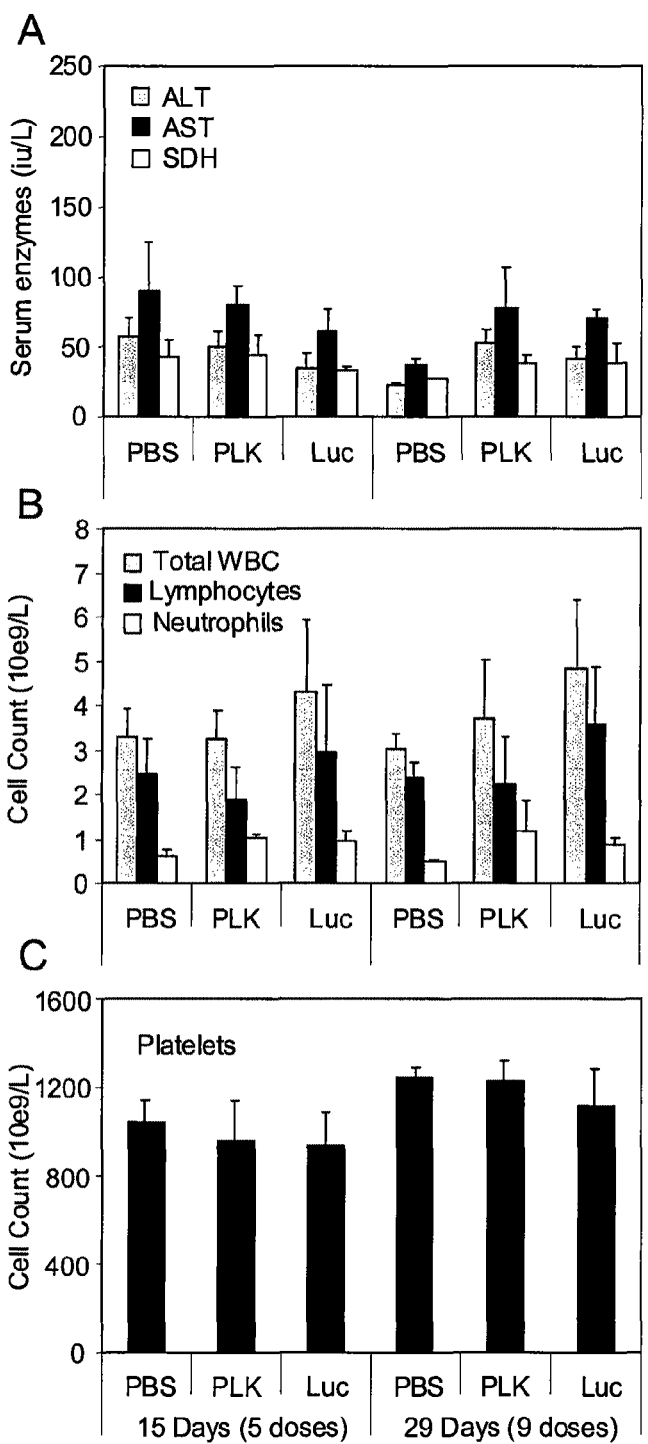
FIG. 32 illustrates data demonstrating that PLK-1 SNALP is well tolerated in mice. Groups of CD1 ICR mice were administered PBS, PLK773-1/B, or Luc-U/U SNALP to assess potential cumulative toxicities associated with either PLK-1 silencing or the lipid vehicle. Mice were treated twice weekly at 2 mg/kg siRNA, equivalent to the efficacious dosing regimen in tumor studies. Clinical chemistry and complete blood counts were evaluated 24 h after dose 5 (day 15) and dose 9 (day 29). siRNA treatment induced no significant changes in (A) serum liver enzymes alanine aminotransferase (ALT), aspartate aminotransferase (AST), or sorbitol dehydrogenase (SDH); (B) Total wbc, lymphocyte or neutrophil counts and (C) platelet counts at either 15 or 29 days treatment duration. All values are mean+/−SD (n=6). No changes in red blood cell parameters were observed.

To examine more closely the tolerability of systemic siRNA administration, multi-dose toxicity studies were conducted using the mouse surrogate PLK773-1/B. Repeat administration of SNALP formulated PLK773-1/B at 2 mg/kg, twice weekly (mirroring the therapeutic dosing regimen) caused no significant changes in serum liver enzymes, total wbc, lymphocyte and neutrophil counts, platelet numbers, or rbc parameters assessed after 15 and 29 days of continuous treatment (FIG. 32). These results indicated that the therapeutic dosing regime established in the orthotopic tumor model caused minimal hepatocellular toxicity and no significant bone marrow dysfunction of the type frequently observed with the systemic administration of small molecule anti-mitotic drugs.

The therapeutic effect of SNALP-formulated KSP2263-U/U siRNA in syngeneic Neuro2a liver tumors was next evaluated. Median survival time of mice receiving Luc-U/U SNALP (4 mg/kg, Q3d x5) was 20 d in this model, compared to 28 d in the KSP2263-U/U treatment group (FIG. 29D), demonstrating therapeutic efficacy with SNALP-formulated siRNA for another oncology target.

Confirmation of RNAi-Mediated Tumor Gene Silencing In Vivo

Figure 33:
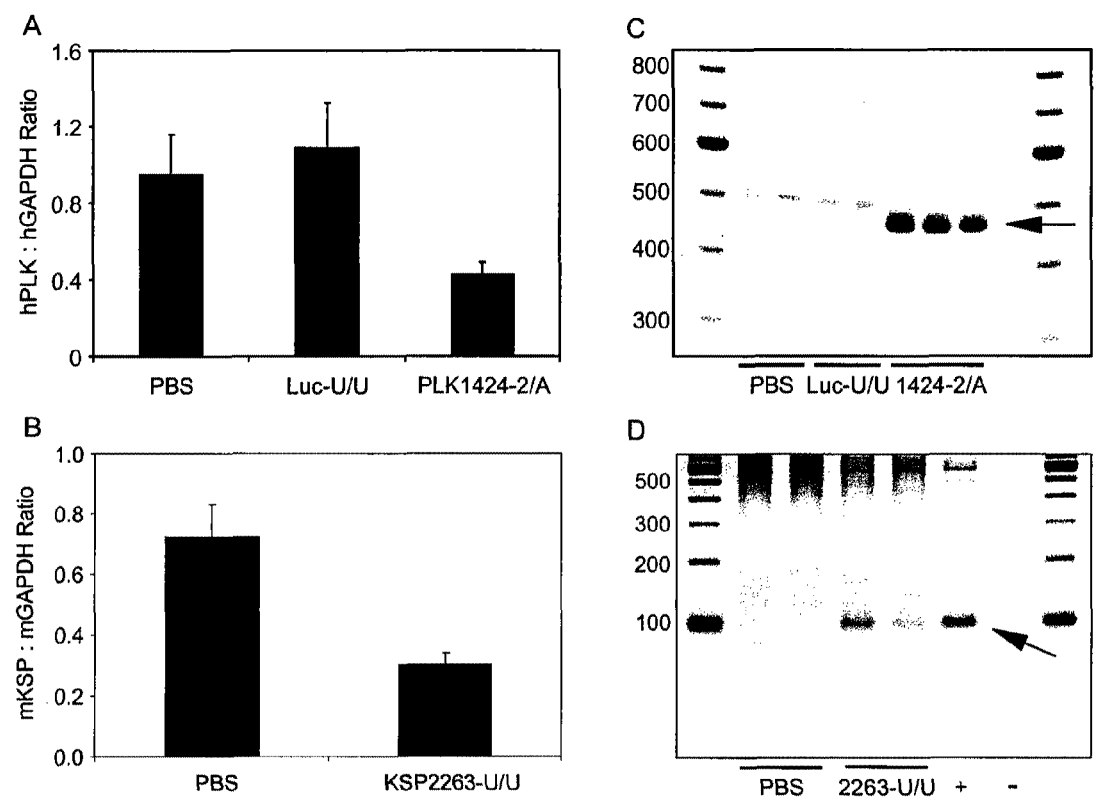
FIG. 33 illustrates data demonstrating target mRNA silencing in hepatic tumors by the RNAi mechanism. (A,B) Target mRNA silencing and (C,D) detection of RNAi-specific mRNA cleavage products in tumors following SNALP formulated siRNA administration. Scid/beige mice with established intrahepatic Hep3B tumors were administered a single 2 mg/kg dose of SNALP formulated PLK1424-2/A or Luc-U/U siRNA and RNAi activity assessed by (A) PLK-1 mRNA in tumor lysates and (C) 5' RACE-PCR analysis. (A) Tumor (human) PLK-1:GAPDH mRNA ratios 24 h after siRNA administration (Mean+/−SD of 4 animals). (C) RACE-PCR detects the specific 5' cleavage product of PLK-1 mRNA from tumors analyzed in (A). Lanes represent PCR products derived from individual PBS (n=2), Luc-U/U (n=2), and PLK1424-2/A (n=3) treated mice. (B) mouse KSP mRNA and (D) 5'RACE-PCR analysis of resected hepatic Neuro2a tumors from mice treated with SNALP formulated KSP2263-U/U siRNA. Data is presented as in (A) and (C). +=positive control from in vitro Neuro2a cell lysates treated with KSP2263-U/U siRNA; −=no template control. RACE-PCR detects the specific 5' cleavage product of mouse KSP mRNA from tumors. Identities of the predicted 476 bp PLK-1 and 102 bp KSP PCR products (arrows) were confirmed by direct DNA sequencing. Mean SNALP particle size and (polydispersity) were 83 (0.09), 90 (0.12), and 88 (0.07) nm for the PLK1424, Luc, and KSP2263 formulations, respectively.

Despite demonstrating that the 2'OMe siRNA did not induce a measurable immune response in mice, it remained critical to show that RNAi was the primary mechanism underlying the potent therapeutic effects of these PLK-1 and KSP siRNA formulations. A single intravenous administration of SNALP-formulated PLK1424-2/A (2 mg/kg) caused a significant reduction in tumor-derived human PLK-1 (hPLK-1) mRNA in hepatic hep3B tumors 24 h after administration (45%+/−6.8% of hPLK-1 mRNA levels in PBS-treated mice; FIG. 33A). A similar reduction in mouse KSP mRNA expression was achieved using an equivalent dose of KSP2263-U/U in the hepatic Neuro2a tumor model (FIG. 33B). In contrast to KSP and PLK-1 expression in tumors, endogenous expression of both these genes in the surrounding non-proliferative liver was found to be very low, below the level of detection of the branched DNA assay employed in these studies. Since the expression of cell cycle genes such as PLK-1 and KSP are typically down-regulated as cells exit cell cycle (22), any non-specific, anti-proliferative effects induced by siRNA or the delivery vehicle would cause a general decrease in their expression within tumors. We therefore confirmed RNAi as the mechanism responsible for mRNA silencing in vivo by the 5'-RACE PCR method. A PCR product of the predicted size was readily amplified from hepatic Hep3B tumor samples taken 24 h after administration of PLK1424-2/A SNALP (FIG. 33C). Oligonucleotide sequencing of the 476 bp PCR product from three individual mice confirmed its identity as the predicted 5' cut end of hPLK-1 mRNA. This PCR product was not evident in tumors taken from Luc-U/U siRNA treated mice or in liver samples from non-tumor bearing animals. RACE-PCR analysis also confirmed the specific induction of RNAi-mediated KSP mRNA cleavage within tumors of KSP2263-U/U treated animals (FIG. 33D).

5'-RACE-PCR to Monitor the Duration of RNAi in Tumors

Figure 34:
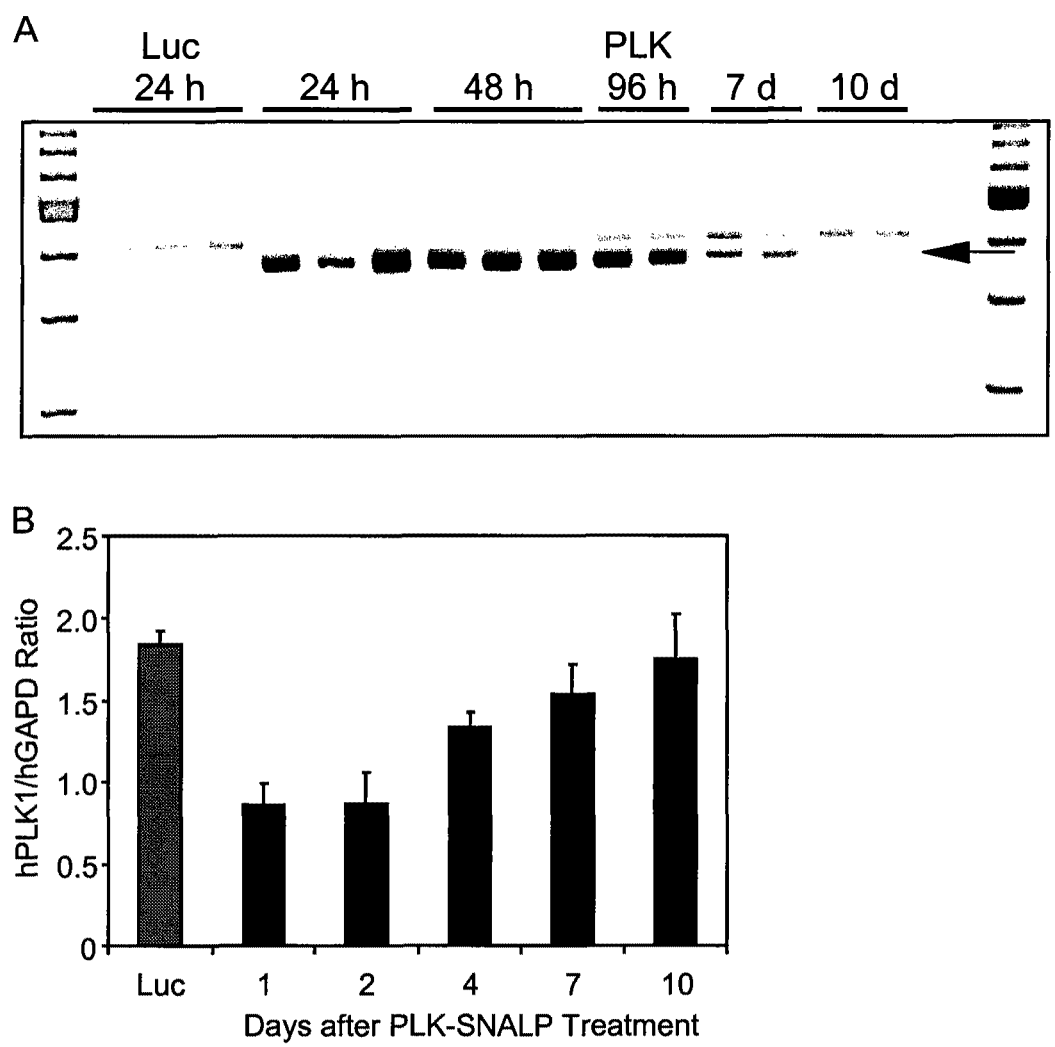
FIG. 34 illustrates data demonstrating the duration of RNAi activity within hepatic tumors. (A) 5'-RACE-PCR analysis of Hep3B liver tumors 24 h, 48 h, 96 h, 7 d, & 10 d after a single intravenous administration of SNALP-formulated PLK1424-2/A siRNA (2 mg/kg). Specificity of the PLK1424-specific RACE-PCR product (arrowed) was confirmed by sequencing at d 1 and d 7. (B) Corresponding levels of PLK-1 mRNA in isolated tumor RNA analyzed in (A). Duration of RNAi correlated with duration of mRNA silencing compared to Luc-U/U SNALP treated mice. Data in represent mean hPLK-1:hGAPDH mRNA ratio+SD (n=3 at each time point). Mean SNALP particle size and (polydispersity) were 83 (0.09) and 90 (0.12) nm for PLK1424 and Luc, respectively.

To determine the duration of active RNAi within the tumor, a cohort of Hep3B tumor-bearing mice was treated with PLK1424-2/A SNALP (2 mg/kg by intravenous administration) and collected tumors 24 h, 48 h, 96 h, 7 d, and 10 d after administration for analysis by 5' RACE-PCR. Active PLK-1 mRNA cleavage remained strong at 48 and 96 h and was still evident 7 d after a single siRNA administration. A weak signal was detected in PLK1424 treated animals on Day 10 (FIG. 34A). The duration of RNAi determined by RACE-PCR closely correlated with the level of hPLK-1 mRNA silencing in these liver tumors (FIG. 34B), providing further confirmation that RNAi was the primary mechanism for reductions in PLK-1 mRNA. Since the cleaved mRNA species are inherently unstable in the cell cytoplasm, it can be concluded that active RISC-mediated cleavage of the target mRNA persisted for 7-10 days after a single siRNA treatment. This suggests that active RNAi continued to occur either within a subset of tumor cells at sub-cytotoxic levels or within an initially non-proliferative population that subsequently entered cell cycle and re-expressed PLK-1 mRNA.

RNAi-Mediated Anti-Tumor Activity Assessed by Histology

Figure 35:
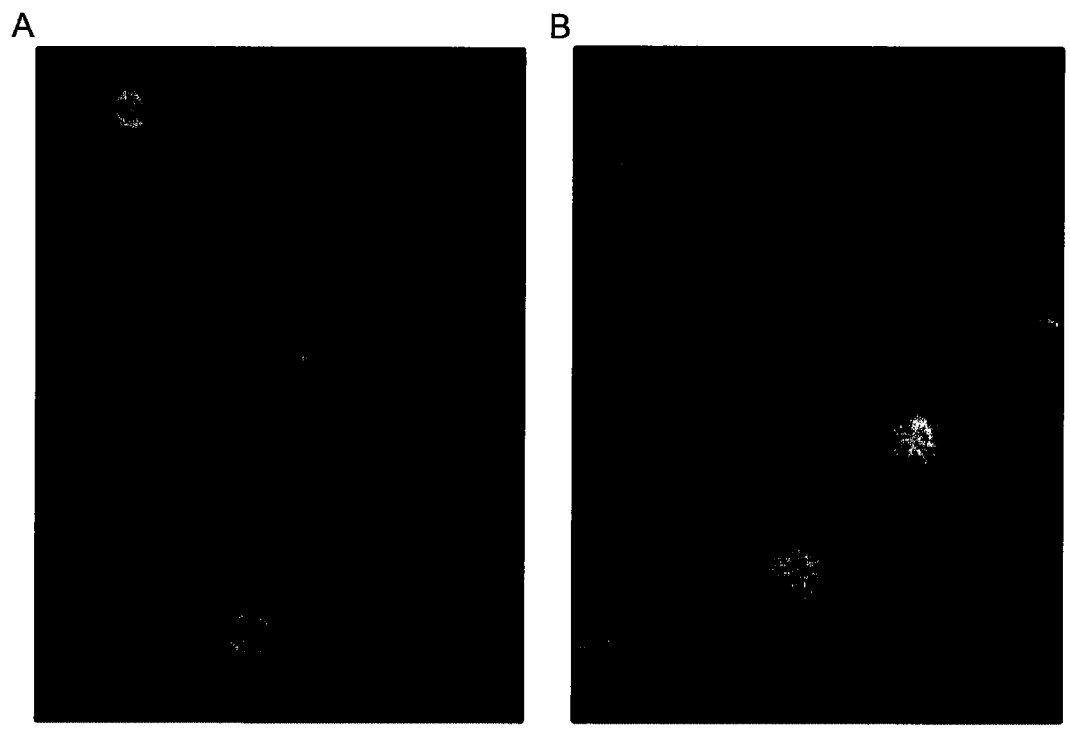
FIG. 35 illustrates data demonstrating the induction of monoastral spindle formation by KSP2263 siRNA. HeLa cells were treated for 16 h with (A) Luc or (B) KSP2263 siRNA at 20 nM then immunostained for α-tubulin (FITC). DNA was stained with DAPI and flourescent images captured and overlayed. Control cells show normal bipolar spindles at metaphase compared to monoastral spindles in KSP2263 treated cells.
Figure 36:
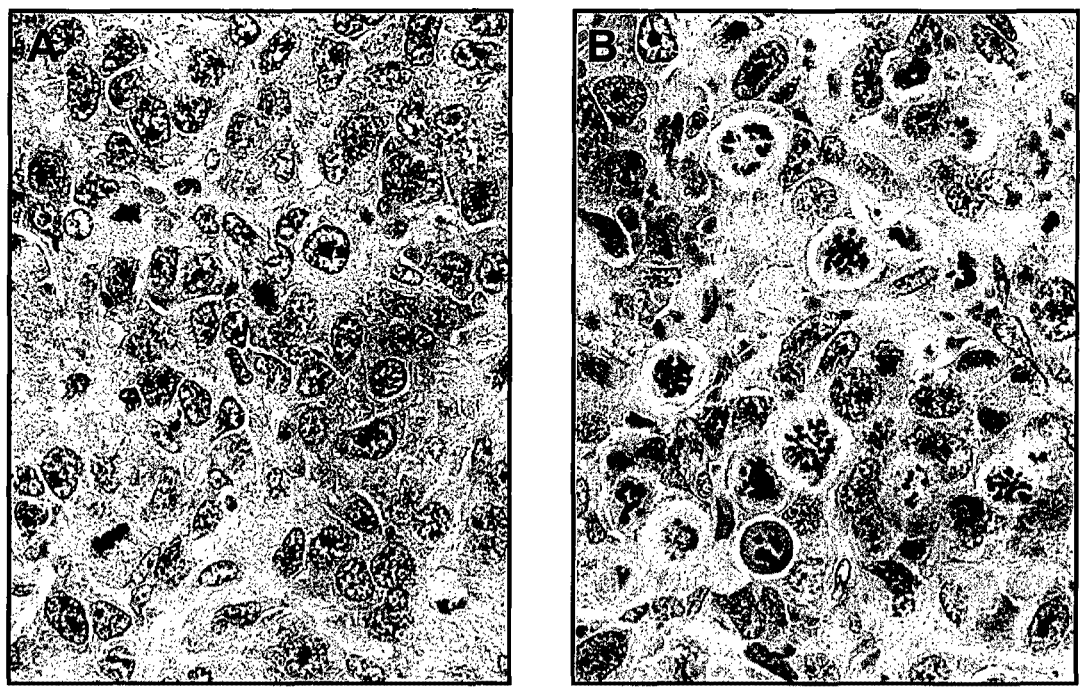
FIG. 36 illustrates data demonstrating that KSP2263-U/U induces distinct phenotypic changes typical of KSP inhibition in hepatic tumor cells. Hepatic Neuro2a tumor histology 24 h after a single intravenous administration of (A) Luc-U/U or (B) KSP2263-U/U siRNA formulated in SNALP (2 mg/kg siRNA). Images are at 200× magnification and representative of tumors from at least 6 individual mice. Hematoxylin and eosin (H&E) staining reveals tumor cells with aberrant nuclear figures typical of monoastral spindles or apoptotic phenotypes in KSP2263-U/U treated mice. (C) Quantitative histology of H&E stained tumor tissues from mice treated with SNALP-formulated KSP2263-U/U at 4, 2, 1, or 0.5 mg/kg siRNA. Tumor cells with condensed chromatin structures were scored positive and calculated as a % of total tumor cells taken from 10 fields of view. Positive cells included aberrant and typical mitotic and apoptotic figures. Values are mean+SD of 3 mice. Mean SNALP particle size and (polydispersity) were 88 (0.07) and 82 (0.08) nm for KSP2263 and Luc, respectively.
Figure 36:
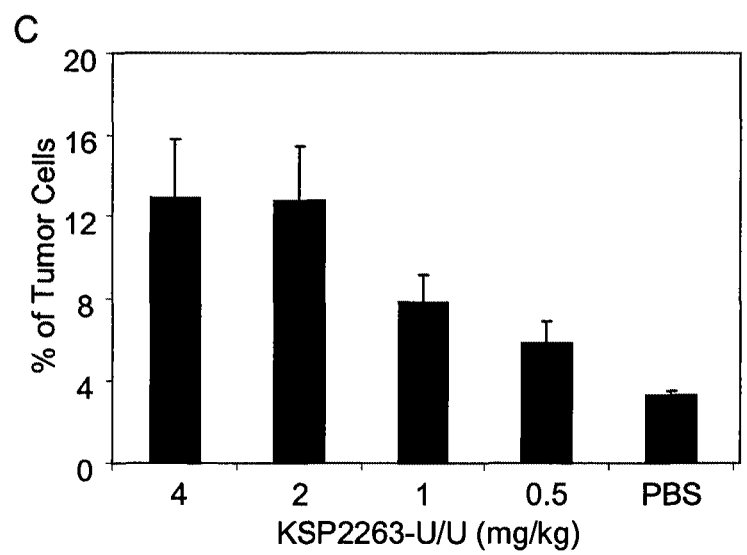

Many anti-mitotic drugs, including KSP (46) and PLK-1 inhibitors (47, 48), induce distinct nuclear phenotypes that reflect their underlying mechanism of action. We therefore used conventional histology as a biomarker to assess whether the degree of RNAi-mediated gene silencing in vivo was sufficient to induce the desired anti-mitotic effect in tumor cells. Inhibition of KSP prevents bipolar spindle formation and centrosome segregation, leading to the formation of characteristic monoastral spindles. We first confirmed that the treatment of tumor cells with KSP2263-U/U siRNA induced the distinct monoastral nuclear phenotype in vitro (FIG. 35). Conventional histology on Neuro2a tumors from KSP2263-U/U treated mice revealed significant numbers of tumor cells with aberrant mitotic figures typical of monoastral and apoptotic cells (46) 24 h after SNALP administration (FIG. 36A, B). This dramatic pharmacodynamic response to KSP2263-U/U treatment was dose-dependent with maximal effects observed at 2 mg/kg siRNA based on quantitative histology scores (FIG. 36C). This analysis estimated ~13% of total Neuro2a tumor cells with condensed chromatin structures at 24 h post siRNA treatment, compared to ~3% of cells displaying typical mitotic figures in control tumors.

Figure 37:
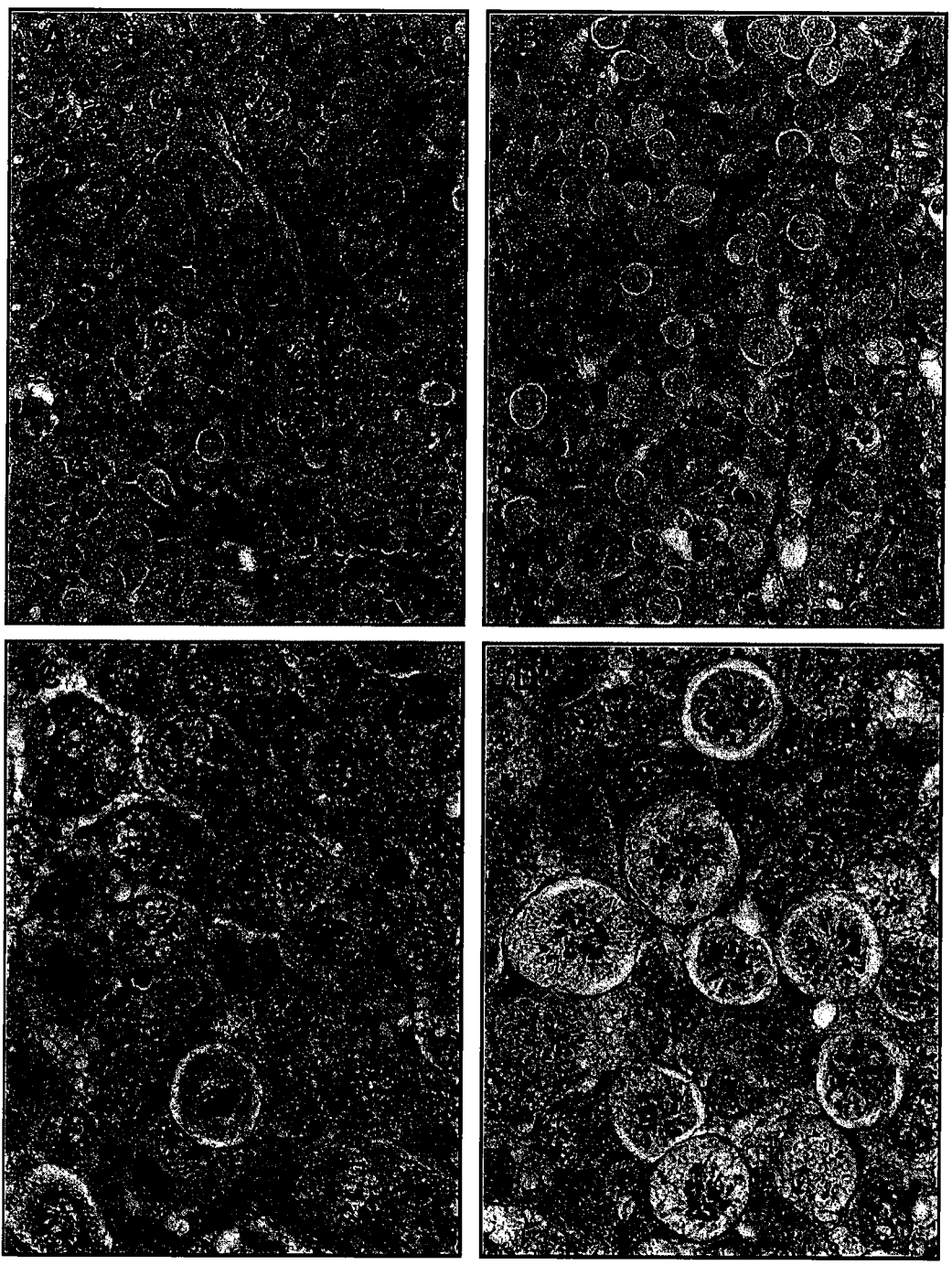
FIG. 37 illustrates data demonstrating that PLK1424-2A induces distinct phenotypic changes typical of PLK-1 inhibition in hepatic tumor cells. H&E tumor histology 24 h after single intravenous administration of 2 mg/kg SNALP formulated (A,C) Luc-U/U or (B,D) PLK1424-2/A siRNA. Images at (A,B) 200× and (C,D) 400× magnification are representative of tumors from at least 7 individual mice. Mean SNALP particle size and (polydispersity) were 72 (0.04) and 72 (0.02) nm for PLK1424 and Luc, respectively.

Histological analysis of Hep3B liver tumors from PLK1424-2/A SNALP treated mice also revealed abundant tumor cells with condensed chromatin structures and aberrant mitotic figures (FIG. 37). These phenotypic changes were consistent with the dysregulated chromosomal segregation and apoptosis that is induced by PLK-1 inhibition (47) and were in striking contrast to the typical mitotic figures evident in the tumor histology of control treated animals.

These molecular and cellular pharmacodynamic studies confirmed that the degree of RNAi-mediated silencing achieved by a single intravenous administration of SNALP-formulated PLK or KSP siRNA was sufficient to cause mitotic dysfunction in a substantial proportion of tumor cells. Histological assessments of drug activity in both models demonstrated that "affected" cells were distributed throughout established tumors, indicating good penetration of the lipidic delivery vehicle. Taken together, this battery of tests provided conclusive evidence that the potent therapeutic effects of these SNALP formulated siRNA, in the absence of a measurable immune response, are the result of RNAi.

Therapeutic Activity of SNALP-Formulated siRNA in Subcutaneous Tumors

Figure 38:
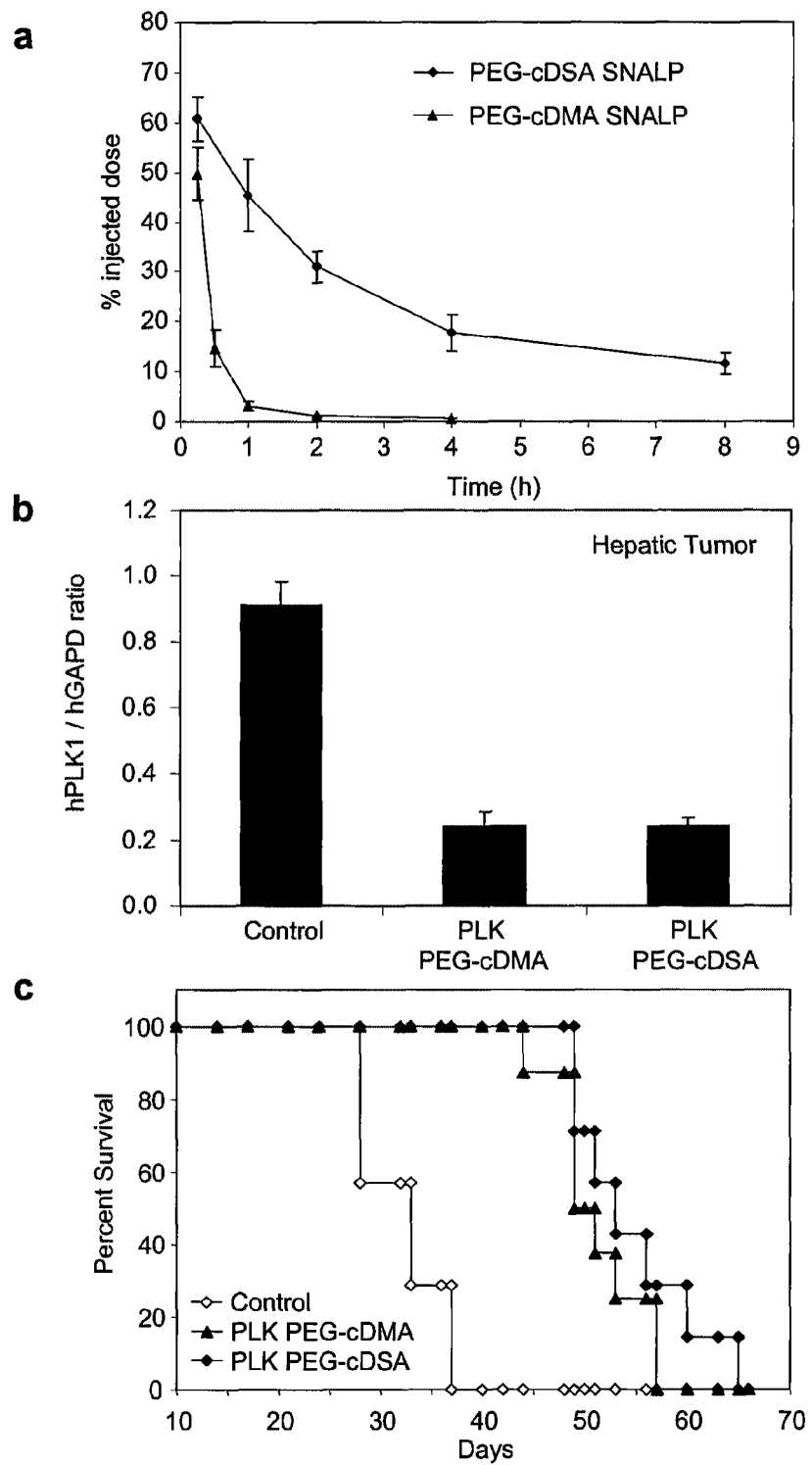
FIG. 38 illustrates data demonstrating a comparison of PLK1424 SNALP comprising either PEG-cDMA or PEG-cDSA in the hepatic tumor model. (A) Blood clearance of $^3$H-labelled SNALP (according to Judge et al., *Mol. Ther.*, 13:328-337 (2006)) comprising either PEG-cDMA or PEG-cDSA following IV administration in mice. Data are expressed as mean % injected dose (+/−SD, n=4) remaining in whole blood at 0.25, 0.5, 1, 2, 4, and 8 h after injection. (B) PLK-1 mRNA silencing in hepatic Hep3B tumors 24 h after single 2 mg/kg administration of either PLK1424-2/A SNALP formulations (mean PLK1:GAPDH ratio+/−SD, n=4 mice). (C) Treatment with PLK1424-2/A SNALP comprising either PEG-cDMA or PEG-cDSA confers significant survival advantages in scid/beige mice bearing intrahepatic Hep3B tumors. Mice were administered PLK1424-2/A SNALP comprising PEG cDMA or PEG-cDSA or Luc-U/U SNALP (PEG-cDMA) at 2 mg/kg twice weekly between d 10 and d 28 after seeding (6 doses). Time to euthanization due to tumor burden was assessed based on clinical scores as a humane surrogate to survival. Both PLK1424-2/A SNALP compositions provided significant survival advantage over control (p<0.05, Log-rank Mantel Cox test).

To expand the general utility of this technology in oncology, the performance of this liver-targeting SNALP formulation (26) was tested for delivering siRNA to tumors outside of the liver. For vehicles containing poly(ethylene)glycol conjugated lipids (PEG-lipids) such as SNALP, increased blood residency time and tumor accumulation can be achieved by incorporating PEG-lipids with longer alkyl chains that associate more strongly with the lipid particle and provide greater shielding in the blood compartment (49). Replacing the C14 PEG-lipid (PEG-cDMA) with the C18 analogue PEG-cDSA (50) had the effect of significantly increasing the blood circulation time of PLK1424-2/A SNALP in mice without altering its therapeutic efficacy in hepatic tumors (FIG. 38; median survival PLK PEG-cDMA=51 d, PLK PEG-cDSA=53 d versus Luc Control PEG-cDMA=33 d; p<0.05).

Despite a relatively short blood circulation time and rapid distribution to the liver, repeat administration of PEG-cDMA SNALP containing PLK1424-2/A caused significant inhibition of subcutaneous Hep3B tumor growth compared to Luc-U/U siRNA treatment controls (FIG. 39A). PLK1424-2/A formulated in an equivalent PEG-cDSA SNALP exhibited more potent anti-tumor effects, inducing regression of established tumors (~7 mm diameter) through the dosing period (FIG. 39A). This difference in activity correlated with the degree of gene silencing induced by these PLK1424-2/A SNALP in subcutaneous tumors (FIG. 39B). As in the hepatic tumor models, this was confirmed as being mediated by RNAi by both RACE-PCR and tumor histology. Finally, the therapeutic dose response of the PEG-cDSA PLK1424-2/A formulation was established in the subcutaneous model. Dose-dependent inhibition of tumor growth was evident from 0.5 to 3.0 mg/kg PLK1424-2/A siRNA (FIG. 39C). At the lowest dose level tested, this represented a total cumulative dose of 3 mg/kg siRNA over a 2 week period.

Discussion

Delineating the mechanism of action for nucleic acid based drugs has historically been confounded by underlying immune stimulation or other non-specific effects induced by the nucleic acid (51, 52). This remains a valid concern for the burgeoning field of siRNA-based therapeutics (11). Assessment of target mRNA or protein down-regulation is necessary, but not sufficient to conclude RNAi as the underlying mechanism as these changes may also be symptomatic of the off-target effects induced by siRNA. This example on the development of SNALP-formulated siRNA for oncology applications describes the methodology used to confirm both the specificity and mechanism of action underlying the potent siRNA-mediated anti-tumor efficacy in preclinical models. This involved a combination of approaches: (1) the design of both active and control siRNA formulations with no apparent capacity to activate an immune response, therefore excluding as best as possible the potential for non-specific efficacy; (2) the selection of validated oncology targets (PLK-1 and KSP) with direct anti-tumor effects and distinctive histological biomarkers of functional target inhibition; (3) the use of RACE-PCR to confirm induction of the RNAi-specific mRNA cleavage product in tumor cells; and (4) the correlation of this active RNAi signature with the duration of target mRNA silencing in tumors. This example is the first report describing anti-tumor effects of siRNA to formally demonstrate RNAi as the primary mechanism of action. Furthermore, this approach to preclinical study design can be generalized to other targets in oncology and readily adopted by researchers in the RNAi field.

To evaluate the therapeutic potential of gene silencing in tumors without the confounding effects of immune stimulation, 2'OMe modified siRNA were designed that completely abolish the immunostimulatory activity of unmodified (native) RNA duplexes when administered in a delivery vehicle. It is well established that the large majority of native siRNA duplexes have the inherent capacity to activate the innate immune response through the endosomal TLR7 and/or TLR8 pathway, particularly when cellular uptake is facilitated by delivery vehicles (2, 3, 18, 53). Naked (non-formulated) siRNA duplexes of 21 bp or longer have also been reported to activate cell surface TLR3 on endothelial cells, causing non-specific anti-angiogenic effects in models of choroidal neovascularization (4). The consequences of immune activation by siRNA in tumor models was recently illustrated by the potent anti-tumor effects elicited by both active and non-targeting immune stimulatory siRNA constructs through the activation of immune effector functions (15). The 2'OMe siRNAs described herein induced no measurable cytokine response in mice. There was also no induction of the IFN inducible gene IFIT1 in either the liver, representing the primary target organ for these delivery vehicles, or within secondary lymphoid tissues. IFIT1 expression is responsive to local IFN signaling within tissues, and is also induced directly via dsRNA receptors, including TLR3, through an IFN-independent pathway (54-56). Its measure can therefore be considered more broadly indicative of siRNA-mediated immune activation compared to the induction of particular systemic cytokines. Taken together, these results indicate that the appropriate design of 2'OMe siRNA can not only circumvent the activation of endosomal TLR7/8 (2, 3, 18, 53), but also TLR3 (56). This likely reflects the fact that encapsulation of siRNA within delivery vehicles such as SNALP effectively shields the RNA from exposure to TLR3 on the cell surface. It is important that researchers confirm the full abrogation of an immune response to their selected siRNA in the context of their preferred delivery vehicle and animal model.

A number of strategies for chemically modifying siRNA have been proposed, primarily with the intent to produce nuclease resistant duplexes (16). This example illustrates that strategies incorporating 2'OMe-G, -U, or -A residues into both strands of the duplex will generate non-immunostimulatory siRNA. One such method for siRNA design employs alternating 2'OMe nucleotides throughout both strands of the duplex (57). Santel and colleagues (58) have tested these 2'OMe siRNA against the angiogenic target CD31 in tumor models using a lipoplex formulation that transfects vascular endothelium. Anti-tumor effects in these studies were correlated with specific reductions in CD31 expression and tumor vasculature in the apparent absence of overt immune stimulation. While the authors did not confirm the induction of RNAi in their models and only looked at systemic IFNα 24 h after siRNA administration, the report represents one of very few published RNAi studies in oncology to use chemically modified siRNA constructs predicted to have minimal immunostimulatory capacity. It should be noted that this siRNA design is based on blunt-ended 19mer duplexes that, as naked molecules, are predicted not to activate TLR3 (4). This assumption needs to be formally tested for these lipoplexed siRNA to ensure complexing of short siRNA does not enable their engagement of cell surface TLR3 or other RNA receptors.

Target silencing by siRNA may offer several advantages over functional inhibition by small molecule drugs. By its nature, RNAi is highly specific and allows for the selective inhibition of closely related proteins compared to the relative promiscuity of kinase inhibitors. Current PLK-1 inhibitors for example also inhibit PLK-2 and PLK-3 kinase activity (23, 59), raising some concern that concomitant inhibition of these family members may have opposing effects in controlling cell division (60). The biological response to protein depletion by RNAi can also differ from its functional inhibition by small molecules, for example, the loss of both kinase and polo-box functionality upon PLK-1 gene silencing (61). The duration of drug effect that can be achieved with siRNA is another attractive advantage. Once RNAi is established within mammalian cells, gene silencing can persist for many days, due to the relative stability of activated RISC in the presence of its complementary mRNA (26, 62). Therefore, the maintenance of drug activity for an siRNA therapeutic is uncoupled from the requirement to maintain an effective drug concentration in the blood. We have found that active RNAi in our tumor models persisted for up to 10 days based on detection of the specific mRNA cleavage product by RACE-PCR. Interestingly, this duration of effect was substantially shorter than that observed in comparable studies targeting ApoB expression in the healthy mouse liver in which silencing at the mRNA level slowly resolved between 14 and 28 days after siRNA administration (26). We believe that the attenuation of RNAi in the tumor most likely results from the effective killing of PLK-1 silenced tumor cells and from the dilution of activated RISC through the proliferation of cells receiving sub-lethal doses of PLK-1 siRNA (62).

This example demonstrates that systemic administration of SNALP-formulated siRNA can trigger RNAi-mediated cleavage of mRNA within solid tumors, silencing target expression at a magnitude sufficient to induce the mitotic disruption and apoptosis of tumor cells. This specific drug effect translates into robust therapeutic anti-cancer activity in models of human HCC. Significant inhibition of tumor growth, correlating with marked improvements in clinical signs, ultimately led to significant increases in survival times.

The multi-kinase inhibitor Sorafenib has recently been approved for the treatment of unresectable HCC based on limited phase III data (63) and it is likely that Sorafenib will become the standard of care for this indication. As a result, there is utility in using SNALP-formulated siRNA in combination with small molecule drugs. In fact, our studies indicate that a combination of Sorafenib and PLK-1 SNALP is well tolerated in mice and shows promising signs of activity in tumor models.

Current treatment options are limited for patients with primary liver cancer or liver metastatic disease and prognoses remain poor. The clinical development of therapeutic siRNAs targeting key genes in cancer development, such as PLK-1 and KSP, coupled with a systemic delivery vehicle capable of targeting hepatic and disseminated tumors, offers an exciting opportunity for this significant unmet medical need.

Methods siRNA. siRNA sequences targeting human PLK-1 (Genbank Accession No. NM_005030) were selected using a standard siRNA design algorithm (40, 64). Target sequences of PLK-1 siRNAs are listed in Table 7. All siRNA were synthesized as oligonucleotides by Integrated DNA Technologies and received as desalted, deprotected RNA. Integrity of annealed duplexes was confirmed by 20% PAGE. siRNA were formulated into SNALP comprised of synthetic cholesterol (Sigma), DSPC (1,2-distearoyl-sn-glycero-3-phosphocholine; Avanti Polar Lipids), PEG-cDMA (3-N-(-Methoxy poly(ethylene glycol)2000)carbamoyl-1,2-dimyrestyloxy-propylamine), and DLinDMA (1,2-Dilinoleyloxy-3-(N,N-dimethyl)aminopropane) as previously described (26). Formulations used for in vivo studies comprised a final lipid:siRNA mass ratio of 9:1. In the experiments indicated, PEG-cDMA was substituted at equimolar concentrations with the C18 analogue PEG-cDSA (50). All stabilized lipid particles were dialyzed in PBS prior to use and were stable as a wet preparation stored at 4° C. for greater than 6 months.

TABLE 7 siRNA sequences targeting human PLK-1.

| siRNA | Sense Strand (5'→3') | SEQ ID NO: |
|---|---|---|
| 126 | GGUCCUAGUGGACCCACGCUU | 235 |
| 272 | AGCCGCACCAGAGGGAGAAUU | 236 |
| 273 | GCCGCACCAGAGGGAGAAGUU | 237 |
| 363 | GGACAACGACUUCGUGUUCUU | 238 |
| 412 | CUCCUGGAGCUGCACAAGAUU | 239 |
| 450 | GCCUGAGGCCCGAUACUACUU | 240 |
| 498 | CCUGCACCGAAACCGAGUUUU | 241 |
| 618 | GAGGAAGAAGACCCUGUGUUU | 242 |
| 627 | GACCCUGUGUGGGACUCCUUU | 243 |
| 629 | CCCUGUGUGGGACUCCUAAUU | 244 |
| 630 | CCUGUGUGGGACUCCUAAUUU | 245 |

TABLE 7-continued siRNA sequences targeting human PLK-1.

| siRNA | Sense Strand (5'→3') | SEQ ID NO: |
|---|---|---|
| 693 | GGUGGAUGUGUGGUCCAUUUU | 246 |
| 694 | GUGGAUGUGUGGUCCAUUGUU | 247 |
| 736 | GUGGGCAAACCACCUUUUGUU | 248 |
| 744 | ACCACCUUUUGAGACUUCUUU | 249 |
| 745 | CCACCUUUUGAGACUUCUUUU | 250 |
| 772 | GAGACCUACCUCCGGAUCAUU | 251 |
| 773 | AGACCUACCUCCGGAUCAAUU | 218 |
| 776 | CCUACCUCCGGAUCAAGAAUU | 252 |
| 780 | CCUCCGGAUCAAGAAGAAUUU | 253 |
| 832 | GCCGCCUCCCUCAUCCAGAUU | 254 |
| 837 | CUCCCUCAUCCAGAAGAUGUU | 255 |
| 1137 | GCAGCUGCACAGUGUCAAUUU | 256 |
| 1195 | GAGGCUGAGGAUCCUGCCUUU | 257 |
| 1229 | GGGUCAGCAAGUGGGUGGAUU | 258 |
| 1232 | UCAGCAAGUGGGUGGACUAUU | 259 |
| 1233 | CAGCAAGUGGGUGGACUAUUU | 260 |
| 1242 | GGUGGACUAUUCGGACAAGUU | 261 |
| 1319 | CACGCCUCAUCCUCUACAAUU | 262 |
| 1321 | CGCCUCAUCCUCUACAAUGUU | 263 |
| 1347 | CAGCCUGCAGUACAUAGAGUU | 264 |
| 1404 | UCCCAACUCCUUGAUGAAGUU | 265 |
| 1409 | ACUCCUUGAUGAAGAAGAUUU | 266 |
| 1424 | AGAUCACCCUCCUUAAAUAUU | 211 |
| 1457 | UGAGCGAGCACUUGCUGAAUU | 267 |
| 1550 | CCCGCAGCGCCAUCAUCCUUU | 268 |
| 1556 | GCGCCAUCAUCCUGCACCUUU | 269 |
| 1577 | GCAACGGCAGCGUGCAGAUUU | 270 |
| 1580 | ACGGCAGCGUGCAGAUCAAUU | 271 |
| 1620 | GCUCAUCUUGUGCCCACUGUU | 272 |
| 1658 | UCGACGAGAAGCGGGACUUUU | 273 |

The number under "siRNA" in Table 7 refers to the nucleotide position of the 5' base of the sense strand relative to the start codon (ATG) of the human PLK-1 mRNA sequence NM_005030. In certain embodiments, the sense strand comprises modified nucleotides such as 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides.

Cell Cultures. The cell lines Hep3B, HepG2, HT29, LS174T, and Neuro2a cells were obtained from the American Type Culture Collection (ATCC; Manassas, Va.) and cultured in the recommended basal media with 10% heat inactivated FBS and 1% penicillin-streptomycin. For in vivo tumor studies, Hep3B or Neuro2a cells were cultured in T175 flasks, harvested and washed once in PBS prior to implantation. For in vitro siRNA activity assays, cell lines were cultured in 96 well plates in the presence of SNALP formulated siRNA. Cell viability was assessed after 72 h using the resazurin dye CellTiter Blue (Promega Corp). Corresponding PLK-1 or KSP mRNA silencing activity was assessed in replicate plates at 24 h by the bDNA assay (Panomics Inc.). The level of Caspase 3 and 7 enzyme activity in siRNA treated cells was assessed using the fluorescent Caspase 3/7 substrate (Z-DEVD)-2-Rhodamine 110 reagent Apo-ONE (Promega Corp.).

In vitro immune stimulation assays. Mouse Flt3L dendritic cell cultures were generated as described previously (65). In brief, bone marrow from Balb/C mice was harvested in complete media (RPMI 1640, 10% FBS, 1% penicillin/streptomycin, 2 mM L-glutamine, 1 mM sodium pyruvate, 25 mM HEPES, 50 uM 2-mercaptoethanol), passed through a 70 micron strainer and resuspended to 2×106 cells/mL in complete media supplemented with 100 ng/mL murine Flt3L (Peprotech). Cells were seeded in 6-well plates and 1 mL fresh Flt3L media added every three days. On day 9 of culture, non-adherent cells were plated into 96 well plates at a concentration 2×105 cells/well. Formulated siRNA were diluted in PBS and added to the cells for 24 h before supernatants were assayed for cytokines by ELISA.

In vivo immune stimulation assays. All animal studies were performed at Protiva Biotherapeutics in accordance with Canadian Council on Animal Care guidelines and following protocol approval by the Institutional Animal Care and Use Committee. 6-8 week old Balb/C mice were obtained from Harlan and subject to a two week acclimation period prior to use. Mice were administered SNALP formulated siRNA (2 mg/kg) in PBS via standard intravenous injection in the lateral tail vein. Blood was collected by cardiac puncture and processed as plasma for cytokine analysis. Liver and spleen were collected into RNALater (Sigma Co.) for IFIT1 mRNA analysis.

Intrahepatic tumor models. Liver tumors were established in mice by direct intrahepatic injection of Hep3B or Neuro2a tumor cells (45). Female scid/beige mice (Charles River Laboratories) and male A/J mice (Jackson Laboratories) were used as hosts for the Hep3B and Neuro2a tumors, respectively. Animals received Anafen by SC injection immediately prior to surgery. Individual mice were anaesthetized by isoflourane gas inhalation and eye lube applied to prevent excessive eye drying. While maintained under gas anaesthesia, a single 1.5 cm incision across the midline was made below the sternum and the left lateral hepatic lobe exteriorized. 1×10$^6$ Hep3B cells or 1×10$^5$ Neuro2a cells suspended in 25 µL PBS were injected slowly into the lobe at a shallow angle using a Hamilton syringe and 30G needle. A swab was then applied to the puncture wound to stop any bleeding prior to suturing. Mice were allowed to recover from anaesthesia in a sterile cage and monitored closely for 2-4 h before being returned to conventional housing.

Eight to 11 days after tumor implantation, mice were randomized into treatment groups. siRNA SNALP formulations or PBS vehicle control were administered by standard intravenous injection via the lateral tail vein, calculated on a mg siRNA/kg basis according to individual animal weights (10 mL/kg injection volume). Body weights were then monitored throughout the duration of the study as an indicator of developing tumor burden and treatment tolerability. For efficacy studies, defined humane endpoints were determined as a surrogate for survival. Assessments were made by qualified veterinary technicians based on a combination of clinical signs, weight loss, and abdominal distension to define the day of euthanization due to tumor burden.

Subcutaneous tumor models. Hep3B tumors were established in female scid/beige mice by subcutaneous injection of 3×10$^6$ cells in 50 µL PBS into the left hind flank. Mice were randomized into treatment groups 10-17 days after seeding as tumors became palpable. siRNA SNALP formulations were administered as described above. Tumors were measured in 2 dimensions (Width×Length) to assess tumor growth using digital calipers. Tumor volume was calculated using the equation a×b×b/2 where a and b=largest and smallest diameters, respectively, and expressed as group mean+/−SD.

Measurement of human PLK-1 and GAPDH mRNA in tumor tissues. Tumors were harvested directly into RNALater and stored at 4° C. until processing. 100 mg tumor tissue was homogenized in Tissue and Lysis Solution (EpiCentre Biotechnologies) containing 50 mg/ml proteinase K (EpiCentre) in a Fastprep tissue homogenizer followed by incubation in a 65° C. waterbath for 15 min and centrifuged to clarify lysates. mRNA analysis in FIG. 33B was performed on purified RNA isolated according the 5'-RACE-PCR protocol. Human PLK-1 and GAPDH mRNA were measured in tumor lystes by the QuantiGene bDNA assay (Panomics) as per the manufacturer's instructions (Quantigene 1.0 Manual). Human-specific PLK-1 (NM_005030) and GAPDH(NM_002046) probe sets were designed by Panomics and demonstrated to have minimal cross-reactivity to the mouse counterpart mRNA. Data were expressed as mean PLK-1:GAPDH ratio+/−SD of individual animals. Tumor burden was assessed by homogenizing the complete liver from tumor bearing mice and measuring the total hGAPDH signal (RLU's) within the liver. Values were expressed as hGAPDH RLU/mg total liver.

Measurement of IFIT1 mRNA in mouse tissues. Murine liver and spleen were processed for bDNA assay to quantitate IFIT1 mRNA as described above. The IFIT1 probe set was specific to mouse IFIT1 mRNA (positions 4-499 of NM_008331) and the GAPDH probe set was specific to mouse GAPDH mRNA (positions 9-319 of NM_008084). Data is shown as the ratio of IFIT1 relative light units (RLU) to GAPDH RLU.

5' RNA Ligase Mediated Rapid Amplification of cDNA ends (5' RLM RACE). Total RNA was isolated from in vitro cultured cells by direct lysis in TRIZOL (Invitrogen, Carlsbad, Calif.). For in vivo tumor samples, tissues were harvested into RNAlater (Sigma Co.) and stored at 4° C. for at least 24 h prior to processing. 30 mg tumor tissue was homogenized in 1 mL TRIZOL then processed to isolate total RNA. RNA quality was confirmed by gel electrophoresis (1% agarose TBE). 5' RLM RACE was performed according to the Invitrogen GeneRacer manual with modifications. Primers were designed using the Primer 3 software. 10 µg total RNA was mixed with 1.3 ng GeneRacer RNA adaptor (5'-CGACUGGAGCACGAGGACACUGACAUG-GACUGAAGGAGUAGAAA-3'; SEQ ID NO:274), heated to 65° C. for 5 min and snap-cooled on ice prior to ligation. RNA ligation was performed at 37° C. for 1 h in 1× ligase buffer, 30 U RNase-Out (Invitrogen) and 30 U RNA ligase (Ambion Inc, Austin, Tex.). Samples were then purified by diafiltration using Microcon 100 filters as per the manufacturer's instructions for nucleic acids (Millipore Inc). 10 µL of the RNA ligation product was reverse transcribed using Superscript III (Invitrogen) and a PLK-1-specific primer (5'-GGACAAGGCTGTAGAACCCACAC-3'; SEQ ID NO:275) designed downstream of the predicted PLK1424 siRNA cut site. Reverse transcription was carried out at 55° C. for 50 min followed by inactivation at 70° C. for 15 min and snapcooling on ice. 5' RLM RACE PCR was performed using forward (GR5) and reverse (PLK1424rev) primers in the GeneRacer adaptor and 3' end of PLK-1 mRNA, respectively, to span the predicted PLK1424 cut site. PCR primer sequences were as follows: GR5-5'-CGACTGGAGCAC-GAGGACACTGA-3' (SEQ ID NO:276); and PLK1424rev-5'-CCAGATGCAGGTGGGAGTGAGGA-3' (SEQ ID NO:277). PCR was performed using a BIO-RAD iCycler using touchdown PCR conditions of 94° C. for 2 min (1 cycle), 94° C. for 30 sec and 72° C. for 1 min (5 cycles), 94° C. for 30 sec and 70° C. for 1 min (5 cycles), 94° C. for 30 sec, 65° C. for 30 sec and 68° C. for 1 min (25 cycles), and 68° C. for 10 min (1 cycle). PCR products were run on a 2% TBE Agarose 1000 (Invitrogen) gel and stained with 1 μg/ml ethidium bromide. The identity of PCR products was confirmed by direct sequencing of the gel-purified products using the following sequencing primers: GeneRacer 5' Seq-5'-ACTGGAGCACGAGGACAC-3' (SEQ ID NO:278); and PLK1424 3' Seq-5'-GAGACGGGCAGGGATATAG-3' (SEQ ID NO:279). Similar assay conditions and primer design were employed to amplify the cleaved KSP mRNA product by KSP2263 siRNA using the following unique primers: KSP-specific cDNA primer 5'-GCTGCTCTCGTGGTTCAGT-TCTC-3' (SEQ ID NO:280), RACE primer KSPrev 5'-GC-CCAACTACTGCTTAACTGGCAAA-3' (SEQ ID NO:281), and KSP sequencing primer 5'-TGGGTTTCCTTTAT-TGTCTT-3' (SEQ ID NO:282).

Histology. Tumors were harvested from mice 24 h after siRNA administration and fixed directly in 10% buffered formalin. Tissues were then processed as paraffin embedded tissue sections and stained with Hematoxylin and Eosin using conventional histological techniques. Quantitative analysis of stained sections was performed by counting the number of mitotic/apoptotic cells displaying condensed chromatin structures as a percentage of total tumor cells. Values for each tumor were derived from means of 10 fields of view at 400× magnification.

Cytokine ELISA. All cytokines were quantified using sandwich ELISA kits. These were mouse interferon-α (PBL Biomedical; Piscataway, N.J.) and human and mouse IL-6 (BD Biosciences; San Diego, Calif.).

ApoB-1 siRNA sequences. The following ApoB-1 siRNA (5'-3') sequences were used in the experiments shown in FIG. 25: Sense-GUCAUCACACUGAAUACCAAU (SEQ ID NO:283); 2'OMe sense-GUCAUCACACUGAAUACCAA U (SEQ ID NO:284); Antisense (AS)-AUUGGUAUU-CAGUGUGAUGACAC (SEQ ID NO:285); 2'OMe AS-AUUGGUAUUCAGUGUGAUGACAC (SEQ ID NO:286). 2'OMe nucleotides are indicated in bold and underlined.

Statistical analysis. Comparison of survival times were performed on Kaplan-Meier plots by the Log-rank (Mantel Cox) test. Differences were deemed significant for P values less than 0.05.

References (1) Elbashir, S. M. et al. 2001. Duplexes of 21-nucleotide RNAs mediate RNA interference in cultured mammalian cells. *Nature* 411: 494-498.

(2) Judge, A. D. et al. 2005. Sequence-dependent stimulation of the mammalian innate immune response by synthetic siRNA. *Nat Biotechnol* 23: 457-462.

(3) Hornung, V. et al. 2005. Sequence-specific potent induction of IFN-alpha by short interfering RNA in plasmacytoid dendritic cells through TLR7. *Nat Med* 11: 263-270.

(4) Kleinman, M. E. et al. 2008. Sequence and target-independent angiogenesis suppression by siRNA via TLR3. *Nature* 452:591-597.

(5) Hornung, V. et al. 2006. 5'-Triphosphate RNA is the ligand for RIG-1. *Science* 314: 994-997.

(6) Marques, J. T. et al. 2006. A structural basis for discriminating between self and nonself double-stranded RNAs in mammalian cells. *Nat Biotechnol* 24: 559-565.

(7) Krieg, A. M. 2006. Therapeutic potential of Toll-like receptor 9 activation. *Nat Rev Drug Discov* 5: 471-484.

(8) von Marschall, Z. et al. 2003. Effects of interferon alpha on vascular endothelial growth factor gene transcription and tumor angiogenesis. *J Natl Cancer Inst* 95:437-448.

(9) Lanuti, M. et al. 2000. Cationic lipid:bacterial DNA complexes elicit adaptive cellular immunity in murine intraperitoneal tumor models. *Cancer Res* 60: 2955-2963.

(10) Buhtoiarov, I. N., Lum, H. D., Berke, G., Sondel, P. M., and Rakhmilevich, A. L. 2006. Synergistic activation of macrophages via CD40 and TLR9 results in T cell independent antitumor effects. *J Immunol* 176: 309-318.

(11) Judge, A., and MacLachlan, I. 2008. Overcoming the innate immune response to small interfering RNA. *Hum Gene Ther* 19: 111-124.

(12) Michie, H. R. et al. 1988. Detection of Circulating Tumor Necrosis Factor after Endotoxin Administration. *N. Engl. J. Med.* 318: 1481-1486.

(13) Stevenson, H. C. et al. 1985. A phase I evaluation of poly(I,C)-LC in cancer patients. *J Biol Response Mod.* 4: 650-655.

(14) Schlee, M., Barchet, W., Hornung, V., and Hartmann, G. 2007. Beyond double-stranded RNA-type I IFN induction by 3pRNA and other viral nucleic acids. *Curr Top Microbiol Immunol* 316: 207-230.

(15) Poeck, H. et al. 2008. 5'-triphosphate-siRNA: turning gene silencing and Rig-I activation against melanoma. *Nat Med.* 14: 1256-1263.

(16) Manoharan, M. 2004. RNA interference and chemically modified small interfering RNAs. *Curr. Opin. Chem. Biol.* 8: 570-579.

(17) Morrissey, D. V. et al. 2005. Potent and persistent in vivo anti-HBV activity of chemically modified siRNAs. *Nat Biotechnol* 23: 1002-1007.

(18) Judge, A. D., Bola, G., Lee, A. C., and MacLachlan, I. 2006. Design of non-inflammatory synthetic siRNA mediating potent gene silencing in vivo. *Mol Ther* 13: 494-505.

(19) Knight, S. D., and Parrish, C. A. 2008. Recent progress in the identification and clinical evaluation of inhibitors of the mitotic kinesin KSP. *Curr Top Med Chem* 8: 888-904.

(20) Strebhardt, K., and Ullrich, A. 2006. Targeting polo-like kinase 1 for cancer therapy. *Nat Rev Cancer* 6: 321-330.

(21) Tao, W. et al. 2005. Induction of apoptosis by an inhibitor of the mitotic kinesin KSP requires both activation of the spindle assembly checkpoint and mitotic slippage. *Cancer Cell* 8: 49-59.

(22) Barr, F. A., Sillje, H. H., and Nigg, E. A. 2004. Polo-like kinases and the orchestration of cell division. *Nat Rev Mol Cell Biol* 5:429-440.

(23) Steegmaier, M. et al. 2007. BI 2536, a potent and selective inhibitor of polo-like kinase 1, inhibits tumor growth in vivo. *Curr Biol* 17: 316-322.

(24) Liu, X., and Erikson, R. L. 2003. Polo-like kinase (Plk)1 depletion induces apoptosis in cancer cells. *Proc Natl Acad Sci USA* 100: 5789-5794.

(25) Spankuch, B., Kurunci-Csacsko, E., Kaufmann, M., and Strebhardt, K. 2007. Rational combinations of siRNAs targeting Plk1 with breast cancer drugs. *Oncogene* 26: 5793-5807.

(26) Zimmermann, T. S. et al. 2006. RNAi-mediated gene silencing in non-human primates. *Nature* 441: 111-114.

(27) de Fougerolles, A., Vomlocher, H. P., Maraganore, J., and Lieberman, J. 2007. Interfering with disease: a progress report on siRNA-based therapeutics. *Nat Rev Drug Discov* 6: 443-453.

(28) Behlke, M. A. 2006. Progress towards in vivo use of siRNAs. *Mol Ther.* 13: 644-670.

(29) Urban-Klein, B., Werth, S., Abuharbeid, S., Czubayko, F., and Aigner, A. 2005. RNAi-mediated gene-targeting through systemic application of polyethylenimine (PEI)-complexed siRNA in vivo. *Gene Ther.* 12: 461-466.

(30) Schiffelers R. M et al. 2004. Cancer siRNA therapy by tumor selective delivery with ligand-targeted sterically stabilized nanoparticle. *Nucleic Acids Res.* 32: e149.

(31) Heidel, J. D. et al. 2007. Administration in non-human primates of escalating intravenous doses of targeted nanoparticles containing ribonucleotide reductase subunit M2 siRNA. *Proc Natl Acad Sci USA* 104: 5715-5721.

(32) Santel, A. et al. 2006. A novel siRNA-lipoplex technology for RNA interference in the mouse vascular endothelium. *Gene Ther* 13: 1222-1234.

(33) Mayer, L., Bally, M., Cullis, P., Wilson, S., and Emerman, J. 1990. Comparison of free and liposome encapsulated doxorubicin tumor drug uptake and anti-tumor efficacy in the SC115 murine mammary tumor. *Cancer Letters* 53: 183-190.

(34) Seymour, L. W. 1992. Passive tumor targeting of soluble macromolecules and drug conjugates. *Crit Rev Ther Drug Carrier Syst* 9: 135-187.

(35) Chono, S., Li, S. D., Conwell, C. C., and Huang, L. 2008. An efficient and low immunostimulatory nanoparticle formulation for systemic siRNA delivery to the tumor. *J Control Release* 131: 64-69.

(36) Peer, D., Park, E. J., Morishita, Y., Carman, C. V., and Shimaoka, M. 2008. Systemic leukocyte-directed siRNA delivery revealing cyclin D1 as an anti-inflammatory target. *Science* 319: 627-630.

(37) Robbins, M. et al. 2008. Misinterpreting the therapeutic effects of siRNA caused by immune stimulation. *Hum Gene Ther*. PMID 18713023.

(38) Weil, D., Garcon, L., Harper, M., Dumenil, D., Dautry, F., and Kress, M. 2002. Targeting the kinesin Eg5 to monitor siRNA transfection in mammalian cells. *Biotechniques* 33: 1244-1248.

(39) Soutschek, J. et al. 2004. Therapeutic silencing of an endogenous gene by systemic administration of modified siRNAs. *Nature* 432: 173-178.

(40) Elbashir, S. M., Lendeckel, W., and Tuschl, T. 2001. RNA interference is mediated by 21- and 22-nucleotide RNAs. *Genes Dev.* 15: 188-200.

(41) Matranga, C., Tomari, Y., Shin, C., Bartel, D. P., and Zamore, P. D. 2005. Passenger-strand cleavage facilitates assembly of siRNA into Ago2-containing RNAi enzyme complexes. *Cell* 123: 607-620.

(42) Leuschner, P. J., Ameres, S. L., Kueng, S., and Martinez, J. 2006. Cleavage of the siRNA passenger strand during RISC assembly in human cells. *EMBO Rep* 7: 314-320.

(43) Prakash, T. et al. 2005. Positional effect of chemical modifications on short interference RNA activity in mammalian cells. *J. Med. Chem.* 48: 4247-4253.

(44) Chiu, Y., and Rana, T. 2003. siRNA function in RNAi: A chemical modification analysis. *RNA* 9: 1034-1048.

(45) Yao, X. et al. 2003. A novel orthotopic tumor model to study growth factors and oncogenes in hepatocarcinogenesis. *Clin Cancer Res* 9: 2719-2726.

(46) Sakowitz, R. et al. 2004. Antitumor activity of kinesin inhibitor. *Cancer Research* 64: 3276-3280.

(47) Lenart, P. et al. 2007. The small-molecule inhibitor BI 2536 reveals novel insights into mitotic roles of polo-like kinase 1. *Curr Biol* 17: 304-315.

(48) Spankuch-Schmitt, B., Bereiter-Hahn, J., Kaufmann, M., and Strebhardt, K. 2002. Effect of RNA silencing of polo-like kinase-1 (PLK1) on apoptosis and spindle formation in human cancer cells. *J Natl Cancer Inst* 94: 1863-1877.

(49) Ambegia, E. et al. 2005. Stabilized plasmid-lipid particles containing PEG-diacylglycerols exhibit extended circulation lifetimes and tumor selective gene expression. *Biochimica et Biophysica Acta* 1669: 155-163.

(50) Heyes, J., Hall, K., Tailor, V., Lenz, R., and MacLachlan, I. 2006. Synthesis and characterisation of novel poly(ethylene glycol)-lipid conjugates suitable for use in drug delivery. *Journal of Controlled Release* 112: 280-290.

(51) Krieg, A. M. 2002. CpG motifs in bacterial DNA and their immune effects. *Annu. Rev. Immunol.* 20: 709-760.

(52) Castro, J. E. et al. 2006. Thymidine-phosphorothioate oligonucleotides induce activation and apoptosis of CLL cells independently of CpG motifs or BCL-2 gene interference. *Leukemia* 20: 680-688.

(53) Diebold, S. S. et al. 2006. Nucleic acid agonists for Toll-like receptor 7 are defined by the presence of uridine ribonucleotides. *Eur J Immunol* 36: 3256-3267.

(54) Der, S. D., Zhou, A., Williams, B. R., and Silverman, R. H. 1998. Identification of genes differentially regulated by interferon alpha, beta, or gamma using oligonucleotide arrays. *Proc Natl Acad Sci USA* 95: 15623-15628.

(55) Geiss, G. et al. 2001. A comprehensive view of regulation of gene expression by double-stranded RNA-mediated cell signaling. *J Biol Chem* 276: 30178-30182.

(56) Sarkar, S. N., Smith, H. L., Rowe, T. M., and Sen, G. C. 2003. Double-stranded RNA signaling by Toll-like receptor 3 requires specific tyrosine residues in its cytoplasmic domain. *J Biol Chem* 278: 4393-4396.

(57) Czauderna, F. et al. 2003. Structural variations and stabilising modifications of synthetic siRNAs in mammalian cells. *Nucl. Acids Res.* 31: 2705-2716.

(58) Santel, A. et al. 2006. RNA interference in the mouse vascular endothelium by systemic administration of siRNA-lipoplexes for cancer therapy. *Gene Ther* 13: 1360-1370.

(59) Johnson, E. F., Stewart, K. D., Woods, K. W., Giranda, V. L., and Luo, Y. 2007. Pharmacological and functional comparison of the polo-like kinase family: insight into inhibitor and substrate specificity. *Biochemistry* 46: 9551-9563.

(60) Malumbres, M., and Barbacid, M. 2007. Cell cycle kinases in cancer. *Curr Opin Genet Dev* 17: 60-65.

(61) McInnes, C. et al. 2006. Inhibitors of Polo-like kinase reveal roles in spindle-pole maintenance. *Nat Chem Biol* 2: 608-617.

(62) Bartlett, D. W., and Davis, M. E. 2006. Insights into the kinetics of siRNA-mediated gene silencing from live-cell and live-animal bioluminescent imaging. *Nucleic Acids Res* 34: 322-333.

(63) Llovet, J. M., and Bruix, J. 2008. Novel advancements in the management of hepatocellular carcinoma in 2008. *J Hepatol* 48 Suppl 1:S20-37.

(64) Schwarz, D. S. et al. 2003. Asymmetry in the assembly of the RNAi enzyme complex. *Cell* 115: 119-208.

(65) Gilliet, M. et al. 2002. The development of murine plasmacytoid dendritic cell precursors is differentially regulated by FLT3-ligand and granulocyte/macrophage colony-stimulating factor. *J Exp Med* 195: 953-958.

EXAMPLE 16

Synthesis of Cholesteryl-2'-Hydroxyethyl Ether

Step 1: A 250 ml round bottom flask containing cholesterol (5.0 g, 12.9 mmol) and a stir bar was sealed and flushed with nitrogen. Toluenesulphonyl chloride (5.0 g, 26.2 mmol) was weighed into a separate 100-mL round bottom flask, also sealed and flushed with nitrogen. Anhydrous pyridine (2×50 ml) was delivered to each flask. The toluenesulphonyl chloride solution was then transferred, via cannula, into the 250 ml flask, and the reaction stirred overnight. The pyridine was removed by rotovap, and methanol (80 ml) added to the residue. This was then stirred for 1 hour until a homogeneous suspension was obtained. The suspension was filtered, washed with acetonitrile (50 ml), and dried under vacuum to yield cholesteryl tosylate as a fluffy white solid (6.0 g, 86%).

Step 2: Cholesteryl tosylate (2.0 g, 3.7 mmol), 1,4-dioxane (50 mL), and ethylene glycol (4.6 g, 74 mmol) were added to a 100 ml flask containing a stir bar. The flask was fitted with a condenser, and refluxed overnight. The dioxane was then removed by rotovap, and the reaction mixture suspended in water (100 ml). The solution was transferred to a separating funnel and extracted with chloroform (3×100 ml). The organic phases were combined, washed with water (2×150 ml), dried over magnesium sulphate, and the solvent removed. The crude product was purified by column chromatography (5% acetone/hexane) to yield the product as a white solid (1.1 g, 69%).

The structures of the cholesterol derivatives cholesteryl-2'-hydroxyethyl ether and cholesteryl-4'-hydroxybutyl ether are as follows:

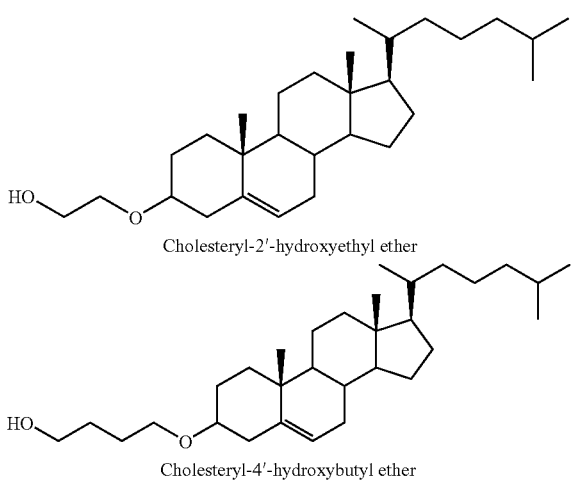

Cholesteryl-2'-hydroxyethyl ether

Cholesteryl-4'-hydroxybutyl ether

EXAMPLE 17

Exemplary aiRNA Molecules Targeting PLK-1

Table 8 provides non-limiting examples of aiRNA molecules that are suitable for modulating (e.g., silencing) PLK-1 expression. The first set of aiRNA molecules comprises the PLK1424 siRNA antisense strand sequence (SEQ ID NO:2). The second set of aiRNA molecules comprises the PLK773 siRNA antisense strand sequence (SEQ ID NO:4).

The 5' antisense overhang may contain one, two, three, four, or more nontargeting nucleotides (e.g., "AA", "UU", "dTdT", etc.). Preferably, the 5' antisense overhang contains two nontargeting nucleotides. The 3' antisense overhang may contain one, two, three, four, or more nontargeting nucleotides. The aiRNA molecules may comprise one or more modified nucleotides, e.g., in the double-stranded (duplex) region and/or in the antisense overhangs. Examples of modified nucleotides are described herein and include 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and locked nucleic acid (LNA) nucleotides. The aiRNA molecules may further comprise one of the carrier systems described herein (e.g., a nucleic acid particle) and find utility in treating cancers such as liver cancer (e.g., hepatocellular carcinoma).

TABLE 8 aiRNA duplexes comprising sense and antisense PLK-1 RNA polynucleotides.

| aiRNA | PLK-1 aiRNA Sequence | |
|---|---|---|
| PLK1424 (12 bp/ 1) | 5'-CCCUCCUUAAAU-3' 3'-UCUAGUGGGAGGAAUUUAU-5' | (SEQ ID NO: 287) (SEQ ID NO: 2) |
| PLK1424 (12 bp/ 2) | 5'-ACCCUCCUUAAA-3' 3'-UCUAGUGGGAGGAAUUUAU-5' | (SEQ ID NO: 288) (SEQ ID NO: 2) |
| PLK1424 (12 bp/ 3) | 5'-CACCCUCCUUAA-3' 3'-UCUAGUGGGAGGAAUUUAU-5' | (SEQ ID NO: 289) (SEQ ID NO: 2) |
| PLK1424 (13 bp/ 1) | 5'-ACCCUCCUUAAAU-3' 3'-UCUAGUGGGAGGAAUUUAU-5' | (SEQ ID NO: 290) (SEQ ID NO: 2) |
| PLK1424 (13 bp/ 2) | 5'-CACCCUCCUUAAA-3' 3'-UCUAGUGGGAGGAAUUUAU-5' | (SEQ ID NO: 291) (SEQ ID NO: 2) |
| PLK1424 (13 bp/ 3) | 5'-UCACCCUCCUUAA-3' 3'-UCUAGUGGGAGGAAUUUAU-5' | (SEQ ID NO: 292) (SEQ ID NO: 2) |
| PLK1424 (14 bp/ 1) | 5'-CACCCUCCUUAAAU-3' 3'-UCUAGUGGGAGGAAUUUAU-5' | (SEQ ID NO: 293) (SEQ ID NO: 2) |
| PLK1424 (14 bp/ 2) | 5'-UCACCCUCCUUAAA-3' 3'-UCUAGUGGGAGGAAUUUAU-5' | (SEQ ID NO: 294) (SEQ ID NO: 2) |
| PLK1424 (14 bp/ 3) | 5'-AUCACCCUCCUUAA-3' 3'-UCUAGUGGGAGGAAUUUAU-5' | (SEQ ID NO: 295) (SEQ ID NO: 2) |
| PLK1424 (15 bp/ 1) | 5'-UCACCCUCCUUAAAU-3' 3'-UCUAGUGGGAGGAAUUUAU-5' | (SEQ ID NO: 296) (SEQ ID NO: 2) |
| PLK1424 (15 bp/ 2) | 5'-AUCACCCUCCUUAAA-3' 3'-UCUAGUGGGAGGAAUUUAU-5' | (SEQ ID NO: 297) (SEQ ID NO: 2) |
| PLK1424 (15 bp/ 3) | 5'-GAUCACCCUCCUUAA-3' 3'-UCUAGUGGGAGGAAUUUAU-5' | (SEQ ID NO: 298) (SEQ ID NO: 2) |
| PLK1424 (16 bp/ 1) | 5'-AUCACCCUCCUUAAAU-3' 3'-UCUAGUGGGAGGAAUUUAU-5' | (SEQ ID NO: 299) (SEQ ID NO: 2) |
| PLK1424 (16 bp/ 2) | 5'-GAUCACCCUCCUUAAA-3' 3'-UCUAGUGGGAGGAAUUUAU-5' | (SEQ ID NO: 300) (SEQ ID NO: 2) |
| PLK1424 (17 bp) | 5'-GAUCACCCUCCUUAAAU-3' 3'-UCUAGUGGGAGGAAUUUAU-5' | (SEQ ID NO: 301) (SEQ ID NO: 2) |
| PLK773 (12 bp/ 1) | 5'-ACCUCCGGAUCA-3' 3'-UCUGGAUGGAGGCCUAGUU-5' | (SEQ ID NO: 302) (SEQ ID NO: 4) |

TABLE 8-continued aiRNA duplexes comprising sense and antisense PLK-1 RNA polynucleotides.

| aiRNA | PLK-1 aiRNA Sequence | |
|---|---|---|
| PLK773 (12 bp/2) | 5'-UACCUCCGGAUC-3'<br>3'-UCUGGAUGGAGGCCUAGUU-5' | (SEQ ID NO: 303)<br>(SEQ ID NO: 4) |
| PLK773 (12 bp/3) | 5'-CUACCUCCGGAU-3'<br>3'-UCUGGAUGGAGGCCUAGUU-5' | (SEQ ID NO: 304)<br>(SEQ ID NO: 4) |
| PLK773 (13 bp/1) | 5'-UACCUCCGGAUCA-3'<br>3'-UCUGGAUGGAGGCCUAGUU-5' | (SEQ ID NO: 305)<br>(SEQ ID NO: 4) |
| PLK773 (13 bp/2) | 5'-CUACCUCCGGAUC-3'<br>3'-UCUGGAUGGAGGCCUAGUU-5' | (SEQ ID NO: 306)<br>(SEQ ID NO: 4) |
| PLK773 (13 bp/3) | 5'-CCUACCUCCGGAU-3'<br>3'-UCUGGAUGGAGGCCUAGUU-5' | (SEQ ID NO: 307)<br>(SEQ ID NO: 4) |
| PLK773 (14 bp/1) | 5'-CUACCUCCGGAUCA-3'<br>3'-UCUGGAUGGAGGCCUAGUU-5' | (SEQ ID NO: 308)<br>(SEQ ID NO: 4) |
| PLK773 (14 bp/2) | 5'-CCUACCUCCGGAUC-3'<br>3'-UCUGGAUGGAGGCCUAGUU-5' | (SEQ ID NO: 309)<br>(SEQ ID NO: 4) |
| PLK773 (14 bp/3) | 5'-ACCUACCUCCGGAU-3'<br>3'-UCUGGAUGGAGGCCUAGUU-5' | (SEQ ID NO: 310)<br>(SEQ ID NO: 4) |
| PLK773 (15 bp/1) | 5'-CCUACCUCCGGAUCA-3'<br>3'-UCUGGAUGGAGGCCUAGUU-5' | (SEQ ID NO: 311)<br>(SEQ ID NO: 4) |
| PLK773 (15 bp/2) | 5'-ACCUACCUCCGGAUC-3'<br>3'-UCUGGAUGGAGGCCUAGUU-5' | (SEQ ID NO: 312)<br>(SEQ ID NO: 4) |
| PLK773 (15 bp/3) | 5'-GACCUACCUCCGGAU-3'<br>3'-UCUGGAUGGAGGCCUAGUU-5' | (SEQ ID NO: 313)<br>(SEQ ID NO: 4) |
| PLK773 (16 bp/1) | 5'-ACCUACCUCCGGAUCA-3'<br>3'-UCUGGAUGGAGGCCUAGUU-5' | (SEQ ID NO: 314)<br>(SEQ ID NO: 4) |
| PLK773 (16 bp/2) | 5'-GACCUACCUCCGGAUC-3'<br>3'-UCUGGAUGGAGGCCUAGUU-5' | (SEQ ID NO: 315)<br>(SEQ ID NO: 4) |
| PLK773 (17 bp) | 5'-GACCUACCUCCGGAUCA-3'<br>3'-UCUGGAUGGAGGCCUAGUU-5' | (SEQ ID NO: 316)<br>(SEQ ID NO: 4) |

EXAMPLE 18

Exemplary miRNA Molecules Targeting PLK-1

Table 9 provides non-limiting examples of miRNA molecules that are suitable for modulating (e.g., silencing) PLK-1 expression. The miRNA molecules described herein may comprise one or more modified nucleotides. Examples of modified nucleotides are described herein and include 2'-O-methyl (2'OMe) nucleotides, 2'-deoxy-2'-fluoro (2'F) nucleotides, 2'-deoxy nucleotides, 2'-O-(2-methoxyethyl) (MOE) nucleotides, and locked nucleic acid (LNA) nucleotides. The 5' and/or 3' ends of the miRNA sequence may contain one, two, three, four, or more nontargeting nucleotides. In certain instances, a fragment of one of the miRNA sequences set forth in Table 9 may be used for modulating (e.g., silencing) PLK-1 expression. In certain other instances, an agent that blocks the interaction between one or more of the miRNA molecules set forth in Table 9 and their target PLK-1 mRNA sequence(s) may be used for modulating (e.g., silencing) PLK-1 expression. The miRNA molecules or blocking agents thereof may further comprise one of the carrier systems described herein (e.g., a nucleic acid particle) and find utility in treating cancers such as hepatocellular carcinoma.

Unmodified or modified pre-miRNA sequences corresponding to any of the mature miRNA sequences listed in Table 9 are also suitable for use in the present invention, e.g., to modulate (e.g., silence) PLK-1 expression. The pre-miRNA molecule may further comprise one of the carrier systems described herein (e.g., a nucleic acid particle) and find utility in treating cancers such as liver cancer (e.g., hepatocellular carcinoma).

TABLE 9 miRNA sequences that target human PLK-1 expression.

| Mature miRNA Name | Mature miRNA Accession No. | Mature miRNA Sequence (5'→3') | Mature miRNA SEQ ID NO: | Pre-miRNA Accession No. |
|---|---|---|---|---|
| hsa-miR-509-3-5p | MIMAT0004975 | UACUGCAGACGUGGCAAUCAUG | 317 | MI0005717 |
| mmu-miR-705 | MIMAT0003495 | GGUGGGAGGUGGGGUGGGCA | 318 | MI0004689 |
| hsa-miR-509-5p | MIMAT0004779 | UACUGCAGACAGUGGCAAUCA | 319 | MI0003196 |
| hsa-miR-505* | MIMAT0004776 | GGGAGCCAGGAAGUAUUGAUGU | 320 | MI0003190 |
| mmu-miR-762 | MIMAT0003892 | GGGGCUGGGGCCGGGACAGAGC | 321 | MI0004215 |
| hsa-miR-149* | MIMAT0004609 | AGGGAGGGACGGGGGCUGUGC | 322 | MI0000478 |
| hsa-miR-183 | MIMAT0000261 | UAUGGCACUGGUAGAAUUCACU | 323 | MI0000273 |
| hsa-miR-9* | MIMAT0000442 | AUAAAGCUAGAUAACCGAAAGU | 324 | MI0000466 |

TABLE 9-continued miRNA sequences that target human PLK-1 expression.

| Mature miRNA Name | Mature miRNA Accession No. | Mature miRNA Sequence (5'→3') | Mature miRNA SEQ ID NO: | Pre-miRNA Accession No. |
|---|---|---|---|---|
| mmu-miR-673-3p | MIMAT0004824 | UCCGGGGCUGAGUUCUGUGCACC | 325 | MI0004601 |
| hsa-miR-630 | MIMAT0003299 | AGUAUUCUGUACCAGGGAAGGU | 326 | MI0003644 |
| hsa-miR-491-3p | MIMAT0004765 | CUUAUGCAAGAUUCCCUUCUAC | 327 | MI0003126 |
| hsa-miR-559 | MIMAT0003223 | UAAAGUAAAUAUGCACCAAAA | 328 | MI0003565 |
| hsa-miR-593* | MIMAT0003261 | AGGCACCAGCCAGGCAUUGCUCAGC | 329 | MI0003605 |
| mmu-miR-327 | MIMAT0004867 | ACUUGAGGGGCAUGAGGAU | 330 | MI0005493 |
| hsa-let-7f-2* | MIMAT0004487 | CUAUACAGUCUACUGUCUUUCC | 331 | MI0000068 |
| hsa-miR-100 | MIMAT0000098 | AACCCGUAGAUCCGAACUUGUG | 332 | MI0000102 |
| hsa-miR-767-3p | MIMAT0003883 | UCUGCUCAUACCCCAUGGUUUCU | 333 | MI0003763 |
| hsa-miR-532-3p | MIMAT0004780 | CCUCCCACACCCAAGGCUUGCA | 334 | MI0003205 |
| hsa-miR-106b* | MIMAT0004672 | CCGCACUGUGGGUACUUGCUGC | 335 | MI0000734 |
| hsa-miR-568 | MIMAT0003232 | AUGUAUAAAUGUAUACACAC | 336 | MI0003574 |
| hsa-miR-652 | MIMAT0003322 | AAUGGCGCCACUAGGGUUGUG | 337 | MI0003667 |
| hsa-let-7e* | MIMAT0004485 | CUAUACGGCCUCCUAGCUUUCC | 338 | MI0000066 |
| hsa-miR-340 | MIMAT0004692 | UUAUAAAGCAAUGAGACUGAUU | 339 | MI0000802 |
| hsa-miR-198 | MIMAT0000228 | GGUCCAGAGGGGAGAUAGGUUC | 340 | MI0000240 |
| hsa-miR-548b-5p | MIMAT0004798 | AAAAGUAAUUGUGGUUUUGGCC | 341 | MI0003596 |
| hsa-miR-452* | MIMAT0001636 | CUCAUCUGCAAAGAAGUAAGUG | 342 | MI0001733 |
| hsa-miR-148b* | MIMAT0004699 | AAGUUCUGUUAUACACUCAGGC | 343 | MI0000811 |
| hsa-let-7g* | MIMAT0004584 | CUGUACAGGCCACUGCCUUGC | 344 | MI0000433 |
| hsa-miR-488 | MIMAT0004763 | UUGAAAGGCUAUUUCUUGGUC | 345 | MI0003123 |
| mmu-miR-693-5p | MIMAT0003472 | CAGCCACAUCCGAAAGUUUUC | 346 | MI0004662 |
| hsa-miR-136 | MIMAT0000448 | ACUCCAUUUGUUUUGAUGAUGGA | 347 | MI0000475 |
| hsa-miR-744 | MIMAT0004945 | UGCGGGGCUAGGGCUAACAGCA | 348 | MI0005559 |
| hsa-miR-324-3p | MIMAT0000762 | ACUGCCCCAGGUGCUGCUGG | 349 | MI0000813 |
| hsa-miR-320 | MIMAT0000510 | AAAAGCUGGGUUGAGAGGGCGA | 350 | MI0000542 |
| hsa-miR-99a | MIMAT0000097 | AACCCGUAGAUCCGAUCUUGUG | 351 | MI0000101 |
| hsa-miR-590-5p | MIMAT0003258 | GAGCUUAUUCAUAAAAGUGCAG | 352 | MI0003602 |
| hsa-miR-622 | MIMAT0003291 | ACAGUCUGCUGAGGUUGGAGC | 353 | MI0003636 |
| hsa-miR-151-5p | MIMAT0004697 | UCGAGGAGCUCACAGUCUAGU | 354 | MI0000809 |
| hsa-miR-142-5p | MIMAT0000433 | CAUAAAGUAGAAAGCACUACU | 355 | MI0000458 |
| hsa-miR-648 | MIMAT0003318 | AAGUGUGCAGGGCACUGGU | 356 | MI0003663 |
| hsa-miR-643 | MIMAT0003313 | ACUUGUAUGCUAGCUCAGGUAG | 357 | MI0003658 |
| hsa-miR-19a* | MIMAT0004490 | AGUUUUGCAUAGUUGCACUACA | 358 | MI0000073 |
| hsa-miR-516b | MIMAT0002859 | AUCGGAGGUAAGAAGCACUUU | 359 | MI0003172 |
| hsa-miR-296-5p | MIMAT0000690 | AGGGCCCCCCCUCAAUCCUGU | 360 | MI0000747 |
| hsa-miR-619 | MIMAT0003288 | GACCUGGACAUGUUUGUGCCCAGU | 361 | MI0003633 |

TABLE 9-continued miRNA sequences that target human PLK-1 expression.

| Mature miRNA Name | Mature miRNA Accession No. | Mature miRNA Sequence (5'→3') | Mature miRNA SEQ ID NO: | Pre-miRNA Accession No. |
|---|---|---|---|---|
| mmu-miR-742 | MIMAT0004237 | GAAAGCCACCAUGCUGGGUAAA | 362 | MI0005206 |
| hsa-miR-147b | MIMAT0004928 | GUGUGCGGAAAUGCUUCUGCUA | 363 | MI0005544 |
| mmu-miR-466h | MIMAT0004884 | UGUGUGCAUGUGCUUGUGUGUA | 364 | MI0005511 |
| mmu-miR-700 | MIMAT0003490 | CACGCGGGAACCGAGUCCACC | 365 | MI0004684 |
| hsa-miR-941 | MIMAT0004984 | CACCCGGCUGUGUGCACAUGUGC | 366 | MI0005763 |
| hsa-miR-21 | MIMAT0000076 | UAGCUUAUCAGACUGAUGUUGA | 367 | MI0000077 |
| mmu-miR-666-6p | MIMAT0003737 | AGCGGGCACAGCUGUGAGAGCC | 368 | MI0004553 |
| hsa-miR-17* | MIMAT0000071 | ACUGCAGUGAAGGCACUUGUAG | 369 | MI0000071 |
| hsa-miR-188-3p | MIMAT0004613 | CUCCCACAUGCAGGGUUUGCA | 370 | MI0000484 |
| hsa-miR-520d-5p | MIMAT0002855 | CUACAAAGGGAAGCCCUUUC | 371 | MI0003164 |
| hsa-miR-19a | MIMAT0000073 | UGUGCAAAUCUAUGCAAAACUGA | 372 | MI0000073 |
| hsa-miR-153 | MIMAT0000439 | UUGCAUAGUCACAAAAGUGAUC | 373 | MI0000463 |
| hsa-miR-554 | MIMAT0003217 | GCUAGUCCUGACUCAGCCAGU | 374 | MI0003559 |
| hsa-miR-610 | MIMAT0003278 | UGAGCUAAAUGUGUGCUGGGA | 375 | MI0003623 |
| hsa-miR-454 | MIMAT0003885 | UAGUGCAAUAUUGCUUAUAGGGU | 376 | MI0003820 |
| hsa-miR-10b* | MIMAT0004556 | ACAGAUUCGAUUCUAGGGGAAU | 377 | MI0000267 |
| hsa-miR-654-5p | MIMAT0003330 | UGGUGGGCCGCAGAACAUGUGC | 378 | MI0003676 |
| mmu-miR-466f-5p | MIMAT0004881 | UACGUGUGUGUGCAUGUGCAUG | 379 | MI0005507 |
| hsa-miR-210 | MIMAT0000267 | CUGUGCGUGUGACAGCGGCUGA | 380 | MI0000286 |
| hsa-miR-603 | MIMAT0003271 | CACACACUGCAAUUACUUUUGC | 381 | MI0003616 |
| hsa-miR-216b | MIMAT0004959 | AAAUCUCUGCAGGCAAAUGUGA | 382 | MI0005569 |
| mmu-miR-704 | MIMAT0003494 | AGACAUGUGCUCUGCUCCUAG | 383 | MI0004688 |
| hsa-miR-331-5p | MIMAT0004700 | CUAGGUAUGGUCCCAGGGAUCC | 384 | MI0000812 |
| mmu-miR-434-3p | MIMAT0001422 | UUUGAACCAUCACUCGACUCCU | 385 | MI0001526 |
| hsa-miR-589 | MIMAT0004799 | UGAGAACCACGUCUGCUCUGAG | 386 | MI0003599 |
| hsa-miR-548b-3p | MIMAT0003254 | CAAGAACCUCAGUUGCUUUUGU | 387 | MI0003596 |
| hsa-miR-10a* | MIMAT0004555 | CAAAUUCGUAUCUAGGGGAAUA | 388 | MI0000266 |
| hsa-miR-604 | MIMAT0003272 | AGGCUGCGGAAUUCAGGAC | 389 | MI0003617 |
| hsa-miR-485-3p | MIMAT0002176 | GUCAUACACGGCUCUCCUCUCU | 390 | MI0002469 |
| mmu-miR-883b-3p | MIMAT0004851 | UAACUGCAACAUCUCUCAGUAU | 391 | MI0005477 |
| hsa-miR-329 | MIMAT0001629 | AACACACCUGGUUAACCUCUUU | 392 | MI0001725 |
| hsa-miR-585 | MIMAT0003250 | UGGGCGUAUCUGUAUGCUA | 393 | MI0003592 |
| hsa-miR-551b | MIMAT0003233 | GCGACCCAUACUUGGUUUCAG | 394 | MI0003575 |
| hsa-miR-886-3p | MIMAT0004906 | CGCGGGUGCUUACUGACCCUU | 395 | MI0005527 |
| mmu-miR-714 | MIMAT0003505 | CGACGAGGGCCGGUCGGUCGC | 396 | MI0004699 |
| mmu-miR-293 | MIMAT0000371 | AGUGCCGCAGAGUUUGUAGUGU | 397 | MI0000391 |

TABLE 9-continued miRNA sequences that target human PLK-1 expression.

| Mature miRNA Name | Mature miRNA Accession No. | Mature miRNA Sequence (5'→3') | Mature miRNA SEQ ID NO: | Pre-miRNA Accession No. |
|---|---|---|---|---|
| hsa-miR-95 | MIMAT0000094 | UUCAACGGGUAUUUAUUGAGCA | 398 | MI0000097 |
| hsa-miR-99b | MIMAT0000689 | CACCCGUAGAACCGACCUUGCG | 399 | MI0000746 |

The Accession Nos. for the mature miRNA and pre-miRNA sequences correspond to entries that can be found in the miRBase Sequence Database from the Sanger Institute. The miRBase Sequence Database is a searchable database of published miRNA sequences and annotation.

EXAMPLE 19

Additional Modified PLK-1 siRNAs are Non-Immunostimulatory and Inhibit the Growth of Cancer Cells PLK-1 siRNA molecules containing 2'-O-methyl (2'OMe) nucleotides at selective positions on the sense and antisense strands of the siRNA were formulated as SNALP and evaluated for their inhibitory effects on cell growth in vitro. The modified PLK-1 siRNA sense and antisense strand sequences are shown in Table 10. Exemplary double-stranded modified PLK-1 siRNA molecules generated from the sequences of Table 10 are shown in Table 11.

TABLE 10

Modified PLK-1 sense and antisense strand siRNA sequences.

| siRNA | 5'→3' Sequence | Strand | SEQ ID NO: |
|---|---|---|---|
| PLK1424-1 | AGAUCACCCUCCUUAAAUAUU | Sense | 214 |
| PLK1424-2 | AGAUCACCCUCCUUAAAUAUU | Sense | 400 |
| PLK1424-3 | UAUUUAAGGAGGGUGAUCUUU | Antisense | 215 |
| PLK1424-4 | UAUUUAAGGAGGGUGAUCUUC | Antisense | 401 |
| PLK1424-5 | UAUUUAAGGAGGGUGAUCUUC | Antisense | 402 |
| PLK1424-6 | UAUUUAAGGAGGGUGAUCUUC | Antisense | 403 |
| PLK1424-7 | UAUUUAAGGAGGGUGAUCUUU | Antisense | 216 |
| PLK1424-8 | UAUUUAAGGAGGGUGAUCUUU | Antisense | 404 |
| PLK773-1 | AGACCUACCUCCGGAUCAAUU | Sense | 220 |
| PLK773-2 | AGACCUACCUCCGGAUCAAGA | Sense | 405 |
| PLK773-3 | UUGAUCCGGAGGUAGGUCUUU | Antisense | 223 |
| PLK773-4 | UUGAUCCGGAGGUAGGUCUCU | Antisense | 406 |
| PLK773-5 | UUGAUCCGGAGGUAGGUCUCU | Antisense | 407 |

Column 1: The number after "PLK" refers to the nucleotide position of the 5' base of the sense strand relative to the start codon (ATG) of the human PLK-1 mRNA sequence NM_005030. Column 2: 2'-O-methyl (2'OMe) nucleotides are indicated in bold and underlined. The siRNA can alternatively or additionally comprise 2'-deoxy-2'-fluoro (2'F) nucleotides, 2'deoxy nucleotides, 2'-O-(2-methoxyethyl) (MOE) nucleotides, and/or locked nucleic acid (LNA) nucleotides.

TABLE 11

PLK-1 siRNA molecules comprising modified sense and antisense strand sequences.

| siRNA | PLK-1 siRNA Sequence | % 2'OMe-Modified | % Modified in DS Region |
|---|---|---|---|
| PLK1424 1/3 | 5'-AGAUCACCCUCCUUAAAUAUU-3' (SEQ ID NO: 214)<br>3'-UUUCUAGUGGGAGGAAUUUAU-5' (SEQ ID NO: 215) | 6/42 = 14.3% | 6/38 = 15.8% |
| PLK1424 1/4 | 5'-AGAUCACCCUCCUUAAAUAUU-3' (SEQ ID NO: 214)<br>3'-CUUCUAGUGGGAGGAAUUUAU-5' (SEQ ID NO: 401) | 6/42 = 14.3% | 6/38 = 15.8% |
| PLK1424 1/5 | 5'-AGAUCACCCUCCUUAAAUAUU-3' (SEQ ID NO: 214)<br>3'-CUUCUAGUGGGAGGAAUUUAU-5' (SEQ ID NO: 402) | 7/42 = 16.7% | 6/38 = 15.8% |
| PLK1424 1/6 | 5'-AGAUCACCCUCCUUAAAUAUU-3' (SEQ ID NO: 214)<br>3'-CUUCUAGUGGGAGGAAUUUAU-5' (SEQ ID NO: 403) | 8/42 = 19% | 7/38 = 18.4% |
| PLK1424 1/7 | 5'-AGAUCACCCUCCUUAAAUAUU-3' (SEQ ID NO: 214)<br>3'-UUUCUAGUGGGAGGAAUUUAU-5' (SEQ ID NO: 216) | 7/42 = 16.7% | 7/38 = 18.4% |
| PLK1424 1/8 | 5'-AGAUCACCCUCCUUAAAUAUU-3' (SEQ ID NO: 214)<br>3'-UUUCUAGUGGGAGGAAUUUAU-5' (SEQ ID NO: 404) | 9/42 = 21.4% | 9/38 = 23.7% |
| PLK1424 2/3 | 5'-AGAUCACCCUCCUUAAAUAUU-3' (SEQ ID NO: 400) | 7/42 = 16.7% | 6/38 = 15.8% |

TABLE 11-continued

PLK-1 siRNA molecules comprising modified sense and antisense strand sequences.

| siRNA | PLK-1 siRNA Sequence | | % 2'OMe-Modified | % Modified in DS Region |
|---|---|---|---|---|
| | 3'-UUUCUAGUGGGAGGAAUUUAU-5' | (SEQ ID NO: 215) | | |
| PLK1424 2/4 | 5'-AGAUCACCCUCCUUAAAUAUU-3' | (SEQ ID NO: 400) | 7/42 = 16.7% | 6/38 = 15.8% |
| | 3'-CUUCUAGUGGGAGGAAUUUAU-5' | (SEQ ID NO: 401) | | |
| PLK1424 2/5 | 5'-AGAUCACCCUCCUUAAAUAUU-3' | (SEQ ID NO: 400) | 8/42 = 19% | 6/38 = 15.8% |
| | 3'-CUUCUAGUGGGAGGAAUUUAU-5' | (SEQ ID NO: 402) | | |
| PLK1424 2/6 | 5'-AGAUCACCCUCCUUAAAUAUU-3' | (SEQ ID NO: 400) | 9/42 = 21.4% | 7/38 = 18.4% |
| | 3'-CUUCUAGUGGGAGGAAUUUAU-5' | (SEQ ID NO: 403) | | |
| PLK1424 2/7 | 5'-AGAUCACCCUCCUUAAAUAUU-3' | (SEQ ID NO: 400) | 8/42 = 19% | 7/38 = 18.4% |
| | 3'-UUUCUAGUGGGAGGAAUUUAU-5' | (SEQ ID NO: 216) | | |
| PLK1424 2/8 | 5'-AGAUCACCCUCCUUAAAUAUU-3' | (SEQ ID NO: 400) | 10/42 = 23.8% | 9/38 = 23.7% |
| | 3'-UUUCUAGUGGGAGGAAUUUAU-5' | (SEQ ID NO: 404) | | |

Column 1: The number after "PLK" refers to the nucleotide position of the 5' base of the sense strand relative to the start codon (ATG) of the human PLK-1 mRNA sequence NM_005030.
Column 2: 2'-O-methyl (2'OMe) nucleotides are indicated in bold and underlined. The siRNA duplex can alternatively or additionally comprise 2'-deoxy-2'-fluoro (2'F) nucleotides, 2'-deoxy nucleotides, 2'-O-(2-methoxyethyl) (MOE) nucleotides, and/or locked nucleic acid (LNA) nucleotides.
Column 3: The number and percentage of 2'OMe-modified nucleotides in the siRNA molecule are provided.
Column 4: The number and percentage of modified nucleotides in the double-stranded (DS) region of the siRNA molecule are provided.

Cell viability assays. For in vitro PLK-1 siRNA activity assays, HT29 cells were cultured in 96 well plates in the presence of SNALP formulated PLK-1 siRNA. Cell viability analysis was performed at 72 hours following transfection with a range of PLK-1 SNALP dosages. FIG. 40 shows that different chemical modification patterns in the PLK1424 siRNA sequence were well tolerated and the modified siRNA molecules retained potent activity in killing human tumor cells.

In vivo immune stimulation assays. Animal studies were performed to test for the immunostimulatory activity of SNALP containing 2'OMe-modified PLK1424 siRNAs. Six-week-old female CD1 ICR mice were used in this study. Mice were administered SNALP formulated siRNA resuspended in PBS via standard intravenous injection in the lateral tail vein and then sacrificed 4 hours after SNALP administration. The tolerability of the treatment regime was monitored by animal appearance and behavior. Blood was collected by cardiac puncture and processed as plasma for cytokine analysis of IFN-α and IL-6 protein levels by ELISA. Liver and spleen from the same animals were collected into RNALater (Sigma Co.) for IFIT1 mRNA analysis by bDNA (QG) assay.
Test Articles of detection (15.6 pg/ml). FIG. 42 shows that there was no significant IFIT1 induction above that of empty SNALP with PLK1424 1/3, PLK1424 2/3, PLK1424 2/4, and PLK1424 2/6 siRNAs. The IFIT1 QG analysis was more sensitive than the IFN-α ELISA for measuring immunogenicity because it resolved low-grade immune stimulation.

Subcutaneous tumor models. Hep3B tumors were established in scid/beige mice by subcutaneous injection of tumor cells into the left hind flank. PLK1424 siRNA SNALP formulations were then administered by intravenous injection as a 3 mg/kg single dose. The extent of PLK-1 mRNA knockdown was determined in the Hep3B tumors about 24 hours after SNALP administration. FIG. 43 shows that all PLK1424 siRNAs tested produced an equivalent level of PLK-1 mRNA silencing in vivo.

In vivo PEG-lipid antibody induction assays. Animal studies were performed to test for the induction of an antibody response to 2'OMe-modified PLK1424 siRNAs that were encapsulated in a 1:57 SNALP formulation containing the lipid conjugate PEG-cDMA. Six-week-old female CD1 ICR mice were used in this study. Mice were administered SNALP

| Group | Test Article | siRNA | n | Lot | siRNA dose | Treat day | End point | Data & Sample collection |
|---|---|---|---|---|---|---|---|---|
| A | PBS | N/A | 4 | | N/A | Day 0 | 4 h | Body weights at dosing |
| B | 1:57 PEG-cDMA | PLK1424 1/3 | 4 | 390-062608-1 | 3 mg/kg | | | Terminal Plasma 4 h after injection |
| C | (28 mM) | PLK1424 2/3 | 4 | 390-062608-2 | | | | |
| D | pH loaded | PLK1424 2/4 | 4 | 390-062608-3 | | | | Half of left lateral lobe of liver into RNAlater and the whole spleen into RNAlater. |
| E | | PLK1424 2/5 | 4 | 390-062608-4 | | | | |
| F | | PLK1424 2/6 | 4 | 390-062608-5 | | | | |
| G | | BimA mod 2/3 | 4 | 390-062608-7 | | | | |
| H | | Empty | 4 | 390-062608-8 | | | | |

FIG. 41 shows that modified PLK1424 siRNAs did not induce an IFN-α response that was greater than the "PBS" and "Empty" negative controls. Only the BimA siRNA positive control induced IFN-α protein in plasma above the level formulated siRNA resuspended in PBS via standard intravenous injection in the lateral tail vein at Days 0, 7, and 14. Mice were then sacrificed on Day 21. The tolerability of the treatment regime was monitored by animal appearance, behavior, and body weight. Anti-PEG-lipid IgG and IgM antibodies in plasma at Days 7, 14, and 21 were measured by ELISA.

SNALP containing PLK1424 1/3 siRNA was substantially less immunogenic than SNALP containing the corresponding unmodified PLK1424 siRNA sequence. In particular, PLK1424 1/3 SNALP had a significantly lower potential for generating an IgG or IgM antibody response against the PEG-lipid conjugate PEG-cDMA. In addition, SNALP containing either PLK1424 2/3, PLK1424 2/4, or PLK1424 2/6 siRNA produced almost no detectable antibody responses against the PEG-lipid. In fact, PLK1424 2/6 SNALP consistently had the lowest antibody response to PEG-cDMA out of all PLK-1 siRNA sequences tested. As such, the present invention provides methods for designing and optimizing PLK-1 siRNA sequences to substantially reduce or abrogate the immunogenic properties of unmodified siRNA sequences.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications, patents, PCT publications, and Genbank Accession Nos., are incorporated herein by reference for all purposes.

What is claimed is:

1. A modified siRNA molecule for silencing polo-like kinase 1 (PLK-1) expression, wherein the modified siRNA molecule comprises a sense strand consisting of SEQ ID NO:57, a complementary antisense strand, and a double-stranded region of 15 to 19 nucleotides in length, and
wherein the antisense strand comprises at least one 2'OMe-guanosine nucleotide and at least one 2'OMe-uridine nucleotide in the double-stranded region.

2. The modified siRNA molecule of claim 1, wherein the 5'-NN-3' sequence in SEQ ID NO:57 corresponds to a 3' overhang in the sense strand of the modified siRNA molecule.

3. The modified siRNA molecule of claim 2, wherein one or more of the nucleotides in the 3' overhang comprise modified nucleotides.

4. The modified siRNA molecule of claim 1, wherein less than 30% of the nucleotides in the double-stranded region comprise modified nucleotides.

5. The modified siRNA molecule of claim 1, wherein the modified siRNA molecule is less immunostimulatory than a corresponding unmodified siRNA sequence.

6. The modified siRNA molecule of claim 1, wherein the antisense strand consists of SEQ ID NO:403.

7. The modified siRNA molecule of claim 1, wherein the sense strand consists of SEQ ID NO:400.

8. The modified siRNA molecule of claim 1, wherein the sense strand consists of SEQ ID NO:400 and the antisense strand consists of SEQ ID NO:403.

9. The modified siRNA molecule of claim 1, further comprising a carrier system.

10. The modified siRNA molecule of claim 9, wherein the carrier system is selected from the group consisting of a nucleic acid-lipid particle, a liposome, a micelle, a virosome, a nucleic acid complex, and mixtures thereof.

11. The modified siRNA molecule of claim 10, wherein the carrier system is a nucleic acid-lipid particle.

12. A pharmaceutical composition comprising a modified siRNA molecule of claim 1 and a pharmaceutically acceptable carrier.

13. A nucleic acid-lipid particle comprising:
a modified siRNA molecule of claim 1;
a cationic lipid comprising from about 50 mol % to about 65 mol % of the total lipid present in the particle;
a non-cationic lipid comprising a mixture of a phospholipid and cholesterol or a derivative thereof, wherein the phospholipid comprises from about 4 mol % to about 10 mol % of the total lipid present in the particle and the cholesterol or derivative thereof comprises from about 30 mol % to about 40 mol % of the total lipid present in the particle; and
a polyethyleneglycol (PEG)-lipid conjugate comprising from about 1 mol % to about 15 mol % of the total lipid present in the particle.

14. The nucleic acid-lipid particle of claim 13, wherein the cationic lipid is a member selected from the group consisting of 1,2-Dilinoleyloxy-N,N-dimethylaminopropane (DLinDMA), 1,2-Dilinolenyloxy-N,N-dimethylaminopropane (DLenDMA), N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), distearyldimethylammonium (DSDMA), N-(1-(2,3-dioleyloxy)propyl)-N,N,N-trimethylammonium chloride (DOTMA), N,N-dimethyl-2,3-dioleyloxypropylamine (DODMA), 3-(N-(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), and a mixture thereof.

15. The nucleic acid-lipid particle of claim 13, wherein the cationic lipid is DLinDMA.

16. The nucleic acid-lipid particle of claim 13, wherein the PEG-lipid conjugate is a member selected from the group consisting of a PEG-diacylglycerol, a PEG dialkyloxypropyl, a PEG-phospholipid, a PEG-ceramide, a PEG-cholesterol, and a mixture thereof.

17. The nucleic acid-lipid particle of claim 13, wherein the PEG-lipid conjugate comprises a polyethyleneglycol (PEG)-dialkyloxypropyl (PEG-DAA) conjugate.

18. The nucleic acid-lipid particle of claim 13, wherein the modified siRNA molecule is fully encapsulated in the nucleic acid-lipid particle.

19. A pharmaceutical composition comprising a nucleic acid-lipid particle of claim 13 and a pharmaceutically acceptable carrier.

20. A method for introducing an siRNA that silences polo-like kinase 1 (PLK-1) expression into a cell, the method comprising:
contacting the cell with a nucleic acid-lipid particle of claim 13.

21. The method of claim 20, wherein the cell is in a mammal.

22. A method for the in vivo delivery of an siRNA that silences polo-like kinase 1 (PLK-1) expression, the method comprising:
administering to a mammalian subject a nucleic acid-lipid particle of claim 13.

23. The method of claim 22, wherein the administration is selected from the group consisting of oral, intranasal, intravenous, intraperitoneal, intramuscular, intra-articular, intralesional, intratracheal, subcutaneous, and intradermal.

24. A method for treating cancer in a mammalian subject in need thereof, the method comprising:
administering to the mammalian subject a therapeutically effective amount of a nucleic acid-lipid particle of claim 13.

25. The method of claim 24, wherein the cancer is liver cancer.

26. The method of claim 25, wherein the liver cancer is hepatocellular carcinoma.

27. The nucleic acid-lipid particle of claim 13, wherein the phospholipid is a member selected from the group consisting of dipalmitoylphosphatidylcholine (DPPC), distearoylphosphatidylcholine (DSPC), dioleoylphosphatidylethanolamine (DOPE), palmitoyloleoylphosphatidylcholine (POPC), palmitoyloleoylphosphatidylethanolamine (POPE), palmitoyloleoylphosphatidylglycerol (POPG), dipalmitoylphosphatidylethanolamine (DPPE), dimyristoylphosphatidylethanolamine (DMPE), distearoylphosphatidylethanolamine (DSPE), monomethylphosphatidylethanolamine, dimethylphosphatidylethanolamine, dielaidoylphosphatidylethanolamine (DEPE), stearoyloleoylphosphatidylethanolamine (SOPE), egg phosphatidylcholine (EPC), and a mixture thereof.

28. The nucleic acid-lipid particle of claim 13, wherein the cholesterol derivative is a member selected from the group consisting of cholestanol, cholestanone, cholestenone, coprostanol, cholesteryl-2'-hydroxyethyl ether, and cholesteryl-4'-hydroxybutyl ether.

29. The nucleic acid-lipid particle of claim 13, wherein the phospholipid comprises DPPC.

30. The nucleic acid-lipid particle of claim 13, wherein the PEG-lipid conjugate comprises from about 4 mol % to about 15 mol % of the total lipid present in the particle.

31. The nucleic acid-lipid particle of claim 17, wherein the PEG-DAA conjugate comprises a PEG-dimyristyloxypropyl (PEG-DMA) conjugate.

32. The nucleic acid-lipid particle of claim 13, wherein the particle has a lipid:siRNA mass ratio of from about 5 to about 15.

33. The nucleic acid-lipid particle of claim 13, wherein the particle has a median diameter of from about 50 nm to about 150 nm.

34. The nucleic acid-lipid particle of claim 13, wherein:
the phospholipid comprises from about 5 mol % to about 9 mol % of the total lipid present in the particle;
the cholesterol or derivative thereof comprises from about 30 mol % to about 35 mol % of the total lipid present in the particle; and
the PEG-lipid conjugate comprises from about 4 mol % to about 10 mol % of the total lipid present in the particle.

35. The modified siRNA molecule of claim 1, wherein the antisense strand comprises a 3' overhang.

36. The modified siRNA molecule of claim 35, wherein one or more of the nucleotides in the 3' overhang comprise modified nucleotides.

37. The modified siRNA molecule of claim 1, wherein the modified siRNA molecule does not comprise 2'OMc-cytosine nucleotides.

38. The modified siRNA molecule of claim 1, wherein the modified siRNA molecule does not comprise phosphate backbone modifications.

39. The modified siRNA molecule of claim 1, wherein from about 15% to about 30% of the nucleotides in the double-stranded region comprise modified nucleotides.

40. The modified siRNA molecule of claim 1, wherein the modified siRNA molecule comprises a double-stranded region of 19 nucleotides in length.

41. The nucleic acid-lipid particle of claim 11, wherein the particle comprises a cationic lipid, a non-cationic lipid, and a polyethyleneglycol (PEG)-lipid conjugate.

* * * * *

SEQUENCE LISTING

```
<160> NUMBER OF SEQ ID NOS: 407

<210> SEQ ID NO 1
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 1
agaucacccu ccuuaaaua                                                19

<210> SEQ ID NO 2
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 2
uauuuaagga gggugaucu                                                19

<210> SEQ ID NO 3
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 3
agaccuaccu ccggaucaa                                                19

<210> SEQ ID NO 4
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 4
uugauccgga gguaggucu                                                19

<210> SEQ ID NO 5
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
```

```
                           siRNA sense strand

<400> SEQUENCE: 5
gguccuagug gacccacgc                                               19

<210> SEQ ID NO 6
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 6 gcguggqucc acuaggacc                                               19
```

(Note: above line as printed: `gcgugggucc acuaggacc`)

```
<210> SEQ ID NO 7
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 7
cuccuggagc ugcacaaga                                               19

<210> SEQ ID NO 8
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 8
ucuugugcag cuccaggag                                               19

<210> SEQ ID NO 9
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 9
guggaugugu gguccauug                                               19

<210> SEQ ID NO 10
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 10
caauggacca cacauccac                                               19

<210> SEQ ID NO 11
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand
```

```
<400> SEQUENCE: 11
gagaccuacc uccggauca                                                    19

<210> SEQ ID NO 12
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 12
ugauccggag guaggucuc                                                    19

<210> SEQ ID NO 13
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 13
gccgccuccc ucauccaga                                                    19

<210> SEQ ID NO 14
<211> LENGTH: 19
<212> TYPE: RNA
<213> ORGANISM: Artificial Sequence
<220> FEATURE:
<223> OTHER INFORMATION: human polo-like kinase 1 (PLK-1) siRNA
      antisense strand

<400> SEQUENCE: 14
ucuggaugag ggaggcggc                                                    19

<210> SEQ ID NO 15
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 15
cucccucauc cagaagaug                                                    19

<210> SEQ ID NO 16
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 16
caucuucugg augagggag                                                    19

<210> SEQ ID NO 17
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand
```

```
<400> SEQUENCE: 17
ccagugguuc gagagacag                                                    19

<210> SEQ ID NO 18
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 18
cugucucucg aaccacugg                                                    19

<210> SEQ ID NO 19
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 19
gaggcugagg auccugccu                                                    19

<210> SEQ ID NO 20
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 20
aggcaggauc cucagccuc                                                    19

<210> SEQ ID NO 21
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 21
gggucagcaa gugggugga                                                    19

<210> SEQ ID NO 22
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 22
uccacccacu ugcugaccc                                                    19

<210> SEQ ID NO 23
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 23
```
ucagcaagug gguggacua                                        19

<210> SEQ ID NO 24
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 24
uaguccaccc acuugcuga                                        19

<210> SEQ ID NO 25
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 25
cagcaagugg guggacuau                                        19

<210> SEQ ID NO 26
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 26
auaguccacc cacuugcug                                        19

<210> SEQ ID NO 27
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 27
gguggacuau ucggacaag                                        19

<210> SEQ ID NO 28
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 28
cuuguccgaa uaguccacc                                        19

<210> SEQ ID NO 29
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 29

```
gacagccugc aguacauag                                                 19

<210> SEQ ID NO 30
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 30
cuauguacug caggcuguc                                                 19

<210> SEQ ID NO 31
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 31
gcgccaucau ccugcaccu                                                 19

<210> SEQ ID NO 32
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 32
aggugcagga ugauggcgc                                                 19

<210> SEQ ID NO 33
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA sense strand

<400> SEQUENCE: 33
cccaucccaa uuccuugau                                                 19

<210> SEQ ID NO 34
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA antisense strand

<400> SEQUENCE: 34
aucaaggaau ugggaugggg                                                19

<210> SEQ ID NO 35
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA sense strand

<400> SEQUENCE: 35
agaucacucu ccucaacua                                                 19
```

<210> SEQ ID NO 36
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA antisense strand

<400> SEQUENCE: 36
uaguugagga gagugaucu                                              19

<210> SEQ ID NO 37
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA sense strand

<400> SEQUENCE: 37
gaucacucuc cucaacuau                                              19

<210> SEQ ID NO 38
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA antisense strand

<400> SEQUENCE: 38
auaguugagg agagugauc                                              19

<210> SEQ ID NO 39
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA sense strand

<400> SEQUENCE: 39
cacucuccuc aacuauuuc                                              19

<210> SEQ ID NO 40
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA antisense strand

<400> SEQUENCE: 40
gaaauaguug aggagagug                                              19

<210> SEQ ID NO 41
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA sense strand

<400> SEQUENCE: 41
ccucaacuau uuccgcaau                                              19

<210> SEQ ID NO 42
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1) siRNA antisense strand

<400> SEQUENCE: 42
auugcggaaa uaguugagg                                               19

<210> SEQ ID NO 43
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1) siRNA sense strand

<400> SEQUENCE: 43
aggaccacac caaacuuau                                               19

<210> SEQ ID NO 44
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1) siRNA antisense strand

<400> SEQUENCE: 44
auaaguuugg uguggccu                                                19

<210> SEQ ID NO 45
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1) siRNA sense strand

<400> SEQUENCE: 45
ggaccacacc aaacuuauc                                               19

<210> SEQ ID NO 46
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1) siRNA antisense strand

<400> SEQUENCE: 46
gauaaguuug guguggucc                                               19

<210> SEQ ID NO 47
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1) siRNA sense strand

<400> SEQUENCE: 47
gaccuacauc aacgagaag                                               19

```
<210> SEQ ID NO 48
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA antisense strand

<400> SEQUENCE: 48
cuucucguug auguagguc                                                      19

<210> SEQ ID NO 49
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA sense strand

<400> SEQUENCE: 49
gagggacuuc caaacguac                                                      19

<210> SEQ ID NO 50
<211> LENGTH: 19
<212> TYPE: RNA
<213> ORGANISM: Artificial Sequence
<220> FEATURE:
<223> OTHER INFORMATION: synthetic mouse polo-like kinase 1 (PLK-1)
      siRNA antisense strand

<400> SEQUENCE: 50
guacguuugg aaguccuc                                                       19

<210> SEQ ID NO 51
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand
<220> FEATURE:
<221> NAME/KEY: modified_base
<222> LOCATION: (20)...(21)
<223> OTHER INFORMATION: n = g, a, c or u

<400> SEQUENCE: 51
agaucacccu ccuuaaauan n                                                   21

<210> SEQ ID NO 52
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA antisense strand
<220> FEATURE:
<221> NAME/KEY: modified_base
<222> LOCATION: (20)...(21)
<223> OTHER INFORMATION: n = g, a, c or u

<400> SEQUENCE: 52
uauuuaagga gggugaucun n                                                   21

<210> SEQ ID NO 53
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
```

```
                              modified siRNA sense strand
<220> FEATURE:
<221> NAME/KEY: modified_base
<222> LOCATION: (4)...(14)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 53
agancacccn ccunaaauan n                                              21

<210> SEQ ID NO 54
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (17)...(17)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 54
uauuuaanga gggugancun n                                              21

<210> SEQ ID NO 55
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (11)...(11)
<223> OTHER INFORMATION: n = gm
<220> FEATURE:
<221> NAME/KEY: modified_base
<222> LOCATION: (14)...(17)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 55
uauunaagga nggngancun n                                              21

<210> SEQ ID NO 56
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (9)...(15)
```

```
<223> OTHER INFORMATION: n = gm
<220> FEATURE:
<221> NAME/KEY: modified_base
<222> LOCATION: (20)...(21)
<223> OTHER INFORMATION: n = g, a, c or u

<400> SEQUENCE: 56
uauuuaagna gngunaucun n                                              21

<210> SEQ ID NO 57
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (4)...(18)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 57
agancacccn ccunaaanan n                                              21

<210> SEQ ID NO 58
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand
<220> FEATURE:
<221> NAME/KEY: modified_base
<222> LOCATION: (20)...(21)
<223> OTHER INFORMATION: n = g, a, c or u

<400> SEQUENCE: 58
agaccuaccu ccggaucaan n                                              21

<210> SEQ ID NO 59
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA antisense strand
<220> FEATURE:
<221> NAME/KEY: modified_base
<222> LOCATION: (20)...(21)
<223> OTHER INFORMATION: n = g, a, c or u

<400> SEQUENCE: 59
uugauccgga gguaggucun n                                              21

<210> SEQ ID NO 60
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (6)...(16)
<223> OTHER INFORMATION: n = um
<220> FEATURE:
<221> NAME/KEY: modified_base
```

```
<222> LOCATION: (20)...(21)
<223> OTHER INFORMATION: n = g, a, c or u

<400> SEQUENCE: 60
agaccnaccn ccggancaan n                                              21

<210> SEQ ID NO 61
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (5)...(17)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 61
uuganccgga ggnaggncun n                                              21

<210> SEQ ID NO 62
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (8)...(16)
<223> OTHER INFORMATION: n = gm
<220> FEATURE:
<221> NAME/KEY: modified_base
<222> LOCATION: (20)...(21)
<223> OTHER INFORMATION: n = g, a, c or u

<400> SEQUENCE: 62
uuganccnga nguagnucun n                                              21

<210> SEQ ID NO 63
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (9)...(12)
<223> OTHER INFORMATION: n = gm
<220> FEATURE:
<221> NAME/KEY: modified_base
<222> LOCATION: (17)...(17)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 63
uugauccgna gnuaggncun n                                              21
```

```
<210> SEQ ID NO 64
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (2)...(13)
<223> OTHER INFORMATION: n = gm
<220> FEATURE:
<221> NAME/KEY: modified_base
<222> LOCATION: (20)...(21)
<223> OTHER INFORMATION: n = g, a, c or u

<400> SEQUENCE: 64
anaccuaccu ccngaucaan n                                              21

<210> SEQ ID NO 65
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand
<220> FEATURE:
<221> NAME/KEY: modified_base
<222> LOCATION: (20)...(21)
<223> OTHER INFORMATION: n = g, a, c or u

<400> SEQUENCE: 65
gaucacccuc cuuaaauaun n                                              21

<210> SEQ ID NO 66
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA antisense strand
<220> FEATURE:
<221> NAME/KEY: modified_base
<222> LOCATION: (20)...(21)
<223> OTHER INFORMATION: n = g, a, c or u

<400> SEQUENCE: 66
auauuuaagg agggugaucn n                                              21

<210> SEQ ID NO 67
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (3)...(17)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 67
gancacccuc cunaaanaun n                                              21

<210> SEQ ID NO 68
<211> LENGTH: 21
<212> TYPE: RNA
```

```
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (9)...(9)
<223> OTHER INFORMATION: n = gm
<220> FEATURE:
<221> NAME/KEY: modified_base
<222> LOCATION: (18)...(18)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 68
auauuuaang agggugancn n                                              21

<210> SEQ ID NO 69
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (10)...(16)
<223> OTHER INFORMATION: n = gm
<220> FEATURE:
<221> NAME/KEY: modified_base
<222> LOCATION: (20)...(21)
<223> OTHER INFORMATION: n = g, a, c or u

<400> SEQUENCE: 69
auauuuaagn agngunaucn n                                              21

<210> SEQ ID NO 70
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (6)...(6)
<223> OTHER INFORMATION: n = um
<220> FEATURE:
<221> NAME/KEY: modified_base
<222> LOCATION: (12)...(12)
<223> OTHER INFORMATION: n = gm
<220> FEATURE:
<221> NAME/KEY: modified_base
<222> LOCATION: (15)...(18)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 70
auauunaagg anggngancn n                                              21

<210> SEQ ID NO 71
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
```

```
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (9)...(16)
<223> OTHER INFORMATION: n = gm
<220> FEATURE:
<221> NAME/KEY: modified_base
<222> LOCATION: (18)...(18)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 71
auaunuaang agggunancn n                                              21

<210> SEQ ID NO 72
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (3)...(17)
<223> OTHER INFORMATION: n = um
<220> FEATURE:
<221> NAME/KEY: modified_base
<222> LOCATION: (20)...(21)
<223> OTHER INFORMATION: n = g, a, c or u

<400> SEQUENCE: 72
gancacccnc cunaaanaun n                                              21

<210> SEQ ID NO 73
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 73
ggucugcagc gcagcuucg                                                 19

<210> SEQ ID NO 74
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 74
cgaagcugcg cugcagacc                                                 19

<210> SEQ ID NO 75
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 75
```
gcgcagcuuc gggagcaug                                              19

<210> SEQ ID NO 76
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 76
caugcucccg aagcugcgc                                              19

<210> SEQ ID NO 77
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 77
agccgcacca gagggagaa                                              19

<210> SEQ ID NO 78
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 78
uucucccucu ggugcggcu                                              19

<210> SEQ ID NO 79
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 79
gccgcaccag agggagaag                                              19

<210> SEQ ID NO 80
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 80
cuucucccuc uggugcggc                                              19

<210> SEQ ID NO 81
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 81
gaagaugucc auggaaaua                                              19

<210> SEQ ID NO 82
<211> LENGTH: 19
<212> TYPE: RNA
<213> ORGANISM: Artificial Sequence
<220> FEATURE:
<223> OTHER INFORMATION: synthetic human polo-like kinase 1 (PLK-1) siRNA antisense strand

<400> SEQUENCE: 82
uauuuccaug gacaucuuc                                                   19

<210> SEQ ID NO 83
<211> LENGTH: 19
<212> TYPE: RNA
<213> ORGANISM: Artificial Sequence
<220> FEATURE:
<223> OTHER INFORMATION: synthetic human polo-like kinase 1 (PLK-1) siRNA sense strand

<400> SEQUENCE: 83
ggacaacgac uucguguuc                                                   19

<210> SEQ ID NO 84
<211> LENGTH: 19
<212> TYPE: RNA
<213> ORGANISM: Artificial Sequence
<220> FEATURE:
<223> OTHER INFORMATION: synthetic human polo-like kinase 1 (PLK-1) siRNA antisense strand

<400> SEQUENCE: 84
gaacacgaag ucguugucc                                                   19

<210> SEQ ID NO 85
<211> LENGTH: 19
<212> TYPE: RNA
<213> ORGANISM: Artificial Sequence
<220> FEATURE:
<223> OTHER INFORMATION: synthetic human polo-like kinase 1 (PLK-1) siRNA sense strand

<400> SEQUENCE: 85
gcugcacaag aggaggaaa                                                   19

<210> SEQ ID NO 86
<211> LENGTH: 19
<212> TYPE: RNA
<213> ORGANISM: Artificial Sequence
<220> FEATURE:
<223> OTHER INFORMATION: synthetic human polo-like kinase 1 (PLK-1) siRNA antisense strand

<400> SEQUENCE: 86
uuuccuccuc uugugcagc                                                   19

<210> SEQ ID NO 87
<211> LENGTH: 19
<212> TYPE: RNA
<213> ORGANISM: Artificial Sequence
<220> FEATURE:
<223> OTHER INFORMATION: synthetic human polo-like kinase 1 (PLK-1) siRNA sense strand

<400> SEQUENCE: 87
gaggaggaaa gcccugacu                                                   19

<210> SEQ ID NO 88
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 88
agucagggcu uuccuccuc                                                    19

<210> SEQ ID NO 89
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 89
ggaggaaagc ccugacuga                                                    19

<210> SEQ ID NO 90
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 90
ucagucaggg cuuuccucc                                                    19

<210> SEQ ID NO 91
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 91
agcccugacu gagccugag                                                    19

<210> SEQ ID NO 92
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 92
cucaggcuca gucagggcu                                                    19

<210> SEQ ID NO 93
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 93
gcccugacug agccugagg                                                    19

```
<210> SEQ ID NO 94
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 94
ccucaggcuc agucagggc                                                19

<210> SEQ ID NO 95
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 95
gccugaggcc cgauacuac                                                19

<210> SEQ ID NO 96
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 96
guaguaucgg gccucaggc                                                19

<210> SEQ ID NO 97
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 97
ggcccgauac uaccuacgg                                                19

<210> SEQ ID NO 98
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 98
ccguagguag uaucgggcc                                                19

<210> SEQ ID NO 99
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 99
ccugcaccga aaccgaguu                                                19

<210> SEQ ID NO 100
```

```
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 100
aacucgguuu cggugcagg                                                   19

<210> SEQ ID NO 101
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 101
ccgaaaccga guuauucau                                                   19

<210> SEQ ID NO 102
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 102
augaauaacu cgguuucgg                                                   19

<210> SEQ ID NO 103
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 103
cuggcaacca aagucgaau                                                   19

<210> SEQ ID NO 104
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 104
auucgacuuu gguugccag                                                   19

<210> SEQ ID NO 105
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 105
gaggaagaag acccugugu                                                   19

<210> SEQ ID NO 106
<211> LENGTH: 19
```

```
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 106
acacaggguc uucuuccuc                                                        19

<210> SEQ ID NO 107
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 107
gacccugugu gggacuccu                                                        19

<210> SEQ ID NO 108
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 108
aggagcccca cacagggguc                                                       19

<210> SEQ ID NO 109
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 109
cccugugugg gacuccuaa                                                        19

<210> SEQ ID NO 110
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 110
uuaggagucc cacacaggg                                                        19

<210> SEQ ID NO 111
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 111
ggugcugagc aagaaaggg                                                        19

<210> SEQ ID NO 112
<211> LENGTH: 19
<212> TYPE: RNA
```

```
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 112
cccuuucuug cucagcacc                                                  19

<210> SEQ ID NO 113
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 113
gguggaugug ugguccauu                                                  19

<210> SEQ ID NO 114
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 114
aauggaccac acauccacc                                                  19

<210> SEQ ID NO 115
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 115
uuggguguau cauguauac                                                  19

<210> SEQ ID NO 116
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 116
guauacauga uacacccaa                                                  19

<210> SEQ ID NO 117
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 117
gugggcaaac caccuuuug                                                  19

<210> SEQ ID NO 118
<211> LENGTH: 19
<212> TYPE: RNA
<213> ORGANISM: Artificial Sequence
```

```
<220> FEATURE:
<223> OTHER INFORMATION: synthetic human polo-like kinase 1 (PLK-1)
      siRNA antisense strand

<400> SEQUENCE: 118
caaaaggugg uuugcccac                                                    19

<210> SEQ ID NO 119
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 119
accaccuuuu gagacuucu                                                    19

<210> SEQ ID NO 120
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 120
agaagucuca aaagguggu                                                    19

<210> SEQ ID NO 121
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 121
ccaccuuuug agacuucuu                                                    19

<210> SEQ ID NO 122
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 122
aagaagucuc aaaaggugg                                                    19

<210> SEQ ID NO 123
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 123
gaccuaccuc cggaucaag                                                    19

<210> SEQ ID NO 124
<211> LENGTH: 19
<212> TYPE: RNA
<213> ORGANISM: Artificial Sequence
<220> FEATURE:
```

```
<223> OTHER INFORMATION: synthetic human polo-like kinase 1 (PLK-1)
     siRNA antisense strand

<400> SEQUENCE: 124
cuugauccgg agguagguc                                                 19

<210> SEQ ID NO 125
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
     siRNA sense strand

<400> SEQUENCE: 125
ccuaccuccg gaucaagaa                                                 19

<210> SEQ ID NO 126
<211> LENGTH: 19
<212> TYPE: RNA
<213> ORGANISM: Artificial Sequence
<220> FEATURE:
<223> OTHER INFORMATION: human polo-like kinase 1 (PLK-1) siRNA
     antisense strand

<400> SEQUENCE: 126
uucuugaucc ggagguagg                                                 19

<210> SEQ ID NO 127
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
     siRNA sense strand

<400> SEQUENCE: 127
ccuccggauc aagaagaau                                                 19

<210> SEQ ID NO 128
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
     siRNA antisense strand

<400> SEQUENCE: 128
auucuucuug auccggagg                                                 19

<210> SEQ ID NO 129
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
     siRNA sense strand

<400> SEQUENCE: 129
ccauuaacga gcugcuuaa                                                 19

<210> SEQ ID NO 130
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
``` siRNA antisense strand

<400> SEQUENCE: 130
uuaagcagcu cguuaaugg                                                    19

<210> SEQ ID NO 131
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 131
gcugcuuaau gacgaguuc                                                    19

<210> SEQ ID NO 132
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 132
gaacucguca uuaagcagc                                                    19

<210> SEQ ID NO 133
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 133
ugacgaguuc uuuacuucu                                                    19

<210> SEQ ID NO 134
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 134
agaaguaaag aacucguca                                                    19

<210> SEQ ID NO 135
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 135
guccucaaua aaggcuugg                                                    19

<210> SEQ ID NO 136
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

```
<400> SEQUENCE: 136
ccaagccuuu auugaggac                                                    19

<210> SEQ ID NO 137
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 137
gcagcugcac agugucaau                                                    19

<210> SEQ ID NO 138
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 138
auugacacug ugcagcugc                                                    19

<210> SEQ ID NO 139
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 139
gcaagugggu ggacuauuc                                                    19

<210> SEQ ID NO 140
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 140
gaauagucca cccacuugc                                                    19

<210> SEQ ID NO 141
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 141
cacgccucau ccucuacaa                                                    19

<210> SEQ ID NO 142
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand
```

<400> SEQUENCE: 142
uuguagagga ugaggcgug                                                19

<210> SEQ ID NO 143
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 143
cgccucaucc ucuacaaug                                                19

<210> SEQ ID NO 144
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 144
cauuguagag gaugaggcg                                                19

<210> SEQ ID NO 145
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 145
cagccugcag uacauagag                                                19

<210> SEQ ID NO 146
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 146
cucuauguac ugcaggcug                                                19

<210> SEQ ID NO 147
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 147
gagcgugacg gcacugagu                                                19

<210> SEQ ID NO 148
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 148
acucagugcc gucacgcuc				19

<210> SEQ ID NO 149
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 149
ucccaacucc uugaugaag				19

<210> SEQ ID NO 150
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 150
cuucaucaag gaguuggga				19

<210> SEQ ID NO 151
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 151
acuccuugau gaagaagau				19

<210> SEQ ID NO 152
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 152
aucuucuuca ucaaggagu				19

<210> SEQ ID NO 153
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 153
gaagaucacc cuccuuaaa				19

<210> SEQ ID NO 154
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 154
uuuaaggagg gugaucuuc                                                    19

<210> SEQ ID NO 155
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 155
cccuccuuaa auauuccg                                                     19

<210> SEQ ID NO 156
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 156
cggaaauauu uaaggaggg                                                    19

<210> SEQ ID NO 157
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 157
ugagcgagca cuugcugaa                                                    19

<210> SEQ ID NO 158
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 158
uucagcaagu gcucgcuca                                                    19

<210> SEQ ID NO 159
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 159
cccgcagcgc caucauccu                                                    19

<210> SEQ ID NO 160
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 160
aggaugaugg cgcugcggg                                                    19

<210> SEQ ID NO 161
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 161
gcaacggcag cgugcagau                                              19

<210> SEQ ID NO 162
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 162
aucugcacgc ugccguugc                                              19

<210> SEQ ID NO 163
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 163
acggcagcgu gcagaucaa                                              19

<210> SEQ ID NO 164
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 164
uugaucugca cgcugccgu                                              19

<210> SEQ ID NO 165
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 165
cggcagcgug cagaucaac                                              19

<210> SEQ ID NO 166
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 166
guugaucugc acgcugccg                                              19

<210> SEQ ID NO 167
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 167
gcgugcagau caacuucuu                                               19

<210> SEQ ID NO 168
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 168
aagaaguuga ucugcacgc                                               19

<210> SEQ ID NO 169
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 169
gcucaucuug ugcccacug                                               19

<210> SEQ ID NO 170
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 170
cagugggcac aagaugagc                                               19

<210> SEQ ID NO 171
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 171
uggcagccgu gaccuacau                                               19

<210> SEQ ID NO 172
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 172
auguagguca cggcugcca                                               19

-continued

<210> SEQ ID NO 173
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
    siRNA sense strand

<400> SEQUENCE: 173
gccgugaccu acaucgacg                                                    19

<210> SEQ ID NO 174
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
    siRNA antisense strand

<400> SEQUENCE: 174
cgucgaugua ggucacggc                                                    19

<210> SEQ ID NO 175
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
    siRNA sense strand

<400> SEQUENCE: 175
ucgacgagaa gcgggacuu                                                    19

<210> SEQ ID NO 176
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
    siRNA antisense strand

<400> SEQUENCE: 176
aagucccgcu ucucgucga                                                    19

<210> SEQ ID NO 177
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
    siRNA sense strand

<400> SEQUENCE: 177
agcgggacuu ccgcacaua                                                    19

<210> SEQ ID NO 178
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
    siRNA antisense strand

<400> SEQUENCE: 178
uaugugcgga agucccgcu                                                    19

<210> SEQ ID NO 179

```
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 179
gcgggacuuc cgcacauac                                                  19

<210> SEQ ID NO 180
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 180
guaugugcgg aagucccgc                                                  19

<210> SEQ ID NO 181
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 181
ggaguacggc ugcugcaag                                                  19

<210> SEQ ID NO 182
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 182
cuugcagcag ccguacucc                                                  19

<210> SEQ ID NO 183
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 183
gcucacgcuc ggccagcaa                                                  19

<210> SEQ ID NO 184
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 184
uugcuggccg agcgugagc                                                  19

<210> SEQ ID NO 185
<211> LENGTH: 19
```

```
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 185
ccgucucaag gccuccuaa                                                    19

<210> SEQ ID NO 186
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 186
uuaggaggcc uugagacgg                                                    19

<210> SEQ ID NO 187
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 187
agaagauguc cauggaaau                                                    19

<210> SEQ ID NO 188
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 188
auuuccaugg acaucuucu                                                    19

<210> SEQ ID NO 189
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 189
gauacuaccu acggcaaau                                                    19

<210> SEQ ID NO 190
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 190
auuugccgua gguaguauc                                                    19

<210> SEQ ID NO 191
<211> LENGTH: 19
<212> TYPE: RNA
```

```
<213> ORGANISM: Artificial Sequence
<220> FEATURE:
<223> OTHER INFORMATION: synthetic human polo-like kinase 1 (PLK-1)
      siRNA sense strand

<400> SEQUENCE: 191
ugcaccgaaa ccgaguuau                                                19

<210> SEQ ID NO 192
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 192
auaacucggu uucggugca                                                19

<210> SEQ ID NO 193
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 193
ggcaaccaaa gucgaauau                                                19

<210> SEQ ID NO 194
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 194
auauucgacu uugguugcc                                                19

<210> SEQ ID NO 195
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 195
ccuguguggg acuccuaau                                                19

<210> SEQ ID NO 196
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 196
auuaggaguc ccacacagg                                                19

<210> SEQ ID NO 197
<211> LENGTH: 19
<212> TYPE: RNA
<213> ORGANISM: Artificial Sequence
```

```
<220> FEATURE:
<223> OTHER INFORMATION: synthetic human polo-like kinase 1 (PLK-1)
      siRNA sense strand

<400> SEQUENCE: 197
ugugugggac uccuaauua                                                    19

<210> SEQ ID NO 198
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 198
uaauuaggag ucccacaca                                                    19

<210> SEQ ID NO 199
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 199
cccucacagu ccucaauaa                                                    19

<210> SEQ ID NO 200
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 200
uuauugagga cugugaggg                                                    19

<210> SEQ ID NO 201
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 201
ccucacaguc cucaauaaa                                                    19

<210> SEQ ID NO 202
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 202
uuuauugagg acugugagg                                                    19

<210> SEQ ID NO 203
<211> LENGTH: 19
<212> TYPE: RNA
<213> ORGANISM: Artificial Sequence
<220> FEATURE:
```

```
<223> OTHER INFORMATION: synthetic human polo-like kinase 1 (PLK-1)
      siRNA sense strand

<400> SEQUENCE: 203
cucacagucc ucaauaaag                                                    19

<210> SEQ ID NO 204
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 204
cuuuauugag gacugugag                                                    19

<210> SEQ ID NO 205
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 205
cgucucaagg ccuccuaau                                                    19

<210> SEQ ID NO 206
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 206
auuaggaggc cuugagacg                                                    19

<210> SEQ ID NO 207
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 207
gucucaaggc cuccuaaua                                                    19

<210> SEQ ID NO 208
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 208
uauuaggagg ccuugagac                                                    19

<210> SEQ ID NO 209
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
```

```
                siRNA sense strand

<400> SEQUENCE: 209
ucucaaggcc uccuaauag                                                    19

<210> SEQ ID NO 210
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 210
cuauuaggag gccuugaga                                                    19

<210> SEQ ID NO 211
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 211
agaucacccu ccuuaaauau u                                                 21

<210> SEQ ID NO 212
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA antisense strand

<400> SEQUENCE: 212
uauuuaagga gggugaucuu u                                                 21

<210> SEQ ID NO 213
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (4)...(14)
<223> OTHER INFORMATION: n = um

<400> SEQUENCE: 213
agancacccn ccunaaauau u                                                 21

<210> SEQ ID NO 214
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (4)...(18)
<223> OTHER INFORMATION: n = um

<400> SEQUENCE: 214
agancacccn ccunaaanau u                                                 21
```

<210> SEQ ID NO 215
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
    modified siRNA antisense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 215
uauuuaanga gggugancuu u                                         21

<210> SEQ ID NO 216
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
    modified siRNA antisense strand
<220> FEATURE:
<221> NAME/KEY: modified_base
<222> LOCATION: (9)...(15)
<223> OTHER INFORMATION: n = gm

<400> SEQUENCE: 216
uauuuaagna gngunaucuu u                                         21

<210> SEQ ID NO 217
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
    modified siRNA antisense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (11)...(11)
<223> OTHER INFORMATION: n = gm
<220> FEATURE:
<221> NAME/KEY: modified_base
<222> LOCATION: (14)...(17)
<223> OTHER INFORMATION: n = um

<400> SEQUENCE: 217
uauunaagga nggngancuu u                                         21

<210> SEQ ID NO 218
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
    siRNA sense strand

<400> SEQUENCE: 218
agaccuaccu ccggaucaau u                                         21

<210> SEQ ID NO 219
<211> LENGTH: 21

```
<212> TYPE: RNA
<213> ORGANISM: Artificial Sequence
<220> FEATURE:
<223> OTHER INFORMATION: synthetic human polo-like kinase 1 (PLK-1)
      siRNA sense antistrand

<400> SEQUENCE: 219
uugauccgga gguaggucuu u                                              21

<210> SEQ ID NO 220
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (2)...(13)
<223> OTHER INFORMATION: n = gm

<400> SEQUENCE: 220
anaccuaccu ccngaucaau u                                              21

<210> SEQ ID NO 221
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (6)...(16)
<223> OTHER INFORMATION: n = um

<400> SEQUENCE: 221
agaccnaccn ccggancaau u                                              21

<210> SEQ ID NO 222
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (5)...(17)
<223> OTHER INFORMATION: n = um

<400> SEQUENCE: 222
uuganccgga ggnaggncuu u                                              21

<210> SEQ ID NO 223
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (9)...(12)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 223
```

```
uugauccgna gnuaggncuu u                                              21

<210> SEQ ID NO 224
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (4)...(16)
<223> OTHER INFORMATION: n = um

<400> SEQUENCE: 224
uuganccnga nguagnucuu u                                              21

<210> SEQ ID NO 225
<211> LENGTH: 21
<212> TYPE: DNA
<213> ORGANISM: Artificial Sequence
<220> FEATURE:
<223> OTHER INFORMATION: synthetic human kinesin spindle protein (KSP,
      Eg5) siRNA sense strand
<220> FEATURE:
<223> OTHER INFORMATION: Description of Combined DNA/RNA Molecule:
      synthetic human kinesin spindle protein (KSP, Eg5) siRNA sense
      strand

<400> SEQUENCE: 225
cugaagaccu gaagacaaut t                                              21

<210> SEQ ID NO 226
<211> LENGTH: 21
<212> TYPE: DNA
<213> ORGANISM: Artificial Sequence
<220> FEATURE:
<223> OTHER INFORMATION: synthetic human kinesin spindle protein (KSP,
      Eg5) siRNA antisense strand
<220> FEATURE:
<223> OTHER INFORMATION: Description of Combined DNA/RNA Molecule:
      synthetic human kinesin spindle protein (KSP, Eg5) siRNA
      antisense strand

<400> SEQUENCE: 226
auugucuuca ggucuucagt t                                              21

<210> SEQ ID NO 227
<211> LENGTH: 21
<212> TYPE: DNA
<213> ORGANISM: Artificial Sequence
<220> FEATURE:
<223> OTHER INFORMATION: synthetic human kinesin spindle protein (KSP,
      Eg5) modified siRNA sense strand
<220> FEATURE:
<223> OTHER INFORMATION: Description of Combined DNA/RNA Molecule:
      synthetic human kinesin spindle protein (KSP, Eg5) modified
      siRNA sense strand
<220> FEATURE:
<221> NAME/KEY: modified_base
<222> LOCATION: (2)...(19)
<223> OTHER INFORMATION: n = um

<400> SEQUENCE: 227
cngaagaccn gaagacaant t                                              21
```

```
<210> SEQ ID NO 228
<211> LENGTH: 21
<212> TYPE: DNA
<213> ORGANISM: Artificial Sequence
<220> FEATURE:
<223> OTHER INFORMATION: synthetic human kinesin spindle protein (KSP,
      Eg5) modified siRNA sense strand
<220> FEATURE:
<223> OTHER INFORMATION: Description of Combined DNA/RNA Molecule:
      synthetic human kinesin spindle protein (KSP, Eg5) modified
      siRNA sense strand
<220> FEATURE:
<221> NAME/KEY: modified_base
<222> LOCATION: (3)...(14)
<223> OTHER INFORMATION: n = gm

<400> SEQUENCE: 228
cunaanaccu naanacaaut t                                            21

<210> SEQ ID NO 229
<211> LENGTH: 21
<212> TYPE: DNA
<213> ORGANISM: Artificial Sequence
<220> FEATURE:
<223> OTHER INFORMATION: synthetic human kinesin spindle protein (KSP,
      Eg5) modified siRNA antisense strand
<220> FEATURE:
<223> OTHER INFORMATION: Description of Combined DNA/RNA Molecule:
      synthetic human kinesin spindle protein (KSP, Eg5) modified
      siRNA antisense strand
<220> FEATURE:
<221> NAME/KEY: modified_base
<222> LOCATION: (8)...(16)
<223> OTHER INFORMATION: n = um

<400> SEQUENCE: 229 augucunca ggncuncagt t                                             21

<210> SEQ ID NO 230
<211> LENGTH: 21
<212> TYPE: DNA
<213> ORGANISM: Artificial Sequence
<220> FEATURE:
<223> OTHER INFORMATION: synthetic human kinesin spindle protein (KSP,
      Eg5) modified siRNA antisense strand
<220> FEATURE:
<223> OTHER INFORMATION: Description of Combined DNA/RNA Molecule:
      synthetic human kinesin spindle protein (KSP, Eg5) modified siRNA
      antisense strand
<220> FEATURE:
<221> NAME/KEY: modified_base
<222> LOCATION: (4)...(19)
<223> OTHER INFORMATION: n = gm

<400> SEQUENCE: 230
auunucuuca gnucuucant t                                            21

<210> SEQ ID NO 231
<211> LENGTH: 21
<212> TYPE: RNA
<213> ORGANISM: Artificial Sequence
<220> FEATURE:
<223> OTHER INFORMATION: synthetic luciferase (Luc) siRNA sense strand

<400> SEQUENCE: 231
gauuaugucc gguuauguau u                                            21

<210> SEQ ID NO 232
<211> LENGTH: 21
<212> TYPE: RNA
```

```
<213> ORGANISM: Artificial Sequence
<220> FEATURE:
<223> OTHER INFORMATION: synthetic luciferase (Luc) siRNA antisense
      strand

<400> SEQUENCE: 232
uacauaaccg gacauaaucu u                                          21

<210> SEQ ID NO 233
<211> LENGTH: 21
<212> TYPE: RNA
<213> ORGANISM: Artificial Sequence
<220> FEATURE:
<223> OTHER INFORMATION: synthetic luciferase (Luc) modified siRNA
      sense strand
<220> FEATURE:
<221> NAME/KEY: modified_base
<222> LOCATION: (3)...(18)
<223> OTHER INFORMATION: n = um

<400> SEQUENCE: 233
ganuangncc ggnnangnau u                                          21

<210> SEQ ID NO 234
<211> LENGTH: 21
<212> TYPE: RNA
<213> ORGANISM: Artificial Sequence
<220> FEATURE:
<223> OTHER INFORMATION: synthetic luciferase (Luc) modified siRNA
      antisense strand
<220> FEATURE:
<221> NAME/KEY: modified_base
<222> LOCATION: (5)...(18)
<223> OTHER INFORMATION: n = um

<400> SEQUENCE: 234
uacanaaccg gacanaancu u                                          21

<210> SEQ ID NO 235
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 235
gguccuagug gacccacgcu u                                          21

<210> SEQ ID NO 236
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 236
agccgcacca gagggagaau u                                          21

<210> SEQ ID NO 237
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 237
```
gccgcaccag agggagaagu u                                              21

<210> SEQ ID NO 238
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 238
ggacaacgac uucguguucu u                                              21

<210> SEQ ID NO 239
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 239
cuccuggagc ugcacaagau u                                              21

<210> SEQ ID NO 240
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 240
gccugaggcc cgauacuacu u                                              21

<210> SEQ ID NO 241
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 241
ccugcaccga aaccgaguuu u                                              21

<210> SEQ ID NO 242
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 242
gaggaagaag acccuguguu u                                              21

<210> SEQ ID NO 243
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 243
gacccugugu gggacuccuu u 21

<210> SEQ ID NO 244
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 244
cccugugugg gacuccuaau u 21

<210> SEQ ID NO 245
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 245
ccuguguggg acuccuaauu u 21

<210> SEQ ID NO 246
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 246
gguggaugug ugguccauuu u 21

<210> SEQ ID NO 247
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 247
guggaugugu gguccauugu u 21

<210> SEQ ID NO 248
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 248
gugggcaaac caccuuuugu u 21

<210> SEQ ID NO 249
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 249
accaccuuuu gagacuucuu u 21

```
<210> SEQ ID NO 250
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 250
ccaccuuuug agacuucuuu u                                             21

<210> SEQ ID NO 251
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 251
gagaccuacc uccggaucau u                                             21

<210> SEQ ID NO 252
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 252
ccuaccuccg gaucaagaau u                                             21

<210> SEQ ID NO 253
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 253
ccuccggauc aagaagaauu u                                             21

<210> SEQ ID NO 254
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 254
gccgccuccc ucauccagau u                                             21

<210> SEQ ID NO 255
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 255
cucccucauc cagaagaugu u                                             21
```

```
<210> SEQ ID NO 256
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 256
gcagcugcac agugucaauu u                                                   21

<210> SEQ ID NO 257
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 257
gaggcugagg auccugccuu u                                                   21

<210> SEQ ID NO 258
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 258
gggucagcaa gugggluggau u                                                  21

<210> SEQ ID NO 259
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 259
ucagcaagug gguggacuau u                                                   21

<210> SEQ ID NO 260
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 260
cagcaagugg guggacuauu u                                                   21

<210> SEQ ID NO 261
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 261 ggluggacuau ucggacaagu u                                                  21
```

```
<210> SEQ ID NO 262
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 262
cacgccucau ccucuacaau u                                              21

<210> SEQ ID NO 263
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 263
cgccucaucc ucuacaaugu u                                              21

<210> SEQ ID NO 264
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 264
cagccugcag uacauagagu u                                              21

<210> SEQ ID NO 265
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 265
ucccaacucc uugaugaagu u                                              21

<210> SEQ ID NO 266
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 266
acuccuugau gaagaagauu u                                              21

<210> SEQ ID NO 267
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 267
ugagcgagca cuugcugaau u                                              21

<210> SEQ ID NO 268
```

```
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 268
cccgcagcgc caucauccuu u                                              21

<210> SEQ ID NO 269
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 269
gcgccaucau ccugcaccuu u                                              21

<210> SEQ ID NO 270
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 270
gcaacggcag cgugcagauu u                                              21

<210> SEQ ID NO 271
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 271
acggcagcgu gcagaucaau u                                              21

<210> SEQ ID NO 272
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 272
gcucaucuug ugcccacugu u                                              21

<210> SEQ ID NO 273
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      siRNA sense strand

<400> SEQUENCE: 273
ucgacgagaa gcgggacuuu u                                              21

<210> SEQ ID NO 274
<211> LENGTH: 44
```

```
<212> TYPE: RNA
<213> ORGANISM: Artificial Sequence
<220> FEATURE:
<223> OTHER INFORMATION: synthetic 5' RNA ligase mediated rapid
      amplification of cDNA ends (5' RLM RACE) GeneRacer
      RNA adaptor

<400> SEQUENCE: 274
cgacuggagc acgaggacac ugacauggac ugaaggagua gaaa              44

<210> SEQ ID NO 275
<211> LENGTH: 23
<212> TYPE: DNA
<213> ORGANISM: Artificial Sequence
<220> FEATURE:
<223> OTHER INFORMATION: synthetic reverse transcription PLK-1-
      specific primer

<400> SEQUENCE: 275
ggacaaggct gtagaaccca cac                                     23

<210> SEQ ID NO 276
<211> LENGTH: 23
<212> TYPE: DNA
<213> ORGANISM: Artificial Sequence
<220> FEATURE:
<223> OTHER INFORMATION: synthetic 5' RNA ligase mediated rapid
      amplification of cDNA ends (5' RLM RACE) PCR
      forward primer GR5

<400> SEQUENCE: 276
cgactggagc acgaggacac tga                                     23

<210> SEQ ID NO 277
<211> LENGTH: 23
<212> TYPE: DNA
<213> ORGANISM: Artificial Sequence
<220> FEATURE:
<223> OTHER INFORMATION: synthetic 5' RNA ligase mediated rapid
      amplification of cDNA ends (5' RLM RACE) PCR
      reverse primer PLK1424rev

<400> SEQUENCE: 277
ccagatgcag gtgggagtga gga                                     23

<210> SEQ ID NO 278
<211> LENGTH: 18
<212> TYPE: DNA
<213> ORGANISM: Artificial Sequence
<220> FEATURE:
<223> OTHER INFORMATION: synthetic sequencing primer GeneRacer 5' Seq

<400> SEQUENCE: 278
actggagcac gaggacac                                           18

<210> SEQ ID NO 279
<211> LENGTH: 19
<212> TYPE: DNA
<213> ORGANISM: Artificial Sequence
<220> FEATURE:
<223> OTHER INFORMATION: synthetic sequencing primer PLK1424 3' Seq

<400> SEQUENCE: 279
gagacgggca gggatatag                                          19

<210> SEQ ID NO 280
<211> LENGTH: 23
```

```
<212> TYPE: DNA
<213> ORGANISM: Artificial Sequence
<220> FEATURE:
<223> OTHER INFORMATION: synthetic unique amplification KSP-specific
      cDNA primer

<400> SEQUENCE: 280
gctgctctcg tggttcagtt ctc                                           23

<210> SEQ ID NO 281
<211> LENGTH: 25
<212> TYPE: DNA
<213> ORGANISM: Artificial Sequence
<220> FEATURE:
<223> OTHER INFORMATION: synthetic unique amplification RACE primer
      KSPrev

<400> SEQUENCE: 281
gcccaactac tgcttaactg gcaaa                                         25

<210> SEQ ID NO 282
<211> LENGTH: 20
<212> TYPE: DNA
<213> ORGANISM: Artificial Sequence
<220> FEATURE:
<223> OTHER INFORMATION: synthetic unique amplification KSP sequencing
      primer

<400> SEQUENCE: 282
tgggtttcct ttattgtctt                                               20

<210> SEQ ID NO 283
<211> LENGTH: 21
<212> TYPE: RNA
<213> ORGANISM: Artificial Sequence
<220> FEATURE:
<223> OTHER INFORMATION: synthetic ApoB-1 siRNA sense strand

<400> SEQUENCE: 283
gucaucacac ugaauaccaa u                                             21

<210> SEQ ID NO 284
<211> LENGTH: 21
<212> TYPE: RNA
<213> ORGANISM: Artificial Sequence
<220> FEATURE:
<223> OTHER INFORMATION: synthetic ApoB-1 modified siRNA 2'OMe sense
      strand
<220> FEATURE:
<221> NAME/KEY: modified_base
<222> LOCATION: (2)...(21)
<223> OTHER INFORMATION: n = um

<400> SEQUENCE: 284
gncancacac ngaanaccaa n                                             21

<210> SEQ ID NO 285
<211> LENGTH: 23
<212> TYPE: RNA
<213> ORGANISM: Artificial Sequence
<220> FEATURE:
<223> OTHER INFORMATION: synthetic ApoB-1 siRNA antisense (AS) strand

<400> SEQUENCE: 285
auugguauuc agugugauga cac                                           23

<210> SEQ ID NO 286
```

```
<211> LENGTH: 23
<212> TYPE: RNA
<213> ORGANISM: Artificial Sequence
<220> FEATURE:
<223> OTHER INFORMATION: synthetic ApoB-1 modified siRNA 2'OMe antisense
      (AS) strand
<220> FEATURE:
<221> NAME/KEY: modified_base
<222> LOCATION: (9)...(9)
<223> OTHER INFORMATION: n = um
<220> FEATURE:
<221> NAME/KEY: modified_base
<222> LOCATION: (12)...(14)
<223> OTHER INFORMATION: n = gm
<220> FEATURE:
<221> NAME/KEY: modified_base
<222> LOCATION: (18)...(18)
<223> OTHER INFORMATION: n = um

<400> SEQUENCE: 286
auugguaunc anunuganga cac                                              23

<210> SEQ ID NO 287
<211> LENGTH: 12
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 287
cccuccuuaa au                                                          12

<210> SEQ ID NO 288
<211> LENGTH: 12
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 288
acccuccuua aa                                                          12

<210> SEQ ID NO 289
<211> LENGTH: 12
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 289
cacccuccuu aa                                                          12

<210> SEQ ID NO 290
<211> LENGTH: 13
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 290
acccuccuua aau                                                         13

<210> SEQ ID NO 291
<211> LENGTH: 13
<212> TYPE: RNA
```

```
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 291
cacccuccuu aaa                                                              13

<210> SEQ ID NO 292
<211> LENGTH: 13
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 292
ucacccuccu uaa                                                              13

<210> SEQ ID NO 293
<211> LENGTH: 14
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 293
cacccuccuu aaau                                                             14

<210> SEQ ID NO 294
<211> LENGTH: 14
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 294
ucacccuccu uaaa                                                             14

<210> SEQ ID NO 295
<211> LENGTH: 14
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 295
aucacccucc uuaa                                                             14

<210> SEQ ID NO 296
<211> LENGTH: 15
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 296
ucacccuccu uaaau                                                            15

<210> SEQ ID NO 297
<211> LENGTH: 15
<212> TYPE: RNA
<213> ORGANISM: Artificial Sequence
```

```
<220> FEATURE:
<223> OTHER INFORMATION: synthetic human polo-like kinase 1 (PLK-1)
      asymmetrical interfering RNA (aiRNA) sense strand

<400> SEQUENCE: 297
aucacccucc uuaaa                                                          15

<210> SEQ ID NO 298
<211> LENGTH: 15
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 298
gaucacccuc cuuaa                                                          15

<210> SEQ ID NO 299
<211> LENGTH: 16
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 299
aucacccucc uuaaau                                                         16

<210> SEQ ID NO 300
<211> LENGTH: 16
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 300
gaucacccuc cuuaaa                                                         16

<210> SEQ ID NO 301
<211> LENGTH: 17
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 301
gaucacccuc cuuaaau                                                        17

<210> SEQ ID NO 302
<211> LENGTH: 12
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 302
accuccggau ca                                                             12

<210> SEQ ID NO 303
<211> LENGTH: 12
<212> TYPE: RNA
<213> ORGANISM: Artificial Sequence
<220> FEATURE:
```

<223> OTHER INFORMATION: synthetic human polo-like kinase 1 (PLK-1)
       asymmetrical interfering RNA (aiRNA) sense strand

<400> SEQUENCE: 303
uaccuccgga uc                                                              12

<210> SEQ ID NO 304
<211> LENGTH: 12
<212> TYPE: RNA
<213> ORGANISM: Artificial Sequence
<220> FEATURE:
<223> OTHER INFORMATION: synthetic human polo-like kinase 1 (PLK-1)
       asymmetrical interfering RNA (aiRNA) sense strand

<400> SEQUENCE: 304
cuaccuccgg au                                                              12

<210> SEQ ID NO 305
<211> LENGTH: 13
<212> TYPE: RNA
<213> ORGANISM: Artificial Sequence
<220> FEATURE:
<223> OTHER INFORMATION: synthetic human polo-like kinase 1 (PLK-1)
       asymmetrical interfering RNA (aiRNA) sense strand

<400> SEQUENCE: 305
uaccuccgga uca                                                             13

<210> SEQ ID NO 306
<211> LENGTH: 13
<212> TYPE: RNA
<213> ORGANISM: Artificial Sequence
<220> FEATURE:
<223> OTHER INFORMATION: synthetic human polo-like kinase 1 (PLK-1)
       asymmetrical interfering RNA (aiRNA) sense strand

<400> SEQUENCE: 306
cuaccuccgg auc                                                             13

<210> SEQ ID NO 307
<211> LENGTH: 13
<212> TYPE: RNA
<213> ORGANISM: Artificial Sequence
<220> FEATURE:
<223> OTHER INFORMATION: synthetic human polo-like kinase 1 (PLK-1)
       asymmetrical interfering RNA (aiRNA) sense strand

<400> SEQUENCE: 307
ccuaccuccg gau                                                             13

<210> SEQ ID NO 308
<211> LENGTH: 14
<212> TYPE: RNA
<213> ORGANISM: Artificial Sequence
<220> FEATURE:
<223> OTHER INFORMATION: synthetic human polo-like kinase 1 (PLK-1)
       asymmetrical interfering RNA (aiRNA) sense strand

<400> SEQUENCE: 308
cuaccuccgg auca                                                            14

<210> SEQ ID NO 309
<211> LENGTH: 14
<212> TYPE: RNA
<213> ORGANISM: Artificial Sequence
<220> FEATURE:
<223> OTHER INFORMATION: synthetic human polo-like kinase 1 (PLK-1)

asymmetrical interfering RNA (aiRNA) sense strand

<400> SEQUENCE: 309
ccuaccuccg gauc                                                         14

<210> SEQ ID NO 310
<211> LENGTH: 14
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 310
accuaccucc ggau                                                         14

<210> SEQ ID NO 311
<211> LENGTH: 15
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 311
ccuaccuccg gauca                                                        15

<210> SEQ ID NO 312
<211> LENGTH: 15
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 312
accuaccucc ggauc                                                        15

<210> SEQ ID NO 313
<211> LENGTH: 15
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 313
gaccuaccuc cggau                                                        15

<210> SEQ ID NO 314
<211> LENGTH: 16
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 314
accuaccucc ggauca                                                       16

<210> SEQ ID NO 315
<211> LENGTH: 16
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

```
<400> SEQUENCE: 315
gaccuaccuc cggauc                                                    16

<210> SEQ ID NO 316
<211> LENGTH: 17
<212> TYPE: RNA
<213> ORGANISM: Artificial Sequence
<220> FEATURE:
<223> OTHER INFORMATION: synthetic human polo-like kinase 1 (PLK-1)
      asymmetrical interfering RNA (aiRNA) sense strand

<400> SEQUENCE: 316
gaccuaccuc cggauca                                                   17

<210> SEQ ID NO 317
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 317
uacugcagac guggcaauca ug                                             22

<210> SEQ ID NO 318
<211> LENGTH: 20
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 318
ggugggaggu ggguggca                                                  20

<210> SEQ ID NO 319
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 319
uacugcagac aguggcaauc a                                              21

<210> SEQ ID NO 320
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 320
gggagccagg aaguauugau gu                                             22

<210> SEQ ID NO 321
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence
```

```
<400> SEQUENCE: 321 ggggcuggggg ccgggacaga gc                                           22

<210> SEQ ID NO 322
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 322
agggagggac gggggcugug c                                             21

<210> SEQ ID NO 323
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 323
uauggcacug guagaauuca cu                                            22

<210> SEQ ID NO 324
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 324
auaaagcuag auaaccgaaa gu                                            22

<210> SEQ ID NO 325
<211> LENGTH: 23
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 325
uccggggcug aguucugugc acc                                           23

<210> SEQ ID NO 326
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 326
aguauucugu accagggaag gu                                            22

<210> SEQ ID NO 327
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 327
```
cuuaugcaag auucccuucu ac                                        22

<210> SEQ ID NO 328
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 328
uaaaguaaau augcaccaaa a                                         21

<210> SEQ ID NO 329
<211> LENGTH: 25
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 329
aggcaccagc caggcauugc ucagc                                     25

<210> SEQ ID NO 330
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 330
acuugagggg caugaggau                                            19

<210> SEQ ID NO 331
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 331
cuauacaguc uacugucuuu cc                                        22

<210> SEQ ID NO 332
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 332
aacccguaga uccgaacuug ug                                        22

<210> SEQ ID NO 333
<211> LENGTH: 23
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 333
ucugcucaua ccccauggun ucu                                              23

<210> SEQ ID NO 334
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 334
ccucccacac ccaaggcuug ca                                               22

<210> SEQ ID NO 335
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 335
ccgcacugug gguacuugcu gc                                               22

<210> SEQ ID NO 336
<211> LENGTH: 20
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 336
auguauaaau guauacacac                                                  20

<210> SEQ ID NO 337
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 337
aauggcgcca cuaggguugu g                                                21

<210> SEQ ID NO 338
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 338
cuauacggcc uccuagcuuu cc                                               22

<210> SEQ ID NO 339
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 339
uuauaaagca augagacuga uu                                               22

```
<210> SEQ ID NO 340
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 340
gguccagagg ggagauaggu uc                                              22

<210> SEQ ID NO 341
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 341
aaaaguaauu gugguuuugg cc                                              22

<210> SEQ ID NO 342
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 342
cucaucugca aagaaguaag ug                                              22

<210> SEQ ID NO 343
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 343
aaguucuguu auacacucag gc                                              22

<210> SEQ ID NO 344
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 344
cuguacaggc cacugccuug c                                               21

<210> SEQ ID NO 345
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 345
uugaaaggcu auuucuuggu c                                               21
```

<210> SEQ ID NO 346
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 346
cagccacauc cgaaaguuuu c                                             21

<210> SEQ ID NO 347
<211> LENGTH: 23
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 347
acuccauuug uuuugaugau gga                                           23

<210> SEQ ID NO 348
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 348
ugcggggcua gggcuaacag ca                                            22

<210> SEQ ID NO 349
<211> LENGTH: 20
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 349
acugccccag gugcugcugg                                               20

<210> SEQ ID NO 350
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 350
aaaagcuggg uugagagggc ga                                            22

<210> SEQ ID NO 351
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 351
aacccguaga uccgaucuug ug                                            22

```
<210> SEQ ID NO 352
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 352
gagcuuauuc auaaaagugc ag                                              22

<210> SEQ ID NO 353
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 353
acagucugcu gagguuggag c                                               21

<210> SEQ ID NO 354
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 354
ucgaggagcu cacagucuag u                                               21

<210> SEQ ID NO 355
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 355
cauaaaguag aaagcacuac u                                               21

<210> SEQ ID NO 356
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 356
aagugugcag ggcacuggu                                                  19

<210> SEQ ID NO 357
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 357
acuuguaugc uagcucaggu ag                                              22

<210> SEQ ID NO 358
```

```
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 358
aguuuugcau aguugcacua ca                                              22

<210> SEQ ID NO 359
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 359
aucuggaggu aagaagcacu uu                                              22

<210> SEQ ID NO 360
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 360 agggccccccc cucaauccug u                                              21

<210> SEQ ID NO 361
<211> LENGTH: 24
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 361
gaccuggaca uguuugugcc cagu                                            24

<210> SEQ ID NO 362
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 362
gaaagccacc augcugggua aa                                              22

<210> SEQ ID NO 363
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 363
gugugcggaa augcuucugc ua                                              22

<210> SEQ ID NO 364
<211> LENGTH: 22
```

```
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 364
ugugugcaug ugcuugugug ua                                              22

<210> SEQ ID NO 365
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 365
cacgcgggaa ccgaguccac c                                               21

<210> SEQ ID NO 366
<211> LENGTH: 23
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 366
cacccggcug ugugcacaug ugc                                             23

<210> SEQ ID NO 367
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 367
uagcuuauca gacugauguu ga                                              22

<210> SEQ ID NO 368
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 368
agcgggcaca gcugugagag cc                                              22

<210> SEQ ID NO 369
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 369
acugcaguga aggcacuugu ag                                              22

<210> SEQ ID NO 370
<211> LENGTH: 21
<212> TYPE: RNA
```

```
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 370
cucccacaug caggguuugc a                                            21

<210> SEQ ID NO 371
<211> LENGTH: 20
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 371
cuacaaaggg aagcccuuuc                                              20

<210> SEQ ID NO 372
<211> LENGTH: 23
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 372
ugugcaaauc uaugcaaaac uga                                          23

<210> SEQ ID NO 373
<211> LENGTH: 22
<212> TYPE: RNA
<213> ORGANISM: Artificial Sequence
<220> FEATURE:
<223> OTHER INFORMATION: human polo-like kinase 1 (PLK-1) silencing
      mature microRNA (miRNA) sequence

<400> SEQUENCE: 373
uugcauaguc acaaaaguga uc                                           22

<210> SEQ ID NO 374
<211> LENGTH: 21
<212> TYPE: RNA
<213> ORGANISM: Artificial Sequence
<220> FEATURE:
<223> OTHER INFORMATION: human polo-like kinase 1 (PLK-1) silencing
      mature microRNA (miRNA) sequence

<400> SEQUENCE: 374
gcuaguccug acucagccag u                                            21

<210> SEQ ID NO 375
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 375
ugagcuaaau gugugcuggg a                                            21

<210> SEQ ID NO 376
<211> LENGTH: 23
<212> TYPE: RNA
<213> ORGANISM: Artificial Sequence
```

<220> FEATURE:
<223> OTHER INFORMATION: synthetic human polo-like kinase 1 (PLK-1)
      silencing mature microRNA (miRNA) sequence

<400> SEQUENCE: 376
uagugcaaua uugcuuauag ggu                                              23

<210> SEQ ID NO 377
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 377
acagauucga uucuagggga au                                               22

<210> SEQ ID NO 378
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 378
uggugggccg cagaacaugu gc                                               22

<210> SEQ ID NO 379
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 379
uacgugugug ugcaugugca ug                                               22

<210> SEQ ID NO 380
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 380
cugugcgugu gacagcggcu ga                                               22

<210> SEQ ID NO 381
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 381
cacacacugc aauuacuuuu gc                                               22

<210> SEQ ID NO 382
<211> LENGTH: 22
<212> TYPE: RNA
<213> ORGANISM: Artificial Sequence
<220> FEATURE:

```
<223> OTHER INFORMATION: synthetic human polo-like kinase 1 (PLK-1)
      silencing mature microRNA (miRNA) sequence

<400> SEQUENCE: 382
aaaucucugc aggcaaaugu ga                                                22

<210> SEQ ID NO 383
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 383
agacaugugc ucugcuccua g                                                 21

<210> SEQ ID NO 384
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 384
cuagguaugg ucccagggau cc                                                22

<210> SEQ ID NO 385
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 385
uuugaaccau cacucgacuc cu                                                22

<210> SEQ ID NO 386
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 386
ugagaaccac gucugcucug ag                                                22

<210> SEQ ID NO 387
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 387
caagaaccuc aguugcuuuu gu                                                22

<210> SEQ ID NO 388
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
```

-continued silencing mature microRNA (miRNA) sequence

<400> SEQUENCE: 388
caaauucgua ucuaggggaa ua                                                22

<210> SEQ ID NO 389
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 389
aggcugcgga auucaggac                                                    19

<210> SEQ ID NO 390
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 390
gucauacacg gcucuccucu cu                                                22

<210> SEQ ID NO 391
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 391
uaacugcaac aucucucagu au                                                22

<210> SEQ ID NO 392
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 392
aacacaccug guuaaccucu uu                                                22

<210> SEQ ID NO 393
<211> LENGTH: 19
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 393
ugggcguauc uguaugcua                                                    19

<210> SEQ ID NO 394
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 394
gcgacccaua cuugguuuca g                                              21

<210> SEQ ID NO 395
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 395
cgcgggugcu uacugacccu u                                              21

<210> SEQ ID NO 396
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 396
cgacgagggc cggucggucg c                                              21

<210> SEQ ID NO 397
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 397
agugccgcag aguuuguagu gu                                             22

<210> SEQ ID NO 398
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 398
uucaacgggu auuuauugag ca                                             22

<210> SEQ ID NO 399
<211> LENGTH: 22
<212> TYPE: RNA
<213> ORGANISM: Artificial Sequence
<220> FEATURE:
<223> OTHER INFORMATION: synthetic human polo-like kinase 1 (PLK-1)
      silencing mature microRNA (miRNA) sequence

<400> SEQUENCE: 399
cacccguaga accgaccuug cg                                             22

<210> SEQ ID NO 400
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:

```
<221> NAME/KEY: modified_base
<222> LOCATION: (4)...(20)
<223> OTHER INFORMATION: n = um

<400> SEQUENCE: 400
agancacccn ccunaaanan u                                              21

<210> SEQ ID NO 401
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 401
uauuuaanga gggugancuu c                                              21

<210> SEQ ID NO 402
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (8)...(8)
<223> OTHER INFORMATION: n = gm
<220> FEATURE:
<221> NAME/KEY: modified_base
<222> LOCATION: (17)...(20)
<223> OTHER INFORMATION: n = um

<400> SEQUENCE: 402
uauuuaanga gggugancun c                                              21

<210> SEQ ID NO 403
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA
      antisense strand
<220> FEATURE:
<221> NAME/KEY: modified_base
<222> LOCATION: (8)...(15)
<223> OTHER INFORMATION: n = gm
<220> FEATURE:
<221> NAME/KEY: modified_base
<222> LOCATION: (17)...(20)
<223> OTHER INFORMATION: n = um

<400> SEQUENCE: 403
uauuuaanga gggunancun c                                              21

<210> SEQ ID NO 404
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
```

```
        modified siRNA antisense strand
<220> FEATURE:
<221> NAME/KEY: modified_base
<222> LOCATION: (8)...(15)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 404
uauuuaanna gngunancuu u                                              21

<210> SEQ ID NO 405
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA sense strand
<220> FEATURE:
<221> NAME/KEY: modified_base
<222> LOCATION: (2)...(13)
<223> OTHER INFORMATION: n = gm

<400> SEQUENCE: 405
anaccuaccu ccngaucaag a                                              21

<210> SEQ ID NO 406
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (9)...(12)
<223> OTHER INFORMATION: n = um
<220> FEATURE:
<221> NAME/KEY: modified_base
<222> LOCATION: (17)...(17)
<223> OTHER INFORMATION: n = um

<400> SEQUENCE: 406
uugauccgna gnuaggncuc u                                              21

<210> SEQ ID NO 407
<211> LENGTH: 21
<212> TYPE: RNA
<213> ORGANISM: Artificial Sequence
<220> FEATURE:
<223> OTHER INFORMATION: synthetic human polo-like kinase 1 (PLK-1)
      modified siRNA antisense strand
<220> FEATURE:
<221> NAME/KEY: modified_base
<222> LOCATION: (5)...(5)
<223> OTHER INFORMATION: n = um
<220> FEATURE:
<221> NAME/KEY: modified_base
<222> LOCATION: (9)...(12)
<223> OTHER INFORMATION: n = gm
<220> FEATURE:
<221> NAME/KEY: modified_base
<222> LOCATION: (17)...(17)
<223> OTHER INFORMATION: n = um

<400> SEQUENCE: 407
uuganccgna gnuaggncuc u                                              21
```